(12) United States Patent
Chan Chun Kong et al.

(10) Patent No.: US 7,402,608 B2
(45) Date of Patent: Jul. 22, 2008

(54) **COMPOUNDS AND METHODS FOR THE TREATMENT OR PREVENTION OF *FLAVIVIRUS* INFECTIONS**

(75) Inventors: Laval Chan Chun Kong, Kirkland (CA); Sanjoy Kumar Das, Laval (CA); Nghe Nguyen-Ba, LaPrairie (CA); Liliane Halab, Outremont (CA); Oswy Z. Pereira, Kirkland (CA); Carl Poisson, Montreal (CA); Melanie Proulx, Knowlton (CA); Thumkunta Jagadeeswar Reddy, St. Laurent (CA); Zhang Ming-Qiang, Kirkland (CA)

(73) Assignee: ViroChem Pharma Inc., Quebec (CA)

( * ) Notice: Subject to any disclaimer, the term of this patent is extended or adjusted under 35 U.S.C. 154(b) by 253 days.

(21) Appl. No.: 10/730,272

(22) Filed: Dec. 9, 2003

(65) Prior Publication Data

US 2005/0009804 A1 Jan. 13, 2005

Related U.S. Application Data

(60) Provisional application No. 60/431,964, filed on Dec. 10, 2002.

(51) Int. Cl.
*A61K 31/381* (2006.01)
*C07D 333/10* (2006.01)

(52) U.S. Cl. ........................ 514/444; 514/447; 514/326; 549/60; 549/63

(58) Field of Classification Search ............... 514/279.7, 514/326, 444, 447; 546/209, 342; 549/60, 549/63
See application file for complete search history.

(56) References Cited

U.S. PATENT DOCUMENTS

| | | | |
|---|---|---|---|
| 4,180,662 | A | 12/1979 | Pfister et al. |
| 6,187,799 | B1 | 2/2001 | Wood et al. |
| 6,380,214 | B1 | 4/2002 | Gant et al. |
| 6,414,013 | B1 | 7/2002 | Fancelli et al. |
| 6,448,290 | B1 | 9/2002 | Ohuchida et al. |
| 6,620,767 | B1 | 9/2003 | Ducray et al. |
| 6,660,728 | B2 | 12/2003 | Scheunemann et al. |
| 6,660,732 | B2 | 12/2003 | Betageri et al. |
| 6,734,207 | B2 | 5/2004 | Uckun et al. |
| 6,747,057 | B2 | 6/2004 | Ruzafa et al. |
| 6,881,741 | B2 * | 4/2005 | Chan Chun Kong et al. .. 514/91 |

FOREIGN PATENT DOCUMENTS

| | | |
|---|---|---|
| DE | 199 03 398 A | 8/2000 |
| DE | 199 20 247 A | 11/2000 |
| JP | 7-48360 | 2/1995 |
| WO | WO 98/52558 | 11/1998 |
| WO | WO 02/28353 | 4/2002 |

OTHER PUBLICATIONS

Roberts et al. "Preparation of nucleoside . . . " CA 139:365176 (2003).*
Hadziyannis et al. "Emerging treatments in chronic hepatitis B" CA 142:253391 (2004).*
Sostegni et al. "wquential versis concomitant administration . . . " CA 129:285628 (1998).*
Vicari et al. "Safety, pharmacokinetics . . . " CA 2007:977620 (2007).*
David McKinnon et al., "The Conversions of Izothiazolium Salts into Thiophenecarboxylic Ester Derivatives", *Can. J. Chem.*, 1984, vol. 62, pp. 1580-1584.
Pilar Goya et al., Synthesis of 4-Oxo- 3,4-dihydro-1 *H*-thieno [3,4-c] and thieno [3,2-c][1,2,6]thiadiazine 2,2-Dioxides, *Synthesis*, Apr. 1989, pp. 280-282.
Bo Sung Kim et al., "Reactions of Thiaroylketene S,N-Acetals with 1,3-Dicarbonyl Compounds in the Presence of Mercury (II) Acetate: A General Route to 2-Acyl-and 2 Aroyl-3-(alkylamino)-5-arylthiopenes and 2-(Ethoxycarbonyl)-3-(methylamino)-5-arylthiopenes", *J. Org. Chem.*, 1998, vol. 63, pp. 6086-6087.
Bo Sung et al., "A Facile and Convenient Synthesis of 3-Alkylamino-5-arylthiopenes with a Variety of Substituents at C-2 and Studies of Reaction Mechanisms", *J. Org. Chem*, 2000, vol. 65, pp. 3690-3699.
Ya. L. Gol'dfarb et al., "Action of Alkali Metals in Liquid Ammonia on Substituted Thiophenes. Communication 9. Preparation of 5-Mercapto-4-Ketoalkanoic Acids by Reductive Cleavage of 4-Acetylamino- and 4-Nitrothiphene-2-Carboxylic Acids", *Izv. Akad. Nauk* SSSR. *Ser. Khim.*, 1984, vol. 10, pp. 2136-2139.
J. R. Desai et al.; J. Ind. Chem. Soc., vol. 74, 1997, p. 160, "Thieno[3,2-d]pyrimidines—Part-I: Preparation and Antimicrobial Activity of 3-N-Substituted-tioureido-2-methyl-6-phenylthieno[3,2-d]pyrimidin-4(3H)-ones", ISR ref. XP002220249.
E. Marchand, G. Morel, Bull. Soc. Chim. Fr. vol. 133, No. 9, 1996, p. 903-912, "Alpha-Thioxothioamides Reactions de cycloaddition [4+2] avec l'acetylenedicarboxylate de dimethyle et le propiolate de methyle", ISR ref. XP002220251.

(Continued)

*Primary Examiner*—Celia Chang
(74) *Attorney, Agent, or Firm*—Millen, White, Zelano, Branigan, P.C.

(57) ABSTRACT

Compounds represented by formula:

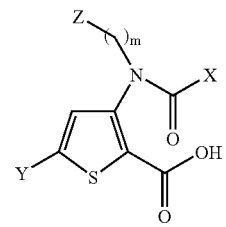

wherein X, Y and Z are as defined herein, pharmaceutically acceptable salts thereof, and related compounds, are suitable for use in treating or preventing a Flaviviridae viral infection in a host.

40 Claims, No Drawings

OTHER PUBLICATIONS

W. Kantlehner et al., J. Prakt. Chem., vol. 338, 1996, p. 403-413; "Orthoamide, IL. Umsetzungen von Orthoamid-Derivaten mit Schwefel und Selen, Synthesen von 1,3-Thiazol- und 1,3-Selenazolderivaten" ISR ref. XP002220245.

S. Vega et al., Eur. J. Med. Chem. vol. 23, No. 4, 1988, p. 329-334; "Thiophene Isosteres: Synthesis and Pharmacological Study of 3-(azol-l-yl)thieno isothiazole-1,1-dioxides" ISR ref. XP002220246.

R.A. Smith et al., Bioorg. Med. Chem. Lett. vol. 11, No. 20, 2001, p. 2775-2778; "Discovery of Heterocyclic Ureas as a New Class of Raf Kinase Inhibitors: Identification of a Second Generation Lead by a Combinatorial Chemistry Approach", ISR ref. XP001118699.

B.S. Kim et al., J. Org. Chem. vol. 63, No. 18, 1998, p. 6086-6087, "Reactions of Thioaroylketene S,N-Acetals with 1,3-Dicarbonyl Compounds in the Presence of Mercury(II) Acetate: A General Route to 2-Acyl- and 2-Aroyl-3-(alkylamino)-5-arylthiophenes and 2-(Etoxycarbonyl)-3-(methylamino)-5-arylthiophenes"; ISR ref. XP001118697.

A.M. Redman et al., Bioorg. Med. Chem. Lett., vol. 11, 2001, p. 9-12; "P38 Kinase Inhibitors for the Treatment of Arthritis and Osteoporosis: Thienyl, Furyl, and Pyrrolyl Ureas", ISR ref. XP004225311.

D.J. Lee et al., Chemical Abstracts Service, Columbus, OH, U.S., "Novel Synthesis of 5,6-Dihydro-4H-thieno[3,2-b]pyrrol-5-ones via the Rhodium(II)-Mediated Wolff Rearrangement of 3-(2-Thienyl)-3-oxo-2-diazopropanoates"; Database accession No. 2002:151873, ISR ref. XP002220252.

M. Sugiyama et al., Chem. Pharm. Bull. vol. 37, No. 8, 1989, p. 2091-2102; "Condensed Thienopyrimidines. I. Synthesis and Gastric Antisecretory Activity of 2,3-Dihydro-5H-oxazolothienopyrimidin-5-one Derivatives", ISR ref. XP001118351.

J.C. Lancelot et al., J. Heterocycl. Chem. vol. 33, No. 2, 1996, p. 427-430; "A Facile Synthesis of New Beta-Lactams", ISR ref. XP002220247.

D.M. McKinnon et al., Can. J. Chem. vol. 62, No. 8, 1984, p. 1580-1584; "The Conversion of Isothiazolium Salts into Thiophenecarboxylic Ester Derivatives", ISR ref. XP002220248.

J.R. Desai et al., J. Inst. Chemists (INDIA) vol. 67, 1995, p. 136-137, "Thieno[3,2-d]pyrimidines—Part-II: Preparation and Antimicrobial Activity of 2-methyl-3-N-Arylsulphonamido-6-Phenylthieno[3,2-d]Pyrimidin-4(3H)-ones", ISR ref. XP002220249.

Co-pending U.S. Appl. No. 10/166,031, filed Jun. 11, 2002.

Co-pending U.S. Appl. No. 11/042,442, filed Jan. 26, 2005.

B.S. Kim, K. Kim; J. Org. Chem. vol. 65, No. 12, 2000, p. 3690-3699, "A Facile and Convenient Synthesis of 3-Alkylamino-5-Arylthiophenes with a Variety of Substituents at C-2 and Studies of Reaction Mechanisms"; ISR ref XP001118698.

J.R. Desai et al., J. Inst. Chemists (INDIA) vol. 67, 1995, p. 160, "Thieno[3,2-d]pyrimidines—Part-I: Preparation and Antimicrobial Activity of 2-methyl-3-N-Arylsulphonamido-6-Phenylthieno[3,2-d]Pyrimidin-4(3H)-ones", ISR ref. XP002220250.

* cited by examiner

SEQUENCE LISTING

<160> NUMBER OF SEQ ID NOS: 4

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 1
gctagcgcta gctcaatgtc ctacacatgg     30

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 2
ctcgagctcg agcgtccatc ggttggggag     30

<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 3
atacatatgg ctagcatgtc aatgtcctac acatgg     36

-continued

```
<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 4
ggatccggat cccgttcatc ggttggggag                              30
```

COMPOUNDS AND METHODS FOR THE TREATMENT OR PREVENTION OF *FLAVIVIRUS* INFECTIONS

This application claims the benefit of U.S. provisional application 60/431,964 filed Dec. 10, 2002 which is herein incorporated by reference.

FIELD OF THE INVENTION

The present invention relates to novel compounds and a method for the treatment or prevention of Flavivirus infections using novel compounds.

BACKGROUND OF THE INVENTION

Hepatitis is a disease occurring throughout the world. It is generally of viral nature, although there are other causes known. Viral hepatitis is by far the most common form of hepatitis. Nearly 750,000 Americans are affected by hepatitis each year, and out of those, more than 150,000 are infected with the hepatitis C virus ("HCV").

HCV is a positive-stranded RNA virus belonging to the Flaviviridae family and has closest relationship to the pestiviruses that include hog cholera virus and bovine viral diarrhea virus (BVDV). HCV is believed to replicate through the production of a complementary negative-strand RNA template. Due to the lack of efficient culture replication system for the virus, HCV particles were isolated from pooled human plasma and shown, by electron microscopy, to have a diameter of about 50-60 nm. The HCV genome is a single-stranded, positive-sense RNA of about 9,600 bp coding for a polyprotein of 3009-3030 amino-acids, which is cleaved co and post-translationally by cellular and two viral proteinases into mature viral proteins (core, E1, E2, p7, NS2, NS3, NS4A, NS4B, NS5A, NS5B). It is believed that the structural proteins, E1 and E2, the major glycoproteins are embedded into a viral lipid envelope and form stable heterodimers. It is also believed that the structural core protein interacts with the viral RNA genome to form the nucleocapsid. The nonstructural proteins designated NS2 to NS5 include proteins with enzymatic functions involved in virus replication and protein processing including a polymerase, protease and helicase.

The main source of contamination with HCV is blood. The magnitude of the HCV infection as a health problem is illustrated by the prevalence among high-risk groups. For example, 60% to 90% of hemophiliacs and more than 80% of intravenous drug abusers in western countries are chronically infected with HCV. For intravenous drug abusers, the prevalence varies from about 28% to 70% depending on the population studied. The proportion of new HCV infections associated with post-transfusion has been markedly reduced lately due to advances in diagnostic tools used to screen blood donors.

The only treatment currently available for HCV infection is interferon-α (IFN-α). However, according to different clinical studies, only 70% of treated patients normalize alanine aminotransferase (ALT) levels in the serum and after discontinuation of IFN, 35% to 45% of these responders relapse. In general, only 20% to 25% of patients have long-term responses to IFN. Clinical studies have shown that combination treatment with IFN and ribavirin (RIBA) results in a superior clinical response than IFN alone. Different genotypes of HCV respond differently to IFN therapy, genotype 1b is more resistant to IFN therapy than type 2 and 3.

There is therefore a great need for the development of anti-viral agents.

SUMMARY OF THE INVENTION

In one aspect, the present invention provides novel compounds represented by formula:

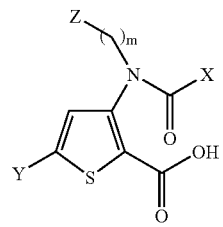

or pharmaceutically acceptable salts thereof;

wherein;

Z is chosen from 3-7 membered heterocycle or 3-7 membered cycloalkyl;

Y is 6-10 membered aryl;

X is 3-10 membered cycloalkyl;

m is an integer from 0-1;

provided that when Y is unsubstituted phenyl then X is other than 4-methylcyclohexane.

In another aspect, there is provided a method for treating or preventing a Flaviviridae viral infection in a host comprising administering to the subject a therapeutically effective amount of a compound, composition or combination of the invention.

In another aspect, there is provided a combination comprising a compound of the invention and one or more additionnal agent chosen from viral serine protease inhibitor, viral polymerase inhibitor and viral helicase inhibitor, immunomudulating agent, antioxydant agent, antibacterial agent or antisense agent.

In another aspect, there is provided a pharmaceutical composition comprising at least one compound of the invention and at least one pharmaceutically acceptable carrier or excipient.

In a further aspect, there is provided the use of compound, composition or combination of the invention for treating or preventing Flaviviridae viral infection in a host.

In still another aspect, there is provided the use of a compound of the invention for inhibiting or reducing the activity of viral polymerase in a host.

In still another aspect, there is provided the use of a compound of the invention for the manufacture of a medicament for treating or preventing a viral Flaviridae infection in a host.

DETAILED DESCRIPTION OF THE INVENTION

In one embodiment, compounds of the present invention comprise those wherein the following embodiments are present, either independently or in combination.

In one embodiment of the present invention, Z is chosen from 3-7 membered heterocycle or 3-7 membered cycloalkyl.

In one embodiment, Z is:

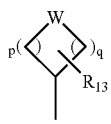

wherein;
w is $CR_{10}R_{11}$, $S(O)n$, O or $NR_{12}$;
wherein, n is 0-2;
$R_{10}$ and $R_{11}$ in each case are independently H, $C_{1-6}$ alkyl, $C_{6-10}$ aryl, $C_{3-10}$ heterocycle, $C_{3-10}$ heteroaralkyl, $C_{6-10}$ aralkyl, $C(O)$—$C_{1-6}$ alkyl, $C_{1-6}$ alkyloxy, hydroxyl or formyl;
or $R_{10}$ and $R_{11}$ are taken together to form =O, =S or =N—Ra, wherein Ra is H, hydroxyl or $C_{1-6}$ alkyl;
$R_{12}$ is H, $C_{1-6}$ alkyl, $c_{6-14}$ aryl, C3-12 heterocycle, $C_{3-12}$ heteroaralkyl, $C_{6-16}$ aralkyl, $C(O)$—$C_{1-6}$ alkyl or $C_{1-6}$ alkyloxy;
P is an integer from 1-3;
q is an integer from 0-2;
$R_{13}$ is one or more optional substituent each of which is independently chosen from halogen, nitro, nitroso, $SO_3Rf$, $SO_2Rf$, $PO_3RcRd$, $CONRgRh$, $C_{1-6}$ alkyl, $C_{2-6}$ alkenyl, $C_{2-6}$ alkynyl, $C_{6-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{6-12}$ aralkyl, $C_{3-10}$ heterocycle, hydroxyl, $NRgRh$, $C(O)ORf$, cyano, azido, amidino or guanido;
wherein Rf, Rc, Rd, Rg and Rh in each case are independently H, $C_{1-6}$ alkyl, $C_{2-6}$ alkenyl, $C_{2-6}$ alkynyl, $C_{6-10}$ aryl, $C_{3-10}$ heterocycle, $C_{3-10}$ heteroaralkyl or $C_{6-10}$ aralkyl;
or Rc and Rd are taken together with the oxygens to form a 5 to 10 membered heterocycle;
or Rg and Rh are taken together with the nitrogen to form a 3 to 10 membered heterocycle.
In a further embodiment, Z is 6-7 membered heterocycle or 6-7 membered cycloalkyl.
In one embodiment, Z is cyclohexyl, piperidinyl or $N(C_{1-6}$ alkyl)-piperidinyl, azepanyl, methylazepanyl, $N(C_{1-6}$alkyl)-piperidinylmethyl, tetrahydropyranyl, piperidinylmethyl, pyridinyl, pyridinylmethyl, tetrahydrothiopyranyl, dioxolanylmethyl or dioxanylmethyl which in each case is unsubstituted or substituted by one or more substituent independently chosen from halogen, nitro, nitroso, $SO_3Rf$, $SO_2Rf$, $PO_3RcRd$, $CONRgRh$, $C_{1-6}$ alkyl, $C_{2-6}$ alkenyl, $C_{2-6}$ alkynyl, $C_{6-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{6-12}$ aralkyl, $C(O)NHRf$, $C_{3-10}$ heterocycle, hydroxyl, $NRgRh$, $C(O)ORf$, cyano, azido, amidino or guanido;
wherein Rf, Rc, Rd, Rg and Rh in each case are independently H, $C_{1-6}$ alkyl, $C_{2-6}$ alkenyl, $C_{2-6}$ alkynyl, $C_{6-10}$ aryl, $C_{3-10}$ heterocycle, $C_{3-10}$ heteroaralkyl or $C_{6-10}$ aralkyl;
or Rc and Rd are taken together with the oxygens to form a 5 to 10 membered heterocycle;
or Rg and Rh are taken together with the nitrogen to form a 3 to 10 membered heterocycle.
In a further embodiment, Z is cyclohexyl, piperidinyl, $N(C_{1-6}$ alkyl)-piperidinyl, azepanyl, methylazepanyl, $N(C_{1-6}$ alkyl)-piperidinylmethyl, tetrahydropyranyl, piperidinylmethyl, pyridinyl, pyridinylmethyl, tetrahydrothiopyranyl, dioxolanylmethyl or dioxanylmethyl which in each case is unsubstituted or substituted by one or more substituent independently chosen from halogen, $SO_2Rf$, $PO_3RcRd$, $CONRgRh$, $C_{1-6}$ alkyl, $C_{6-12}$ aralkyl, $C_{6-12}$ aryl, $C_{1-6}$ alkyloxy, $C_{6-12}$ aryloxy, $C(O)C_{1-6}$ alkyl, $C(O)C_{6-12}$ aryl, $C(O)C_{6-12}$ aralkyl, $C(O)NHRf$, $C_{3-10}$ heterocycle, hydroxyl, $NRgRh$, $C(O)ORf$, cyano, azido, amidino or guanido;
wherein Rf, Rc, Rd, Rg and Rh in each case are independently H, $C_{1-6}$ alkyl, $C_{2-6}$ alkenyl, $C_{2-6}$ alkynyl, $C_{6-10}$ aryl, $C_{3-10}$ heterocycle, $C_{3-10}$ heteroaralkyl or $C_{6-10}$ aralkyl.
In one embodiment, Z is cyclohexyl, piperidinyl, $N(C_{1-6}$ alkyl)-piperidinyl, azepanyl, methylazepanyl, $N(C_{1-6}$ alkyl)-piperidinylmethyl, tetrahydropyranyl, piperidinylmethyl, pyridinyl, pyridinylmethyl, tetrahydrothiopynnyl, dioxolanylmethyl or dioxanylmethyl which in each case is unsubstituted or substituted by one or more substituent independently chosen from halogen, $SO_2Rf$, $CONRgRh$, $C_{1-6}$ alkyl, $C_{6-12}$ aralkyl, $C_{6-12}$ aryl, $C_{1-6}$ alkyloxy, $C(O)C_{1-6}$ alkyl, $C(O)NHRf$, $C_{3-10}$ heterocycle, hydroxyl, $NRgRh$, $C(O)Orf$ or cyano;
wherein Rf, Rg and Rh in each case are independently H or $C_{1-6}$ alkyl.
In one embodiment, Z is cyclohexyl unsubstituted or substituted by one or more substituent independently chosen from halogen, $SO_2Rf$, $CONRgRh$, $C_{1-6}$ alkyl, $C_{6-12}$ aralkyl, $C_{6-12}$ aryl, $C_{1-6}$ alkyloxy, $C(O)C_{1-6}$ alkyl, $C_{3-10}$ heterocycle, hydroxyl, $NRgRh$, $C(O)Orf$ or cyano;
wherein Rf, Rg and Rh in each case are independently H or $C_{1-6}$ alkyl.
In one embodiment, Z is piperidinyl unsubstituted or substituted by one or more substituent independently chosen from halogen, $SO_2Rf$, $CONRgRh$, $C_{1-6}$ alkyl, $C_{6-12}$ aralkyl, $C_{6-12}$ aryl, $C_{1-6}$ alkyloxy, $C(O)C_{1-6}$ alkyl, $C(O)NHRf$, $C_{3-10}$ heterocycle, hydroxyl, $NRgRh$, $C(O)Orf$ or cyano;
wherein Rf, Rg and Rh in each case are independently H or $C_{1-6}$ alkyl.
In one embodiment, Z is $N(C_{1-6}$ alkyl)-piperidinyl unsubstituted or substituted by one or more substituent independently chosen from halogen, $SO_2Rf$, $CONRgRh$, $C_{1-6}$ alkyl, $C_{6-12}$ aralkyl, $C_{6-12}$ aryl, $C_{1-6}$ alkyloxy, $C(O)C_{1-6}$ alkyl, $C(O)NHRf$, $C_{3-10}$ heterocycle, hydroxyl, $NRgRh$, $C(O)Orf$ or cyano;
wherein Rf, Rg and Rh in each case are independently H or $C_{1-6}$ alkyl.
In further embodiments:
Z is cyclohexyl, piperidinyl or $N(C_{1-6}$ alkyl)-piperidinyl;
Z is cyclohexyl;
Z is piperidinyl;
Z is $N(C_{1-6}$ alkyl)-piperidinyl.
In one embodiment, Z is N-methyl-piperidinyl, N-ethyl-piperidinyl, N-propyl-piperidinyl, N-isopropyl-piperidinyl, N-butyl-piperidinyl, N-pentyl-piperidinyl, N-hexylpiperidinyl, N-cyclohexyl-piperidinyl, N-acetyl-piperidinyl, N-benzyl-piperidinyl, hydroxycyclohexyl, oxocyclohexyl, Hydroxyiminocyclohexyl, aminocyclohexyl, methanesulfonyl, methylcarbamoyl or methoxycyclohexyl.
In further embodiments:
Z is N-methyl-piperidinyl or hydroxycyclohexyl;
Z is N-methyl-piperidinyl;
Z is from. N-methyl-4-piperidinyl;
Z is hydroxycyclohexyl;
Z is 4-hydroxycyclohexyl;
Z is N-methyl-4-piperidinyl.
In one embodiment, X is 3-10 membered cycloalkyl.
In one embodiment, X is 6-membered cycloalkyl.
In one embodiment, X is cyclohexyl unsubstituted or substituted by one or more substituent independently chosen from halogen, nitro, nitroso, $SO_3Rf$, $SO_2Rf$, $PO_3RcRd$, $CONRgRh$, $C_{1-6}$ alkyl, $C_{2-6}$ alkenyl, $C_{2-6}$ alkynyl, $C_{6-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{6-12}$ aralkyl, $C(O)$NHRf, $C_{3-10}$ heterocycle, hydroxyl, NRgRh, C(O)ORf, cyano, azido, amidino or guanido;

wherein Rf, Rc, Rd, Rg and Rh in each case are independently H, $C_{1-6}$ alkyl, $C_{2-6}$ alkenyl, $C_{2-6}$ alkynyl, $C_{6-10}$ aryl, $C_{3-10}$ heterocycle, $C_{3-10}$ heteroaralkyl or $C_{6-10}$ aralkyl;

or Rc and Rd are taken together with the oxygens to form a 5 to 10 membered heterocycle;

or Rg and Rh are taken together with the nitrogen to form a 3 to 10 membered heterocycle.

In a further embodiment, X is cyclohexyl unsubstituted or substituted by one or more substituent independently chosen from halogen, nitro, nitroso, $SO_3Rf$, $SO_2Rf$, $PO_3RcRd$, $CONRgRh$, $C_{1-6}$ alkyl, $C_{6-12}$ aralkyl, $C_{6-12}$ aryl, $C_{1-6}$ alkyloxy, $C_{6-12}$ aryloxy, $C(O)C_{1-6}$ alkyl, $C(O)C_{6-12}$ aryl, $C(O)$ $C_{6-12}$ aralkyl, C(O)NHRf, $C_{3-10}$ heterocycle, hydroxyl, NRgRh, C(O)ORf, cyano, azido, amidino or guanido;

wherein Rf, Rc, Rd, Rg and Rh in each case are independently H, $C_{1-6}$ alkyl, $C_{2-6}$ alkenyl, $C_{2-6}$ alkynyl, $C_{6-10}$ aryl, $C_{3-10}$ heterocycle, $C_{3-10}$ heteroaralkyl, $C_{6-10}$ aralkyl.

In still a further embodiment, X is cyclohexyl unsubstituted or substituted by one or more substituent independently chosen from halogen, $SO_2Rf$, $CONRgRh$, $C_{1-6}$ alkyl, $C_{6-12}$ aralkyl, $C_{6-12}$ aryl, $C_{1-6}$ alkyloxy, $C_{6-12}$ aryloxy, $C(O)C_{1-6}$ alkyl, $C(O)C_{6-12}$ aryl, $C(O)C_{6-12}$ aralkyl, C(O)NHRf, $C_{3-10}$ heterocycle, hydroxyl, NRgRh, C(O)ORf, cyano or azido;

wherein Rf, Rc, Rd, Rg and Rh in each case are independently H, $C_{1-6}$ alkyl, $C_{6-10}$ aryl, $C_{3-10}$ heterocycle, $C_{3-10}$ heteroaralkyl or $C_{6-10}$ aralkyl.

In one embodiment, X is cyclohexyl substituted by one or more substituent independently chosen from $C_{1-6}$ alkyl, halogen, $C_{2-6}$ alkenyl, $C_{2-6}$ alkynyl or $C_{1-6}$ alkyloxy.

In further embodiments:
X is cyclohexyl substituted by $C_{1-6}$ alkyl;
X is cyclohexyl substituted by $C_{1-3}$ alkyl;
X is 4-methyl-cyclohexyl or 2-hydroxy-4-methyl-cyclohexyl;
X is 4-methylcyclohexyl.

In one embodiment, Y is 6-10 membered aryl.

In one embodiment, Y is phenyl unsubstituted or substituted by one or more substituent independently chosen from halogen, nitro, nitroso, $SO_3Rf$, $SO_2Rf$, $PO_3RcRd$, CONRgRh, $C_{1-6}$ alkyl, $C_{2-6}$ alkenyl, $C_{2-6}$ alkynyl, $C_{6-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{6-12}$ aralkyl, C(O)NHRf, $C_{3-10}$ heterocycle, hydroxyl, NRgRh, C(O)ORf, cyano, azido, amidino or guanido;

wherein Rf, Rc, Rd, Rg and Rh in each case are independently H, $C_{1-6}$ alkyl, $C_{2-6}$ alkenyl, $C_{2-6}$ alkynyl, $C_{6-10}$ aryl, $C_{3-10}$ heterocycle, $C_{3-10}$ heteroaralkyl or $C_{6-10}$ aralkyl;

or Rc and Rd are taken together with the oxygens to form a 5 to 10 membered heterocycle;

or Rg and Rh are taken together with the nitrogen to form a 3 to 10 membered heterocycle.

In a further embodiment, Y is phenyl unsubstituted or substituted by one or more substituent independently chosen from halogen, nitro, nitroso, $SO_3Rf$, $SO_2Rf$, $PO_3RcRd$, CONRgRh, $C_{1-6}$ alkyl, $C_{2-6}$ alkenyl, $C_{2-6}$ alkynyl, $C_{6-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{6-12}$ aralkyl, C(O)NHRf, $C_{3-10}$ heterocycle, hydroxyl, NRgRh, C(O)ORf, cyano, azido, amidino or guanido;

wherein Rf, Rc, Rd, Rg and Rh in each case are independently H, $C_{1-6}$ alkyl, $C_{2-6}$ alkenyl, $C_{2-6}$ alkynyl, $C_{6-10}$ aryl, $C_{3-10}$ heterocycle, $C_{3-10}$ heteroaralkyl or $C_{6-10}$ aralkyl.

In still a further embodiment, Y is phenyl unsubstituted or substituted by one or more substituent independently chosen from halogen, nitro, nitroso, $SO_3Rf$, $SO_2Rf$, $PO_3RcRd$, CONRgRh, $C_{1-6}$ alkyl, $C_{6-12}$ aralkyl, $C_{6-12}$ aryl, $C_{1-6}$ alkyloxy, $C_{6-12}$ aryloxy, $C(O)C_{1-6}$ alkyl, $C(O)C_{6-12}$ aryl, $C(O)$ $C_{6-12}$ aralkyl, C(O)NHRf, $C_{3-10}$ heterocycle, hydroxyl, NRgRh, C(O)ORf, cyano, azido, amidino or guanido;

wherein Rf, Rc, Rd, Rg and Rh in each case are independently H, $C_{1-6}$ alkyl, $C_{2-6}$ alkenyl, $C_{2-6}$ alkynyl, $C_{6-10}$ aryl, $C_{3-10}$ heterocycle, $C_{3-10}$ heteroaralkyl or $C_{6-10}$ aralkyl.

In one embodiment, Y is phenyl unsubstituted or substituted by one or more substituent independently chosen from halogen, nitro, $SO_2Rf$, CONRgRh, $C_{1-6}$ alkyl, $C_{6-12}$ aralkyl, $C_{6-12}$ aryl, $C_{1-6}$ alkyloxy, $C_{6-12}$ aryloxy, $C(O)C_{1-6}$ alkyl, $C(O)$ $C_{6-12}$ aryl, $C(O)C_{6-12}$ aralkyl, C(O)NHRf, $C_{3-10}$ heterocycle, hydroxyl, NRgRh, C(O)ORf, cyano, amidino or guanido;

wherein Rf, Rg and Rh in each case are independently H, $C_{1-6}$ alkyl, $C_{6-10}$ aryl, $C_{3-10}$ heterocycle, $C_{3-10}$ heteroaralkyl or $C_{6-10}$ aralkyl.

In one embodiment, Y is phenyl substituted by one or more substituent independently chosen from halogen, nitro, $SO_2Rf$, $C_{1-6}$ alkyl, $C_{1-6}$ alkyloxy, $C(O)C_{1-6}$ alkyl, C(O)Orf, cyano or azido.

In one embodiment, Y is phenyl substituted by one or more substituent independently chosen from halogen, nitro, $C_{1-6}$ alkyl, $C_{1-6}$ alkyloxy or cyano.

In further embodiments:
Y is phenyl substituted by one or more halogen;
Y is phenyl substituted by one or more $C_{1-6}$ alkyloxy;
Y is phenyl substituted by one or more methyloxy;
Y is phenyl substituted by one or more $C_{1-6}$ alkyl;
Y is phenyl substituted by one or more methyl;
Y is phenyl;
Y is 3-fluorophenyl, 4-fluorophenyl 4-chlorophenyl, 4-cyanophenyl, 4-methoxyphenyl, 4-nitrophenyl or p-tolyl.

In one embodiment, P is an integer from 1-3 and q is an integer from 0-2;

In further embodiments:
P is 2 and q is 2;
p is 3 and q is 2;
P is 1 and q is 2;
P is 1 and q is 1;
P is 2 and q is 1;
P is 3 and q is 1;
P is 1 and q is 0;
P is 2 and q is 0;
P is 3 and q is 0.

In one embodiment, W is $CR_{10}R_{11}$, S(O)n, O or $NR_{12}$;
wherein n, $R_{10}$, $R_{11}$, and $R_{12}$ are as defined in herein.

In further embodiments:
W is $CR_{10}R_{11}$ or $NR_{12}$;
wherein $R_{10}$, $R_{11}$ and $R_{12}$ are as defined herein;
W is $CR_{10}R_{11}$;
wherein $R_{10}$ and $R_{11}$ are as defined in herein;
W is $NR_{12}$;
wherein $R_{12}$ is as defined in herein;
W is O;
W is S(O)n;
wherein n is as defined in herein.

In one embodiment, $R_{10}$ and $R_{11}$ are each independently chosen from H, $C_{1-6}$ alkyl, $C_{6-10}$ aryl, $C_{3-10}$ heterocycle, $C_{3-10}$ heteroaralkyl, $C_{6-10}$ aralkyl, C(O)—$C_{1-6}$ alkyl, $C_{1-6}$ alkyloxy, hydroxyl or formyl;

or $R_{10}$ and $R_{11}$ are taken together to form =O, =S or =N—Ra, wherein Ra is H, hydroxyl or $C_{1-6}$ alkyl.

In one embodiment, $R_{10}$ is H, $C_{1-6}$ alkyl, $C_{6-10}$ aryl, $C_{3-10}$ heterocycle, $C_{3-10}$ heteroaralkyl, $C_{6-10}$ aralkyl, C(O)—$C_{1-6}$ alkyl, $C_{1-6}$ alkyloxy, hydroxyl or formyl; and R11 is H.

In one embodiment, $R_{10}$ is $C_{1-6}$ alkyl, $C_{6-10}$ aralkyl, C(O)—$C_{1-6}$ alkyl, $C_{1-6}$ alkyloxy, hydroxyl or formyl; and $R_{11}$ is H.

In one embodiment, $R_{10}$ is C1-3 alkyl, $C_{6-10}$ aralkyl, C(O)—C1-3 alkyl, $C_{1-3}$ alkyloxy, hydroxyl or formyl; and R11 is H.

In one embodiment, $R_{10}$ is chosen from methyl, ethyl, propyl, isopropyl benzyl, acetyl, hydroxyl or formyl; and R11 is H.

In one embodiment, $R_{10}$ and $R_{11}$ are taken together to form =O, =S or =N—Ra, wherein Ra is H, hydroxyl or $C_{1-6}$ alkyl.

In one embodiment, $R_{10}$ and $R_{11}$ are taken together to form =O.

In a further embodiment, $R_{10}$ and $R_{11}$ are taken together to form =S.

In a further embodiment, $R_{10}$ and $R_{11}$ are taken together to form =N—Ra, wherein Ra is H, hydroxyl or $C_{1-6}$ alkyl.

In one embodiment, Ra is chosen from H, hydroxyl, methyl, ethyl, propyl or isopropyl.

In one embodiment, $R_{13}$ is one or more optional substituent each of which is independently chosen from halogen, nitro, nitroso, $SO_3Rf$, $SO_2Rf$, $PO_3RcRd$, CONRgRh, $C_{1-6}$ alkyl, $C_{2-6}$ alkenyl, $C_{2-6}$ alkynyl, $C_{6-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, C(O)$C_{1-6}$ alkyl, C(O)$C_{2-6}$ alkenyl, C(O)$C_{2-6}$ alkynyl, C(O)$C_{6-12}$ aryl, C(O)$C_{6-12}$ aralkyl, $C_{3-10}$ heterocycle, hydroxyl, NRgRh, C(O)ORf, cyano, azido, amidino or guanido;
wherein Rf, Rc, Rd, Rg and Rh in each case are independently H, $C_{1-6}$ alkyl, $C_{2-6}$ alkenyl, $C_{2-6}$ alkynyl, $C_{6-10}$ aryl, $C_{3-10}$ heterocycle, $C_{3-10}$ heteroaralkyl or $C_{6-10}$ aralkyl;
or Rc and Rd are taken together with the oxygens to form a 5 to 10 membered heterocycle;
or Rg and Rh are taken together with the nitrogen to form a 3 to 10 membered heterocycle.

In one embodiment, $R_{13}$ is one or more substituent each of which is independently chosen from halogen, nitro, $SO_2Rf$, CONRgRh, $C_{1-6}$ alkyl, $C_{6-12}$ aralkyl, $C_{6-12}$ aryl, $C_{1-6}$ alkyloxy, C(O)$C_{1-6}$ alkyl, $C_{3-10}$ heterocycle, hydroxyl, NRgRh, C(O)ORf, cyano or azido;
wherein Rf, Rg and Rh are as defined herein.

In one embodiment, $R_{13}$ is one or more substituent each of which is independently chosen from halogen, nitro, $SO_2Rf$, CONRgRh, C1-3 alkyl, $C_{6-12}$ aralkyl, C6 aryl, C1-3 alkyloxy, C(O)C1-3 alkyl, C3-6 heterocycle, hydroxyl, NRgRh, C(O)ORf, cyano or azido;
wherein Rf, Rg and Rh are as defined herein.

In one embodiment, $R_{13}$ is one or more substituent each of which is independently chosen from halogen, nitro, $SO_2CH_3$, $CONH_2$, $CONHCH_3$, $CONH(CH_3)2$, methyl, ethyl, propyl, isopropyl, benzyl, phenyl, acetyl, methoxy, ethoxy, propyloxy, isopropyloxy, piperidinyl, piperazinyl, pyrrolidinyl, azetidinyl, aziridinyl, pyridinyl, dioxanyl, dioxolanyl, azepanyl, hydroxyl, NH2, N(H)CH3, NH(CH3)2, cyano or azido;
wherein Rf, Rg and Rh are as defined herein.

A person of ordinary skill will readily understand that $R_{13}$ may be attached to any position of the ring. A person of skill will also realize that the position of $R_{13}$ on the ring will be dependant on the valencies of the ring atoms and will respect normal rules of chemistry.

In one embodiment, the present invention provides compounds represented by formula:

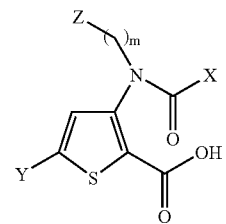

or pharmaceutically acceptable salts thereof;
wherein;
Z is cyclohexyl unsubstituted or substituted by one or more substituent independently chosen from halogen, $SO_2Rf$, CONRgRh, $C_{1-6}$ alkyl, $C_{6-12}$ aralkyl, $C_{6-12}$ aryl, $C_{1-6}$ alkyloxy, C(O)$C_{1-6}$ alkyl, $C_{3-10}$ heterocycle, hydroxyl, NRgRh, C(O).ORf or cyano;
wherein Rf, Rg and Rh in each case are independently H or $C_{1-6}$ alkyl;
Y is phenyl unsubstituted or substituted by one or more substituent independently chosen from halogen, nitro, $SO_2Rf$, CONRgRh, $C_{1-6}$ alkyl, $C_{6-12}$ aralkyl, $C_{6-12}$ aryl, C1-6 alkyloxy, $C_{6-12}$ aryloxy, C(O)$C_{1-6}$ alkyl, C(O)$C_{6-12}$ aryl, C(O) $C_{6-12}$ aralkyl, C(O)NHRf, $C_{3-10}$ heterocycle, hydroxyl, NRgRh, C(O)ORf, cyano, amidino or guanido;
wherein Rf, Rg and Rh in each case are independently H, $C_{1-6}$ alkyl, $C_{6-10}$ aryl, $C_{3-10}$ heterocycle, $C_{3-10}$ heteroaralkyl or $C_{6-10}$ aralkyl;
X is cyclohexyl unsubstituted or substituted by one or more substituent independently chosen from halogen, $SO_2Rf$, CONRgRh, $C_{1-6}$ alkyl, $C_{6-12}$ aralkyl, $C_{6-12}$ aryl, $C_{1-6}$ alkyloxy, $C_{6-12}$ aryloxy, C(C)$C_{1-6}$ alkyl, C(O)$C_{6-12}$ aryl, C(O)C aralkyl, C(O)NHRf, $C_{3-10}$ heterocycle, hydroxyl, NRgRh, C(O)ORf, cyano or azido;
wherein Rf, Rc, Rd, Rg and Rh in each case are independently H, $C_{1-6}$ alkyl, $C_{6-10}$ aryl, $C_{3-10}$ heterocycle, $C_{3-10}$ heteroaralkyl or $C_{6-10}$ aralkyl;
m is O;
provided that when Y is unsubstituted phenyl then X is other than 4-methylcyclohexane.

In one aspect, the present invention provides novel compounds including:
Compound 1 3-{[(2-CARBOXY-5-PHENYL-THIOPHEN-3-YL)-(4-METHYL-CYCLOHEXANECARBONYL)-AMINO]-METHYL}-PIPERIDINIUM; TRIFLUORO-ACETATE;
Compound 2 2-{[(2-CARBOXY-5-PHENYL-THIOPHEN-3-YL)-(4-METHYL-CYCLOHEXANECARBONYL)-AMINO]-METHYL}-PIPERIDINIUM; TRIFLUORO-ACETATE;
Compound 3 3-[(4-METHYL-CYCLOHEXANECARBONYL)-PYRIDIN-3-YLMETHYL-AMINO]-5-PHENYL-THIOPHENE-2-CARBOXYLIC ACID;
Compound 4 3-[(4-METHYL-CYCLOHEXANECARBONYL)-PYRIDIN-4-YLMETHYL-AMINO]-5-PHENYL-THIOPHENE-2-CARBOXYLIC ACID;
Compound 5 5-(3-FLUORO-PHENYL)-3-[ISOPROPYL-(4-METHYL-CYCLOHEXANECARBONYL)-AMINO]-THIOPHENE-2-CARBOXYLIC ACID;

Compound 6 3-[AZEPAN-4-YL-(4-METHYL-CYCLOHEXANECARBONYL)-AMINO]-5-PHENYL-THIOPHENE-2-CARBOXYLIC ACID;

Compound 7 3-[(2,4-DICHLORO-BENZOYL)-[1,3]DIOXOLAN-2-YLMETHYL-AMINO]-5-PHENYL-THIOPHENE-2-CARBOXYLIC ACID;

Compound 8 3-[[1,3]DIOXOLAN-2-YLMETHYL-(4-METHYL-CYCLOHEXANECARBONYL)-AMINO]-5-PHENYL-THIOPHENE-2-CARBOXYLIC ACID;

Compound 9 3-[(1-FLUORO-4-METHYL-CYCLOHEXANECARBONYL)-ISOPROPYL-AMINO]-5-PHENYL-THIOPHENE-2-CARBOXYLIC ACID;

Compound 10 3-[(1-FLUORO-4-METHYL-CYCLOHEXANECARBONYL)-ISOPROPYL-AMINO]-5-PHENYL-THIOPHENE-2-CARBOXYLIC ACID;

Compound 11 4-[(2-CARBOXY-5-PHENYL-THIOPHEN-3-YL)-(4-METHYL-CYCLOHEXANECARBONYL)-AMINO]-1-METHYL-PIPERIDINIUM CHLORIDE;

Compound 12 3-[(2-ACETYLAMINO-4-METHYL-CYCLOHEXANECARBONYL)-ISOPROPYL-AMINO]-5-PHENYL-THIOPHENE-2-CARBOXYLIC ACID;

Compound 13 3-[(4-METHYL-CYCLOHEXANECARBONYL)-(4-OXO-CYCLOHEXYL)-AMINO]-5-PHENYL-THIOPHENE-2-CARBOXYLIC ACID;

Compound 14 3-[(4-METHYL-CYCLOHEXANECARBONYL)-PYRIDIN-2-YLMETHYL-AMINO]-5-PHENYL-THIOPHENE-2-CARBOXYLIC ACID;

Compound 15 3-[(4-HYDROXY-CYCLOHEXYL)-(4-METHYL-CYCLOHEXANECARBONYL)-AMINO]-5-PHENYL-THIOPHENE-2-CARBOXYLIC ACID;

Compound 16 3-[(4-HYDROXYIMINO-CYCLOHEXYL)-(4-METHYL-CYCLOHEXANECARBONYL)-AMINO]-5-PHENYL-THIOPHENE-2-CARBOXYLIC ACID;

Compound 17 3-[ISOPROPYL-(4-METHYL-CYCLOHEX-3-ENECARBONYL)-AMINO]-5-PHENYL-THIOPHENE-2-CARBOXYLIC ACID;

Compound 18 3-[(1-AZIDOMETHYL-2-METHYL-BUTYL)-(2,4-DICHLORO-BENZOYL)-AMINO]-5-PHENYL-THIOPHENE-2-CARBOXYLIC ACID;

Compound 19 2-[(2-Carboxy-5-phenyl-thiophen-3-yl)-(2-chloro-benzoyl)-amino]-3-methyl-pentyl-ammonium trifluoroacetate;

Compound 20 3-[(1-AMINOMETHYL-2-METHYL-BUTYL)-(2,4-DICHLORO-BENZOYL)-AMINO]-5-PHENYL-THIOPHENE-2-CARBOXYLIC ACID;

Compound 21 {2-[(2-CARBOXY-5-PHENYL-THIOPHEN-3-YL)-(2,4-DICHLORO-BENZOYL)-AMINO]-PROPYL}-TRIMETHYL-AMMONIUM; TRIFLUORO-ACETATE;

Compound 22 3-[ISOPROPYL-(5-METHYL-[1,3]DIOXANE-2-CARBONYL)-AMINO]-5-PHENYL-THIOPHENE-2-CARBOXYLIC ACID;

Compound 23 4-[[2-CARBOXY-5-(4-FLUORO-PHENYL)-THIOPHEN-3-YL]-(4-METHYL-CYCLOHEXANECARBONYL)-AMINO]-1-METHYL-PIPERIDINIUM CHLORIDE;

Compound 24 5-(4-FLUORO-PHENYL)-3-[(2-HYDROXY-4-METHYL-CYCLOHEXANECARBONYL)-ISOPROPYL-AMINO]-THIOPHENE-2-CARBOXYLIC ACID;

Compound 25 3-[(4-METHOXYIMINO-CYCLOHEXYL)-(4-METHYL-CYCLOHEXANECARBONYL)-AMINO]-5-PHENYL-THIOPHENE-2-CARBOXYLIC ACID;

Compound 26 5-(4-FLUORO-PHENYL)-3-[ISOPROPYL-(4-METHYL-CYCLOHEX-1-ENECARBONYL)-AMINO]-THIOPHENE-2-CARBOXYLIC ACID;

Compound 27 3-[ISOPROPYL-(5-METHYL-TETRAHYDRO-PYRAN-2-CARBONYL)-AMINO]-5-PHENYL-THIOPHENE-2-CARBOXYLIC ACID;

Compound 28 3-[ISOPROPYL-(4-METHYLENE-CYCLOHEXANECARBONYL)-AMINO]-5-PHENYL-THIOPHENE-2-CARBOXYLIC ACID;

Compound 29 3-[ISOPROPYL-(5-METHYL-TETRAHYDRO-PYRAN-2-CARBONYL)-AMINO]-5-PHENYL-THIOPHENE-2-CARBOXYLIC ACID;

Compound 30 3-[ISOPROPYL-(5-METHYL-3,6-DIHYDRO-2H-PYRAN-2-CARBONYL)-AMINO]-5-PHENYL-THIOPHENE-2-CARBOXYLIC ACID;

Compound 31 3-[(2-HYDROXY-4-METHYL-CYCLOHEXANECARBONYL)-(TETRAHYDRO-PYRAN-4-YL)-AMINO]-5-PHENYL-THIOPHENE-2-CARBOXYLIC ACID;

Compound 32 3-[(2-AZIDO-1-METHYL-ETHYL)-(4-METHYL-CYCLOHEXANECARBONYL)-AMINO]-5-PHENYL-THIOPHENE-2-CARBOXYLIC ACID;

Compound 33 3-[(4-METHYL-CYCLOHEXANECARBONYL)-(1-METHYL-PIPERIDIN-4-YLMETHYL)-AMINO]-5-PHENYL-THIOPHENE-2-CARBOXYLIC ACID;

Compound 34 3-[(4-METHYL-CYCLOHEXANECARBONYL)-(TETRAHYDRO-THIOPYRAN-4-YL)-AMINO]-5-PHENYL-THIOPHENE-2-CARBOXYLIC ACID;

Compound 35 3-{[(2-CARBOXY-5-PHENYL-THIOPHEN-3-YL)-(4-METHYL-CYCLOHEXANECARBONYL)-AMINO]-METHYL}-1-METHYL-PIPERIDINIUM CHLORIDE;

Compound 36 3-[(2-AMINO-1-METHYL-ETHYL)-(4-METHYL-CYCLOHEXANECARBONYL)-AMINO]-5-PHENYL-THIOPHENE-2-CARBOXYLIC ACID;

Compound 37 3-[(4-METHYL-CYCLOHEXANECARBONYL)-(1-OXO-HEXAHYDRO-THIOPYRAN-4-YL)-AMINO]-5-PHENYL-THIOPHENE-2-CARBOXYLIC ACID;

Compound 38 4-{[(2-CARBOXY-5-PHENYL-THIOPHEN-3-YL)-(4-METHYL-CYCLOHEXANECARBONYL)-AMINO]-METHYL}-1-METHYL-PIPERIDINIUM CHLORIDE;

Compound 39 3-[(1-ETHYL-PIPERIDIN-4-YL)-(4-METHYL-CYCLOHEXANECARBONYL)-AMINO]-5-PHENYL-THIOPHENE-2-CARBOXYLIC ACID;

Compound 40 3-[(1-ISOPROPYL-PIPERIDIN-4-YL)-(4-METHYL-CYCLOHEXANECARBONYL)-AMINO]-5-PHENYL-THIOPHENE-2-CARBOYLIC ACID;

Compound 41 3-[(4-METHYL-CYCLOHEXANECARBONYL)-PIPERIDIN-4-YL-AMINO]-5-PHENYL-THIOPHENE-2-CARBOXYLIC ACID;

Compound 42 3-[[1-(4-METHOXY-BENZYL)-2-OXO-PIPERIDIN-4-YL]-(4-METHYL-CYCLOHEXANECARBONYL)-AMINO]-5-PHENYL-THIOPHENE-2-CARBOXYLIC ACID;

Compound 43 3-[(2-AZIDO-1-METHYL-ETHYL)-(4-METHYL-CYCLOHEXANECARBONYL)-AMINO]-5-PHENYL-THIOPHENE-2-CARBOXYLIC ACID;

Compound 44 5-(3-FLUORO-PHENYL)-3-[(2-HYDROXY-4-METHYL-CYCLOHEXANECARBONYL)-ISOPROPYL-AMINO]-THIOPHENE-2-CARBOXYLIC ACID;

Compound 45 4-[(2-CARBOXY-5-#P!-TOLYL-THIOPHEN-3-YL)-(4-METHYL-CYCLOHEXANECARBONYL)-AMINO]-1-METHYL-PIPERIDINIUM CHLORIDE;

Compound 46 3-[(4-METHOXY-CYCLOHEXYL)-(4-METHYL-CYCLOHEXANECARBONYL)-AMINO]-5-PHENYL-THIOPHENE-2-CARBOXYLIC ACID;

Compound 47 3-[(4-METHYL-CYCLOHEXANECARBONYL)-(4-HYDROXYCYCLOHEXYL)-AMINO]-5-PHENYL-THIOPHENE-2-CARBOXYLIC ACID;

Compound 48 3-[(1-ACETYL-PIPERIDIN-4-YL)-(4-METHYL-CYCLOHEXANECARBONYL)-AMINO]-5-PHENYL-THIOPHENE-2-CARBOXYLIC ACID;

Compound 49 4-[(2-CARBOXY-5-PHENYL-THIOPHEN-3-YL)-(4-METHYL-CYCLOHEXANECARBONYL)-AMINO]-1-METHYL-AZEPANIUM CHLORIDE;

Compound 50 5-(4-FLUORO-PHENYL)-3-[(4-HYDROXY-CYCLOHEXYL)-(4-METHYL-CYCLOHEXANECARBONYL)-AMINO]-THIOPHENE-2-CARBOXYLIC ACID;

Compound 51 5-(3-FLUORO-PHENYL)-3-[(4-HYDROXY-CYCLOHEXYL)-(4-METHYL-CYCLOHEXANECARBONYL)-AMINO]-THIOPHENE-2-CARBOXYLIC ACID;

Compound 52 3-[(1-BENZYL-PIPERIDIN-4-YL)-(4-METHYL-CYCLOHEXANECARBONYL)-AMINO]-5-PHENYL-THIOPHENE-2-CARBOXYLIC ACID;

Compound 53 5-(4-FLUORO-PHENYL)-3-[ISOPROPYL-(4-METHYL-CYCLOHEX-3-ENECARBONYL)-AMINO]-THIOPHENE-2-CARBOXYLIC ACID;

Compound 54 4-[[2-CARBOXY-5-(3-FLUORO-PHENYL)-THIOPHEN-3-YL]-(4-METHYL-CYCLOHEXANECARBONYL)-AMINO]-1-METHYL-PIPERIDINIUM; CHLORIDE;

Compound 55 4-[[2-CARBOXY-5-(4-METHOXY-PHENYL)-THIOPHEN-3-YL]-(4-METHYL-CYCLOHEXANECARBONYL)-AMINO]-1-METHYL-PIPERIDINIUM; CHLORIDE;

Compound 56 4-[[2-CARBOXY-5-(4-NITRO-PHENYL)-THIOPHEN-3-YL]-(4-METHYL-CYCLOHEXANECARBONYL)-AMINO]-1-METHYL-PIPERIDINIUM; CHLORIDE;

Compound 57 4-[[2-CARBOXY-5-(4-CHLORO-PHENYL)-THIOPHEN-3-YL]-(4-METHYL-CYCLOHEXANECARBONYL)-AMINO]-1-METHYL-PIPERIDINIUM CHLORIDE;

Compound 58 4-[[2-CARBOXY-5-(4-CYANO-PHENYL)-THIOPHEN-3-YL]-(4-METHYL-CYCLOHEXANECARBONYL)-AMINO]-1-METHYL-PIPERIDINIUM CHLORIDE;

Compound 59 5-(4-CHLORO-PHENYL)-3-[(4-HYDROXY-CYCLOHEXYL)-(4-METHYL-CYCLOHEXANECARBONYL)-AMINO]-THIOPHENE-2-CARBOXYLIC ACID;

Compound 60 3-[(4-HYDROXY-CYCLOHEXYL)-(4-METHYL-CYCLOHEXANECARBONYL)-AMINO]-5-(4-METHOXY-PHENYL)-THIOPHENE-2-CARBOXYLIC ACID;

Compound 61 5-(4-CYANO-PHENYL)-3-[(4-HYDROXY-CYCLOHEXYL)-(4-METHYL-CYCLOHEXANECARBONYL)-AMINO]-THIOPHENE-2-CARBOXYLIC ACID;

Compound 62 3-[(2-HYDROXY-4-METHYL-CYCLOHEXANECARBONYL)-ISOPROPYL-AMINO]-5-(4-METHOXY-PHENYL)-THIOPHENE-2-CARBOXYLIC ACID;

Compound 63 3-[(1-FORMYL-PIPERIDIN-4-YL)-(4-METHYL-CYCLOHEXANECARBONYL)-AMINO]-5-PHENYL-THIOPHENE-2-CARBOXYLIC ACID;

Compound 64 3-[N',N'-Dimethyl-N-(4-methyl-cyclohexanecarbonyl)-hydrazino]-5-phenyl-thiophene-2-carboxylic acid;

Compound 65 3-[(4-METHYL-CYCLOHEXANECARBONYL)-(1-METHYL-1-OXY-PIPERIDIN-4-YL)-AMINO]-5-PHENYL-THIOPHENE-2-CARBOXYLIC ACID;

Compound 66 3-[(4-METHYL-CYCLOHEXANECARBONYL)-(1-METHYL-1-OXY-PIPERIDIN-4-YL)-AMINO]-5-PHENYL-THIOPHENE-2-CARBOXYLIC ACID;

Compound 67 3-[(2-AMINO-CYCLOHEXYL)-(2,4-DICHLORO-BENZOYL)-AMINO]-5-PHENYL-THIOPHENE-2-CARBOXYLIC ACID;

Compound 68 3-[(4-METHYL-CYCLOHEXANECARBONYL)-(1-OXO-TETRAHYDRO-THIOPYRAN-4-YL)-AMINO]-5-PHENYL-THIOPHENE-2-CARBOXYLIC ACID;

Compound 69 5-(4-FLUOROPHENYL)-((4-METHYL-CYCLOHEXANECARBONYL)-1-(METHYL-PIPERIDIN-3-YLMETHYL)-AMINO)-THIOPHENE-2-CARBOXYLIC ACID;

Compound 70 3-[(1-METHANESULFONYL-PIPERIDIN-4-YL)-(4-METHYL-CYCLOHEXANECARBONYL)-AMINO]-5-PHENYL-THIOPHENE-2-CARBOXYLIC ACID;

Compound 71 3-[(1-METHYLCARBAMOYL-PIPERIDIN-4-YL)-(4-METHYL-CYCLOHEXANECARBONYL)-AMINO]-5-PHENYL-THIOPHENE-2-CARBOXYLIC ACID;

Compound 72 3-[N-(2,4-Dichloro-benzoyl)-N',N'-dimethyl-hydrazino]-5-phenyl-thiophene-2-carboxylic acid; or pharmaceutically acceptable salts thereof.

In one aspect, the present invention provides novel compounds including:

Compound 73 5-(4-FLUORO-PHENYL)-3-[(4-HYDROXY-CYCLOHEXYL)-(4-METHYL-CYCLOHEXANECARBONYL)-AMINO]-THIOPHENE-2-CARBOXYLIC ACID;

Compound 74 3-[(1-METHYLCARBAMOYL-PIPERIDIN-4-YL)-(4-METHYL-CYCLOHEXANECARBONYL)-AMINO]-5-PHENYL-THIOPHENE-2-CARBOXYLIC ACID;

Compound 75 3-[(4-METHYL-CYCLOHEXANECARBONYL)-(1-METHYL-2-OXO-PIPERIDIN-4-YL)-AMINO]-5-PHENYL-THIOPHENE-2-CARBOXYLIC ACID;

Compound 76 3-[(4-CARBOXY-CYCLOHEXYL)-(4-METHYL-CYCLOHEXANECARBONYL)-AMINO]-5-PHENYL-THIOPHENE-2-CARBOXYLIC ACID;

Compound 77 3-[(1-CYANO-PIPERIDIN-4-YL)-(4-METHYL-CYCLOHEXANECARBONYL)-AMINO]-5-PHENYL-THIOPHENE-2-CARBOXYLIC ACID;

Compound 78 3-[(4-CARBOXY-CYCLOHEXYL)-(4-METHYL-CYCLOHEXANECARBONYL)-AMINO]-5-PHENYL-THIOPHENE-2-CARBOXYLIC ACID;

Compound 79 5-(3,4-DIFLUORO-PHENYL)-3-[(4-HYDROXY-CYCLOHEXYL)-(4-METHYL-CYCLOHEXANECARBONYL)-AMINO]-THIOPHENE-2-CARBOXYLIC ACID;

Compound 80 5'-ACETYL-4-[(4-HYDROXY-CYCLOHEXYL)-(4-METHYL-CYCLOHEXANECARBONYL)-AMINO]-[2,2']BITHIOPHENYL-5-CARBOXYLIC ACID;

Compound 81 3-[(1-CARBAMOYL-PIPERIDIN-4-YL)-(4-METHYL-CYCLOHEXANECARBONYL)-AMINO]-5-PHENYL-THIOPHENE-2-CARBOXYLIC ACID;

Compound 82 3-[(4-METHYL-CYCLOHEXANECARBONYL)-(7-OXO-AZEPAN-4-YL)-AMINO]-5-PHENYL-THIOPHENE-2-CARBOXYLIC ACID;

Compound 83 3-[(1-AMINOOXALYL-PIPERIDIN-4-YL)-(4-METHYL-CYCLOHEXANECARBONYL)-AMINO]-5-PHENYL-THIOPHENE-2-CARBOXYLIC ACID;

Compound 84 3-[ETHYL-(4-METHYL-BENZOYL)-AMINO]-5-PHENYL-THIOPHENE-2-CARBOXYLIC ACID;

Compound 85 5-(4-ACETYL-PHENYL)-3-[(4-HYDROXY-CYCLOHEXYL)-(4-METHYL-CYCLOHEXANECARBONYL)-AMINO]-THIOPHENE-2-CARBOXYLIC ACID;

Compound 86 3-[(4-HYDROXY-4-METHYL-CYCLOHEXYL)-(4-METHYL-CYCLOHEXANECARBONYL)-AMINO]-5-PHENYL-THIOPHENE-2-CARBOXYLIC ACID;

Compound 87 3-[(3-HYDROXY-CYCLOHEXYL)-(4-METHYL-CYCLOHEXANECARBONYL)-AMINO]-5-PHENYL-THIOPHENE-2-CARBOXYLIC ACID;

Compound 88 3-[(4-HYDROXY-4-METHYL-CYCLOHEXYL)-(4-METHYL-CYCLOHEXANECARBONYL)-AMINO]-5-PHENYL-THIOPHENE-2-CARBOXYLIC ACID;

Compound 89 3-[(3-HYDROXY-CYCLOHEXYL)-(4-METHYL-CYCLOHEXANECARBONYL)-AMINO]-5-PHENYL-THIOPHENE-2-CARBOXYLIC ACID;

Compound 90 3-[(3-HYDROXY-CYCLOPENTYL)-(4-METHYL-CYCLOHEXANECARBONYL)-AMINO]-5-PHENYL-THIOPHE-2-CARBOXYLIC ACID;

or pharmaceutically acceptable salts thereof.

In one embodiment, the present invention provides novel 3-[(6-membered cycloalkyl-carbonyl)-amino]-5-phenyl-thiophene-2-carboxylic acid compounds selected from:

Compound 1 3-{[(2-CARBOXY-5-PHENYL-THIOPHEN-3-YL)-(4-METHYL-CYCLOHEXANECARBONYL)-AMINO]-METHYL}-PIPERIDINIUM; TRIFLUORO-ACETATE;

Compound 2 2-{[(2-CARBOXY-5-PHENYL-THIOPHEN-3-YL)-(4-METHYL-CYCLOHEXANECARBONYL)-AMINO]-METHYL}-PIPERIDINIUM; TRIFLUORO-ACETATE;

Compound 3 3-[(4-METHYL-CYCLOHEXANECARBONYL)-PYRIDIN-3-YLMETHYL-AMINO]-5-PHENYL-THIOPHENE-2-CARBOXYLIC ACID;

Compound 4 3-[(4-METHYL-CYCLOHEXANECARBONYL)-PYRIDIN-4-YLMETHYL-AMINO]-5-PHENYL-THIOPHENE-2-CARBOXYLIC ACID;

Compound 6 3-[AZEPAN-4-YL-(4-METHYL-CYCLOHEXANECARBONYL)-AMINO]-5-PHENYL-THIOPHENE-2-CARBOXYLIC ACID;

Compound 8 3-[[1,3]DIOXOLAN-2-YLMETHYL-(4-METHYL-CYCLOHEXANECARBONYL)-AMINO]-5-PHENYL-THIOPHENE-2-CARBOXYLIC ACID;

Compound 9 3-[(1-FLUORO-4-METHYL-CYCLOHEXANECARBONYL)-ISOPROPYL-AMINO]-5-PHENYL-THIOPHENE-2-CARBOXYLIC ACID;

Compound 10 3-[(1-FLUORO-4-METHYL-CYCLOHEXANECARBONYL)-ISOPROPYL-AMINO]-5-PHENYL-THIOPHENE-2-CARBOXYLIC ACID;

Compound 11 4-[(2-CARBOXY-5-PHENYL-THIOPHEN-3-YL)-(4-METHYL-CYCLOHEXANECARBONYL)-AMINO]-1-METHYL-PIPERIDINIUM CHLORIDE;

Compound 12 3-[(2-ACETYLAMINO-4-METHYL-CYCLOHEXANECARBONYL)-ISOPROPYL-AMINO]-5-PHENYL-THIOPHENE-2-CARBOXYLIC ACID;

Compound 13 3-[(4-METHYL-CYCLOHEXANECARBONYL)-(4-OXO-CYCLOHEXYL)-AMINO]-5-PHENYL-THIOPHENE-2-CARBOXYLIC ACID;

Compound 14 3-[(4-METHYL-CYCLOHEXANECARBONYL)-PYRIDIN-2-YLMETHYL-AMINO]-5-PHENYL-THIOPHENE-2-CARBOXYLIC ACID;

Compound 15 3-[(4-HYDROXY-CYCLOHEXYL)-(4-METHYL-CYCLOHEXANECARBONYL)-AMINO]-5-PHENYL-THIOPHENE-2-CARBOXYLIC ACID;

Compound 16 3-[(4-HYDROXYIMINO-CYCLOHEXYL)-(4-METHYL-CYCLOHEXANECARBONYL)-AMINO]-5-PHENYL-THIOPHENE-2-CARBOXYLIC ACID;

Compound 17 3-[ISOPROPYL-(4-METHYL-CYCLOHEX-3-ENECARBONYL)-AMINO]-5-PHENYL-THIOPHENE-2-CARBOXYLIC ACID;

Compound 25 3-[(4-METHOXYIMINO-CYCLOHEXYL)-(4-METHYL-CYCLOHEXANECARBONYL)-AMINO]-5-PHENYL-THIOPHENE-2-CARBOXYLIC ACID;

Compound 28 3-[ISOPROPYL-(4-METHYLENE-CYCLOHEXANECARBONYL)-AMINO]-5-PHENYL-THIOPHENE-2-CARBOXYLIC ACID;

Compound 31 3-[(2-HYDROXY-4-METHYL-CYCLOHEXANECARBONYL)-(TETRAHYDRO-PYRAN-4-YL)-AMINO]-5-PHENYL-THIOPHENE-2-CARBOXYLIC ACID;

Compound 32 3-[(2-AZIDO-1-METHYL-ETHYL)-(4-METHYL-CYCLOHEXANECARBONYL)-AMINO]-5-PHENYL-THIOPHENE-2-CARBOXYLIC ACID;

Compound 33 3-[(4-METHYL-CYCLOHEXANECARBONYL)-(1-METHYL-PIPERIDIN-4-YLMETHYL)-AMINO]-5-PHENYL-THIOPHENE-2-CARBOXYLIC ACID;

Compound 34 3-[(4-METHYL-CYCLOHEXANECARBONYL)-(TETRAHYDRO-THIOPYRAN-4-YL)-AMINO]-5-PHENYL-THIOPHENE-2-CARBOXYLIC ACID;

Compound 35 3-{[(2-CARBOXY-5-PHENYL-THIOPHEN-3-YL)-(4-METHYL-CYCLOHEXANECARBONYL)-AMINO]-METHYL}-1-METHYL-PIPERIDINIUM CHLORIDE;

Compound 36 3-[(2-AMINO-1-METHYL-ETHYL)-(4-METHYL-CYCLOHEXANECARBONYL)-AMINO]-5-PHENYL-THIOPHENE-2-CARBOXYLIC ACID;

Compound 37 3-[(4-METHYL-CYCLOHEXANECARBONYL)-(1-OXO-HEXAHYDRO-THIOPYRAN-4-YL)-AMINO]-5-PHENYL-THIOPHENE-2-CARBOXYLIC ACID;

Compound 38 4-{[(2-CARBOXY-5-PHENYL-THIOPHEN-3-YL)-(4-METHYL-CYCLOHEXANECARBONYL)-AMINO]-METHYL}-1-METHYL-PIPERIDINIUM CHLORIDE;

Compound 39 3-[(1-ETHYL-PIPERIDIN-4-YL)-(4-METHYL-CYCLOHEXANECARBONYL)-AMINO]-5-PHENYL-THIOPHENE-2-CARBOXYLIC ACID;

Compound 40 3-[(1-ISOPROPYL-PIPERIDIN-4-YL)-(4-METHYL-CYCLOHEXANECARBONYL)-AMINO]-5-PHENYL-THIOPHENE-2-CARBOYLIC ACID;

Compound 41 3-[(4-METHYL-CYCLOHEXANECARBONYL)-PIPERIDIN-4-YL-AMINO]-5-PHENYL-THIOPHENE-2-CARBOXYLIC ACID;

Compound 42 3-[[1-(4-METHOXY-BENZYL)-2-OXO-PIPERIDIN-4-YL]-(4-METHYL-CYCLOHEXANECARBONYL)-AMINO]-5-PHENYL-THIOPHENE-2-CARBOXYLIC ACID;

Compound 43 3-[(2-AZIDO-1-METHYL-ETHYL)-(4-METHYL-CYCLOHEXANECARBONYL)-AMINO]-5-PHENYL-THIOPHENE-2-CARBOXYLIC ACID;

Compound 46 3-[(4-METHOXY-CYCLOHEXYL)-(4-METHYL-CYCLOHEXANECARBONYL)-AMINO]-5-PHENYL-THIOPHENE-2-CARBOXYLIC ACID;

Compound 47 3-[(4-METHYL-CYCLOHEXANECARBONYL)-(4-METHYL-CYCLOHEXYL)-AMINO]-5-PHENYL-THIOPHENE-2-CARBOXYLIC ACID;

Compound 48 3-[(1-ACETYL-PIPERIDIN-4-YL)-(4-METHYL-CYCLOHEXANECARBONYL)-AMINO]-5-PHENYL-THIOPHENE-2-CARBOXYLIC ACID;

Compound 49 4-[(2-CARBOXY-5-PHENYL-THIOPHEN-3-YL)-(4-METHYL-CYCLOHEXANECARBONYL)-AMINO]-1-METHYL-AZEPANIUM CHLORIDE;

Compound 52 3-[(1-BENZYL-PIPERIDIN-4-YL)-(4-METHYL-CYCLOHEXANECARBONYL)-AMINO]-5-PHENYL-THIOPHENE-2-CARBOXYLIC ACID;

Compound 63 3-[(1-FORMYL-PIPERIDIN-4-YL)-(4-METHYL-CYCLOHEXANECARBONYL)-AMINO]-5-PHENYL-THIOPHENE-2-CARBOXYLIC ACID;

Compound 64 3-[N',N'-Dimethyl-N-(4-methyl-cyclohexanecarbonyl)-hydrazino]-5-phenyl-thiophene-2-carboxylic acid;

Compound 65 3-[(4-METHYL-CYCLOHEXANECARBONYL)-(1-METHYL-1-OXY-PIPERIDIN-4-YL)-AMINO]-5-PHENYL-THIOPHENE-2-CARBOXYLIC ACID;

Compound 66 3-[(4-METHYL-CYCLOHEXANECARBONYL)-(1-METHYL-1-OXY-PIPERIDIN-4-YL)-AMINO]-5-PHENYL-THIOPHENE-2-CARBOXYLIC ACID;

Compound 68 3-[(4-METHYL-CYCLOHEXANECARBONYL)-(1-OXO-HEXAHYDRO-THIOPYRAN-4-YL)-AMINO]-5-PHENYL-THIOPHENE-2-CARBOXYLIC ACID;

Compound 70 3-[(1-METHANESULFONYL-PIPERIDIN-4-YL)-(4-METHYL-CYCLOHEXANECARBONYL)-AMINO]-5-PHENYL-THIOPHENE-2-CARBOXYLIC ACID;

Compound 71 3-[(1-METHYLCARBAMOYL-PIPERIDIN-4-YL)-(4-METHYL-CYCLOHEXANECARBONYL)-AMINO]-5-PHENYL-THIOPHENE-2-CARBOXYLIC ACID;

Compound 74 3-[(1-METHYLCARBAMOYL-PIPERIDIN-4-YL)-(4-METHYL-CYCLOHEXANECARBONYL)-AMINO]-5-PHENYL-THIOPHENE-2-CARBOXYLIC ACID;

Compound 75 3-[(4-METHYL-CYCLOHEXANECARBONYL)-(1-METHYL-2-OXO-PIPERIDIN-4-YL)-AMINO]-5-PHENYL-THIOPHENE-2-CARBOXYLIC ACID;

Compound 76 3-[(4-CARBOXY-CYCLOHEXYL)-(4-METHYL-CYCLOHEXANECARBONYL)-AMINO]-5-PHENYL-THIOPHENE-2-CARBOXYLIC ACID;

Compound 77 3-[(1-CYANO-PIPERIDIN-4-YL)-(4-METHYL-CYCLOHEXANECARBONYL)-AMINO]-5-PHENYL-THIOPHENE-2-CARBOXYLIC ACID;

Compound 78 3-[(4-CARBOXY-CYCLOHEXYL)-(4-METHYL-CYCLOHEXANECARBONYL)-AMINO]-5-PHENYL-THIOPHENE-2-CARBOXYLIC ACID;

Compound 81 3-[(1-CARBAMOYL-PIPERIDIN-4-YL)-(4-METHYL-CYCLOHEXANECARBONYL)-AMINO]-5-PHENYL-THIOPHENE-2-CARBOXYLIC ACID;

Compound 82 3-[(4-METHYL-CYCLOHEXANECARBONYL)-(7-OXO-AZEPAN-4-YL)-AMINO]-5-PHENYL-THIOPHENE-2-CARBOXYLIC ACID;

Compound 83 3-[(1-AMINOOXALYL-PIPERIDIN-4-YL)-(4-METHYL-CYCLOHEXANECARBONYL)-AMINO]-5-PHENYL-THIOPHENE-2-CARBOXYLIC ACID;

Compound 86 3-[(4-HYDROXY-4-METHYL-CYCLOHEXYL)-(4-METHYL-CYCLOHEXANECARBONYL)-AMINO]-5-PHENYL-THIOPHENE-2-CARBOXYLIC ACID;

Compound 87 3-[(3-HYDROXY-CYCLOHEXYL)-(4-METHYL-CYCLOHEXANECARBONYL)-AMINO]-5-PHENYL-THIOPHENE-2-CARBOXYLIC ACID;

Compound 88 3-[(4-HYDROXY-4-METHYL-CYCLOHEXYL)-(4-METHYL-CYCLOHEXANECARBONYL)-AMINO]-5-PHENYL-THIOPHENE-2-CARBOXYLIC ACID;

Compound 89 3-[(3-HYDROXY-CYCLOHEXYL)-(4-METHYL-CYCLOHEXANECARBONYL)-AMINO]-5-PHENYL-THIOPHENE-2-CARBOXYLIC ACID;

Compound 90 3-[(3-HYDROXY-CYCLOPENTYL)-(4-METHYL-CYCLOHEXANECARBONYL)-AMINO]-5-PHENYL-THIOPHE-2-CARBOXYLIC ACID;

or pharmaceutically acceptable salts thereof.

In one embodiment, the present invention provides novel 3-[(4-methyl-cyclohexane-carbonyl)-amino]-5-phenyl-thiophene-2-carboxylic acid compounds.

In one embodiment, the present invention provides novel compounds having 3-[(unsubstituted or substituted-benzoyl)-amino]-5-phenyl-thiophene-2-carboxylic acid selected from:

Compound 7 3-[(2,4-DICHLORO-BENZOYL)-[1,3]DIOXOLAN-2-YLMETHYL-AMINO]-5-PHENYL-THIOPHENE-2-CARBOXYLIC ACID;

Compound 18 3-[(1-AZIDOMETHYL-2-METHYL-BUTYL)-(2,4-DICHLORO-BENZOYL)-AMINO]-5-PHENYL-THIOPHENE-2-CARBOXYLIC ACID;

Compound 19 2-[(2-Carboxy-5-phenyl-thiophen-3-yl)-(2-chloro-benzoyl)-amino]-3-methyl-pentyl-ammonium trifluoroacetate;

Compound 20 3-[(1-AMINOMETHYL-2-METHYL-BUTYL)-(2,4-DICHLORO-BENZOYL)-AMINO]-5-PHENYL-THIOPHENE-2-CARBOXYLIC ACID;

Compound 21 {2-[(2-CARBOXY-5-PHENYL-THIOPHEN-3-YL)-(2,4-DICHLORO-BENZOYL)-AMINO]-PROPYL}-TRIMETHYL-AMMONIUM; TRIFLUORO-ACETATE;

Compound 67 3-[(2-AMINO-CYCLOHEXYL)-(2,4-DICHLORO-BENZOYL)-AMINO]-5-PHENYL-THIOPHENE-2-CARBOXYLIC ACID;

Compound 72 3-[N-(2,4-Dichloro-benzoyl)-N',N'-dimethyl-hydrazino]-5-phenyl-thiophene-2-carboxylic acid;

Compound 84 3-[ETHYL-(4-METHYL-BENZOYL)-AMINO]-5-PHENYL-THIOPHENE-2-CARBOXYLIC ACID;

or pharmaceutically acceptable salts thereof.

In one embodiment, the present invention provides novel 3-[(6-membered heterocycle -2-carbonyl)-amino]-5-phenyl-thiophene-2-carboxylic acid compounds selected from:

Compound 22 3-[ISOPROPYL-(5-METHYL-[1,3]DI-OXANE-2-CARBONYL)-AMINO]-5-PHENYL-THIOPHENE-2-CARBOXYLIC ACID;

Compound 27 3-[ISOPROPYL-(5-METHYL-TETRAHYDRO-PYRAN-2-CARBONYL)-AMINO]-5-PHENYL-THIOPHENE-2-CARBOXYLIC ACID;

Compound 29 3-[ISOPROPYL-(5-METHYL-TETRAHYDRO-PYRAN-2-CARBONYL)-AMINO]-5-PHENYL-THIOPHENE-2-CARBOXYLIC ACID;

Compound 30 3-[ISOPROPYL-(5-METHYL-3,6-DIHYDRO-2H-PYRAN-2-CARBONYL)-AMINO]-5-PHENYL-THIOPHENE-2-CARBOXYLIC ACID;

or pharmaceutically acceptable salts thereof.

In one embodiment, the viral infection is chosen from Flavivirus infections.

In one embodiment, the Flavivirus infection is chosen from Hepatitis C virus (HCV), bovine viral diarrhea virus (BVDV), hog cholera virus, dengue fever virus, Japanese encephalitis virus and yellow fever virus.

In another embodiment, the Flavivirus infection is Hepatitis C viral infection.

In one embodiment, the present invention provides a method for treating or preventing a Flaviviridae viral infection in a host comprising administering to the host a therapeutically effective amount of at least one compound according to the invention described herein.

In one embodiment, the present invention provides a method for treating or preventing a Flaviviridae viral infection in a host comprising administering to the host a therapeutically effective amount of at least one compound according to the invention described herein and further comprising administering at least one additional agent chosen from viral serine protease inhibitor, viral polymerase inhibitor, viral helicase inhibitor, immunomudulating agent, antioxydant agent, antibacterial agent, therapeutic vaccine, hepatoprotectant agent or antisense agent.

In one embodiment, the additional agent is interferon α, ribavirin, silybum marianum, interleukine-12, amantadine, ribozyme, thymosin, N-acetyl cysteine or cyclosporin.

In one embodiment, the *Flaviviridea* viral infection is hepatitis C viral infection (HCV).

In one embodiment, the present invention provides a pharmaceutical composition comprising at least one compound according to the invention described herein and at least one pharmaceutically acceptable carrier or excipient.

In one embodiment, the present invention provides a pharmaceutical composition comprising at least one compound according to the invention described herein and at least one pharmaceutically acceptable carrier or excipient and further comprising at least one additional agent chosen from viral serine protease inhibitor, viral polymerase inhibitor, viral helicase inhibitor, immunomudulating agent, antioxydant agent, antibacterial agent, therapeutic vaccine, hepatoprotectant agent or antisense agent.

In another embodiment, the additional agent is interferon a, ribavirin, silybum marianum, interleukine-12, amantadine, ribozyme, thymosin, N-acetyl cysteine or cyclosporin.

In one embodiment, viral serine protease inhibitor is a *flaviviridae* serine protease inhibitor.

In one embodiment, viral polymerase inhibitor is a *flaviviridae* polymerase inhibitor.

In one embodiment, viral helicase inhibitor is a *flaviviridae* helicase inhibitor.

In further embodiments:
viral serine protease inhibitor is HCV serine protease inhibitor;
viral polymerase inhibitor is HCV polymerase inhibitor;
viral helicase inhibitor is HCV helicase inhibitor.

In one embodiment, there is provided a method for inhibiting or reducing the activity of viral polymerase in a host comprising administering a therapeutically effective amount of a compound according to the invention described herein.

In one embodiment, there is provided a method for inhibiting or reducing the activity of viral polymerase in a host comprising administering a therapeutically effective amount of a compound according to the invention described herein and further comprising administering one or more viral polymerase inhibitor.

In one embodiment, viral polymerase is a Flaviviridae viral polymerase.

In one embodiment, viral polymerase is a RNA-dependant RNA-polymerase.

In one embodiment, viral polymerase is HCV polymerase.

In one embodiment, there is provided a combination comprising a least one compound according to the invention described herein and one or more additionnal agent chosen from viral serine protease inhibitor, viral polymerase inhibitor and viral helicase inhibitor, immunomudulating agent, antioxydant agent, antibacterial agent, therapeutic vaccine, hepatoprotectant agent or antisense agent.

In one embodiment, the compound and additionnal agent are administered sequentially.

In one embodiment, the compound and additionnal agent are administered simultaneously.

The combinations referred to above may conveniently be presented for use in the form of a pharmaceutical formulation and thus pharmaceutical formulations comprising a combination as defined above together with a pharmaceutically acceptable carrier therefor comprise a further aspect of the invention.

The individual components for use in the method of the present invention or combinations of the present invention may be administered either sequentially or simultaneously in separate or combined pharmaceutical formulations.

In one embodiment, the present invention provides the use of a compound according to the invention described herein for treating or preventing Flaviviridae viral infection in a host.

In one embodiment, the present invention provides the use of a compound according to the invention described herein for the manufacture of a medicament for treating or preventing a viral Flaviridea infection in a host.

In one embodiment, the present invention provides the use of a compound according to the invention described herein for inhibiting or reducing the activity of viral polymerase in a host.

It will be appreciated by those skilled in the art that the compounds in accordance with the present invention can contain chiral centre. The compounds of formula may thus exist in the form of two different optical isomers (i.e. (+) or (−) enantiomers). All such enantiomers and mixtures thereof including racemic mixtures are included within the scope of the invention. The single optical isomer or enantiomer can be obtained by method well known in the art, such as chiral HPLC, enzymatic resolution and chiral auxiliary.

Preferably, the compounds of the present invention are provided in the form of a single enantiomer at least 95%, more preferably at least 97% and most preferably at least 99% free of the corresponding enantiomer.

More preferably the compound of the present invention are in the form of the (+) enantiomer at least 95% free of the corresponding (−) enantiomer.

More preferably the compound of the present invention are in the form of the (+) enantiomer at least 97% free of the corresponding (−) enantiomer.

More preferably the compound of the present invention are in the form of the (+) enantiomer at least 99% free of the corresponding (−) enantiomer.

In a more preferred embodiment, the compounds of the present invention are in the form of the (−) enantiomer at least 95% free of the corresponding (+) enantiomer.

Most preferably the compound of the present invention are in the form of the (−) enantiomer at least 97% free of the corresponding (+) enantiomer.

More preferably the compound of the present invention are in the form of the (−) enantiomer at least 99% free of the corresponding (+) enantiomer.

It will also be appreciated that the compounds in accordance with the present invention can contain more than one chiral centres. The compounds of formula may thus exist in the form of different diastereomers. All such diastereomers and mixtures thereof are included within the scope of the invention. The single diastereomer can be obtained by method well known in the art, such as HPLC, crystalisation and chromatography.

There is also provided a pharmaceutically acceptable salts of the compounds of the present invention. By the term pharmaceutically acceptable salts of compounds are meant those derived from pharmaceutically acceptable inorganic and organic acids and bases. Examples of suitable acids include hydrochloric, hydrobromic, sulphuric, nitric, perchloric, fumaric, maleic, phosphoric, glycollic, lactic, salicylic, succinic, toleune-p-sulphonic, tartaric, acetic, trifluoroacetic, citric, methanesulphonic, formic, benzoic, malonic, naphthalene-2-sulphonic and benzenesulphonic acids. Other acids such as oxalic, while not in themselves pharmaceutically acceptable, may be useful as intermediates in obtaining the compounds of the invention and their pharmaceutically acceptable acid addition salts.

Salts derived from appropriate bases include alkali metal (e.g. sodium, lithium, potassium), alkaline earth metal (e.g. magnesium), ammonium and $NR_4+$ (where R is $C_{1-4}$ alkyl) salts.

References hereinafter to a compound according to the invention includes compounds and their pharmaceutically acceptable salts.

In one embodiment of the invention, the pharmaceutically acceptable salt is a sodium salt.

In one embodiment of the invention, the pharmaceutically acceptable salt is a lithium salt.

In one embodiment of the invention, the pharmaceutically acceptable salt is a potassium salt.

Applicant has also filed a co-pending U.S. regular application Ser. No. 10/166,031 on Jun. 11, 2002 entitled: "COMPOUNDS AND METHODS FOR THE TREATMENT OR PREVENTION OF FLAVIVIRUS INFECTIONS" the content of which is herein incorporated by reference.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In case of conflict, the present specification, including definitions, will control. In addition, the materials, methods, and examples are illustrative only and not intended to be limiting.

As used in this application, the term "alkyl" represents a straight chain or branched chain hydrocarbon moiety which may optionally be substituted by one or more of: halogen, nitro, nitroso, $SO_3R_{12}$, $PO_3RcRd$, $CONR_{13}R_{14}$, $C_{1-6}$ alkyl, $C_{2-6}$ alkenyl, $C_{2-6}$ alkynyl, $C_{6-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{6-12}$ aralkyl, $C_{3-10}$ heterocycle, hydroxyl, $NR_{13}R_{14}$, $C(O)OR_{12}$, cyano, azido, amidino or guanido;

wherein $R_{12}$, Rc, Rd, $R_{13}$ and $R_{14}$ are each independently chosen from H, C1-12 alkyl, C2-12 alkenyl, C2-12 alkynyl, C6-14 aryl, C3-12 heterocycle, C3-18 heteroaralkyl, C6-18 aralkyl;

or Rc and Rd are taken together with the oxygens to form a 5 to 10 membered heterocycle;

or $R_{13}$ and $R_{14}$ are taken together with the nitrogen to form a 3 to 10 membered heterocycle. Useful examples of alkyls include isopropyl, ethyl, fluorohexyl or cyclopropyl. The term alkyl is also meant to include alkyls in which one or more hydrogen atoms is replaced by an oxygen, (e.g. a benzoyl) or an halogen, more preferably, the halogen is fluoro (e.g. $CF_3$— or $CF_3CH_2$—).

The term "cycloalkyl" represents a cyclic alkyl. The term cycloalkyl is also meant to include a cycloalkyl containing at least one unsaturated group. Useful examples of cycloalkyl include cyclopropyl, cyclobutyl, cyclohexenyl, cyclohex-dienyl and cyclohexyl.

The terms "alkenyl" and "alkynyl", represent an alkyl containing at least one unsaturated group (e.g. allyl, acetylene, ethylene).

The term "aryl" represents a carbocyclic moiety containing at least one benzenoid-type ring which may optionally be substituted by one or more of halogen, nitro, nitroso, $SO_3R_{12}$, $PO_3RcRd$, $CONR_{13}R_{14}$, $C_{1-6}$ alkyl, $C_{2-6}$ alkenyl, $C_{2-6}$ alkynyl, $C_{6-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C6-12$ aryl, $C(O)C_{6-12}$ aralkyl, $C_{3-10}$ heterocycle, hydroxyl, $NR_{13}R_{14}$, $C(O)OR_{12}$, cyano, azido, amidino or guanido;

wherein $R_{12}$, Rc, Rd, $R_{13}$ and $R_{14}$ are each independently chosen from H, C1-12 alkyl, C2-12 alkenyl, C2-12 alkynyl, C6-14 aryl, C3-12 heterocycle, C3-18 heteroaralkyl, C6-18 aralkyl;

or Rc and Rd are taken together with the oxygens to form a 5 to 10 membered heterocycle;

or $R_{13}$ and $R_{14}$ are taken together with the nitrogen to form a 3 to 10 membered heterocycle. Examples of aryl include phenyl and naphthyl.

The term "aralkyl", represents an aryl group attached to the adjacent atom by a $C_{1-6}$alkyl, $C_{1-6}$alkenyl, or $C_{1-6}$alkynyl (e.g., benzyl).

The term "heterocycle" represents a saturated or unsaturated, cyclic moiety wherein said cyclic moeity is interrupted by at least one heteroatom, (e.g. oxygen, sulfur or nitrogen) which may optionally be substituted halogen, nitro, nitroso, $SO_3R_{12}$, $PO_3RcRd$, $CONR_{13}R_{14}$, $C_{1-6}$ alkyl, $C_{2-6}$ alkenyl, $C_{2-6}$ alkynyl, $C_{6-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{6-12}$ aralkyl, $C_{3-10}$ heterocycle, hydroxyl, $NR_{13}R_{14}$, $C(O)OR_{12}$, cyano, azido, amidino or guanido;

wherein $R_{12}$, Rc, Rd, $R_{13}$ and $R_{14}$ are each independently chosen from H, C1-12 alkyl, C2-12 alkenyl, C2-12 alkynyl, C6-14 aryl, C3-12 heterocycle, C3-18 heteroaralkyl, C6-18 aralkyl;

or Rc and Rd are taken together with the oxygens to form a 5 to 10 membered heterocycle;

or $R_{13}$ and $R_{14}$ are taken together with the nitrogen to form a 3 to 10 membered heterocycle. It is understood that the term heterocyclic ring represents a mono or polycyclic (e.g., bicyclic) ring. Examples of heterocyclic rings include but are not limited to epoxide; furan; benzofuran; isobenzofuran; oxathiolane; dithiolane; dioxolane; pyrrole; pyrrolidine; imidazole;

pyridine; pyrimidine; indole; piperidine; morpholine; thiophene and thiomorpholine.

The term "heteroaralkyl" represents an heterocycle group attached to the adjacent atom by a $C_{1-6}$ alkyl, $C_{1-6}$ alkenyl, or $C_{1-6}$ alkynyl.

When there is a sulfur atom present, the sulfur atom can be at different oxidation levels, ie. S, SO, or $SO_2$. All such oxidation levels are within the scope of the present invention.

When there is a nitrogen atom present, the nitrogen atom can be at different oxidation levels, ie. N or NO. All such oxidation levels are within the scope of the present invention.

The term "independently" means that a substituent can be the same or different definition for each item.

It will be appreciated that the amount of a compound of the invention required for use in treatment will vary not only with the particular compound selected but also with the route of administration, the nature of the condition for which treatment is required and the age and condition of the patient and will be ultimately at the discretion of the attendant physician or veterinarian. In general however a suitable dose will be in the range of from about 0.1 to about 750 mg/kg of body weight per day, preferably in the range of 0.5 to 60 mg/kg/day, most preferably in the range of 1 to 20 mg/kg/day.

The desired dose may conveniently be presented in a single dose or as divided dose administered at appropriate intervals, for example as two, three, four or more doses per day.

The compound is conveniently administered in unit dosage form; for example containing 10 to 1500 mg, conveniently 20 to 1000 mg, most conveniently 50 to 700 mg of active ingredient per unit dosage form.

Ideally the active ingredient should be administered to achieve peak plasma concentrations of the active compound of from about 1 to about 75 µM, preferably about 2 to 50 µM, most preferably about 3 to about 30 µM. This may be achieved, for example, by the intravenous injection of a 0.1 to 5% solution of the active ingredient, optionally in saline, or orally administered as a bolus containing about 1 to about 500 mg of the active ingredient. Desirable blood levels may be maintained by a continuous infusion to provide about 0.01 to about 5.0 mg/kg/hour or by intermittent infusions containing about 0.4 to 20 about 15 mg/kg of the active ingredient.

When the compounds of the present invention or a pharmaceutically acceptable salts thereof is used in combination with a second therapeutic agent active against the same virus the dose of each compound may be either the same as or differ from that when the compound is used alone. Appropriate doses will be readily appreciated by those skilled in the art.

While it is possible that, for use in therapy, a compound of the invention may be administered as the raw chemical it is preferable to present the active ingredient as a pharmaceutical composition. The invention thus further provides a pharmaceutical composition comprising compounds of the present invention or a pharmaceutically acceptable derivative thereof together with one or more pharmaceutically acceptable carriers therefor and, optionally, other therapeutic and/or prophylactic ingredients. The carrier(s) must be "acceptable" in the sense of being compatible with the other ingredients of the formulation and not deleterious to the recipient thereof.

Pharmaceutical compositions include those suitable for oral, rectal, nasal, topical (including buccal and sub-lingual), transdermal, vaginal or parenteral (including intramuscular, sub-cutaneous and intravenous) administration or in a form suitable for administration by inhalation or insufflation. The formulations may, where appropriate, be conveniently presented in discrete dosage units and may be prepared by any of the methods well known in the art of pharmacy. All methods include the step of bringing into association the active compound with liquid carriers or finely divided solid carriers or both and then, if necessary, shaping the product into the desired formulation.

Pharmaceutical compositions suitable for oral administration may conveniently be presented as discrete units such as capsules, cachets or tablets each containing a predetermined amount of the active ingredient; as a powder or granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds according to the invention may also be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing an/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

For topical administration to the epidermis, the compounds according to the invention may be formulated as ointments, creams or lotions, or as a transdermal patch. Such transdermal patches may contain penetration enhancers such as linalool, carvacrol, thymol, citral, menthol and t-anethole. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or colouring agents.

Compositions suitable for topical administration in the mouth include lozenges comprising active ingredient in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Pharmaceutical compositions suitable for rectal administration herein the carrier is a solid are most preferably presented as unit dose suppositories. Suitable carriers include cocoa butter and other materials commonly used in the art, and the suppositories may be conveniently formed by admixture of the active compound with the softened or melted carrier(s) followed by chilling and shaping in moulds.

Compositions suitable for vaginal administration may be presented as pessaries, tampons, creams, gels, pastes, foams or sprays containing in addition to the active ingredient such carriers as are known in the art to be appropriate.

For intra-nasal administration the compounds of the invention may be used as a liquid spray or dispersible powder or in the form of drops. Drops may be formulated with an aqueous or non-aqueous base also comprising one more dispersing agents, solubilising agents or suspending agents. Liquid sprays are conveniently delivered from pressurized packs.

For administration by inhalation the compounds according to the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form in, for example, capsules or cartridges or e.g. gelatin or blister packs from which the powder may be administered with the aid of an inhalator or insufflator.

When desired the above described formulations adapted to give sustained release of the active ingredient may be employed.

The following general schemes and examples are provided to illustrate various embodiments of the present invention and shall not be considered as limiting in scope.

EXAMPLE 1

3-{[(2-carboxy-5-phenyl-thiophen-3-yl)-(4-methyl-cyclohexanecarbonyl)-amino]-methyl}-piperidinium trifluoro-acetate compound 1

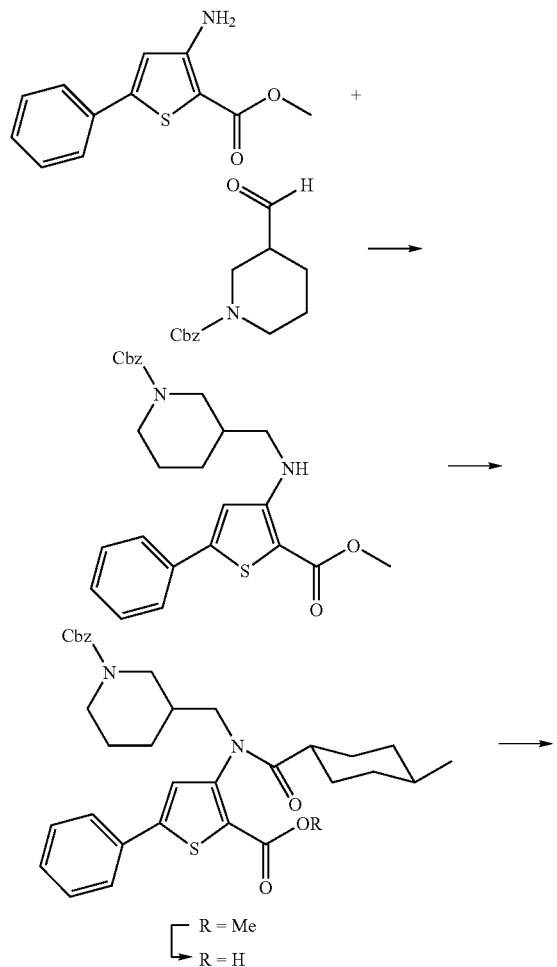

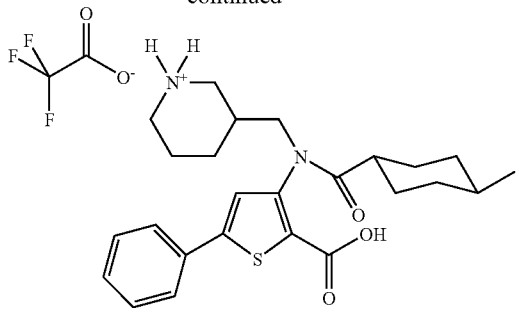

Step I

A suspension of 3-amino-5-phenyl-thiophene-2-carboxylic acid methyl ester (0.268 g, 1.15 mmol) and 3-formyl N-Cbz-piperidine (0.284 g, 1.15 mmol) in THF (0.5 mL) was treated with dibutyltin dichloride (17 mg, 0.057 mmol). After 5 min, phenylsilane (156 □L, 1.26 mmol) was added and the mixture was stirred for 6 days at room temperature. The solvent was then evaporated and the residue was purified by silica gel column chromatography using $CH_2Cl_2$:hexanes: EtOAc as eluent to provide 3-[(1-Methyl-piperidin-3-ylmethyl)-amino]-5-phenyl-thiophene-2-carboxylic acid methyl ester as an oil (0.2723 g, 51% yield). $^1$H NMR ($CDCl_3$, 400 MHz): 7.63-7.59 (m, 2H), 7.40-7.28 (m, 9H), 7.18-6.84 (br s, 1H), 5.20 (d, 1H), 5.10 (d, 1H), 4.55 (m, 1H), 4.15 (m, 1H), 3.82 (s, 3H), 3.58-3.40 (m, 2H), 2.90 (t, 1H), 1.88-1.40 (m, 6H).

Step II

3-[(1-Methyl-piperidin-3-ylmethyl)-amino]-5-phenyl-thiophene-2-carboxylic acid methyl ester (162 mg, 0.348 mmol) was dissolved in 1,2-dichloroethane (3.0 mL) and treated with trans-4-Methyl-cyclohexanecarbonyl chloride in 1,2-dichloroethane (1.0 mL, 0.43 mol). The solution was heated at reflux for 1 day. The solvent was then evaporated and the residue purified by silica gel column chromatography using hexanes:EtOAc as eluent to provide 3-[(4-Methyl-cyclohexanecarbonyl)-(1-methyl-piperidin-3-ylmethyl)-amino]-5-phenyl-thiophene-2-carboxylic acid methyl ester as an oil (0.194 g, 95% yield). $^1$H NMR ($CDCl_3$, 400 MHz) Rotamer 65/35: 7.90 (s, 0.35H), 7.70 (d, 0.65 H), 7.62-7.10 (m, 10H), 5.20-5.00 (m, 2H), 4.70(m, 0.35H), 4.60-4.40 (m, 0.65H), 4.12 (m, 1H), 3.82 (s, 3H), 3.52 (t, 0.65H), 3.20 (t, 0.35H), 2.70 (d, 0.65H), 2.52 (t, 0.35H), 1.90 (m, 1H), 1.80-1.20 (m, 13H), 1.00-0.85 (m, 1H), 0.76 (d, 3H), 0.64 (m, 2H).

Step III

3-[(4-Methyl-cyclohexanecarbonyl)-(1-methyl-piperidin-3-ylmethyl)-amino]-5-phenyl-thiophene-2-carboxylic acid methyl ester (162 mg, 0.27 mmol) was dissolved in a mixture of THF:MeOH:$H_2O$ (3:2:1, 2.8 mL) and treated with LiOH.$H_2O$ (35 mg, 0.81 mmol). The solution was heated at 55° C. for 3 h. The solvents were removed and the residue was acidified using HCl to pH 4. The product was extracted with EtOAc and the organic layers were washed with brine, dried and evaporated to provide 3-[(4-Methyl-cyclohexanecarbonyl)-(1-methyl-piperidin-3-ylmethyl)-amino]-5-phenyl-thiophene-2-carboxylic acid (146 mg, 92% yield). $^1$H NMR ($CDCl_3$, 400 MHz): 9.98 (br s, 1H), 7.80 (d, 1H), 7.62 (d, 1H), 7.48-7.24 (m, 9H), 5.20-5.05 (m, 2H), 4.35-3.95(m, 3H), 3.00 (m, 1H), 2.85-2.52 (m, 2H), 2.15 (m, 1H), 1.82-1.18 (m, 12H), 0.78 (d, 3H), 0.68 (m, 2H).

Step IV

3-[(4-Methyl-cyclohexanecarbonyl)-(1-methyl-piperidin-3-ylmethyl)-amino]-5-phenyl-thiophene-2-carboxylic acid (145 mg, 0.25 mmol) was dissolved in $CH_3CN$ (2.5 mL), cooled at 0° C. and treated with TMSI (144 mL, 1.0 mmol). The reaction was stirred at 0° C. for 1 h and at room temperature for 3 h. The solvent was removed and the residue was acidified using HCl. The product was extracted with EtOAc and the organic layers were washed with brine and dried. The solvent was then evaporated and the residue was first purified by reverse-phase HPLC followed by silica gel column chromatography purification using $CH_2Cl_2$:MeOH:AcOH as eluent to provide 3-{[(2-carboxy-5-phenyl-thiophen-3-yl)-(4-methyl-cyclohexanecarbonyl)-amino]-methyl}-piperidinium trifluoro-acetate (compound 1) (91.6 mg, 66% yield). $^1$H NMR (DMSO-d6, 400 MHz): 7.92 (br s, 1H), 7.66 (m, 2H), 7.49 (s, 1H), 7.42 (m, 2H), 7.33 (m, 1H), 4.50 (m, 1H), 3.33 (m, 3H), 2.80 (m, 1H), 2.56 (m, 1H), 2.30 (m, 2H), 1.80-1.30 (m, 8H), 1.20 (m, 3H), 0.73 (d, 3H), 0.73-0.45 (m, 2H).

The following compounds were prepared in a similar manner: Compound 2, Compound 3, Compound 4, Compound 6 and Compound 14.

EXAMPLE 2

4-{[(2-carboxy-5-phenyl-thiophen-3-yl)-(4-methyl-cyclohexanecarbonyl)-amino]-methyl}-1-methyl-piperidinium chloride Compound 38

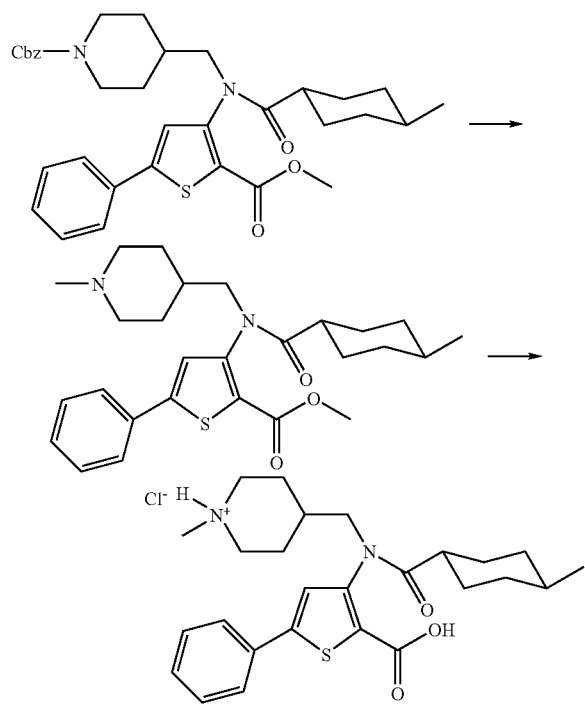

Step I

4-{[(2-Methoxycarbonyl-5-phenyl-thiophen-3-yl)-(4-methyl-cyclohexanecarbonyl)-amino]-methyl}-piperidine-1-carboxylic acid benzyl ester (190 mg, 0.32 mmol) was dissolved in MeOH (3.2 mL) and treated with formaldehyde (37% solution, 0.36 mL, 3.2 mmol), AcOH (1 drop) and 10% Pd/C (97 mg) under $H_2$ (30 psi). The reaction was stirred at room temperature for 48 h and the mixture was filtered on celite. The solution was evaporated to a residue that was purified by silica gel column chromatography using $CH_2Cl_2$: MeOH as eluent to provide 3-[(4-Methyl-cyclohexanecarbonyl)-(1-methyl-piperidin-4-ylmethyl)-amino]-5-phenyl-thiophene-2-carboxylic acid methyl ester as an oil (46.5 mg, 31% yield). $^1$H NMR ($CDCl_3$, 400 MHz): 7.62 (d, 2H), 7.43 (m, 3H), 7.10 (s, 1H), 3.97 (m, 1 H), 3.85 (s, 3H), 3.20 (m, 3H), 2.48 (s, 3H), 2.42 (m, 1H), 2.10 (m, 1H), 1.85 (m, 3H), 1.70-1.40 (m, 8H), 1.30 (m, 2H), 0.78 (d, 3H), 0.68 (m, 2H).

Step II

3-[(4-Methyl-cyclohexanecarbonyl)-(1-methyl-piperidin-4-ylmethyl)-amino]-5-phenyl-thiophene-2-carboxylic acid methyl ester (46 mg, 0.098 mmol) was dissolved in a mixture of THF:MeOH:$H_2O$ (3:2:1, 1.0 mL) and treated with LiOH.$H_2O$ (12 mg, 0.29 mmol). The solution was heated at 55° C. for 3 h. The solvents were removed and the residue was acidified using HCl to pH 4. The precipitate was filtered, washed and triturated with hexanes to provide 4-{[(2-carboxy-5-phenyl-thiophen-3-yl)-(4-methyl-cyclohexanecarbonyl)-amino]-methyl}-1-methyl-piperidinium chloride (Compound 38) as a solid (35.3 mg, 73% yield). $^1$H NMR ($CD_3OD$, 400 MHz): 7.66 (d, 2H), 7.40 (t, 3H), 7.32 (t, 1H), 7.25 (s, 1H), 3.85 (dd, 1 H), 3.52 (dd, 1H), 3.34 (m, 2H), 2.78 (q, 2H), 2.70 (s, 3H), 2.35 (m, 1H), 2.05 (m, 1H), 1.84 (m, 2H), 1.72 (m, 1H), 1.65-1.20 (m, 8H), 0.76 (d, 3H), 0.68 (m, 2H).

The following compounds were prepared in a similar manner: Compound 33, Compound 35, Compound 49 and Compound 69.

EXAMPLE 3

3-[Isopropyl-(5-methyl-[1,3]dioxane-2-carbonyl)-amino]-5-phenyl-thiophene-2-carboxylic acid Compound 22

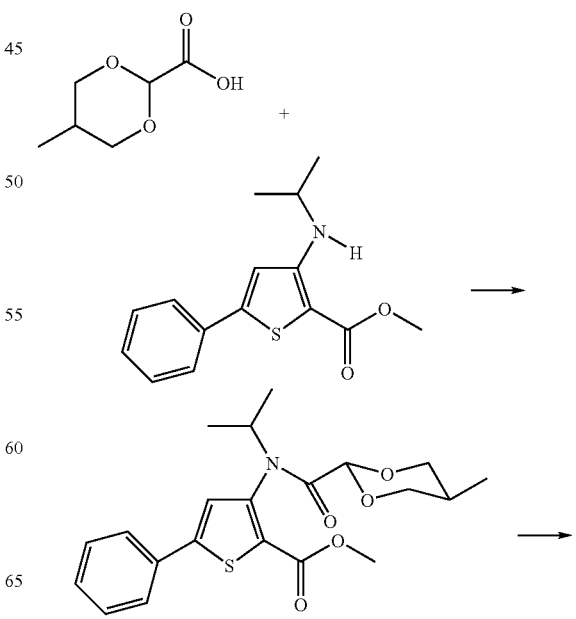

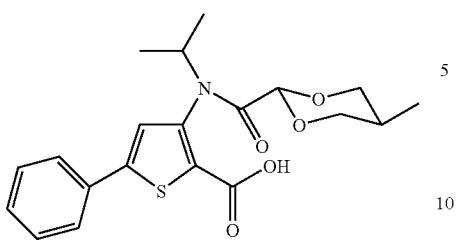

Procedure for the synthesis of 5-methyl-[1,3]dioxane-2-carboxylic acid: Tetrahedron (1989) 45, PP 6987-6998.

Step I

A solution 5-methyl-[1,3]dioxane-2-carboxylic acid (53 mg, 0.47 mmol) in 1,2-dichloroethane at 0° C. was treated with PPh$_3$ (124 mg, 0.47 mmol), NCS (63 mg, 0.47 mmol) and isopropylamino-5-phenyl-thiophene-2-carboxylic acid methyl ester (100 mg, 0.36 mmol). The reaction was heated at reflux for 3 days. The mixture was evaporated to a residue that was purified by silica gel column chromatography using EtOAc:hexanes as eluent to furnished 3-[isopropyl-(5-methyl-[1,3]dioxane-2-carbonyl)-amino]-5-phenyl-thiophene-2-carboxylic acid methyl ester (51.8 mg, 35% yield). $^1$H NMR (CDCl$_3$, 400 MHz): 7.65 (d, 2H), 7.42 (m, 3H), 7.10 (s, 1H), 4.90 (q, 1H), 4.55 (s, 1H), 4.00 (dd, 1H), 3.90 (dd, 1H), 3.85 (s, 3H), 3.10 (t, 1H), 2.95 (t, 1H), 2.10 (m, 1H), 1.25 (d, 3H), 1.05 (d, 3H), 0.58 (d, 3H).

Step II

3-[isopropyl-(5-methyl-[1,3]dioxane-2-carbonyl)-amino]-5-phenyl-thiophene-2-carboxylic acid methyl ester (49 mg, 0.12 mmol) was dissolved in a mixture of THF:MeOH:H$_2$O (3:2:1, 1.1 mL) and treated with LiOH.H$_2$O (14 mg, 0.36 mmol). The solution was heated at 55° C. for 3 h. The solvents were removed and the residue was acidified using HCl to pH 4. The product was extracted with EtOAc and the organic layers were washed with brine, dried and evaporated to provide 3-[Isopropyl-(5-methyl-[1,3]dioxane-2-carbonyl)-amino]-5-phenyl-thiophene-2-carboxylic acid (Compound 22) as a solid (46.7 mg, 98% yield). $^1$H NMR (CD$_3$OD, 400 MHz): 7.65 (d, 2H), 7.45 (m, 3H), 7.30 (s, 1H) 4.80 (q, 1H), 4.80 (s, 1H), 4.00 (dd, 1H), 3.88 (dd, 1H), 3.08 (t, 1H), 2.98 (t, 1H), 2.00 (m, 1H), 1.30 (d, 3H), 1.05 (d, 3H), 0.60 (d, 3H).

EXAMPLE 4

5-(3-fluoro-phenyl)-3-[(4-hydroxy-cyclohexyl)-(4-methyl-cyclohexanecarbonyl)-amino]-thiophene-2-carboxylic acid Compound 51

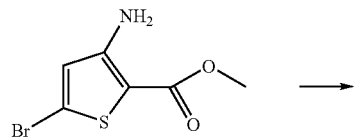

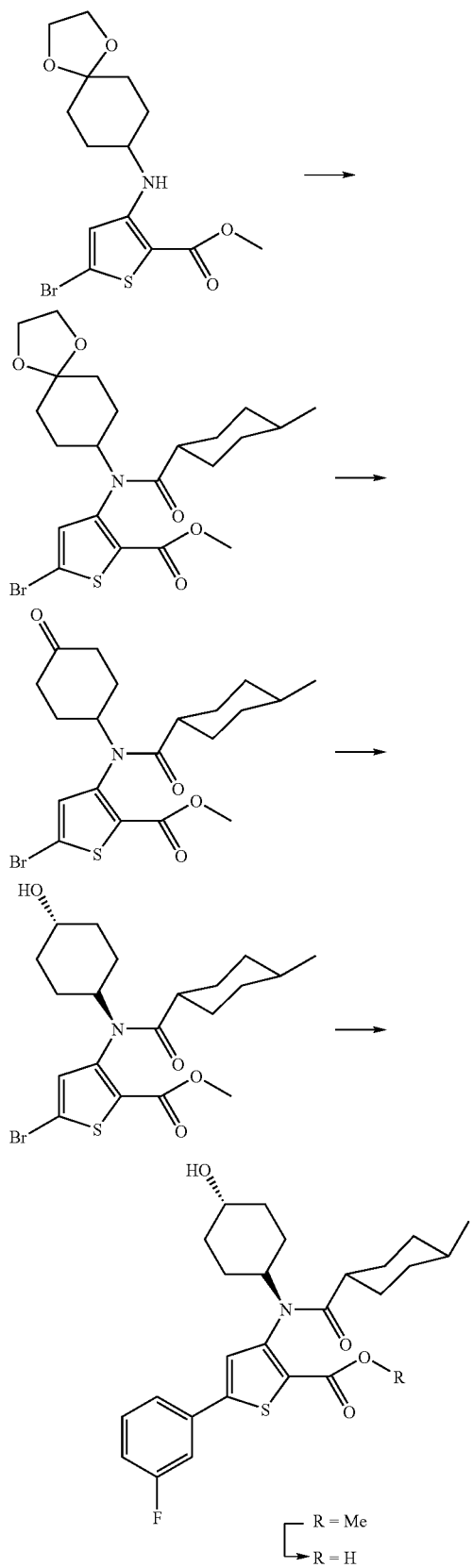

Step I

A suspension of 3-Amino-5-bromo-thiophene-2-carboxylic acid methyl ester (1.03 g, 4.38 mmol) in dry THF (1.1 ml) was treated with 1,4-cyclohexanedione monoethylene ketal (684 mg, 4.38 mmol), followed by dibutyltin dichloride (133 mg, 0.44 mmol). After 5 min, phenyl silane (877 μL, 4.8 mmol) was added and the reaction mixture was stirred at room temperature for 2 days when a clear solution resulted. The solution was then concentrated and the residue purified by silica gel column chromatography using EtOAc:hexanes as eluent to furnished 5-Bromo-3-(1,4-dioxa-spiro[4.5]dec-8-ylamino)-thiophene-2-carboxylic acid methyl ester (1.11 g, 68% yield). $^1$H NMR (CDCl$_3$, 400 MHz): 6.90 (br s, 1H), 6.65 (s, 1H), 3.95 (s, 4H), 3.78 (s, 3H), 3.35 (m, 1H), 2.00 (m, 2H), 1.80 (m, 2H), 1.65 (m, 4H).

Step II

A solution of trans 4-methyl-cyclohexanecarboxylic acid (0.629 g, 4.42 mmol) in 1,2-dichloroethane (30 ml) at 0° C. was treated with triphenylphosphine (1.16 g, 4.42 mmol), N-chlorosuccinimide (0.59 g, 4.42 mmol) and 5-Bromo-3-(1,4-dioxa-spiro[4.5]dec-8-ylamino)-thiophene-2-carboxylic acid methyl ester (1.10 g, 2.92 mmol). The resulting mixture was then stirred for 36 h at 90° C. and then concentrated. The residue was purified by silica gel column chromatography using EtOAc:hexanes as eluent to furnished a mixture of 1:1 (537 mg) of the desired product, 5-Bromo-3-[(1,4-dioxa-spiro[4.5]dec-8-yl)-(4-methyl-cyclohexanecarbonyl)-amino]-thiophene-2-carboxylic acid methyl ester, and the corresponding ketone, 5-Bromo-3-[(4-methyl-cyclohexanecarbonyl)-(4-oxo-cyclohexyl)-amino]-thiophene-2-carboxylic acid methyl ester.

Step III

The mixture of 5-Bromo-3-[(1,4-dioxa-spiro[4.5]dec-8-yl)-(4-methyl-cyclohexanecarbonyl)-amino]-thiophene-2-carboxylic acid methyl ester and 5-Bromo-3-[(4-methyl-cyclohexanecarbonyl)-(4-oxo-cyclohexyl)-amino]-thiophene-2-carboxylic acid methyl ester (352 mg) were dissolved in tetrahydrofuran (4 ml) and treated with 3N HCl solution (4 ml). The reaction was stirred at room temperature for 20 hours and was then diluted with ethyl acetate (10 ml). The organic layer was separated, and the aqueous phase was washed twice with ethyl acetate (2×10 mL). The combined ethyl acetate layers were washed with brine (10 ml), dried on Na$_2$SO$_4$, filtered and concentrated. The residue was purified by silica gel column chromatography using EtOAc:hexanes as eluent to furnished 5-Bromo-3-[(4-methyl-cyclohexanecarbonyl)-(4-oxo-cyclohexyl)-amino]-thiophene-2-carboxylic acid methyl ester as a solid (296 mg). $^1$H NMR (CDCl$_3$, 400 MHz): 6.85 (s, 1H), 5.04 (m, 1H), 3.82 (s, 3H), 2.58-2.30 (m, 4H), 2.18 (m, 1H), 2.06 (m, 1H), 1.90 (m, 1H), 1.70-1.52 (m, 6H), 1.48-1.28 (m, 3H), 0.80 (d, 3H), 0.68 (m, 2H).

Step IV

5-Bromo-3-[(4-methyl-cyclohexanecarbonyl)-(4-oxo-cyclohexyl)-amino]-thiophene-2-carboxylic acid methyl ester (473 mg, 1.04 mmol) was dissolved in methanol (10.4 ml), cooled to 0° C. and treated with sodium borohydride (43 mg, 1.14 mmol). After 30 minutes of stirring at 0° C., the reaction was left stirring at room temperature for 30 min and quenched with a 10% solution of hydrochloric acid (20 ml). The aqueous phase was extracted with ethyl acetate (3×10 mL) and the combined ethyl acetate layer was dried (Na$_2$SO4) and concentrated. The residue was purified by silica gel column chromatography using EtOAc:hexanes as eluent to furnished 5-Bromo-3-[(4-hydroxy-cyclohexyl)-(4-methyl-cyclohexanecarbonyl)-amino]-thiophene-2-carboxylic acid methyl ester (365 mg, 77% yield) as a solid. $^1$H NMR (CDCl$_{13}$, 400 MHz): 6.82 (s, 1H), 4.56 (m, 1H), 3.82 (s, 3H), 3.45 (m, 1H), 2.08-1.72 (m, 4H), 1.75 (m, 1H), 1.68-1.23 (m, 11H), 0.98 (m, 1H), 0.80 (d, 3H), 0.68 (m, 2H).

Step V

A degassed solution of 5-Bromo-3-[(4-hydroxy-cyclohexyl)-(4-methyl-cyclohexanecarbonyl)-amino]-thiophene-2-carboxylic acid methyl ester (70 mg, 0.15 mmol) and 3-fluorophenyl boronic acid (32 mg, 0.23 mmol) in a mixture of DME (2.0 mL) and 2M aqueous Na$_2$CO$_3$ (1.0 mL) was treated with Pd(PPh$_3$)$_4$ (17.6 mg, 0.015 mmol). The reaction was heated at reflux for 18 h. The reaction mixture was diluted with ethyl acetate and water. The organic layer was separated, washed with brine, dried and concentrated to a residue that was purified by preparative chromatography using EtOAc:hexanes as eluent to provide 5-(3-Fluoro-phenyl)-3-[(4-hydroxy-cyclohexyl)-(4-methyl-cyclohexanecarbonyl)-amino]-thiophene-2-carboxylic acid methyl ester as an oil contaminated with triphenylphosphine oxide that could not be removed (61.7 mg). $^1$H NMR (CDCl$_3$, 400 MHz): 7.65 (dd, 3H), 7.53 (t, 2H), 7.43 (m, 5H), 7.32 (m, 1H), 7.1 (m, 1H), 7.02 (s, 1H), 4.56 (m, 1H), 3.82 (s, 3H), 3.40 (m, 1H), 2.14 (br s, 1H), 2.05-1.88 (m, 4H), 1.78 (m, 1H), 1.68-1.54 (m, 5H), 1.51-1.26 (m, 4H), 0.98 (m, 1H), 0.75 (d, 3H), 0.72-0.54 (m, 2H).

Step VI 5-(3-Fluoro-phenyl)-3-[(4-hydroxy-cyclohexyl)-(4-methyl-cyclohexanecarbonyl)-amino]-thiophene-2-carboxylic acid methyl ester (61 mg, 0.13 mmol) was dissolved in a 4:1 mixture of dioxane:H$_2$O (1.3 ml) and treated with LiOH.H$_2$O (20 mg, 0.476 mmol). After 3 hours of stirring at 55° C., the solvents were removed and then partitioned between 5 ml of H$_2$O acidified to pH 4 and 5 ml of EtOAc. The organic layer was separated and the aqueous phase was washed twice with ethyl acetate (2×5 mL). The combined ethyl acetate layer was dried (Na$_2$SO$_4$) and concentrated. The residue was purified by preparative chromatography (10% MeOH/CH$_2$Cl$_2$) to obtain 5-(3-fluoro-phenyl)-3-[(4-hydroxy-cyclohexyl)-(4-methyl-cyclohexanecarbonyl)-amino]-thiophene-2-carboxylic acid (Compound 51) as a white solid (20.1 mg, 34% yield). $^1$H NMR (DMSO-d$_6$, 400 MHz): 7.72 (d, 1H), 7.60 (m, 2H), 7.50 (m, 1H), 7.24 (m, 1H), 4.50 (d, 1H), 4.28 (m, 1H), 3.18 (m, 1H), 1.95 (m, 1H), 1.85-1.10 (m, 14H) 0.88 (m, 1H), 0.75 (d, 3H), 0.68-0.45 (m, 2H).

The following compounds were prepared in a similar manner: Compound 50, Compound 59, Compound 60 and Compound 61.

EXAMPLE 5

3-[(1-methylcarbamoyl-piperidin-4-yl)-(4-methyl-cyclohexanecarbonyl)-amino]-5-phenyl-thiophene-2-carboxylic acid compound 71

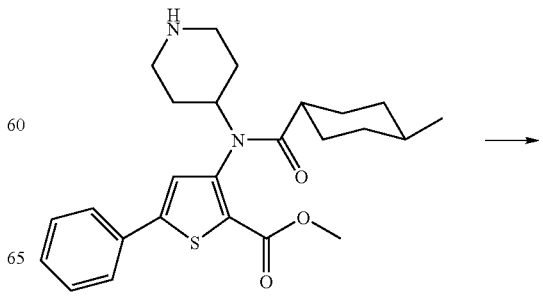

-continued

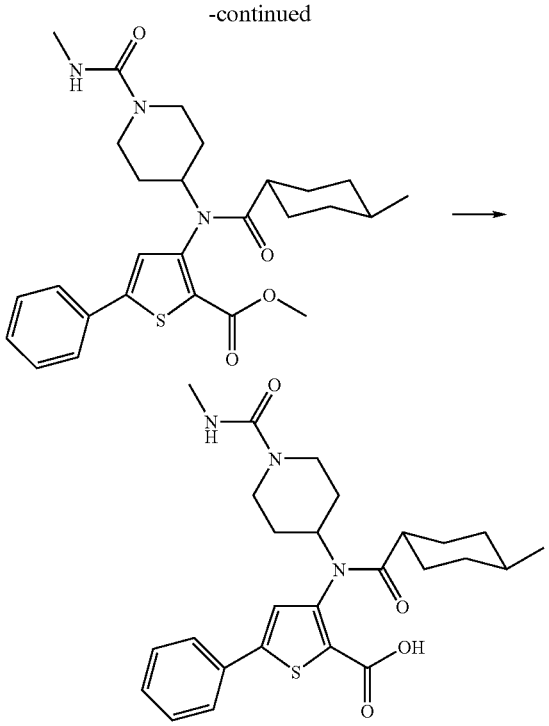

Step I

A solution of 3-[(4-methyl-cyclohexanecarbonyl)-piperidin-4-yl-amino]-5-phenyl-thiophene-2-carboxylic acid methyl ester (145 mg, 0.33 mmol) in CH$_2$Cl$_2$ (3.3 mL) was treated with Et$_3$N (69 mL, 0.49 mmol) and methyl isocyanate (28.2 mg, 0.49 mmol). After stirring at room temperature for 18 h, starting material remained. Methyl isocyanate (28.2 mg, 0.49 mmol) was added to the reaction that was stirred for another 4 h. The solvent was evaporated and the residue was dissolved in EtOAc, washed with HCl (0.1 M) and brine, dried (Na$_2$SO$_4$) and concentrated. The residue was purified by silica gel column chromatography using (5% MeOH/CH$_2$Cl$_2$) to provide 3-[(1-Methylcarbamoyl-piperidin-4-yl)-(4-methyl-cyclohexanecarbonyl)-amino]-5-phenyl-thiophene-2-carboxylic acid methyl ester (142 mg, 87% yield). $^1$H NMR (CDCl$_3$, 400 MHz): 7.65 (m, 2H), 7.45 (m, 3H), 7.00 (s, 1H), 4.78 (m, 1H), 4.35 (q, 1H), 4.05 (dd, 1H), 3.90 (m, 1H), 3.85 (s, 3H), 2.85 (m, 2H), 2.75 (d, 3H), 1.95 (m, 2H), 1.80 (m, 1H), 1.70-1.55 (m, 5H), 1.50-1.25 (m, 3H), 1.10 (m, 1H), 0.78 (d, 3H), 0.75-0.58 (m, 2H).

Step II

3-[(1-Methylcarbamoyl-piperidin-4-yl)-(4-methyl-cyclohexanecarbonyl)-amino]-5-phenyl-thiophene-2-carboxylic acid methyl ester (139 mg, 0.28 mmol) was dissolved in a 4:1 mixture of dioxane:H$_2$O (2.8 ml) and treated with LiOH.H$_2$O (35.3 mg, 0.84 mmol). After 3 hours of stirring at 55° C., the solvents were removed and then partitioned between 5 ml of H$_2$O acidified to pH 4 and 5 ml of EtOAc. The organic layer was separated and the aqueous phase was washed twice with ethyl acetate (2×5 mL). The combined ethyl acetate layer was dried (Na$_2$SO$_4$) and concentrated. The residue was purified by silica gel column chromatography using (10% MeOH/CH$_2$Cl$_2$) to provide 3-[(1-Methylcarbamoyl-piperidin-4-yl)-(4-methyl-cyclohexanecarbonyl)-amino]-5-phenyl-thiophene-2-carboxylic acid (compound 71) as a white solid (101.8 mg, 75% yield). $^1$H NMR (CD$_3$OD, 400 MHz): 7.72 (m, 2H), 7.47-7.37 (m, 3H), 7.32 (s, 1H), 4.65 (m, 1H), 4.00 (m, 1H), 2.82 (q, 2H), 2.65 (d, 3H), 2.10 (m, 1H), 1.90 (m, 2H), 1.80-1.22 (m, 8H), 1.14 (m, 1H), 0.78 (d, 3H), 0.75-0.55 (m, 2H).

EXAMPLE 6

3-[[1,3]Dioxolan-2-ylmethyl-(4-methyl-cyclohexanecarbonyl)-amino]-5-phenyl-thiophene-2-carboxylic acid Compound 8

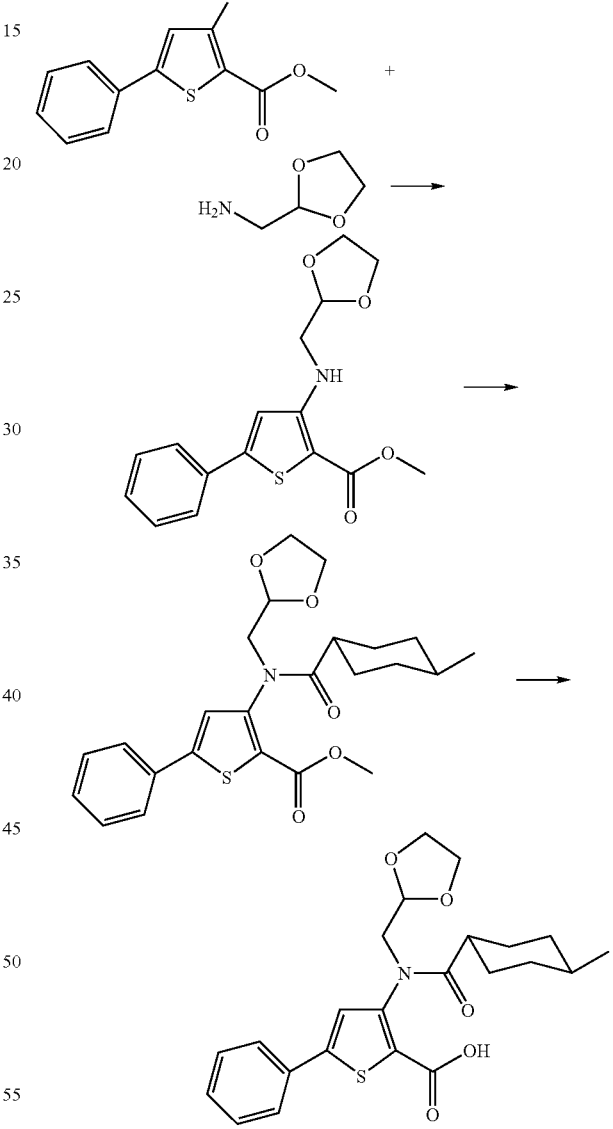

Step I

3-[([1,3]Dioxolan-2-ylmethyl)-amino]-5-phenyl-thiophene-2-carboxylic acid methyl ester was prepared using Pd coupling procedure described in example 32.

Step II

3-[[1,3]Dioxolan-2-ylmethyl-(4-methyl-cyclohexanecarbonyl)-amino]-5-phenyl-thiophene-2-carboxylic acid methyl ester using a procedure similar to the procedure described in example 32.

Step III

3-[[1,3]Dioxolan-2-ylmethyl-(4-methyl-cyclohexanecarbonyl)-amino]-5-phenyl-thiophene-2-carboxylic acid using a similar procedure to the procedure described in example 32.

Compound 7 was prepared using similar method.

EXAMPLE 7

5-(3-fluoro-phenyl)-3-[(2-hydroxy-4-methyl-cyclohexanecarbonyl)-isopropyl-amino]-thiophene-2-carboxylic acid Compound 44

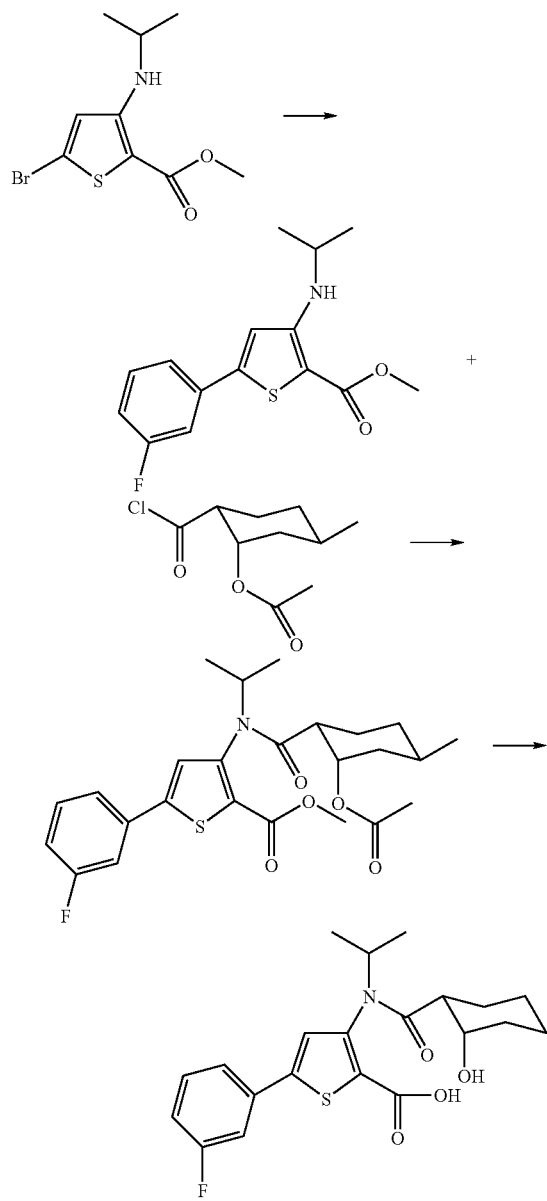

Step I

To a degassed solution of 5-bromo-3-isopropylamino-2-carboxylic acid methyl ester (210 mg, 0.755 mmol) and 3-fluorophenylboronic acid (140 mg, 0.116 mmol) in a mixture of DME (8 mL) and 2M aqueous $Na_2CO_3$ (4 mL), $Pd(PPh_3)_4$ (43 mg) was added and the reaction mixture was stirred at reflux conditions for 3 h under a $N_2$ atmosphere. The reaction mixture was diluted with ethyl acetate and water. The organic layer was separated, dried ($Na_2SO_4$) and concentrated. 5-(3-Fluoro-phenyl)-3-isopropylamino-thiophene-2-carboxylic acid methyl ester (200 mg, 91%) was isolated as thick syrup. $^1H$ NMR ($CDCl_3$, 400 MHz): δ7.50-7.25 (m, 3H), 7.13-7.05 (m, 1H), 6.88 (s, 1H), 6.74 (bs, 1H), 3.80 (s, 3H), 3.75 (m, 1H), 1.35, 1.30 (2s, 6H).

Step II

To a solution of 5-(3-Fluoro-phenyl)-3-isopropylamino-thiophene-2-carboxylic acid methyl ester (200 mg, 0.683 mmol) in 1,2-dichloroethane (5 mL), acetic acid 2-chlorocarbonyl-5-methyl-cyclohexyl ester (148 mg, 0.679 mmol) and triphenylphosphine (197 mg, 0.751 mmol) were added under an atmosphere of $N_2$. The reaction mixture was refluxed for 12 h and then diluted with chloroform and water. The organic layer was separated, dried ($Na_2SO_4$) and concentrated. The residue was purified by preparative TLC plate using 15% ethyl acetate in hexane to obtain 3[(2-Acetoxy-4-methyl-cyclohexanecarbonyl)-isopropyl-amino]-5-(3-fluoro-phenyl)-thiophene-2-carboxylic acid methyl ester as a white solid (40 mg, 12%). $^1H$ NMR ($CDCl_3$, 400 MHz): δ7.45-7.25 (m, 4H), 7.13-6.95 (m, 1H), 5.13 (m, 1H) 4.87-4.75 (m, 1H), 3.80 (s, 3H), 2.37-0.62 (m, 20H).

Step III

3[(2-Acetoxy-4-methyl-cyclohexanecarbonyl)-isopropyl-amino]-5-(3-fluoro-phenyl)-thi-ophene-2-carboxylic acid methyl ester (30 mg, 0.063 mmol) was taken in a mixture of THF:MeOH:$H_2O$ (3:2:1, 2 mL) and then added 1N aqueous solution of LiOH.$H_2O$ (0.38 mL, 0.380 mmol). The reaction mixture was stirred at room temperature for 12 h. Solvents were removed and the residue was partitioned between water and ethyl acetate. The aqueous layer was acidified using 10% $KHSO_4$ solution. The organic layer was separated, dried ($Na_2SO_4$) and concentrated. The residue was purified by silica gel column chromatography using chloroform and methanol (8:2) to obtain 5-(3-fluoro-phenyl)-3-[(2-hydroxy-4-methyl-cyclohexanecarbonyl)-isopropyl-amino]-thiophene-2-carboxylic acid (Compound 44) (15 mg, 58%) as a white solid with two rotamers. $^1H$ NMR ($CDCl_3$, 400 MHz): δ7.50-7.25 (m, 3H), 7.06 (m, 2H), 6.25 (bs, 1H), 5.25 (s, 1H, minor), 4.87 (s, 1H, major), 4.13 (s, 1H, major), 3.87 (s, 1H, minor), 2.38-0.45 (m, 17H). ESI⁻ (M–H): 418.

Compound 62 was prepared in a similar manner.

EXAMPLE 8

3-[Isopropyl-(4-methylene-cyclohexanecarbonyl)-amino]-5-phenyl-thiophene-2-carboxylic acid Compound 28

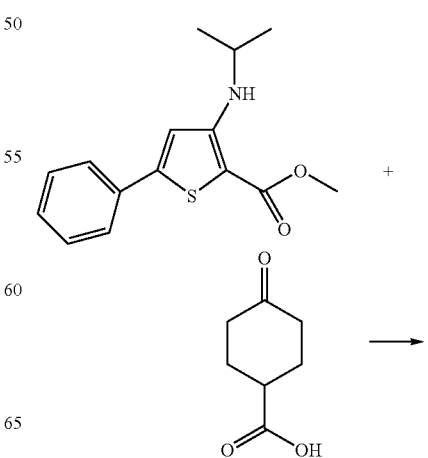

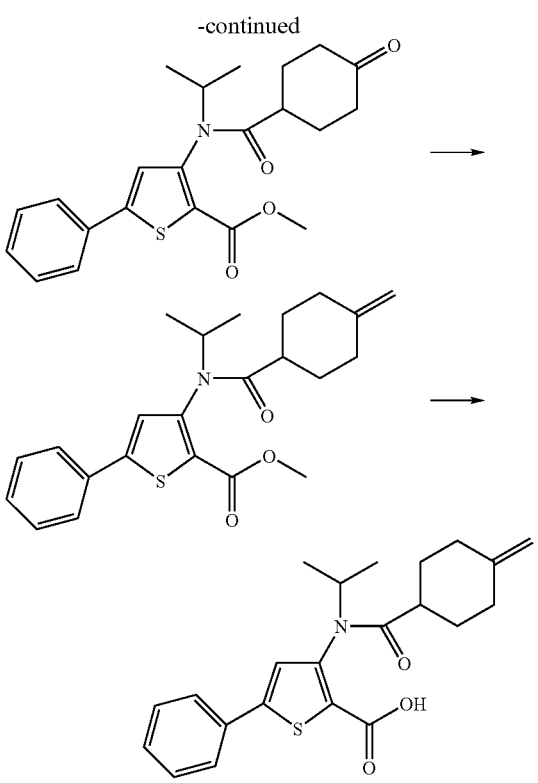

Step I

To a solution of 3-Isopropylamino-5-phenyl-thiophene-2-carboxylic acid methyl ester (1.5 g, 5.45 mmol) in 1,2-dichloroethane, N-chlorosuccinamide (0.940 g, 7.091 mmol), triphenylphosphine (1.9 g, 7.091 mmol) and 4-oxo-cyclohexanecarboxylic acid (800 mg, 5.455 mmol) were added. The reaction mixture was stirred at reflux for overnight under an atmosphere of $N_2$. The reaction mixture was diluted with $CH_2Cl_2$ and extracted with saturated solution oh $NaHCO_3$. The organic layer was separated, dried ($Na_2SO_4$) and concentrated. The residue was purified using silica gel column chromatography using ethyl acetate: hexane (1:4) as eluent to obtain 3-[Isopropyl-(4-oxo-cyclohexanecarbonyl)-amino]-5-phenyl-thiophene-2-carboxylic acid methyl ester.

(1.2 g, 55%) as syrup. $^1$H NMR (CDCl$_3$, 400 MHz): δ7.75-7.50 (m, 2H), 7.70-7.38 (m, 3H), 7.12 (s, 1H), 4.95 (m, 1H), 3.87 (s, 3H), 2.75-0.83 (m, 15H).

Step II

Butyllithium (2.5 M, 0.9 mL, 2.280 mmol) was added to a cold solution (−78° C.) of methyltriphenylphosphonium bromide (939 g, 2.630 mmol) in THF (10 mL). The reaction mixture was stirred at room temperature for 1 h and then 3-[Isopropyl-(4-oxo-cyclohexanecarbonyl)-amino]-5-phenyl-thiophene-2-carboxylic acid methyl ester. (700 mg, 1.754) in THF (5 mL) was added at −78° C. The reaction mixture was allowed to stir at room temperature for 12 h. The reaction was quenched by adding saturated solution of NH$_4$Cl and diluted with ethyl acetate. The organic layer was separated, dried (Na$_2$SO$_4$) and concentrated. The residue was purified by silica gel column chromatography using ethyl acetate: hexane (1:4) to obtain 3-[Isopropyl-(4-methylene-cyclohexanecarbonyl)-amino]-5-phenyl-thiophene-2-carboxylic acid methyl ester (300 mg, 43%) as a solid. $^1$H NMR (CDCl$_3$, 400 MHz): δ7.63 (d, 2H), 7.50-7.38 (m, 3H), 7.12 (s, 1H), 4.99 (m, 1H), 4.55 (d, 2H), 3.85 (s, 3H), 2.25 (m, 3H), 1.83-1.63 (m, 5H), 1.50 (m, 1H), 1.25 (d, 3H), 0.99 (d, 3H).

Step III

3-[Isopropyl-(4-methylene-cyclohexanecarbonyl)-amino]-5-phenyl-thiophene-2-carboxylic acid methyl ester (50 mg, 0.126 mmol) was taken in a mixture of THF:MeOH:H$_2$O (3:2:1, 3 mL) and then 1N aqueous solution of LiOH.H$_2$O (0.8 mL, 0.800 mmol) was added. The reaction mixture was stirred at room temperature for 12 h. Solvents were removed and the residue was partitioned between water and ethyl acetate. The aqueous layer was acidified using 10% KHSO$_4$ solution. The organic layer was separated, dried (Na$_2$SO$_4$) and concentrated. The residue was purified by silica gel column chromatography using chloroform and methanol (8:2) to obtain 3-[Isopropyl-(4-methylene-cyclohexanecarbonyl)-amino]-5-phenyl-thiophene-2-carboxylic acid (compound 28) (25 mg, 52%) as a white solid. $^1$H NMR (CDCl$_3$, 400 MHz): δ7.61 (d, J=7 Hz, 2H), 7.40-7.38 (m, 3H), 7.04 (s, 1H), 4.92 (m, 1H), 4.50 (d, J=7.6 Hz, 2H), 2.21-1.43 (m, 9H), 1.15 (bd, 3H), 0.93 (bd, 3H).

EXAMPLE 9

5-(4-Fluoro-phenyl)-3-[isopropyl-(4-methyl-cyclohex-3-enecarbonyl)-amino]-thiophene-2-carboxylic acid Compound 53

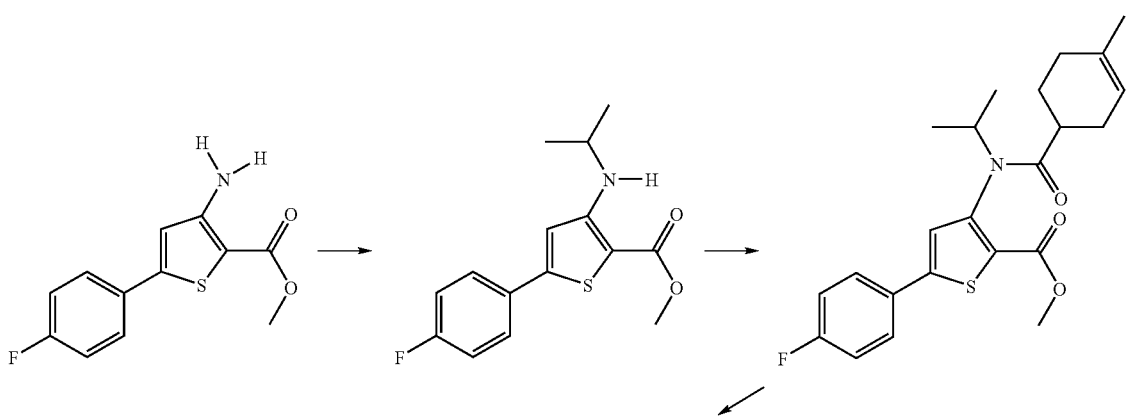

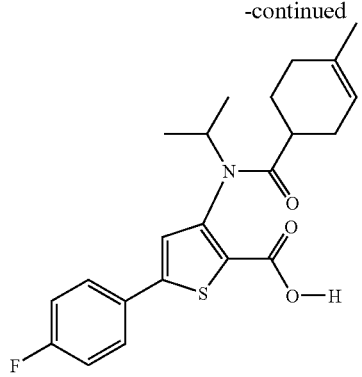

Step I

To a stirred solution of 3-Amino-5-(4-fluoro-phenyl)-thiophene-2-carboxylic acid methyl ester (500 mg, 2.0 mmol) in 1,2-dichloroethane (10 mL) was added sequentially 2-methoxypropene (0.76 mL, 8.0 mmol), AcOH (0.12 mL, 4.0 mmol) and NaBH(OAc)$_3$ (0.848 mg, 8.0 mmol) and stirred for 16 h. It was then diluted with EtOAc and H$_2$O. The aqueous solution was adjusted to pH=7 by adding NaHCO$_3$. The aqueous phase was extracted with EtOAc, the combined extract was washed with brine and dried on MgSO4 and filtered. Purification on bond elute with hexane to 5% EtOAc-hexane furnished 5-(4-Fluoro-phenyl)-3-isopropylamino-thiophene-2-carboxylic acid methyl ester (0.530 mg, 91% yield). $^1$H NMR (CDCl$_3$, 400 MHz): δ 7.62 (d, 2H), 7.09 (m, 2H), 6.81 (s, 1H), 3.84 (s, 3H), 3.71 (m, 1H), 1.35 (d, 6H).

Step II

4-Methyl-cyclohex-3-enecarbonyl chloride was prepared according to the procedure reported in Journal of Organic Chemistry (1986) 51(23), PP4485-8. This 4-Methyl-cyclohex-3-enecarbonyl chloride (0.121 g, 0.77 mmol) was dissolved along with 5-(4-Fluoro-phenyl)-3-isopropylamino-thiophene-2-carboxylic acid methyl ester (0.150 g, 0.51 mmol) in anhydrous 1,2-dichloroethane (2 mL). The reaction mixture was stirred for 16 h at reflux. Then, the solvents were removed and the residue was purified by flash chromatography (8:2 Hexane/EtOAc) to obtain 140 mg (66%) of 5-(4-Fluoro-phenyl)-3-[isopropyl-(4-methyl-cyclohex-3-enecarbonyl)-amino]-thiophene-2-carboxylic acid methyl ester. $^1$H NMR(CDCl$_3$, 400 MHz): δ 7.60 (m, 2H), 7.15 (m, 2H), 7.02 (d, 1H), 5.42-5.20 (m, 1H), 4.99 (m, 1H), 3.83 (d, 3H), 2.41-1.50 (m, 10H), 1.20 (m,3H), 0.98 (d, 3H).

Step III 5-(4-Fluoro-phenyl)-3-[isopropyl-(4-methyl-cyclohex-3-enecarbo-nyl)-amino]-thiophene-2-carboxylic acid methyl ester (0.140 g, 0.34 mmol) was taken in a mixture of THF: MeOH:H$_2$O (3:2:1, 10 mL) and then added 1N aqueous solution of LiOH.H$_2$O (2.1 mL, 2.04 mmol). The reaction mixture was stirred at 50° C. for 1 h. Solvents were removed and the residue was partitioned between water and ethyl acetate. The aqueous layer was acidified using 10% KHSO$_4$ solution. The organic layer was separated, dried (Na$_2$SO$_4$) and concentrated. The residue was purified by preparative TLC using dicholomethane:methanol(9:1) to obtain 5-(4-Fluoro-phenyl)-3-[isopropyl-(4-methyl-cyclohex-3-enecarbonyl)-amino]-thiophene-2-carboxylic acid (compound 53) (31 mg, 23%). $^1$H NMR (CDCl$_3$, 400 MHz): δ 7.81 (m, 2H), 7.43 (d, 1H), 7.28 (m, 2H), 5.38-5.16 (m, 1H), 4.72 (m, 1H), 2.20 (d, 2H), 1.95-1.20 (m, 8H), 1.12 (m, 3H), 0.90 (d, 3H).

The following compound was synthesised a similar manner: Compound 17.

EXAMPLE 10

Trans-3-[(1-Fluoro-4-methyl-cyclohexanecarbonyl)-isopropyl-amino]-5-phenyl-thiophene-2-carboxylic acid Compound 9

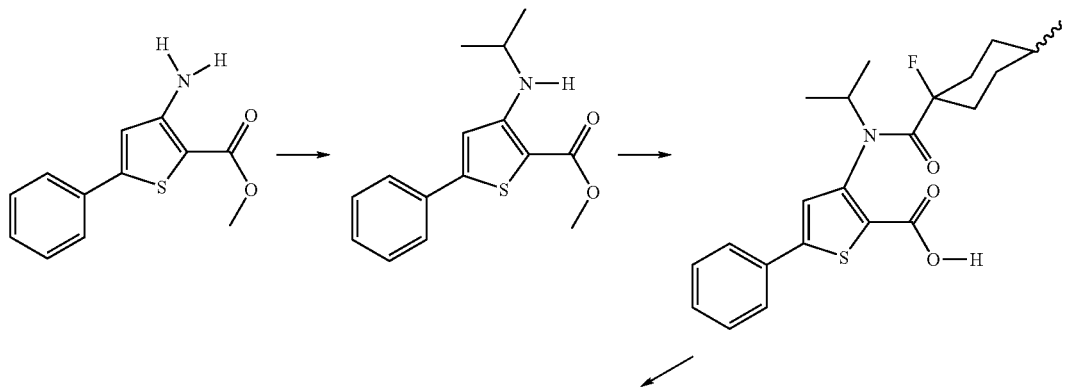

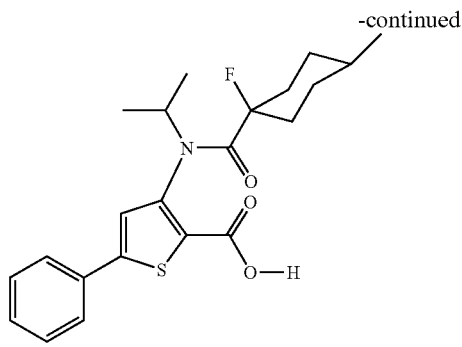

Step I

To a stirred solution of 3-Amino-5-phenyl-thiophene-2-carboxylic acid methyl ester (1.82 g, 7.8 mmol) in 1,2-dichloroethane (40 mL) was added sequentially 2-methoxypropene (3.0 mL, 31.2 mmol), AcOH (1.8 mL, 31.2 mmol) and NaBH(OAc)$_3$ (3.31 g, 15.6 mmol) and stirred for 2 hrs. It was then diluted with EtOAc and H$_2$O. The aqueous solution was adjusted to pH=7 by adding NaHCO$_3$. The aqueous phase was extracted with EtOAc, the combined extract was washed with brine and dried on MgSO4 and filtered. Purification on bond elute with hexane to 5% EtOAc-hexane furnished 3-Isopropylamino-5-phenyl-thiophene-2-carboxylic acid methyl ester (2.07 g, 96% yield). $^1$H NMR (CDCl$_3$, 400 MHz): δ 7.62 (d, 2H) 7.40 (m, 3H), 6.91 (s, 1H), 3.84 (s, 3H), 3.71 (m, 1H), 1.35 (d, 6H).

Step II

Cis/trans-1-Fluoro-4-methyl-cyclohexanecarboxylic acid was prepared according to the procedure reported in *Synthesis*, April (1998) PP310-313. Cis/trans-1-Fluoro-4-methyl-cyclohexanecarboxylic acid (0.220 g, 1.37 mmol) was dissolved along with PPh$_3$ (0.360 g, 1.37 mmol) in anhydrous 1,2-dichloroethane (20 mL) at 0° C. Then NCS (0.181 g, 1.37 mmol) and 3-Isopropylamino-5-phenyl-thiophene-2-carboxylic acid methyl ester (0.290 g, 1.05 mmol) were add and the reaction mixture was stirred for 16 h at reflux. After cooling to room temerature, the crude was wash with NaHCO$_3$ sat. The organic layer was dried (MgSO$_4$), concentrated and the residue was purified by preparative TLc plate chromatography (20% EtOAc/Hexane) to obtain 171 mg (39%) of cis/trans 3-[(1-Fluoro-4-methyl-cyclohexanecarbonyl)-isopropyl-amino]-5-phenyl-thiophene-2-carboxylic acid methyl ester. $^1$H NMR(CDCl$_3$, 400 MHz): major δ 6.61 (d, 2H), 6.40 (m, 3H), 7.03 (s, 1H), 4.93 (m, 1H), 3.81 (s, 3H), 2.18-1.30 (m, 7H), 1.20 (d, 3H), 1.10 (m, 2H), 0.96 (d, 3H), 0.81 (d, 3H).

Step III

3-[(1-Fluoro-4-methyl-cyclohexanecarbonyl)-isopropyl-amino]-5-phenyl-thiophene-2-carboxylic acid methyl ester (0.049 g, 0.12 mmol) was taken in a mixture of THF:MeOH:H$_2$O (3:2:1, 10 mL) and then added 1N aqueous solution of LiOH.H$_2$O (0.35 mL, 0.35 mmol). The reaction mixture was stirred at 50° C. for 3 h. Solvents were removed and the residue was partitioned between water and ethyl acetate. The aqueous layer was acidified using 10% KHSO$_4$ solution. The organic layer was separated, dried (Na$_2$SO$_4$) and concentrated. The residue was purified by preparative TLC using dicholomethane:methanol (9:1) to obtain Trans-3-[(1-Fluoro-4-methyl-cyclohexanecarbonyl)-isopropyl-amino]-5-phenyl-thiophene-2-carboxylic acid (Compound 9) (9 mg, 19%). $^1$H NMR (MeOD, 400 MHz): δ6.75 (d, 2H), 6.41 (m, 3H), 7.29 (s, 1H), 4.85 (m, 1H), 2.1-1.85 (m, 4H), 1.59-1.24 (m, 3H), 1.22 (d, 3H), 1.10 (m, 2H), 0.99 (d, 3H), 0.81 (d, 3H).

The following compound was synthesised a similar manner Compound 10.

EXAMPLE 11

3-[N-(2,4-Dichloro-benzoyl)-N',N'-dimethyl-hydrazino]-5-phenyl-thiophene-2-carboxylic acid Compound 72

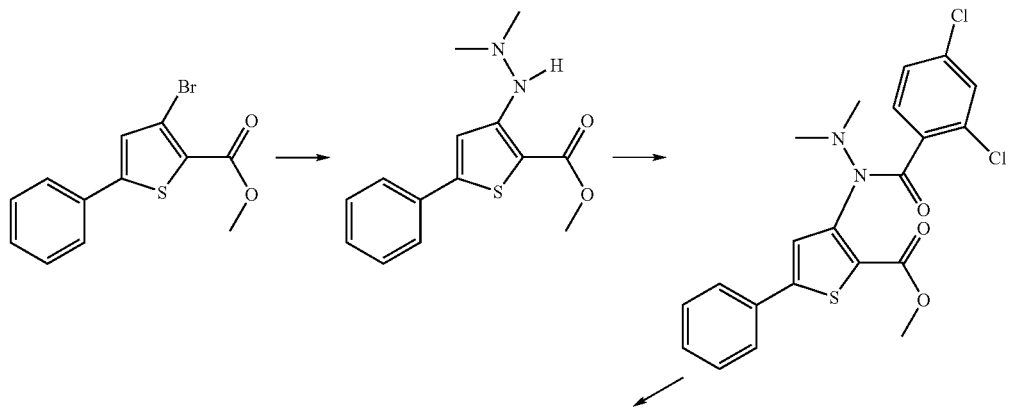

-continued

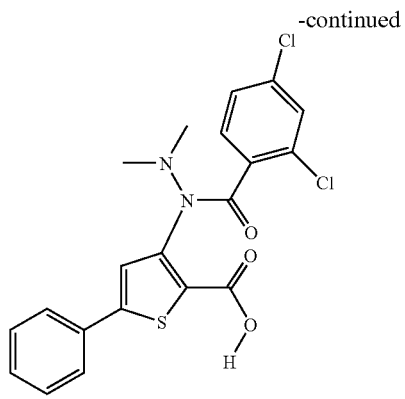

Step I

To a solution of 3-Bromo-5-phenyl-thiophene-2-carboxylic acid methyl ester (0.500 g, 1.68 mmol) in toluene (10 ml) was added N,N-Dimethyl-hydrazine (0.121 g, 2.02 mmol), cesium carbonate (0.767 g, 2.36 mmol), BINAP (0.106 g, 0.17 mmol) and paladium(II) acetate (0.019 g, 0.08 mmol). The reaction mixture was stirred for 16 h at 110° C. The mixture was partitioned between toluene (20 mL) and water (20 mL) and the organic layer was separated. The aqueous phase was washed twice with toluene (2×10 mL) and the combined toluenelayer was dried (MgSO4), concentrated and the residue was purified by preparative tlc (10% EtOAc/Hexane) to obtain 0.350 g (75%) of 3-(N',N'-Dimethyl-hydrazino)-5-phenyl-thiophene-2-carboxylic acid methyl ester. NMR $^1$H (CDCl$_3$, 400 MHz): δ 7.71(d, 2H), 7.40 (m, 3H), 7.13 (s, 1H), 3.87 (s, 3H), 2.65 (s, 6H).

Step II

To a solution of 3-(N',N'-Dimethyl-hydrazino)-5-phenyl-thiophene-2-carboxylic acid methyl ester (0.200 g, 0.72 mmol) in 1,2-dichloroethane (10 ml) in an atmosphere of N$_2$ was added 2,4-dichloro-benzoyl chloride (0.228 g, 1.08 mmol). The reaction mixture was stirred for 1.5 h at reflux. Then, the solvents were removed and the residue was purified by preparative tlc (8:2 Hexane/EtOAc) to obtain 0.017 g (5%) of 3-[N-(2,4-Dichloro-benzoyl)-N',N'-dimethyl-hydrazino]-5-phenyl-thiophene-2-carboxylic acid methyl ester. NMR $^1$H (CDCl$_3$, 400 MHz): δ 7.62(m, 2H), 7.40 (m, 3H), 7.23 (d, 1H), 3.87 (s, 3H), 2.52 (s, 6H).

Step III

3-[N-(2,4-Dichloro-benzoyl)-N',N'-dimethyl-hydrazino]-5-phenyl-thiophene-2-carboxylic acid methyl ester (0.050 g, 0.11 mmol) was taken in a mixture of THF:MeOH:H$_2$O (3:2:1, 10 mL) and then added 1N aqueous solution of LiOH.H$_2$O (0.67 mL, 0.67 mmol). The reaction mixture was stirred at 60° C. for 2 h. Solvents were removed and the residue was partitioned between water and ethyl acetate. The aqueous layer was acidified using 10% KHSO$_4$ solution. The organic layer was separated, dried (Na$_2$SO$_4$) and concentrated. The residue was purified by preparative TLC using dicholomethane:methanol (9:1) to obtain 3-[N-(2,4-Dichloro-benzoyl)-N',N'-dimethyl-hydrazino]-5-phenyl-thiophene-2-carboxy-lic acid (Compound 72) (0.008 g, 17%). $^1$H NMR (DMSO, 400 MHz): δ 7.81 (d, 2H), 7.69 (d, 2H), 7.54-7.40 (m, 5H), 2.42 (s, 6H).

The following compound was synthesised in a similar manner Compound 64.

EXAMPLE 12

5-(3-Fluoro-phenyl)-3-[isopropyl-(4-methyl-cyclohexanecarbonyl)-amino]-thiophene-2-carboxylic acid Compound 5

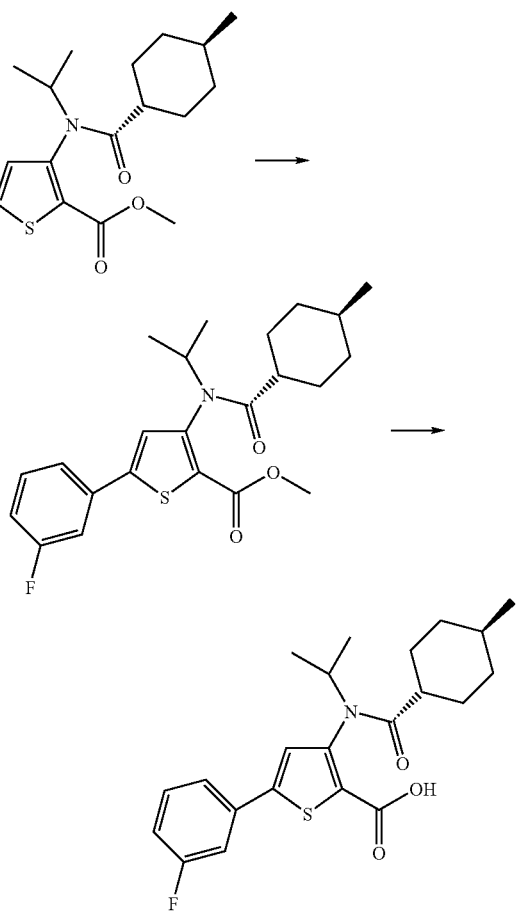

Step I

To the mixture of 3-fluorobenzeneboronic acid (25.0 mg, 0.180 mmol) and 5-Bromo-3-[isopropyl-(4-methyl-cyclohexanecarbonyl)-amino]-thiophene-2-carboxylic acid methyl ester (24 mg, 0.060 mmol) in 5:1 mixture of toluene/

MeOH (1.0 mL) was added a solution of Pd(PPh$_3$)$_4$ (7.0 mg, 0.006 mmol, 10 mol %) in toluene (0.5 mL) followed by aqueous 2M Na$_2$CO$_3$ solution (0.06 mL, 0.120 mmol). The resultant reaction mixture was heated at 70° C. for 18 h, cooled to room temperature, filtered off through MgSO$_4$ and washed with EtOAc. Evaporation of the solvent and purification of the residue over preparative TLC using ethyl acetate/hexane (20:80) as an eluent furnished (25.0 mg, 99% yield) of 5-(3-Fluoro-phenyl)-3-[isopropyl-(4-methyl-cyclohexanecarbonyl)-amino]-thiophene-2-carboxylic acid methyl ester.

$^1$H NMR (CDCl$_3$, 400 MHz) 7.45-7.39 ppm (m, 2H); 7.34-7.31 ppm (m, 1H); 7.13-7.07 ppm (m, 1H); 7.06 ppm (s, 1H); 5.00-4.93 ppm (m, 1H); 3.85 ppm (s, 3H); 2.04-1.95 ppm (m, 1H); 1.74-1.57 ppm (m, 5H); 1.48-1.38 ppm (m, 1H); 1.36-1.27 ppm (m, 1H); 1.17 ppm (d, 3H); 0.94 ppm (d, 3H); 0.77 ppm (d, 3H); 0.73-0.55 ppm (m, 2H).

Step II 5-(3-Fluoro-phenyl)-3-[isopropyl-(4-methyl-cyclohexanecarbonyl)-amino]-thiophene-2-carboxylic acid methyl ester (25 mg, 0.060 mmol) was dissolved in a 4:1 mixture of dioxane:H$_2$O (0.8 mL) and then LiOH 1N (0.3 ml, 0.300 mmol) was added. After 3 hours of stirring at room temperature, solvents were removed and then partitioned between 10 ml of H$_2$O acidified to pH 4 and 10 ml of EtOAc. The organic layer was separated and the aqueous phase was washed twice with ethyl acetate (2×10 mL). The combined ethyl acetate layer was dried (Na$_2$SO4), concentrated and the residue was purified by preparative chromatography (10% MeOH/CH$_2$Cl$_2$) to obtain 20 mg (83%) of 5-(3-Fluoro-phenyl)-3-[isopropyl-(4-methyl-cyclohexanecarbonyl)-amino]-thiophene-2-carboxylic acid (Compound 5).

$^1$H NMR (CD$_3$OD, 400 MHz) 7.57-7.44 ppm (m, 3H); 7.39 ppm (s, 1H); 7.17-7.11 ppm (m, 1H); 4.87-4.81 ppm (m, 1H); 2.15-2.09 ppm (m, 1H); 1.82-1.78 ppm (m, 1H); 1.71-1.52 ppm (m, 4H); 1.42-1.25 ppm (m, 2H); 1.22 ppm (d, 3H); 1.00 ppm (d, 3H); 0.78 ppm (d, 3H); 0.73-0.56 ppm (m, 2H).

EXAMPLE 13

3-[(2-Acetylamino-4-methyl-cyclohexanecarbonyl)-isopropyl-amino]-5-phenyl-thiophene-2-carboxylic acid Compound 12

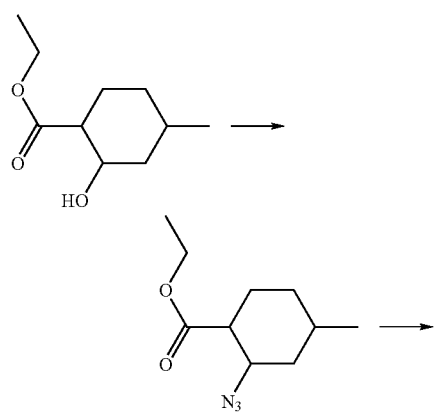

-continued

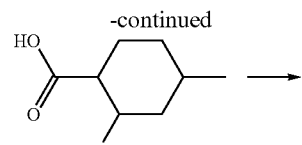

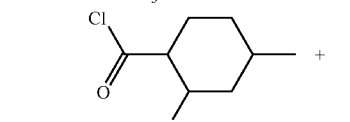

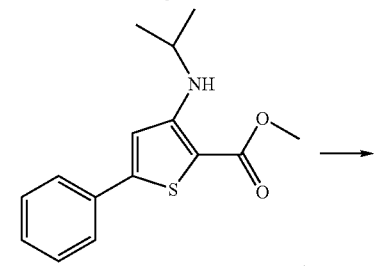

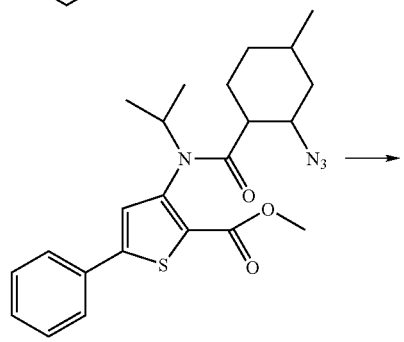

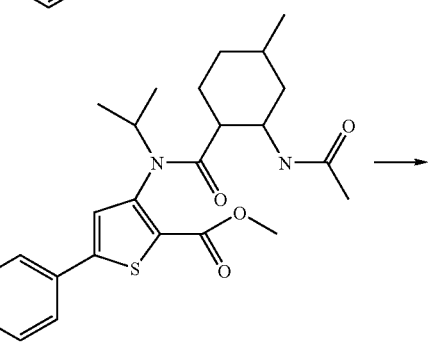

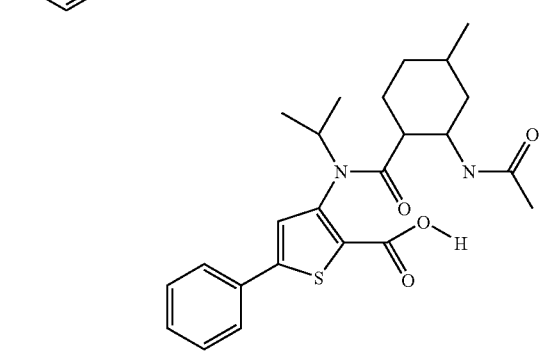

Step I

2-Hydroxy-4-methyl-cyclohexanecarboxylic acid ethyl ester (495 mg, 2.66 mmol) was dissolved in THF (13 ml) and then diphenylphosphoryl azide (680 ul, 3.19 mmol) and triphenylphosphine (837 mg, 3.19 mmol) were added. The resulting solution was cooled in an ice bath and diethyl azodicarboxylate (502 ul, 3.19 mmol) was added. After stirring at room temperature for 20 hours, the solvents were removed and the residue was purified by flash chromatography (0% to 3% EtOAc/Hexane) to obtain 365 mg (65%) of 2-Azido-4-methyl-cyclohexanecarboxylic acid ethyl ester.

Step II 15 2-Azido-4-methyl-cyclohexanecarboxylic acid ethyl ester (425 mg, 2.01 mmol) was dissolved in a 4:1 mixture of dioxane:$H_2O$ (20 ml) and then LiOH 1N (10 ml, 10.05 mmol) was added. After 35 minutes of stirring at room temperature, solvents were removed and then partitioned between 15 ml of $H_2O$ acidified to pH 4 and 15 ml of EtOAc. The organic layer was separated and the aqueous phase was washed twice with ethyl acetate (2×10 mL). The combined ethyl acetate layer was dried ($Na_2SO4$) and concentrated to obtain 166 mg of a 2:1 mixture of 2-Azido-4-methyl-cyclohexanecarboxylic acid and 4-Methyl-cyclohex-1-enecarboxylic acid.

Step III

To a solution of the 2:1 mixture of 2-Azido-4-methyl-cyclohexanecarboxylic acid and 4-Methyl-cyclohex-1-enecarboxylic acid (166 mg, 0.91 mmol) in dichloromethane (9 ml) was added a 2.0 M solution of oxalyl chloride (905 ul, 1.82 mmol) followed by 1 drop of dimethylformamide. The reaction mixture was stirred for 3 hours at room temperature. The solvents were then removed to obtain 182 mg (99%) of a 2:1 mixture of 2-Azido-4-methyl-cyclohexanecarboxylic acid chloride and 4-Methyl-cyclohex-1-enecarboxylic acid chloride.

Step IV

To a solution of 3-Isopropylamino-5-phenyl-thiophene-2-carboxylic acid methyl ester (227 mg, 0.824 mmol) in 1,2-dichloroethane (2.5 ml) was added the 2:1 mixture of 2-Azido-4-methyl-cyclohexanecarboxylic acid chloride and 4-Methyl-cyclohex-1-enecarboxylic acid chloride (182 mg, 0.906 mmol) dissolved in 1,2-dichloroethane (0.5 ml). The resulting solution was stirred for 18 h at 90° C. and then cooled to room temperature. It was then diluted with ethyl acetate (10 ml) and a solution of saturated $NaHCO_3$ (10 ml). The aqueous phase was separated and washed with ethyl acetate (2×10 ml) and the combined organic layers were dried ($Na_2SO_4$), filtered and concentrated. The residue was purified by flash chromatography (0% to 20% EtOAc/Hexane) to obtain 178 mg (49%) of 3-[(2-Azido-4-methyl-cyclohexanecarbonyl)-isopropyl-amino]-5-phenyl-thiophene-2-carboxylic acid methyl ester.

Step V

To 3-[(2-Azido-4-methyl-cyclohexanecarbonyl)-isopropyl-amino]-5-phenyl-thiophene-2-carboxylic acid methyl ester (17.5 mg, 0.04 mmol) in methanol (400 ul) was added concentrated hydrochloric acid (15 ul) followed by 10% palladium on charcoal (4 mg, 0.004 mmol). The reaction vessel was introduced with 20 psi of hydrogen and then stirred at room temperature for 17 hours. The residue was then filtered off through celite, washed with methanol and evaporated to give the crude product. To the crude product in dichloromethane (400 ul) was added pyridine (19 ul, 0.24 mmol), followed by acetic anhydride (15 ul, 0.16 mmol) and a catalytic amount of DMAP. The resulting solution was stirred for 24 hours at room temperature and then quenched with a saturated solution of $NaHCO_3$ (5 ml). The aqueous phase was separated and washed with dichloromethane (2×5 ml). The combined organic layers were dried ($Na_2SO_4$), filtered and concentrated. The residue was then purified by preparative chromatography (60% EtOAc/Hexane) to obtain 8.5 mg (47% for two steps) of 3-[(2-Acetylamino-4-methyl-cyclohexanecarbonyl)-isopropyl-amino]-5-phenyl-thiophene-2-carboxylic acid methyl ester.

Step VI

3-[(2-Acetylamino-4-methyl-cyclohexanecarbonyl)-isopropyl-amino]-5-phenyl-thiophene-2-carboxylic acid methyl ester (8.5 mg, 0.019 mmol) was dissolved in a 4:1 mixture of dioxane:$H_2O$ (250 ul) and then LiOH 1N (22 ul, 0.023 mmol) was added. After 22 hours of stirring at room temperature, solvents were removed and then partitioned between 5 ml of $H_2O$ acidified to pH 4 and 5 ml of EtOAc. The organic layer was separated and the aqueous phase was washed twice with ethyl acetate (2×5 mL). The combined ethyl acetate layer was dried ($Na_2SO4$) and concentrated to give 7.5 mg (91%) of 3-[(2-Acetylamino-4-methyl-cyclohexanecarbonyl)-isopropyl-amino]-5-phenyl-thiophene-2-carboxylic acid (Compound 12).

1H NMR ($CDCl_3$, 400 MHz) 7.78-7.73 ppm (m, 2H); 7.60 ppm (s, 1H); 7.49-7.39 ppm (m, 3H); 4.84-4.77 ppm (m, 1H); 4.36-4.33 ppm (m, 5 1H); 2.50-2.45 ppm (m, 1H); 1.98 ppm (s 3H); 1.95-1.85 ppm (m, 2H); 1.73-1.49 ppm (m, 5H); 1.17 ppm (d, 3H); 0.94 ppm (d, 3H); 0.83-0.77 ppm (m et d, 4H).

EXAMPLE 13

3-[(4-Methyl-cyclohexanecarbonyl)-(4-oxo-cyclohexyl)-amino]-5-phenyl-thiophene-2-carboxylic acid
Compound 13

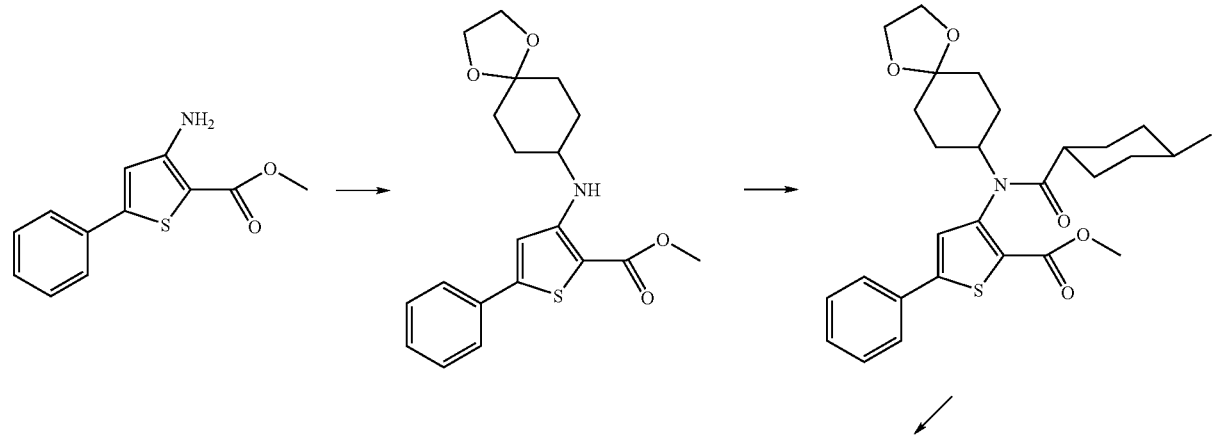

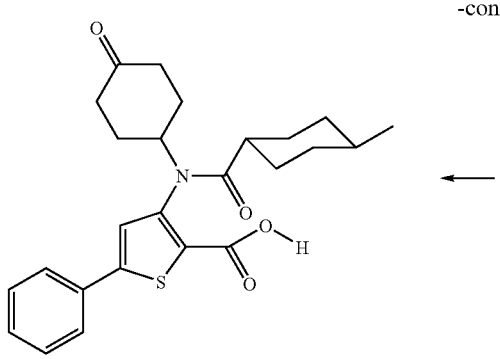 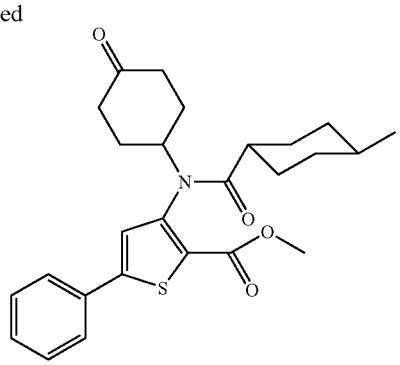

Step I

To a suspension of 3-amino-5-phenyl-thiophene-2-carboxylic acid methyl ester (987 mg, 4.23 mmol) in dry THF (1.0 ml), at room temperature, was added 1,4-cyclohexanedione monoethylene ketal (661 mg, 4.23 mmol), followed by dibutyltin dichloride (129 mg, 0.42 mmol). After 5 min, phenyl silane (575 μL, 4.65 mmol) was added and the reaction mixture was stirred at room temperature for 4 days when a clear solution resulted. It was then concentrated and the residue purified by flash chromatography (0% to 30% EtOAc/Hexane) to obtain 1.22 g (77%) of 3-(1,4-Dioxa-spiro[4.5]dec-8-ylamino)-5-phenyl-thiophene-2-carboxylic acid methyl ester.

$^1$H NMR (CDCl$_3$, 400 MHz) 7.64-7.61 ppm (m, 2H); 7.42-7.33 ppm (m, 3H); 6.85 ppm (s, 1H); 3.96 ppm (s, 4H); 3.82 ppm (s, 3H); 3.49 ppm (bs, 1H); 2.06-2.00 ppm (m, 2H); 1.85-1.81 ppm (m, 2H); 1.79-1.63 ppm (m, 4H).

Step II

To trans 4-methyl-cyclohexanecarboxylic acid (148 mg, 1.044 mmol) and triphenylphosphine (274 mg, 1.044 mmol) dissolved in 1,2-dichloroethane (1.5 ml) was added N-chlorosuccinimide (145 mg, 1.084 mmol). After 15 minutes of stirring at room temperature, a solution of 3-(1,4-Dioxa-spiro[4.5]dec-8-ylamino)-5-phenyl-thiophene-2-carboxylic acid methyl ester (300 mg, 0.803 mmol) in 1,2-dichloroethane (1.5 ml) was added. The resulting mixture was then stirred for 18 h at 90° C. and then cooled to room temperature. It was then diluted with ethyl acetate (10 ml) and a solution of saturated NaHCO$_3$ (10 ml) was added. The aqueous phase was separated and washed with ethyl acetate (2×10 ml) and the combined organic layers were dried (Na$_2$SO$_4$), filtered and concentrated. The residue was purified by flash chromatography (0% to 30% EtOAc/Hexane) to obtain 265 mg (66%) of 3-[(1,4-Dioxa-spiro[4.5]dec-8-yl)-(trans 4-methyl-cyclohexanecarbonyl)-amino]-5-phenyl-thiophene-2-carboxylic acid methyl ester.

$^1$H NMR (CDCl$_3$, 400 MHz) 7.66-7.61 ppm (m, 2H); 7.47-7,38 ppm (m, 3H); 7.04 ppm (s, 1H); 4.72-4.64 ppm (m, 1H); 3.90-3.65 ppm (m, 7H); 2.04-1.89 ppm (m, 2H); 1.79-1.50 ppm (m, 10H); 1.49-1.37 ppm (m, 1H); 1.35-1.17 ppm (m, 3H); 0.77 ppm (d, 3H); 0.73-0.55 ppm (m, 2H).

Step III

To 3-[(1,4-Dioxa-spiro[4.5]dec-8-yl)-(trans 4-methyl-cyclohexanecarbonyl)-amino]-5-phenyl-thiophene-2-carboxylic acid methyl ester (401 mg, 0.806 mmol) in tetrahydrofuran (4 ml) was added 3N HCl solution (4 ml) and the reaction was stirred at room temperature for 20 hours. It was then diluted with ethyl acetate (10 ml), the organic layer was separated, and the aqueous phase was washed twice with ethyl acetate (2×10 mL). The combined ethyl acetate layer was washed with brine (10 ml) and dried on Na$_2$SO$_4$, filtered and concentrated. The residue was purified by flash chromatography (0% to 40% EtOAc/Hexane) to obtain 315 mg (86%) of 3-[(4-Methyl-cyclohexanecarbonyl)-(4-oxo-cyclohexyl)-amino]-5-phenyl-thiophene-2-carboxylic acid methyl ester.

$^1$H NMR (CDCl$_3$, 400 MHz) 7.64-7.62 ppm (m, 2H); 7.48-7.40 ppm (m, 3H); 7.02 ppm (s, 1H); 5.13-5.05 ppm (m, 1H); 3.86 ppm (s, 3H); 2.59-2.24 ppm (m, 5H); 2.15-2.09 ppm (m, 1H); 2.04-1.99 ppm (m, 1H); 1.78-1.60 ppm (m, 6H); 1.50-1.32 ppm (m, 3H); 0.78 ppm (d, 3H); 0.74-0.57 ppm (m, 2H).

Step IV

3-[(4-Methyl-cyclohexanecarbonyl)-(4-oxo-cyclohexyl)-amino]-5-phenyl-thiophene-2-carboxylic acid methyl ester (34 mg, 0.075 mmol) was dissolved in a 4:1 mixture of dioxane:H$_2$O (1 ml) and then LiOH 1N (375 ul, 0.375 mmol) was added. After 3 hours of stirring at room temperature, solvents were removed and then partitioned between 5 ml of H$_2$O acidified to pH 4 and 5 ml of EtOAc. The organic layer was separated and the aqueous phase was washed twice with ethyl acetate (2×5 mL). The combined ethyl acetate layer was dried (Na$_2$SO4) and concentrated. The residue was purified by preparative chromatography (10% MeOH/CH$_2$Cl$_2$) to obtain 17 mg (52%) of 3-[(4-Methyl-cyclohexanecarbonyl)-(4-oxo-cyclohexyl)-amino]-5-phenyl-thiophene-2-carboxylic acid (Compound 13).

$^1$H NMR (CD$_3$OD, 400 MHz) 7.64-7.62 ppm (m, 2H); 7.38-7.28 ppm (m, 3H); 7.26 ppm (s, 1H); 4.88-4.81 ppm (m, 1H); 2.55-2.41 ppm (m, 1H); 2.26-1.91 ppm (m, 3H); 1.88-1.26 ppm (m, 11H); 0.88-0.78 ppm (m, 1H); 0.69 ppm (d, 3H); 0.63-0.48 ppm (m, 2H).

EXAMPLE 15

3-[(4-Hydroxy-cyclohexyl)-(4-methyl-cyclohexanecarbonyl)-amino]-5-phenyl-thiophene-2-carboxylic acid Compound 15

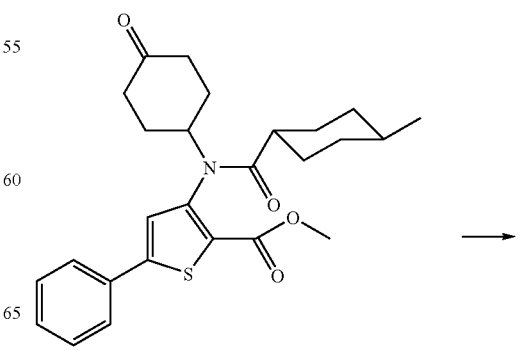

-continued

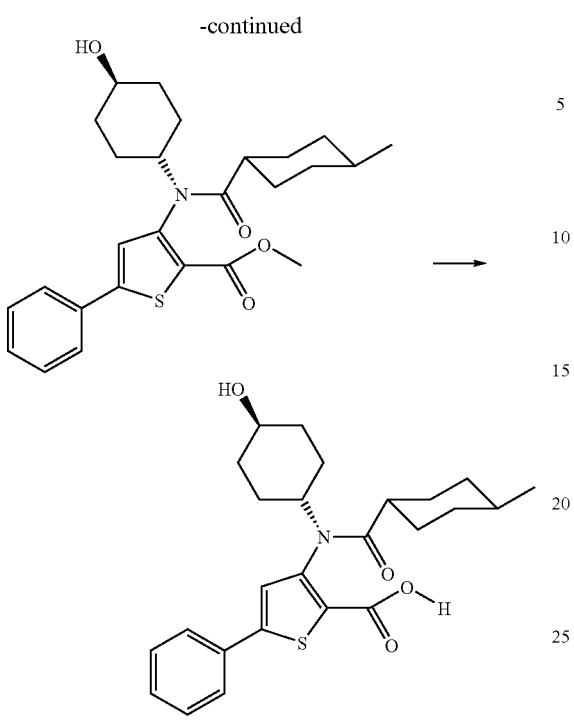

Step I

3-[(4-Methyl-cyclohexanecarbonyl)-(4-oxo-cyclohexyl)-amino]-5-phenyl-thiophene-2-carboxylic acid methyl ester (55 mg, 0.121 mmol) was dissolved in methanol (1.2 ml), cooled to 0° C. and then sodium borohydride (4.6 mg, 0.121 mmol) was added. After 30 minutes of stirring at 0° C., the reaction was quenched with a 10% solution of hydrochloric acid (5 ml) and the aqueous phase was extracted with ethyl acetate (3×10 mL). The combined ethyl acetate layer was dried (Na$_2$SO4) and concentrated. The residue was then purified by preparative chromatography (3% MeOH/CH$_2$Cl$_2$) to obtain 34 mg (62%) of 3-[(trans-4-Hydroxy-cyclohexyl)-(trans-4-methyl-cyclohexanecarbonyl)-amino]-5-phenyl-thiophene-2-carboxylic acid methyl ester.

$^1$H NMR (CDCl$_3$, 400 MHz) 7.66-7.63 ppm (m, 2H); 7.48-7.39 ppm (m, 3H); 7.02 ppm (s, 1H); 4.62-4.54 ppm (m, 1H); 3.85 ppm (s, 3H); 3.46-3.39 ppm (m, 1H); 2.03-1.91 ppm (m, 4H); 1.83-1.78 ppm (m, 1H); 1.72-1.23 ppm (m, 10H); 1.07-0.97 ppm (m, 1H); 0.76 ppm (d, 3H); 0.73-0.55 ppm (m, 2H).

Step II

3-[(trans-4-Hydroxy-cyclohexyl)-(trans-4-methyl-cyclohexanecarbonyl)-amino]-5-phenyl-thiophene-2-carboxylic acid methyl ester (34 mg, 0.075 mmol) was dissolved in a 4:1 mixture of dioxane:H$_2$O (1 ml) and then LiOH 1N (375 ul, 0.375 mmol) was added. After 4 hours of stirring at room temperature, solvents were removed and then partitioned between 5 ml of H$_2$O acidified to pH 4 and 5 ml of EtOAc. The organic layer was separated and the aqueous phase was washed twice with ethyl acetate (2×5 mL). The combined ethyl acetate layer was dried (Na$_2$SO4) and concentrated. The residue was purified by preparative chromatography (10% MeOH/CH$_2$Cl$_2$) to obtain 21 mg (64%) of 3-[(trans-4-Hydroxy-cyclohexyl)-(trans-4-methyl-cyclohexanecarbonyl)-amino]-5-phenyl-thiophene-2-carboxylic acid (Compound 15).

$^1$H NMR (CD$_3$OD, 400 MHz) 7.73-7.70 ppm (m, 2H); 7.46-7.37 ppm (m, 3H); 7.28 ppm (s, 1H); 4.47-4.41 ppm (m, 1H); 3.38-3.32 ppm (m, 1H); 2.14-2.08 ppm (m, 1H); 1.99-1.88 ppm (m, 4H); 1.80-1.77 ppm (bd, 1H); 1.70-1.51 ppm (m, 4H); 1.44-1.27 ppm (m, 5H); 1.10-1.03 ppm (m, 1H); 0.77 ppm (d, 3H); 0.72-0.55 ppm (m, 2H).

EXAMPLE 16

3-[(4-Hydroxy-cyclohexyl)-(4-methyl-cyclohexanecarbonyl)-amino]-5-phenyl-thiophene-2-carboxylic acid Compound 47

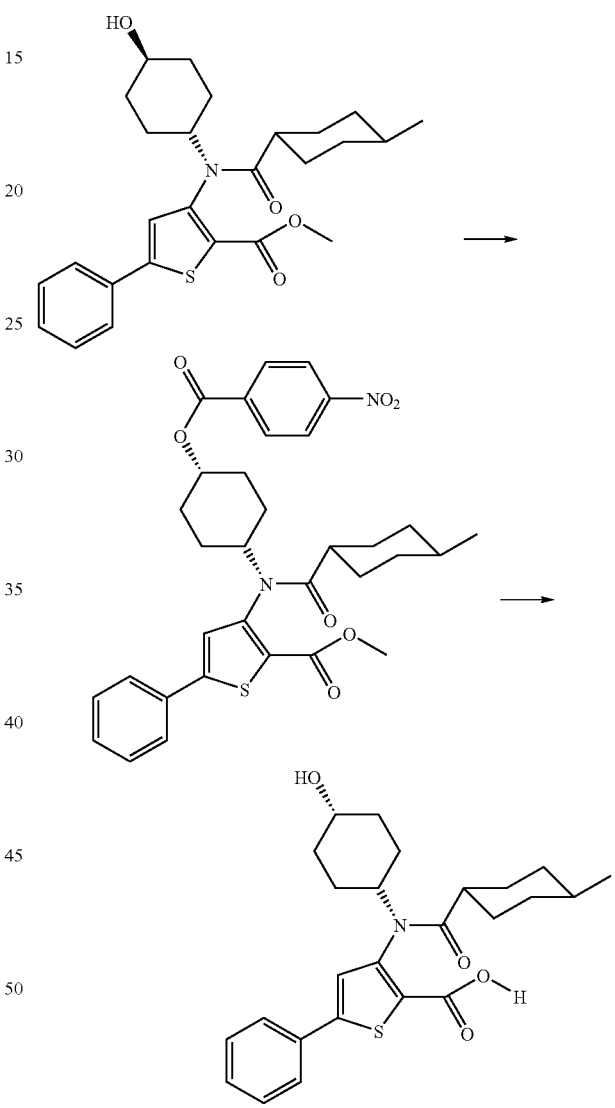

Step I

3-[(4-Hydroxy-cyclohexyl)-(4-methyl-cyclohexanecarbonyl)-amino]-5-phenyl-thiophene-2-carboxylic acid methyl ester (62 mg, 0.136 mmol) was dissolved in benzene (0.7 ml) and then p-nitrobenzoic acid (27 mg, 0.163 mmol) and triphenylphosphine (43 mg, 0.163 mmol) were added. The resulting solution was cooled in an ice bath and diethyl azodicarboxylate (26 ul, 0.163 mmol) was added. After stirring at room temperature for 22 hours, the solvents were removed and the residue was purified by preparative chromatography (30% EtOAc/Hexane) to obtain 44 mg (54%) of 3-{(4-Methyl-cyclohexanecarbonyl)-[4-(4-nitro-benzoyloxy)-cyclohexyl]-amino}-5-phenyl-thiophene-2-carboxylic acid methyl ester.

$^1$H NMR (CDCl$_3$, 400 MHz) 7.91-7.83 ppm (m, 4H); 7.69-7.64 ppm (m, 2H); 7.50-7.47 ppm (m, 3H); 7.16 ppm (s, 1H); 5.24 ppm (bs, 1H); 4.82-4.74 ppm (m, 1H); 3.86 ppm (s, 3H); 2.13-1.90 ppm (m, 4H); 1.82-1.59 ppm (m, 9H); 1.50-1.39 ppm (m, 1H); 1.37-1.24 ppm (m, 2H); 0.78 ppm (d, 3H); 0.75-0.59 ppm (m, 2H).

Step II

3-{(4-Methyl-cyclohexanecarbonyl)-[4-(4-nitro-benzoyloxy)-cyclohexyl]-amino}-5-phenyl-thiophene-2-carboxylic acid methyl ester (44 mg, 0.073 mmol) was dissolved in a 4:1 mixture of dioxane:H$_2$O (1 ml) and then LiOH 1N (365 ul, 0.365 mmol) was added. After 4 hours of stirring at room temperature, solvents were removed and then partitioned between 5 ml of H$_2$O acidified to pH 4 and 5 ml of EtOAc. The organic layer was separated and the aqueous phase was washed twice with ethyl acetate (2×5 mL). The combined ethyl acetate layer was dried (Na$_2$SO4) and concentrated. The residue was purified by preparative chromatography (10% MeOH/CH$_2$Cl$_2$) to obtain 15 mg (47%) of 3-[(4-Hydroxy-cyclohexyl)-(4-methyl-cyclohexanecarbonyl)-amino]-5-phenyl-thiophene-2-carboxylic acid.

$^1$H NMR (CD$_3$OD, 400 MHz) 7.64-7.61 ppm (m, 2H); 7.37-7.27 ppm (m, 3H); 7.20 ppm (s, 1H); 4.43-4.37 ppm (m, 1H); 3.79 ppm (bs, 1H); 2.08-2.02 ppm (m, 1H); 1.77-1.43 ppm (m, 13H); 1.36-1.24 ppm (m, 2H); 0.68 ppm (d, 3H); 0.64-0.50 ppm (m, 2H).

EXAMPLE 17

3-[(4-Methoxy-cyclohexyl)-(4-methyl-cyclohexanecarbonyl)-amino]-5-phenyl-thiophene-2-carboxylic acid Compound 46

Step I

3-[(4-Hydroxy-cyclohexyl)-(4-methyl-cyclohexanecarbonyl)-amino]-5-phenyl-thiophene-2-carboxylic acid methyl ester (27 mg, 0.059 mmol) was dissolved in THF (0.6 ml), cooled to 0° C. in an ice bath and 60% sodium hydride (5 mg, 0.118 mmol) was added, followed by a catalytic amount of tetrabutylammonium iodide. After stirring for 1 hour, iodomethane (37 ul, 0.590 mmol) was added and the reaction further stirred for 3 hours. It was then quenched with water (5 ml) and extracted with ethyl acetate (3×5 ml). The combined ethyl acetate layer was dried (Na$_2$SO4) and concentrated. The residue was purified by preparative chromatography (10% MeOH/CH$_2$Cl$_2$) to obtain 5 mg (18%) of 3-[(4-Methoxy-cyclohexyl)-(4-methyl-cyclohexanecarbonyl)-amino]-5-phenyl-thiophene-2-carboxylic acid (compound 46).

$^1$H NMR (CDCl$_3$, 400 MHz) 7.67-7.65 ppm (m, 2H); 7.47-7.40 ppm (m, 3H); 7.05 ppm (s, 1H); 4.59 ppm (bs, 1H); 3.28 ppm (s, 3H); 3.06-2.97 ppm (m, 1H); 2.18-2.01 ppm (m, 4H); 1.94-1.90 ppm (m, 1H); 1.74-1.25 ppm (m, 11H); 0.77 ppm (d, 3H); 0.71-0.61 ppm (m, 2H).

EXAMPLE 18

3-[(4-Hydroxyimino-cyclohexyl)-(4-methyl-cyclohexanecarbonyl)-amino]-5-phenyl-thiophene-2-carboxylic acid Compound 16

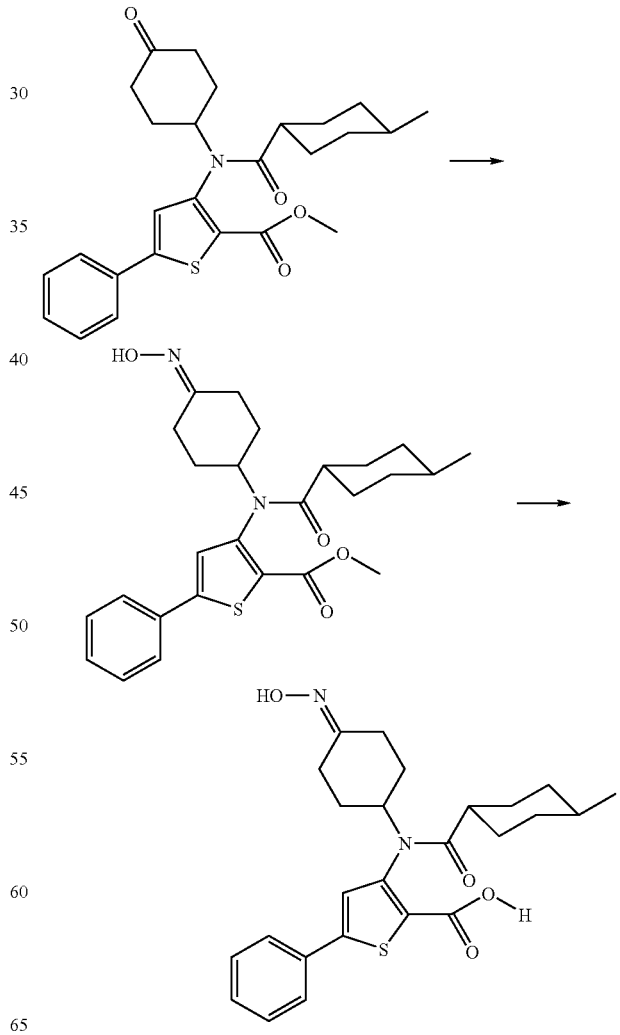

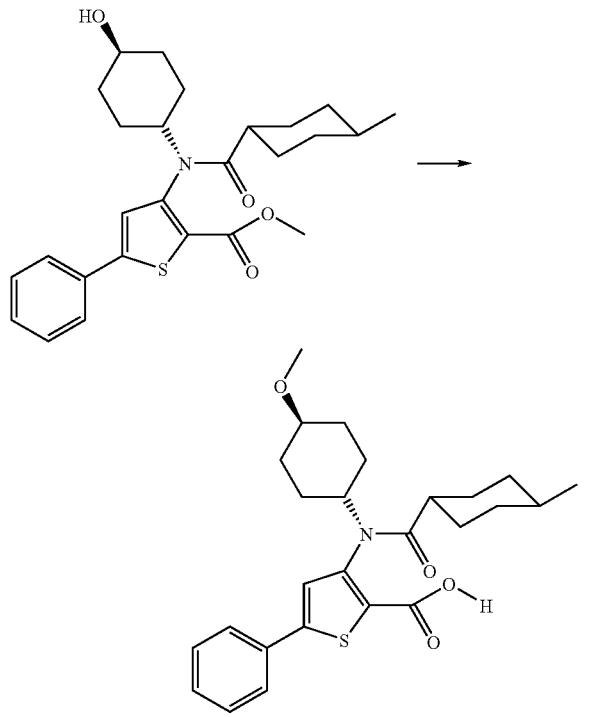

Step I

3-[(4-Methyl-cyclohexanecarbonyl)-(4-oxo-cyclohexyl)-amino]-5-phenyl-thiophene-2-carboxylic acid methyl ester (67 mg, 0.148 mmol) was dissolved in methanol (1.5 ml) and hydroxylamine hydrochloride salt (62 mg, 0.888 mmol) was added. After stirring for 2 hours at room temperature and 2 hours at reflux, the pH of the solution was adjusted to 8-9 by addition of a 10% sodium hydroxide solution. The resulting solution was then refluxed for 30 minutes and cooled to room temperature. It was then quenched with water (5 ml) and extracted with ethyl acetate (3×5 ml). The combined ethyl acetate layer was washed with brine, dried (Na$_2$SO4) and concentrated. The residue was purified by flash chromatography (0% to 60% EtOAc/Hex) to obtain 49 mg (71%) of 3-[(4-Hydroxyimino-cyclohexyl)-(4-methyl-cyclohexanecarbonyl)-amino]-5-phenyl-thiophene-2-carboxylic acid methyl ester.

$^1$H NMR (CDCl$_3$, 400 MHz) 7.63-7.60 ppm (m, 2H); 7.47-7.39 ppm (m, 3H); 6.98 ppm (s, 1H); 4.90-4.82 ppm (m, 1H); 3.84 ppm (s, 3H); 3.39-3.29 ppm (m, 1H); 2.44-2.20 ppm (m, 2H); 2.13-2.09 ppm (m, 1H); 2.04-1.73 ppm (m, 4H); 1.70-1.57 ppm (m, 4H); 1.50-1.22 ppm (m, 4H); 1.13-1.02 ppm (m, 1H); 0.77 ppm (d, 3H); 0.73-0.55 ppm (m, 2H).

Step II

3-[(4-Hydroxyimino-cyclohexyl)-(4-methyl-cyclohexanecarbonyl)-amino]-5-phenyl-thiophene-2-carboxylic acid methyl ester (34 mg, 0.073 mmol) was dissolved in a 4:1 mixture of dioxane:H$_2$O (1 ml) and then LiOH 1N (365 ul, 0.365 mmol) was added. After 3 hours of stirring at room temperature, solvents were removed and then partitioned between 5 ml of H$_2$O acidified to pH 4 and 5 ml of EtOAc. The organic layer was separated and the aqueous phase was washed twice with ethyl acetate (2×5 mL). The combined ethyl acetate layer was dried (Na$_2$SO4) and concentrated. The residue was purified by preparative chromatography (10% MeOH/CH$_2$Cl$_2$) to obtain 15 mg (45%) of 3-[(4-Hydroxy-imino-cyclohexyl)-(4-methyl-cyclohexanecarbonyl)-amino]-5-phenyl-thiophene-2-carboxylic acid Compound 16.

$^1$H NMR (CD$_3$OD, 400 MHz) 7.72-7.69 ppm (m, 2H); 7.50-7.36 ppm (m, 3H); 7.29 ppm (s, 1H); 4.73-4.70 ppm (m, 1H); 3.42-3.31 ppm (m, 1H); 2.42-2.07 ppm (m, 5H); 1.89-1.28 ppm (m, 9H); 1.18-1.03 ppm (m, 1H); 0.78 ppm (d, 3H); 0.73-0.56 ppm (m, 2H).

Compound 25 was prepared in a similar manner.

EXAMPLE 19

3-[(1-Ethyl-3-methylamino-propyl)-(4-methyl-cyclohexanecarbonyl)-amino]-5-phenyl-thiophene-2-carboxylic acid Compound 41

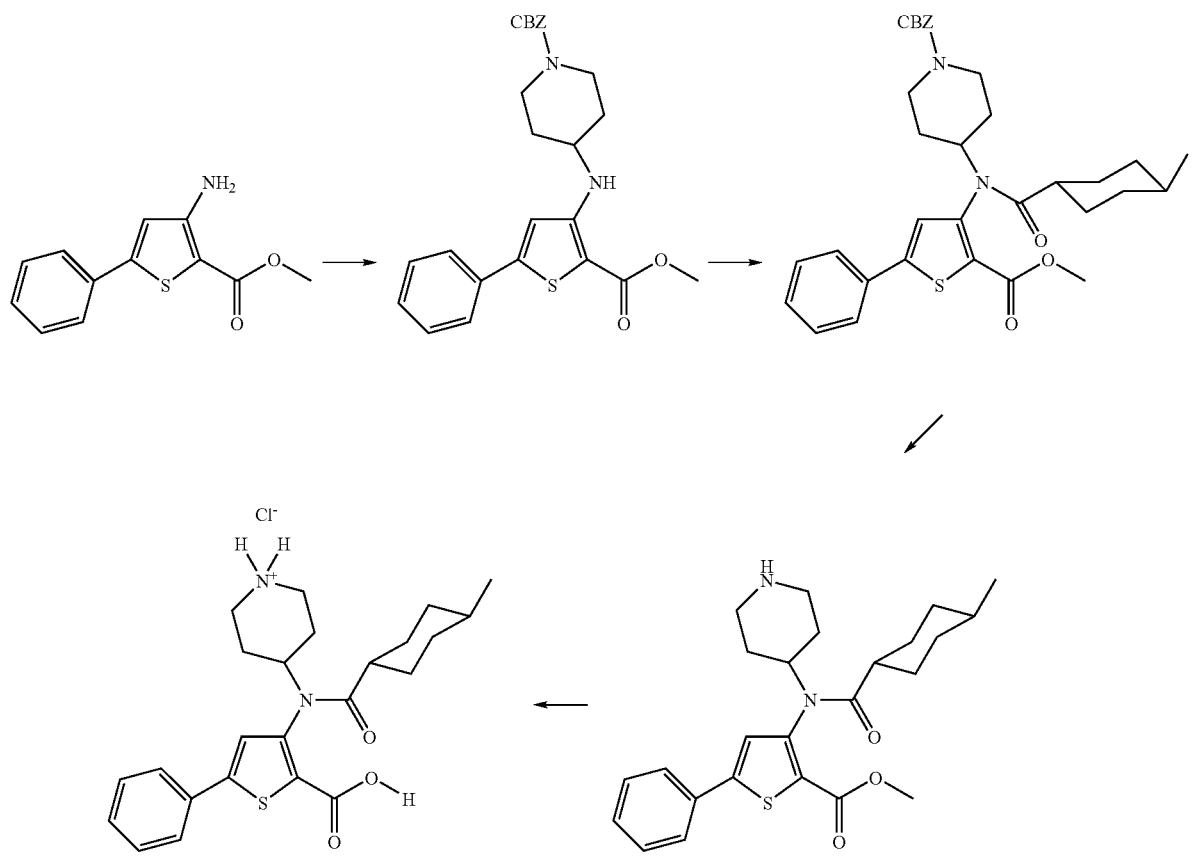

Step I

To a stirred solution of 3-Amino-5-phenyl-thiophene-2-carboxylic acid methyl ester (1.0 g, 4.29 mmol) in THF (1.0 ml) was added the ketone (1.0 g, 4.29 mmol), dibutyltin dichloride (130 mg, 0.43 mmol) and phenylsilane (582 ul, 4.72 mmol) and the reaction mixture was stirred at room temperature for 2 days. The reaction was then quenched with a saturated NaHCO₃ solution, and the mixture was extracted 3 times with EtOAc. The combined extracts were then washed with brine and dried on $Na_2SO_4$, filtered and concentrated. The crude product was purified by flash chromatography (0% to 30% EtOAc/Hex) to give 1.86 g (96%) of 4-(2-Methoxycarbonyl-5-phenyl-thiophen-3-ylamino)-piperidine-1-carboxylic acid benzyl ester.

Step II

To a stirred solution of trans-4-methylcyclohexyl acid (637 mg, 4.48 mmol) in dichloromethane (22 ml) was added a solution of oxalyl chloride (2M in $CH_2Cl_2$, 4.5 ml), followed by 2 drops of DMF. The reaction mixture was stirred at room temperature for 2 h and then evaporated to remove solvent and excess oxalyl chloride. The crude product was used in the next step without further purification.

To a stirred solution of 4-(2-Methoxycarbonyl-5-phenyl-thiophen-3-ylamino)-piperidine-1-carboxylic acid benzyl ester (1.01 g, 2.24 mmol) in dichloroethane (7.5 ml) was added trans-4-methylcyclohexylchloride (720 mg, 4.48 mmol). The resulting reaction mixture was heated for 17 h at 90° C., cooled to room temperature, quenched with a saturated NaHCO₃ solution, and then extracted 3 times with EtOAc. The combined extracts were then washed with brine and dried on $Na_2SO_4$, filtered and concentrated. The crude product was purified by flash chromatography (0% to 25% EtOAc/Hex) to give 1.00 g (78%) of 4-[(2-Methoxycarbonyl-5-phenyl-thiophen-3-yl)-(4-methyl-cyclohexanecarbonyl)-amino]-piperidine-1-carboxylic acid benzyl ester.

¹H NMR (CDCl₃, 400 MHz) 7.65-7.62 ppm (m, 2H); 7.49-7.40 ppm (m, 3H); 7.31-7.23 ppm (m, 5H); 7.0 ppm (s, 1H); 5.5 ppm (s, 2H); 4.82-4.76 ppm (m, 1H); 4.19 ppm (bs, 2H); 3.85 ppm (s, 3H); 2.87 ppm (bs, 2H); 2.03-1.58 ppm (m, 9H); 1.49-1.28 ppm (m, 2H); 1.10 ppm (bs, 2H); 0.78 ppm (d, 3H); 0.73-0.56 ppm (m, 2H).

Step III

To a solution of 4-[(2-Methoxycarbonyl-5-phenyl-thiophen-3-yl)-(4-methyl-cyclohexanecarbonyl)-amino]-piperidine-1-carboxylic acid benzyl ester (506 mg, 0.88 mmol) in a 6:1 mixture of ethyl acetate and methanol (7 ml) was added the 10% palladium on charcoal (103 mg, 0.097 mmol). The resulting reaction mixture was placed under H₂ atmosphere (25 psi), stirred at room temperature for 3 days, and then filtered on celite and evaporated to dryness. The crude product was purified by flash chromatography (100/90/16/1 $CH_2Cl_2/CHCl_3/MeOH/Et_3N$) to give 287 mg (74%) of 3-[(4-Methyl-cyclohexanecarbonyl)-piperidin-4-yl-amino]-5-phenyl-thiophene-2-carboxylic acid methyl ester.

¹H NMR (CDCl₃, 400 MHz) 7.64-7.61 ppm (m, 2H); 7.46-7.38 ppm (m, 3H); 7.04 ppm (s, 1H); 4.74-4.68 ppm (m, 1H); 3.84 ppm (s, 3H); 3.13-3.03 ppm (m, 2H); 2.78-2.67 ppm (m, 2H); 2.03-1.92 ppm (m, 2H); 1.77-1.74 ppm (m, 1H); 1.69-1.13 ppm (m, 9H); 0,77 ppm (d, 3H); 0.72-0.59 ppm (m, 2H).

Step IV

3-[(4-Methyl-cyclohexanecarbonyl)-piperidin-4-yl-amino]-5-phenyl-thiophene-2-carboxylic acid methyl ester (20 mg, 0.045 mmol) was dissolved in a 4:1 mixture of dioxane:H₂O (0.5 ml) and then LiOH 1N (135 ul, 0.135 mmol) was added. After 4 hours of stirring at room temperature, the reaction mixture was acidified to pH 3-4 with a 10% solution of hydrochloric acid and then the solvents were removed. It was further diluted in cold water (1 ml) and filtered out to give 16 mg (84%) of 3-[(4-Methyl-cyclohexanecarbonyl)-piperidin-4-yl-amino]-5-phenyl-thiophene-2-carboxylic acid (Compound 41).

¹H NMR (CD₃OD, 400 MHz) 7.78-7.75 ppm (m, 2H); 7.50-7.41 ppm (m, 4H); 4.77-4.69 ppm (m, 1H); 3.47-3.36 ppm (m, 2H); 3.16-3.06 ppm (m, 2H); 2.24-2.21 ppm (m, 1H); 2.15-2.07 ppm (m, 2H); 1.91-1.80 ppm (m, 1H); 1.76-1.51 ppm (m, 6H); 1.44-1.26 ppm (m, 2H); 0.79 ppm (d, 3H); 0.76-0.60 ppm (m, 2H).

EXAMPLE 20

3-[(1-((Benzyl-piperidin-4-yl)-(4-methyl-cyclohexanecarbonyl)-amino]-5-phenyl-thiophene-2-carboxylic acid Compound 52

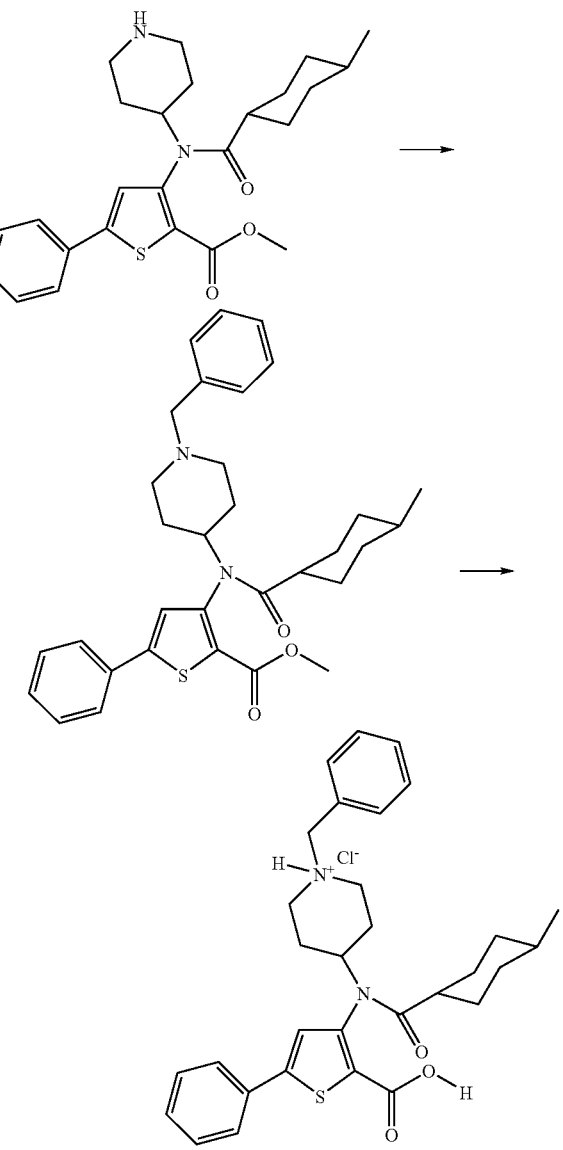

Step I

To 3-[(4-Methyl-cyclohexanecarbonyl)-piperidin-4-yl-amino]-5-phenyl-thiophene-2-carboxylic acid methyl ester (43 mg, 0.098 mmol) in dichloroethane (1.0 ml) was added benzaldehyde (15 ul, 0.146 mmol), followed by sodium triacetoxyborohydride (41 mg, 0.195 mmol). The reaction mixture was stirred at room temperature for 4 h, quenched with a saturated $NaHCO_3$ solution, and then extracted with Ethyl acetate (3×5 ml). The combined extracts were then washed with brine and dried on $Na_2SO_4$, filtered and concentrated. The residue was purified by preparative chromatography (50% EtOAc/Hex) to give 32 mg (61%) of 3-[(1-Benzyl-piperidin-4-yl)-(4-methyl-cyclohexanecarbonyl)-amino]-5-phenyl-thiophene-2-carboxylic acid methyl ester.

Step II

3-[(1-Benzyl-piperidin-4-yl)-(4-methyl-cyclohexanecarbonyl)-amino]-5-phenyl-thiophene-2-carboxylic acid methyl ester (32 mg, 0.060 mmol) was dissolved in a 4:1 mixture of dioxane:$H_2O$ (0.5 ml) and then LiOH 1N (180 ul, 0.180 mmol) was added. After 2 hours of stirring at room temperature and 4 hours at reflux, solvents were removed and then partitioned between 5 ml of $H_2O$ acidified to pH 4 and 5 ml of EtOAc. The organic layer was separated and the aqueous phase was washed twice with ethyl acetate (2×5 mL). The combined ethyl acetate layer was dried ($Na_2SO4$) and concentrated. The residue was purified by reparative chromatography (10% MeOH/$CH_2Cl_2$) to obtain 22 mg (71%) of 3-[(1-(Benzyl-piperidin-4-yl)-(4-methyl-cyclohexanecarbonyl)-amino]-5-phenyl-thiophene-2-carboxylic acid (compound 52).

$^1$H NMR ($CD_2Cl_2$, 400 MHz) 7.41-7.36 ppm (m, 4H); 7.31-7.28 ppm (m, 6H); 6.82 ppm (s, 1H); 4.80-4.73 ppm (m, 1H); 4.37 ppm (d, 1H); 3.65 ppm (bd, 1H); 3.53 ppm (d, 1H); 3.10 ppm (bd, 1H); 2.63 ppm (t, 1H); 2.47 ppm (t, 1H); 2.10-2.06 ppm (m, 2H); 1.85-1.63 ppm (m, 4H); 1.57-1.38 ppm (m, 4H); 1.28-1.18 ppm (m, 2H); 0.66 ppm (d, 3H); 0.62-0.50 ppm (m, 2H).

EXAMPLE 21

3-[(1-Acetyl-piperidin-4-yl)-(4-methyl-cyclohexanecarbonyl)-amino]-5-phenyl-thiophene-2-carboxylic acid Compound 48

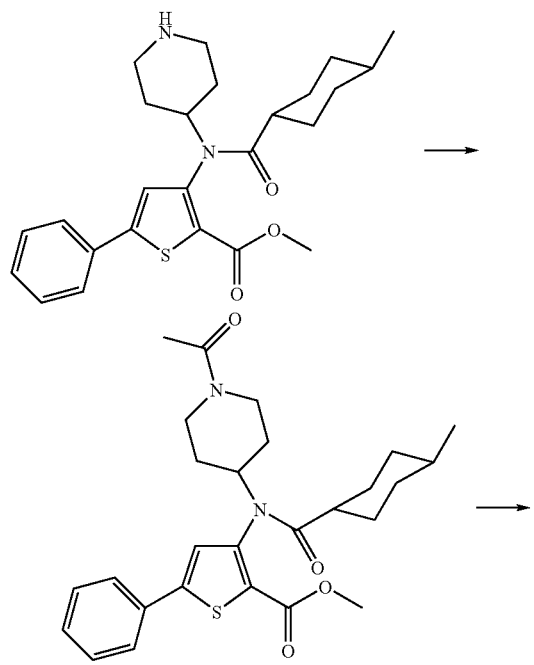

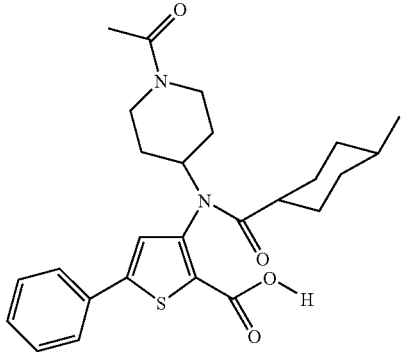

Step I

To 3-[(4-Methyl-cyclohexanecarbonyl)-piperidin-4-yl-amino]-5-phenyl-thiophene-2-carboxylic acid methyl ester (58 mg, 0.132 mmol) in dichloromethane (1.3 ml) was added pyridine (64 ul, 0.789 mmol), followed by acetic anhydride (50 ul, 0.526 mmol) and a catalytic amount of DMAP. The resulting solution was stirred for 18 hours at room temperature and then quenched with a saturated solution of $NaHCO_3$ (5 ml). The aqueous phase was separated and washed with ethyl acetate (2×5 ml). The combined organic layers were dried ($Na_2SO_4$), filtered and concentrated. The residue was then purified by preparative chromatography (100/90/16/1 $CH_2Cl_2$/$CHCl_3$/MeOH/$Et_3N$) to obtain 50 mg (78%) of 3-[(1-Acetyl-piperidin-4-yl)-(4-methyl-cyclohexanecarbonyl)-amino]-5-phenyl-thiophene-2-carboxylic acid methyl ester.

Step II

3-[(1-Acetyl-piperidin-4-yl)-(4-methyl-cyclohexanecarbonyl)-amino]-5-phenyl-thiophene-2-carboxylic acid methyl ester (50 mg, 0.104 mmol) was dissolved in a 4:1 mixture of dioxane:$H_2O$ (1 ml) and then LiOH 1N (310 ul, 0.310 mmol) was added. After 5 hours of stirring at room temperature and 4 hours at reflux, 10 solvents were removed and then partitioned between 5 ml of $H_2O$ acidified to pH 4 and 5 ml of EtOAc. The organic layer was separated and the aqueous phase was washed twice with ethyl acetate (2×5 mL). The combined ethyl acetate layer was dried ($Na_2SO4$) and concentrated. The residue was purified by preparative chromatography (100/90/16/1 $CH_2Cl_2$/$CHCl_3$/MeOH/$Et_3N$) to obtain 27 mg (56%) of 3-[(1-Acetyl-piperidin-4-yl)-(4-methyl-cyclohexanecarbonyl)-amino]-5-phenyl-thiophene-2-carboxylic acid (Compound 48).

$^1$H NMR ($CD_3OD$, 400 MHz) 1:1 mixture of rotamers 7.75-7.73 ppm (m, 2H); 7.48-7.40 ppm (m, 3H); 7.37 ppm (s, 1H); 4.74-4.51 ppm (m, 1H); 3.99-3.90 ppm (m, 1H); 3.23-3.12 ppm (m, 1H); 2.70-2.60 ppm (m, 1H); 2.27-2.00 ppm (m, 2H); 2.04 ppm (s, 1.5H); 2.00 ppm (s, 1.5H); 1.96-1.87 ppm (m, 1H); 1.77-1.06 ppm (m, 9H); 0.78 ppm (d, 3H); 0.73-0.57 ppm (m, 2H).

Compound 63 was prepared in a similar manner $^1$H NMR ($CD_3OD$, 400 MHz) 1:1 mixture of rotamers 7.91 ppm (s, 0.5H); 7.88 ppm (s, 0.5H); 7.75-7.72 ppm (m, 2H); 7.48-7.39 ppm (m, 3H); 7.37 ppm (s, 0.5H); 7.36 ppm (s, 0.5H); 4.78-4.68 ppm (m, 1H); 4.42-4.31 ppm (m, 1H); 3.79-3.63 ppm (m, 1H); 3.26-3.15 ppm (m, 1H); 2.78-2.66 ppm (m, 1H); 2.12-1.91 ppm (m, 3H); 1.76-1.04 ppm (m, 9H); 0.78 ppm (d, 3H); 0.73-0.57 ppm (m, 2H). Compound 23, Compound 39, Compound 40 were prepared as described in Example 24.

Compound 23: $^1$H NMR (CD$_3$OD, 400 MHz) 7.65-7.63 ppm (m, 2H); 7.25 ppm (s, 1H); 7.16-7.12 ppm (m, 2H); 4.76-4.70 ppm (m, 1H); 3.53-3.46 ppm (m, 1H); 3.17-3.04 ppm (m, 2H); 2.80 ppm (s, 3H); 2.23-2.09 ppm (m, 3H); 2.01-1.92 ppm (m, 1H); 1.82-1.79 ppm (m, 1H); 1.70-1.48 ppm (m, 5H); 1.41-1.25 ppm (m, 2H); 0.77 ppm (d, 3H); 0.73-0.54 ppm (m, 2H).

Compound 39: $^1$H NMR (CD$_3$OD, 400 MHz) 7.77-7.74 ppm (m, 2H); 7.50-7.40 ppm (m, 4H); 4.77-4.71 ppm (m, 1H); 3.62-3.54 ppm (m, 2H); 3.15-3.04 ppm (m, 4H); 2.29-2.08 ppm (s, 3H); 1.97-1.88 ppm (m, 1H); 1.78-1.51 ppm (m, 6H); 1.45-1.34 ppm (m, 1H); 1.30-1.26 ppm (m, 1H); 1.28 ppm (t, 3H); 0.79 ppm (d, 3H); 0.76-0.59 ppm (m, 2H).

Compound 40: $^1$H NMR (CD$_3$OD, 400 MHz) 7.76-7.74 ppm (m, 2H); 7.49-7.40 ppm (m, 4H); 4.78-4.72 ppm (m, 1H); 3.51-3.42 ppm (m, 3H); 3.22-3.13 ppm (m, 2H); 2.30-2.09 ppm (s, 3H); 2.00-1.91 ppm (m, 1H); 1.78-1.51 ppm (m, 7H); 1.47-1.34 ppm (m, 1H); 1.30 ppm (d, 6H); 0.79 ppm (d, 3H); 0.74-0.59 ppm (m, 2H).

EXAMPLE 22

3-[(4-Methyl-cyclohexanecarbonyl)-(1-methyl-1-oxy-piperidin-4-yl)-amino]-5-phenyl-thiophene-2-carboxylic acid Compound 65

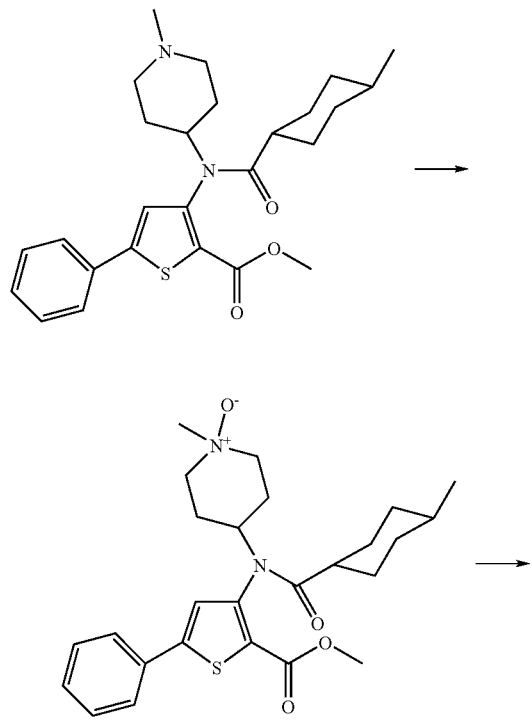

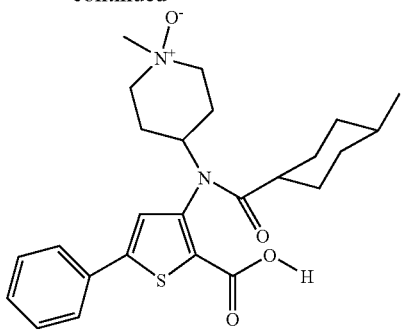

Step I

3-[(4-Methyl-cyclohexanecarbonyl)-(1-methyl-piperidin-4-yl)-amino]-5-phenyl-thiophene-2-carboxylic acid methyl ester (42 mg, 0.092 mmol) was dissolved in dichloromethane (1.8 ml) and then m-chloroperoxybenzoic acid (27 mg, 0.111 mmol) was added. After stirring at room temperature for 2 hours, the solvents were removed and the residue was diluted with ethyl acetate (5 ml). This solution was further washed with a 10% sodium hydroxide solution (2×5 ml), brine (5 ml) and then dried (Na$_2$SO$_4$), filtered and concentrated. The residue was purified by preparative chromatography (10% MeOH/CH$_2$Cl$_2$) to obtain 33 mg (77%) of 3-[(4-Methyl-cyclohexanecarbonyl)-(1-methyl-1-oxy-piperidin-4-yl)-amino]-5-phenyl-thiophene-2-carboxylic acid methyl ester.

$^1$H NMR (CDCl$_3$, 400 MHz) 7.64-7.61 ppm (m, 2H); 7.45-7.37 ppm (m, 3H); 7.10 ppm (s, 1H); 4.76-4.68 ppm (m, 1H); 3.83 ppm (s, 3H); 3.34-3.22 ppm (m, 4H); 3.18 ppm (s, 3H); 2.85 ppm (bs, 2H); 2.57-2.47 ppm (m, 1H); 2.23-2.14 ppm (m, 1H); 2.03-1.96 ppm (m, 1H); 1.90-1.87 ppm (m, 1H); 1.70-1.58 ppm (m, 3H); 1.46-1.35 ppm (m, 1H); 1.31-1.22 ppm (m, 2H); 0.76 ppm (d, 3H); 0.71-0.56 ppm (m, 2H).

Step II

3-[(4-Methyl-cyclohexanecarbonyl)-(1-methyl-1-oxy-piperidin-4-yl)-amino]-5-phenyl-thiophene-2-carboxylic acid methyl ester (33 mg, 0.070 mmol) was dissolved in a 4:1 mixture of dioxane:H$_2$O (0.7 ml) and then LiOH 1N (210 ul, 0.210 mmol) was added. After 4 hours of stirring at room temperature, the reaction mixture was acidified to pH 3-4 with a 10% solution of hydrochloric acid and then the solvents were removed. It was further diluted in cold water (1 ml) and filtered out to give 23 mg (72%) of 3-[(4-Methyl-cyclohexanecarbonyl)-(1-methyl-1-oxy-piperidin-4-yl)-amino]-5-phenyl-thiophene-2-carboxylic acid (Compound 65).

$^1$H NMR (CD$_3$OD, 400 MHz) 7.74-7.72 ppm (m, 2H); 7.48-7.39 ppm (m, 3H); 7.38 ppm (s, 1H); 4.75-4.67 ppm (m, 1H); 3.80-3.65 ppm (m, 4H); 3.42 ppm (s, 3H); 2.32-2.21 ppm (m, 1H); 2.17-1.95 ppm (m, 4H); 1.81-1.71 ppm (m, 2H); 1.66-1.28 ppm (m, 5H); 0.78 ppm (d, 3H); 0.76-0.59 ppm (m, 2H).

EXAMPLE 23

3-[(2-Hydroxy-4-methyl-cyclohexanecarbonyl)-(tetrahydro-pyran-4-yl)-amino]-5-phenyl-thiophene-2-carboxylic acid Compound 31

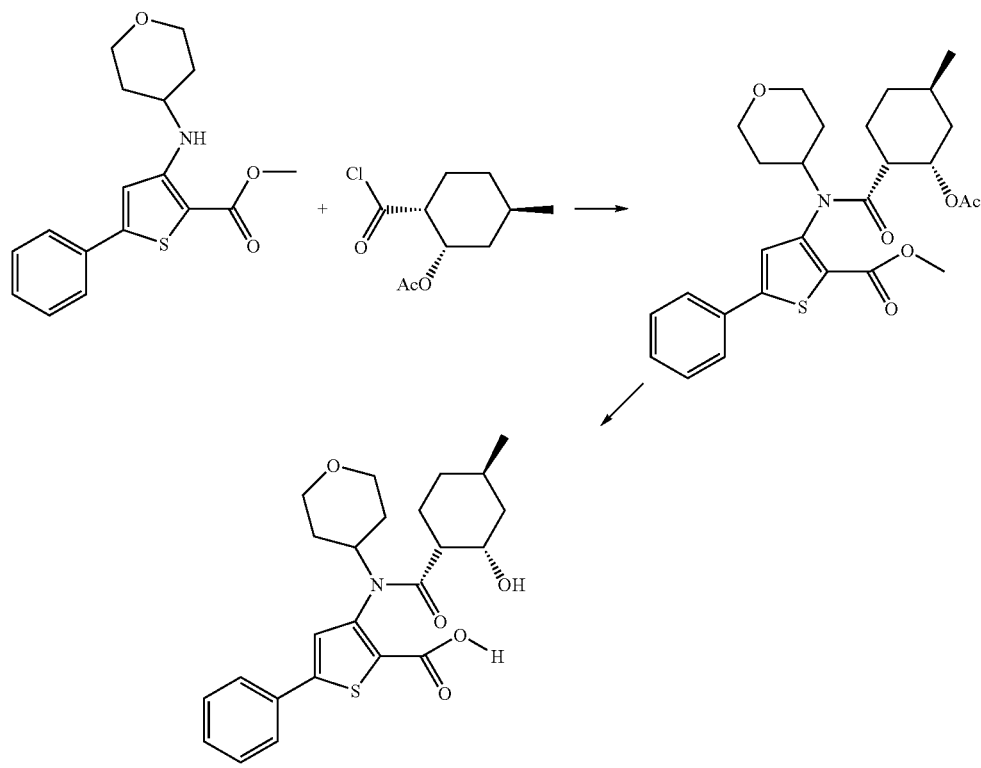

Step I

Acylation using triphenylphosphine in 1,2-dichloroethane at reflux as described for Example 25, Step VI.

Step II

3-[(2-Hydroxy-4-methyl-cyclohexanecarbonyl)-(tetrahydro-pyran-4-yl)-amino]-5-phenyl-thiophene-2-carboxylic acid methyl ester (31 mg, 0.062 mmol) was dissolved in a 4:1 mixture of dioxane:$H_2O$ (0.6 ml) and then LiOH 1N (310 ul, 0.310 mmol) was added. After 4 hours of stirring at room temperature, solvents were removed and then partitioned between 5 ml of $H_2O$ acidified to pH 4 and 5 ml of EtOAc. The organic layer was separated and the aqueous phase was washed twice with ethyl acetate (2×5 mL). The combined ethyl acetate layer was dried ($Na_2SO4$) and concentrated. The residue was purified by preparative HPLC to obtain 14 mg (52%) of 3-[(2-Hydroxy-4-methyl-cyclohexanecarbonyl)-(tetrahydro-pyran-4-yl)-amino]-5-phenyl-thiophene-2-carboxylic acid (Compound 31).

$^1$H NMR (CD$_3$OD, 400 MHz) 7.80-7.75 ppm (m, 2H); 7.50-7.40 ppm (m, 4H); 4.80-4.68 ppm (m, 1H); 4.15 ppm (s, 1H); 4.00-3.85 ppm (m, 2H); 3.55-3.40 ppm (m, 2H); 2.35-2.15 ppm (m, 1H); 2.00-1.45 ppm (m, 4H); 1.40-1.25 ppm (m, 2H); 0.75 ppm (d, 3H); 0.73-0.55 ppm (m, 2H).

EXAMPLE 24

4-[(2-Carboxy-5-phenyl-thiophen-3-yl)-(trans-4-methyl-cyclohexanecarbonyl)-amino]-1-methyl-piperidinium chloride Compound 11

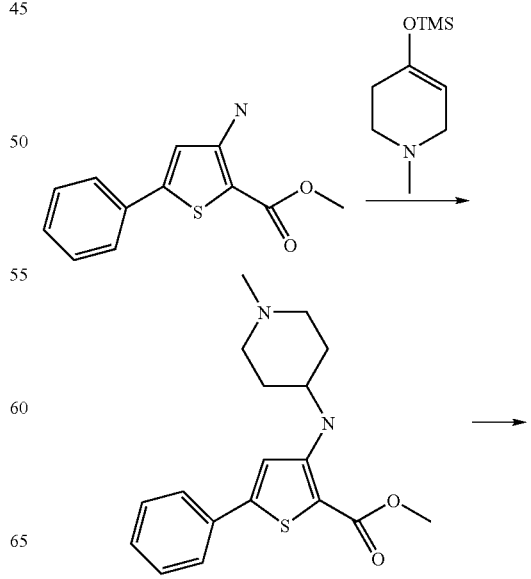

-continued

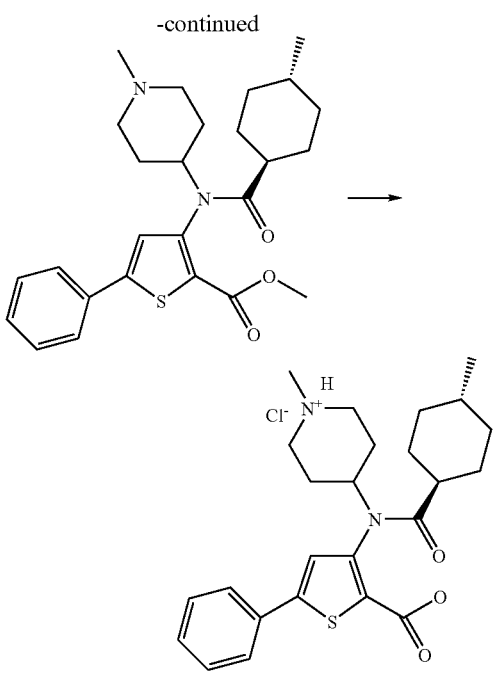

Step I (a) To a stirred solution of 1-methyl-piperidin-4-one (6.0 g, 53 mmol, 6.52 mL) and Et₃N (14.16 g, 140 mmol, 19.5 mL) in 1,4-dioxane (20 mL) was added chlorotrimethylsilane (7.6 g, 70 mmol, 8.88 mL) drop wise during 30 min. The resultant reaction mixture was slowly heated to reflux at 110° C., stirred at the same temperature for 24 h, an additional amount of chlorotrimethylsilane (4.44 mL), heated for 24 h (take aliquot of it and run 1H NMR), cooled to room temp, filtered off the solid, solid was washed with n-pentane. The filtrate was concentrated on rotavaporator, and then diluted with n-pentane and filtered off the solid. The resultant solution was concentrated on rotavaporator followed by high vacuum furnished the 1-methyl-4-trimethylsilanyloxy-1,2,3,6-tetrahydro-pyridine (9.68 g, 1H NMR showed about 10:1 ratio of silylenolether and the starting material). The crude product was as such used in the next step without further purification.

(b) To a stirred solution of methyl-3-amino-5-phenylthiophene-carboxylate (233 mg, 1.0 mmol) and 1-methyl-4-trimethylsilanyloxy-1,2,3,6-tetrahydro-pyridine (370 mg, 2.0 mmol) in dichloroethane (3.0 mL) was added AcOH (0.114 mL, 2.0 eq) and followed addition of NaBH(OAc)₃ (424 mg, 2.0 mmol) in one portion. The resultant reaction mixture was stirred at RT for weekend, aq. 10% NaOH (until basic) was added, after 30 min, reaction mixture was extracted with dichloromethane. The organic extract was washed with brine and dried. The crude product was purified on silica gel column using 20% EtOAc/hexane for unreacted starting material followed by CHCl₃/MeOH/Et3N (180/16/1) furnished the 3-(1-methyl-piperidin-4-ylamino)-5-phenyl-thiophene-2-carboxylic acid methyl ester (240 mg, 73%). NMR ¹H (CDCl₃, 400 MHz): 7.64-7.6 (m, 2H), 7.43-7.34 (m, 3H), 6.83 (brs, 2H), 3.83 (s, 3H), 3.46-3.4 (m, 1H), 2.82-2.74 (m, 1H), 2.3 (s, 3H), 2.26-2.2 (m, 4H), 1.72-1.62 (m, 2H).

Step II (a) To a stirred solution of trans-4-methylcyclohexyl acid (656 mg, 4.6 mmol) in dichloromethane (23 mL) was added a solution of oxalyl chloride (2 M, 4.6 mL) in dichloromethane followed by 2-3 drops of DMF (with 22 G needle), After stirred for 2 h, solvent and excess oxalyl chloride was removed on rotavaporator, trace amount of solvents removed under low vacuum (note: the product is very volatile, do not apply vacuum for long time, around 1-2 min). The crude 4-methyl-cyclohexanecarbonyl chloride was immediately used in the next step.

(b) To a stirred solution of the 3-(1-methyl-piperidin-4-ylamino)-5-phenyl-thiophene-2-carboxylic acid methyl ester (540 mg, 1.636 mmol) in 1,2-dichloroethane (15 mL) was added trans-4-methyl-cyclohexanecarbonyl chloride followed by PPh3 (429 mg, 1.635). The resultant reaction mixture was heated for 48 h at 90° C., cooled to room temperature, basified with aq. 10% NaOH solution, and then extracted with dichloromethane. The combined organic extract was washed with brine and dried, concentrated, purified on silica gel column chromatography using 200/90/16/1 (CH₂Cl₂/CHCl₃/MeOH/Et₃N) eluted first 3-[(trans-4-methyl-cyclohexanecarbonyl)-(1-methyl-piperidin-4-yl)-amino]-5-phenyl-thiophene-2-carboxylic acid methyl ester (760 mg, which contaminated with cyclohexyl acid) followed by starting material (270 mg). NMR ¹H (CDCl₃, 400 MHz): 7.64-7.6 (m, 2H), 7.47-7.38 (m, 3H), 7.04 (s, 1H), 4.68-4.58 (m), 3.84 (s, 3H), 2.95-2.8 (m, 2H), 2.26 (s, 3H), 2.2-1.26 (m, 14H), 0.767 (d, J=6.6, 3H), 0.74-0.56 (m, 2H).

Step III

A mixture of 3-[(trans-4-methyl-cyclohexanecarbonyl)-(1-methyl-piperidin-4-yl)-amino]-5-phenyl-thiophene-2-carboxylic acid methyl ester (176 mg, 0.387 mmol) and LiOH.monohydrate (48.8 mg, 1.16 mmol, 4.0 eq) in dioxane: water (3:1, 3.9 mL, 0.1 M) was heated at 50° C. for 5 h, cooled to room temp, acidified with aq.1N HCl, concentrated, diluted with small amount of water and filtered off the product, and then dried (136 mg), which was triturated with hexanes several times to remove 4-methylcyclohexylacid furnished 4-[(2-carboxy-5-phenyl-thiophen-3-yl)-(trans-4-methyl-cyclohexanecarbonyl)-amino]-1-methyl-piperidinium chloride (Compound 11), 101 mg, 60% yield).

NMR ¹H (CD₃OD, 400 MHz): 7.76-7.72 (m, 2H), 7.5-7.38 (m, 4H) 4.8-4.65 (m, 1H), 3.6-3.4 (m, 2H), 3.25-3.2 (m, 2H), 2.8 (s, 3H), 2.3-1.2 (m, 12H), 0.78 (d, J=6.6 Hz, 3H), 0.96-0.58 (m, 2H).

EXAMPLES 25

(4R)-5-(4-Fluoro-phenyl)-3-[isopropyl-(4-methyl-cyclohex-1-enecarbonyl)-amino]-thiophene-2-carboxylic acid Compound 26 and (1R,2S,4R)-5-(4-Fluoro-phenyl)-3-[(2-hydroxy-4-methyl-cyclohexanecarbonyl)-isopropyl-amino]-thiophene-2-carboxylic acid Compound 24.

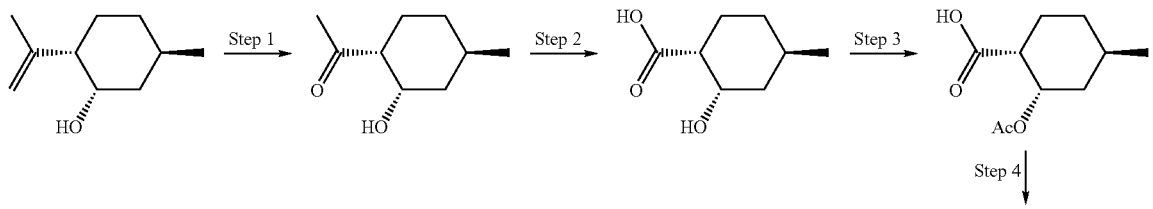

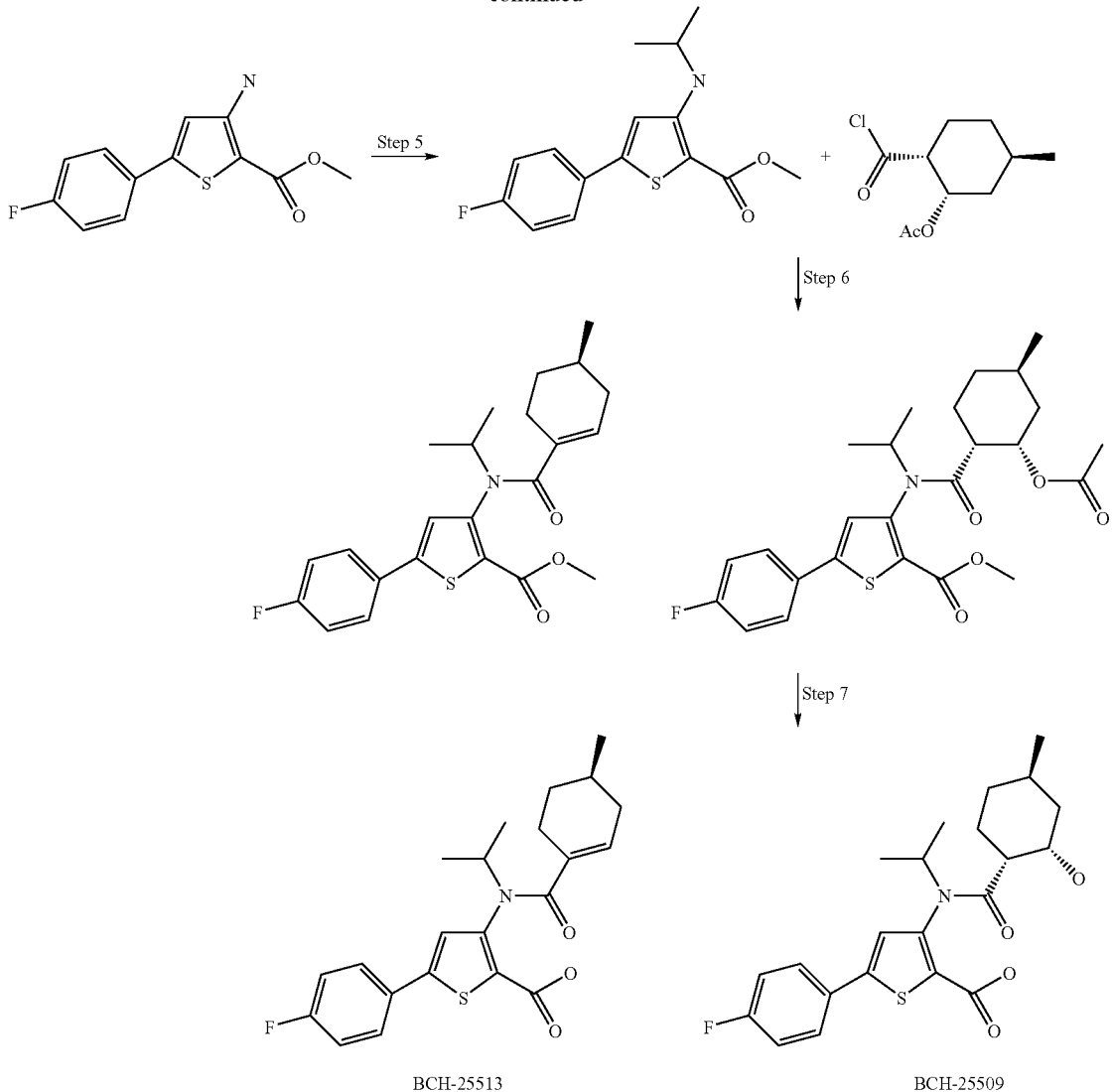

The compound (1S, 2R, 5R)-2-Isopropenyl-5-methyl-cyclohexanol was prepared as described in *Tetrahedron Letter*, (1993), vol.49, pp6429-6436.

NMR $^1$H (CDCl$_3$, 400 MHz) 4.95 ppm (s, 1H); 4.78 ppm (s, 1H); 3.99 ppm (s, 1H); 2.01-1.95 ppm (m, 2H); 1.79 ppm (s, 3H); 1.79-1.66 ppm (m, 3H); 1.48-1.42 ppm (m, 1H); 1.16-1.09 ppm (m, 1H); 1.00-0.87 ppm (m, 2H); 0.88 ppm (d, 3H).

Step I

To the (1S, 2R, 5R)-2-Isopropenyl-5-methyl-cyclohexanol (2.07 g, 13.42 mmol) in DCM (67 mL) and MeOH (1.6 mL) at −78° C. was bubbled ozone/oxygen gas until the reaction mixture was turned blue and the excess ozone was flushed off with oxygen, Dimethyl sulfide (4.9 mL) was added at the same temperature, slowly warmed up to room temperature, stirred for over night, concentrated, purified on column chromatography using 10-20% EtOAc/hexane to give (1R, 2S, 4R)-1-(2-Hydroxy-4-methyl-cyclohexyl)-ethanone (1.40 g, 67%) as an oil. NMR $^1$H (CDCl$_3$, 400 MHz): 4.29-4.27 ppm (m, 1H); 2.40-2.35 ppm (m, 1H); 2.19 ppm (s, 3H); 1.91-1.73 ppm (m, 5H); 1.05-0.91 ppm (m, 2H); 0.88 ppm (d, 3H).

Step II

To a ice-cold solution of NaOH (4.8 g, 119.2 mmol) in water (40 mL) and 1,4-dioxane (30 mL) was added bromine (1.5 mL, 29.57 mmol). To the resultant NaoBr yellow solution was added drop wise a solution (1R, 2S, 4R)-1-(2-Hydroxy-4-methyl-cyclohexyl)-ethanone (1.4 g, 8.962 mmol) in dioxane (130 mL) and water (35 mL). The resulting solution was stirred for 3 h at 10-15° C. The excess NaOBr solution was decomposed by adding a solution of Na$_2$SO$_3$ (1.1 g in 11 mL water), acidified with 10% HCl, extracted with DCM. The combined organic extract was washed with brine, dried and concentrated to give (1R, 2S, 4R)-2-hydroxy-4-methyl-cyclohexanecarboxylic acid (1.30 g, 92%). NMR $^1$H (CDCl$_3$, 400 MHz): 4.34 ppm (s, 1H); 2.43-2.39 ppm (m, 1H); 1.96-1.76 ppm (m, 5H); 1.14-1.08 ppm (m, 1H); 1.02-0.93 ppm (m, 1H); 0.90 ppm (d, 3H).

Step III

To a solution of (1R, 2S, 4R)-2-Hydroxy-4-methyl-cyclohexanecarboxylic acid (162 mg, 1.02 mmol) in dichloromethane (5 ml) was added pyridine (495 ul, 6.12 mmol) followed by acetic anhydride (385 ul, 4.08 mmol). The reaction mixture was stirred for 20 h at room temperature. Then, the solvents were removed and 10 ml of 3N HCl solution was added. This mixture was stirred for 30 minutes and then a saturated solution of NaHCO$_3$ was slowly added until PH=9-10. This solution was then extracted with ethyl acetate (2×5 ml). The aqueous phase was then acidified with a 10% HCl solution and extracted with ethyl acetate (3×5 ml). The following ethyl acetate layers were combined, dried (Na$_2$SO$_4$) and concentrated to obtain 109 mg (53%) of (1R, 2S, 4R)-2-Acetoxy-4-methyl-cyclohexanecarboxylic acid.

NMR $^1$H (CDCl$_3$, 400 MHz): 4.34-4.32 ppm (m, 1H); 2.42-2.37 ppm (m, 1H); 1.95-1.76 ppm (m, 5H); 1.13-1.06 ppm (m, 1H); 1.01-0.92 ppm (m, 1H); 0.89 ppm (d, 3H).

Step IV

To a solution of (1R, 2S, 4R)-2-Acetoxy-4-methyl-cyclohexanecarboxylic acid (109 mg, 0.54 mmol) in dichloromethane (2.7 ml) was added oxalyl chloride (545 ul, 1.09 mmol) followed by 1 drop of dimethylformamide. The reaction mixture was stirred for 4 h at room temperature. The solvents were then removed to obtain 119 mg (99%) of (1R*, 2S*, 4R*)-2-Acetoxy-4-methyl-cyclohexanecarboxylic acid chloride. NMR $^1$H (CDCl$_3$, 400 MHz): 5.45 ppm (s, 1H); 2.46-2.42 ppm (m, 1H); 2.02 ppm (s, 3H); 2.02-1.96 ppm (m, 1H); 1.91-1.76 ppm (m, 3H); 1.70-1.61 ppm (m, 1H); 1.16-1.08 ppm (m, 1H); 0.99-0.88 ppm (m, 1H); 0.87 ppm (d, 3H).

Step V

To a stirred solution of 3-amino-5-(4-fluoro-phenyl)-thiophene-2-carboxylic acid methyl ester (0.502 g, 2.0 mmol) in 1,2-dichloroethane (6.0 mL) was added sequentially 2-methoxypropene (0.38 mL, 4.0 mmol), AcOH (0.114 mL, 2.0 mmol) and NaBH(OAc)3 (0.84 g, 4.0 mmol) and stirred for 2 hrs. It was then diluted with EtOAc and H2O. The aqueous solution was adjusted to pH=7 by adding NaHCO3. The aqueous phase was extracted with EtOAc, the combined extract was washed with brine and dried on MgSO4 and filtered. Purification on bond elute with hexane to 10% EtOAc-hexane furnished 5-(4-fluoro-phenyl)-3-isopropylamino thiophene-2-carboxylic acid methyl ester (0.538 g, 92% yield).

Step VI:

(4R)-5-(4-Fluoro-phenyl)-3-[isopropyl-(4-methyl-cyclohex-1-enecarbonyl)-amino]-thiophene-2-carboxylic acid methyl ester and (1R,2S,4R)-3-[(2-Acetoxy-4-methyl-cyclohexanecarbonyl)-isopropyl-amino]-5-(4-fluoro-phenyl)-thiophene-2-carboxylic acid methyl ester To a solution of 5-(4-fluoro-phenyl)-3-isopropylamino-thiophene-2-carboxylic acid methyl ester (146 mg, 0.50 mmol) in 1,2-dichloroethane (1.5 ml) was added (1R,2S,4R)-2-Acetoxy-4-methyl-cyclohexanecarboxylic acid chloride (119 mg, 0.54 mmol) dissolved in 1,2-dichloroethane (0.5 ml) followed by PPh$_3$ (131 mg, 0.5 mmol). The resulting solution was stirred for 24 h at 90° C. and then cooled to room temperature. It was then diluted with ethyl acetate (10 ml) and a solution of saturated NaHCO$_3$ (10 ml). The aqueous phase was separated and washed with ethyl acetate (2×10 ml) and the combined organic layers were dried (Na$_2$SO$_4$), filtered and concentrated. The residue was purified by flash chromatography (0% to 25% EtOAc/Hexane) to obtain 96 mg as a mixture of title compound.

Step VII

Compounds (95 mg), from step VI was dissolved in a mixture of dioxane:H$_2$O (4:1) (1.0 mL) and then 600 µl of LiOH 1N was added to it. After 24 h at 60° C. the reaction mixture was cooled to room temperature and the solvents were removed. The residue was then partitioned between 10 ml of H$_2$O acidified to pH 4 and 10 ml of EtOAc. The organic layer was separated and the aqueous phase was washed with ethyl acetate (2×10 ml). The combined ethyl acetate layers were dried (Na$_2$SO$_4$), concentrated and the residue was purified by preparative chromatography to obtain (4R)-5-(4-fluoro-phenyl)-3-[isopropyl-(4-methyl-cyclohex-1-enecarbonyl)-amino]-thiophene-2-carboxylic acid (Compound 26) (21 mg). NMR $^1$H (CD$_3$OD, 400 MHz): 7.76-7.68 (m, 2H), 7.3-7.1 (m,3H), 5.78 (brs, 1H), 4.9-4.75 (m, 1H), 2.3-1.4 (m), 1.33 (d, J=4.3, 3H), 1.09 (d, J=4.5, 3H), 0.815 (d, J=3.5, 3H).and (1R, 2S, 4R)-5-(4-Fluoro-phenyl)-3-[(2-hydroxy-4-methyl-cyclohexanecarbonyl)-isopropyl-amino]-thiophene-2-carboxylic acid (Compound 24) (41 mg). NMR $^1$H (CD$_3$OD, 400 MHz): 7.75-7.7 (m, 2H), 7.23 (s, 1H), 7.2-7.15 (m, 2H), 4.9-4.8 (m, 1H), 2.0-1.4 (m, 5H), 1.206 (d, J=6.6, 3H), 1.017 (d, J=6.4, 3H), 0.76 (d, J=6.6, 3H).

EXAMPLE 26

3-[Isopropyl-(5-methyl-3,6-dihydro-2H-pyran-2-carbonyl)-amino]-5-phenyl-thiophene-2-carboxylic acid Compound 30

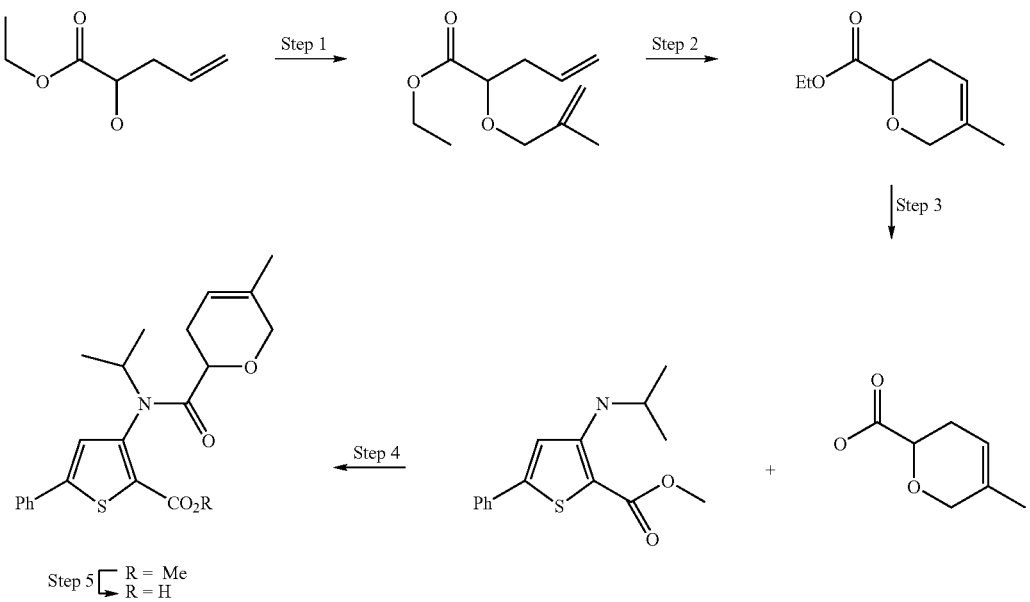

Step I

To a cold (00C) stirred suspension of NaH (55% disperson in oil, 227.9 mg, 5.2 mmol, 1.3 eq) in THF (20 mL) was added drop wise a solution of 2-hydroxy-pent-4-enoic acid ethyl ester (0.576 g, 4.0 mmol) in THF (20 mL) and stirred for 1 h. The reaction mixture was then treated with 3-bromo-2-methylpropene (0.81 g, 6.0 mmol, 0.61 mL), slowly warmed up to rt, and stirred for 1 h. It was carefully quenched with saturated NH$_4$Cl solution. Reaction mixture was extracted with EtOAc (3×20 mL) organic solution was washed with brine, dried (Na$_2$SO$_4$), concentrated. Purification of the residue on silica gel column chromatography using 5% EtOAc-Hexane furnished 2-(2-methyl-allyloxy)-pent-4-enoic acid ethyl ester (0.521 g, 66%) as oil. NMR $^1$H (CDCl$_3$, 400 MHz): 5.9-5.78 (m, 1H), 5.16-5.06 (m, 2H), 4.97 (s, 1H), 4.91 (s, 1H), 4.26-4.16 (m, 2H), 4.072 (d, J=12.3, 1H), 3.93 (t, J=6.5, 1H), 3.813 (d, J=12.4, 1H), 1.15 (s, 3H), 1.28 (t, J=7.2, 3H).

Step II

To a refluxing stirred solution of 2-(2-methyl-allyloxy)-pent-4-enoic acid ethyl ester (396 mg, 2.0 mmol) in CH$_2$Cl$_2$ (100 mL, 0.02 M solution) was added drop wise a solution of the tricyclohexylphosphine (1,3-Bis(2,4,6-trimethylphenyl)-4,5-dihydroimidazol-2-ylidene)(benzylidine)ruthenium (IV) dichloride (85 mg, 0.1 mmol) in CH$_2$Cl$_2$ (3.0 mL). After 50 min, the reaction mixture was cooled to room temperature, concentrated and purified on silica gel bond elute using EtOAc/hexane (1:20) as an eluent furnished 5-methyl-3,6-dihydro-2H-pyran-2-carboxylic acid ethyl ester (320 mg, 92% yield) as a brown oil. NMR $^1$H (CDCl$_3$, 400 MHz): 5.51 (br s, 1H), 4.28-4.08 (m, 4H), 2.32 (brs, 3H), 1.29 (t, J=7.2, 3H).

Step III

A solution of 5-methyl-3,6-dihydro-2H-pyran-2-carboxylic acid ethyl ester (140 mg, 0.823 mmol) in MeOH (3.5 mL) and 10% aq. NaOH (1.0 mL, 2.5 mmol) was heated at 65° C. for 3 h, reaction mixture was cooled to room temperature, solvent was evaporated, diluted with water. The aqueous solution was washed with ether, and acidified with aq. 1 N HCl, extracted with ether. The ethereal solution was washed with brine and dried. Evaporation of the solvent furnished 5-methyl-3,6-dihydro-2H-pyran-2-carboxylic acid (82 mg, 70% yield). NMR $^1$H (CDCl$_3$, 400 MHz): 5.54-5.5 (m, 1H), 4.24-4.1 (m, 3H), 2.4-2.3 (m, 2H), 1.6 (s, 3H).

Step IV

The coupling of 3-isopropylamino-5-phenyl-thiophene-2-carboxylic acid methyl ester (63.3 mg, 0.23 mmol) and 5-methyl-3,6-dihydro-2H-pyran-2-carboxylic acid (40 mg, 0.28 mmol) using PPh3 (78.6 mg, 0.3 mmol) and NCS (39.9 mg, 0.3 mmol) furnished 3-[isopropyl-(5-methyl-3,6-dihydro-2H-pyran-2-carbonyl) -amino]-5-phenyl-thiophene-2-carboxylic acid methyl ester (60 mg, 65.3% yield). NMR $^1$H (CDCl$_3$, 400 MHz, for major rotamer): 7.68-7.62 (m, 2H), 7.4-7.5 (m, 3H), 7.22 (s, 1H), 5.46 (m, 1H), 3.86 (s, 3H), 1.48 (s, 3H), 1.24 (d, 3H), 1.0 (d, 3H)

Step V

Hydrolysis of 3-[isopropyl-(5-methyl-3,6-dihydro-2H-pyran-2-carbonyl)-amino]-5-phenyl-thiophene-2-carboxylic acid methyl ester (38 mg, 0.095 mmol) using LiOH.H20 (12 mg) as described for example 25, step 7 furnished 3-[isopropyl-(5-methyl-3,6-dihydro-2H-pyran-2-carbonyl)-amino]-5-phenyl-thiophene-2-carboxylic acid (Compound 30) (13 mg, 35.5% yield). NMR $^1$H (CD$_3$OD, 400 MHz, for major rotamer): 7.8-7.7 (m, 2H), 7.5-7.3 (m, 4H), 5.45 (brs, 1H), 4.95-4.8 (m, 1H), 2.56-1.82 (m), 1.46 (brs, 3H), 1.26 (d, 3H), 1.2 (d, 3H), 1.0-0.84 (m).

EXAMPLE 27

3-[Isopropyl-(cis-5-methyl-tetrahydro-pyran-2-carbonyl)-amino]-5-phenyl-thiophene-2-carboxylic acid Compound 29 and 3-[Isopropyl-(trans-5-methyl-tetrahydro-pyran-2-carbonyl)-amino]-5-phenyl-thiophene-2-carboxylic acid Compound 27.

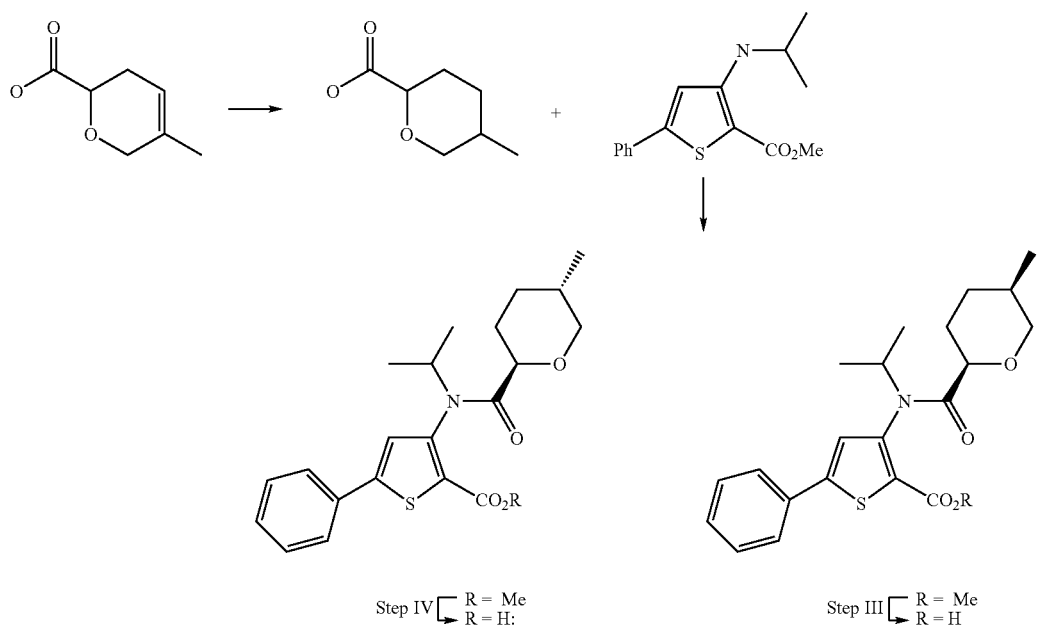

Step I

To a solution of 5-methyl-3,6-dihydro-2H-pyran-2-carboxylic acid (40 mg, 0.28 mmol) in MeOH (2.0 mL) was added 5% Pt-C (20 mg), hydrogenated for 16 h at 20 psi. The reaction mixture was filtered off through celite, washed with MeOH and concentration of the filtrate gave 2:1 ratio of geometrical isomers of 5-methyl-tetrahydro-pyran-2-carboxylic acid (37 mg, 91%).

Step II

Using the procedure as described for example 26, step 4 gave separable mixture of 3-[isopropyl-(cis-5-methyl-tetrahydro-pyran-2-carbonyl)-amino]-5-phenyl-thiophene-2-carboxylic acid methyl ester (30 mg, 35.5%). NMR $^1$H (CDCl$_3$, 400 MHz, For major rotamer): 7.66-7.6 (m, 2H), 7.48-7.36 (m, 3H), 7.162 (s, 1H), 5.0-4.88 (m, 1H), 3.98-3.94 (m), 3.86 (s, 3H), 3.29 (m), 2.18-1.4 (m), 1.25 (d, 3H), 0.98 (d, 3H), 0.72 (d, 3H) and 3-[isopropyl-(trans-5-methyl-tetrahydro-pyran-2-carbonyl)-amino]-5-phenyl-thiophene-2-carboxylic acid methyl ester (14.0 mg, 16.6%). NMR $^1$H (CDCl$_3$, 400 MHz, For major rotamer): 7.65-7.63 (m, 2H), 7.48-7.38 (m, 3H), 7.184 (s, 1H), 4.96-4.86 (m, 1H), 3.86-3.52 (m), 2.55 (t, 1H), 1.96-1.46 (m), 1.218 (d, J=3.7, 3H), 0.985 (d, J=6.7, 3H), 0.657 (d, J=6.7, 3H).

Step III

Hydrolysis of 3-[isopropyl-(cis-5-methyl-tetrahydro-pyran-2-carbonyl)-amino]-5-phenyl-thiophene-2-carboxylic acid methyl ester (30 mg, 0.075 mmol) using LiOH as described for example 25, step 7 gave 3-[isopropyl-(cis-5-methyl-tetrahydro-pyran-2-carbonyl)-amino]-5-phenyl-thiophene-2-carboxylic acid (Compound 29) (13 mg, 44.8%). NMR $^1$H (CD$_3$OD, 400 MHz, For major rotamer): 7.7-7.64 (m, 2H), 7.44-7.3 (m, 3H), 7.15 (s, 1H), 4.88-4.78 (m, 1H), 4.06-4.0 (m, 1H), 3.46-3.4 (m, 1H), 2.06-1.4 (m), 1.24 (d, J=6.7, 3H), 1.057 (d, J=6.9, 3H), 1.01 (d, J=6.7, 3H).

Step IV

3-[Isopropyl-(trans-5-methyl-tetrahydro-pyran-2-carbonyl)-amino]-5-phenyl-thiophene-2-carboxylic acid methyl ester (15 mg, 0.038 mmol) was transformed into 3-[isopropyl-(trans-5-methyl-tetrahydro-pyran-2-carbonyl).-amino]-5-phenyl-thiophene-2-carboxylic acid (Compound 27) (10 mg, 68%) as described for example 25, step 7. NMR $^1$H (CD$_3$OD, 400 MHz, For major rotamer): 7.7-7.64 (m, 2H), 7.44-7.3 (m, 3H), 7.142 (s, 1H), 5.0-4.75 (m), 3.9-3.65 (m), 2.63 (t), 2.0-1.4 (m), 1.24 (d, 3H), 1.07 (d, 3H), 0.67 (d, 3H).

EXAMPLE 28

3-[(trans-4-Methyl-cyclohexanecarbonyl)-(tetrahydro-thiopyran-4-yl)-amino]-5-phenyl-thiophene-2-carboxylic acid Compound 34, 3-[(1,1-Dioxo-tetrahydro-thiopyran-4-yl)-(trans-4-methyl-cyclohexanecarbonyl)-amino]-5-phenyl-thiophene-2-carboxylic acid Compound 37, and Step VII:
3-[(trans-4-Methyl-cyclohexanecarbonyl)-(1-oxo-tetrahydro-thiopyran-4-yl)-amino]-5-phenyl-thiophene-2-carboxylic acid Compound 68.

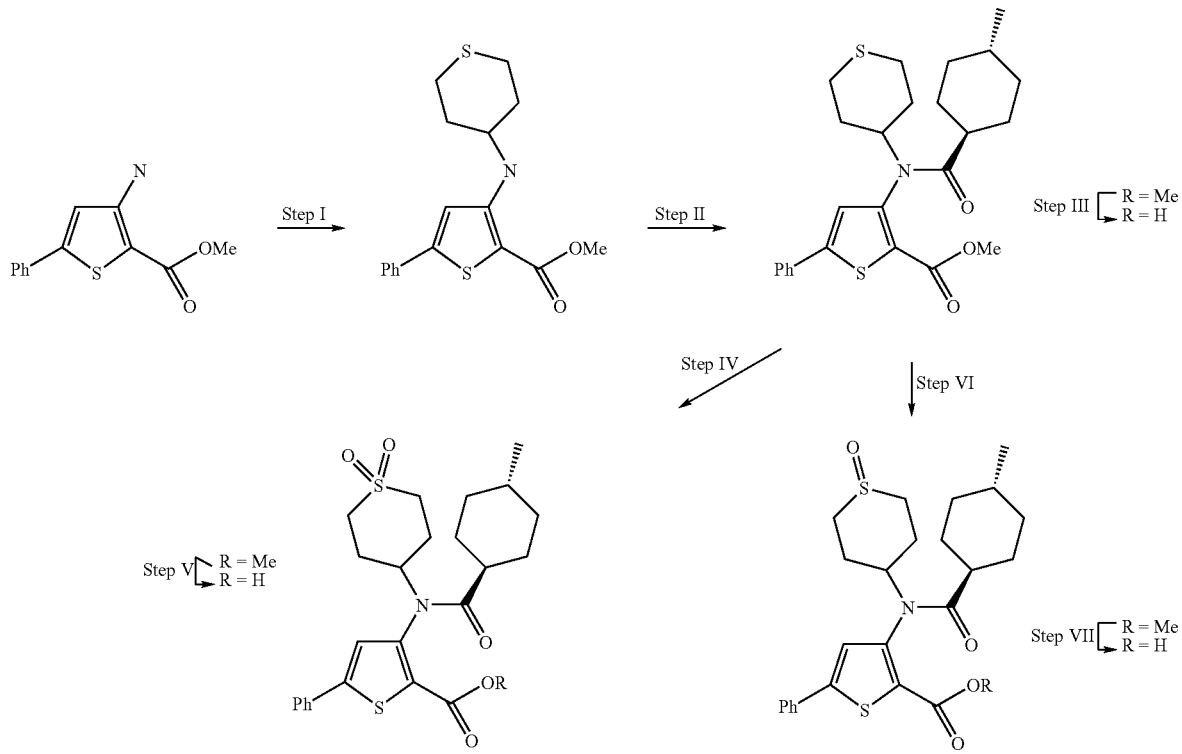

Reductive amination of 3-amino-5-phenyl-thiophene-2-carboxylic acid methyl ester (0.933 g, 4.0 mmol) and tetrahydro-thiopyran-4-one (0.464 g, 4.0 mmol)in THF (1.0 mL) employing $Bu_2SnCl_2$ (60.5 mg, 0.2 mmol) and $PhSiH_3$ (0.476 g, 0.542 mL) was carried out as described for example 13, step 1 gave 5-phenyl-3-(tetrahydro-thiopyran-4-ylamino)-thiophene-2-carboxylic acid methyl ester (0.753 g, 56.3%). NMR $^1$H ($CDCl_3$, 400 MHz): 7.64-7.6 (m, 2H), 7.44-7.34 (m, 3H), 6.9 (brm, 1H), 6.81 (brs, 1H), 3.84 (s, 3H), 3.5-3.4 (m, 1H), 2.85-2.7 (m, 4H), 2.4-2.25 (m, 2H), 1.85-1.7 (m, 2H).

Step II

Amidation of 5-phenyl-3-(tetrahydro-thiopyran-4-ylamino)-thiophene-2-carboxylic acid methyl ester (0.2 g, 0.6 mmol) and 4-Methyl-cyclohexanecarbonyl chloride was carried out as described for example 19, step 2 gave 3-[(trans-4-methyl-cyclohexanecarbonyl)-(tetrahydro-thiopyran-4-yl)-amino]-5-phenyl-thiophene-2-carboxylic acid methyl ester (0.208 g, 75.7%). NMR $^1$H ($CDCl_3$, 400 MHz): 7.68-7.62 (m, 2H), 7.5-7.4 (m, 3H), 7.04 (s, 1H), 4.68-4.58 (m, 1H), 3.86 (s, 3H), 2.9-1.2 (m, 16H), 0.78 (d, 3H), 0.76-0.56 (m, 2H).s Step III Hydrolysis of 3-[(trans-4-methyl-cyclohexanecarbonyl)-(tetrahydro-thiopyran-4-yl)-amino]-5-phenyl-thiophene-2-carboxylic acid methyl ester (60 mg, 0.13 mmol) with LiOH was carried out as described for example 24, step 3 gave 3-[(trans-4-methyl-cyclohexanecarbonyl)-(tetrahydro-thiopyran-4-yl)-amino]-5-phenyl-thiophene-2-carboxylic acid (Compound 34) (38 mg, 65.9%). NMR $^1$H ($CD_3OD$, 400 MHz): 7.76-7.72 (m, 2H), 7.48-7.38 (m, 3H), 7.34 (s, 1H), 4.52-4.42 (brt, 1H), 2.9-2.5 (m, 4H), 1.8-1.2 (m, 9H), 0.773 (d, J=6.4, 3H), 0.76-0.56 (m, 2H).

Step IV

To a ice-cold stirred solution of 3-[(trans-4-methyl-cyclohexanecarbonyl)-(tetrahydro-thiopyran-4-yl)-amino]-5-phenyl-thiophene-2-carboxylic acid methyl ester (119 mg, 0.26 mmol) from step 2 in DCM (1.0 mL) was added m-chloroperbenzoic acid (90 mg,60%, 0.312 mmol) in one portion, and stirred for 1 h. Reaction mixture was then diluted with DCM, washed with saturated aq. $NaHCO_3$, brine, dried and concentrated. Purification of the residue on preparative TLC using 50% EtOAc-hexane as an eluent gave 3-[(1,1-dioxo-tetrahydro thiopyran-4-yl)-(trans-4-methyl-cyclohexanecarbonyl)-amino]-5-phenyl-thiophene-2-carboxylic acid methyl ester (88 mg, 69%)as a white solid. NMR $^1$H ($CDCl_3$, 400 MHz): 7.68-7.6 (m, 2H), 7.5-7.4 (m, 3H), 7.03 (s, 1H), 4.96-4.84 (m, 1H), 3.86 (s, 3H), 3.28-2.94 (m, 4H), 2.36-1.2 (m, 11H), 0.776 (d, J=4.8, 3H), 0.76-0.54 (m, 2H).

Step V

Hydrolysis of 3-[(1,1-dioxo-tetrahydro-thiopyran-4-yl)-(4-methyl-cyclohexanecarbonyl)-amino]-5-phenyl-thiophene-2-carboxylic acid methyl ester (47 mg, 0.095 mmol)with LiOH was carried out as described for example 25, step 7 gave 3-[(1,1-dioxo-tetrahydro-thiopyran-4-yl)-(trans-4-methyl-cyclohexanecarbonyl)-amino]-5-phenyl-thiophene-2-carboxylic acid (Compound 37) (38 mg,84%). NMR $^1$H ($CD_3OD$, 400 MHz): 7.697 (d, J=7.17, 2H), 7.426 (t, 2H), 7.35 (t, 1H), 7.23 (s, 1H), 4.72 (brt, 1H), 3.4-3.26 (m, 2H), 3.3-2.54 (m, 2H), 2.48-2.14 (m, 4H), 1.96-1.2 (m, 8H), 0.76-0.56 (m, 2H), 0.776 (d, J=6.6, 3H).

Step VI

To a stirred solution of 3-[(trans-4-methyl-cyclohexanecarbonyl)-(tetrahydro-thiopyran-4-yl)-amino]-5-phenyl-thiophene-2-carboxylic acid methyl ester (57 mg, 0.124 mmol)in EtOH (1.2 mL) from step 2 was added magnesium monoperoxyphthalic acid (29.6 ing, 0.06 mmol) in one portion, stirred for 24 h. Reaction mixture was diluted with water, extracted with EtOAc. The combined organic solution was washed with brine, dried, and concentrated. Purification of the residue on Preparative TLC using 5% MeOH-DCM gave 3-[(trans-4-methyl-cyclohexanecarbonyl)-(1-oxo-4tetrahydro-thiopyran-4-yl)-amino]-5-phenyl-thiophene-2-carboxylic acid methyl ester (30 mg, 51%). NMR $^1$H ($CDCl_3$, 400 MHz, For major isomer): 7.66-7.6 (m, 2H), 7.5-7.4 (m, 3H), 7.09 (s, 1H), 4.84-4.76 (t, 1H), 3.85 (s, 3H), 3.4-1.2 (m), 0.772 (d, J=6.6, 3H), 0.74-0.56 (m, 2H).

Step VII

Hydrolysis of 3-[(trans-4-methyl-cyclohexanecarbonyl)-(1-oxo-tetrahydro-thiopyran-4-yl)-amino]-5-phenyl-thiophene-2-carboxylic acid methyl ester (30 mg, 0.063 mmol)with LiOH was carried out as described for example 25, step 7 gave 3-[(trans-4-methyl-cyclohexanecarbonyl)-(1-oxo-tetrahydro-thiopyran-4-yl)-amino]-5-phenyl-thiophene-2-carboxylic acid (Compound 68) (15 mg, 51.8%). NMR $^1$H ($CD_3OD$, 400 MHz, For major isomer): 7.76-7.7 (m, 2H), 7.5-7.38 (m, 3H), 7.39 (s, 1H), 4.74-4.56 (m, 1H), 3.5-1.2 (m), 0.782 (d, J=6.4, 1H), 0.75-0.55 (m, 2H).

EXAMPLE 29

5-(4-Chloro-phenyl)-3-[(4-methyl-cyclohexanecarbonyl)-(1-methyl-piperidin-4-yl)-amino]-thiophene-2-carboxylic acid Compound 57

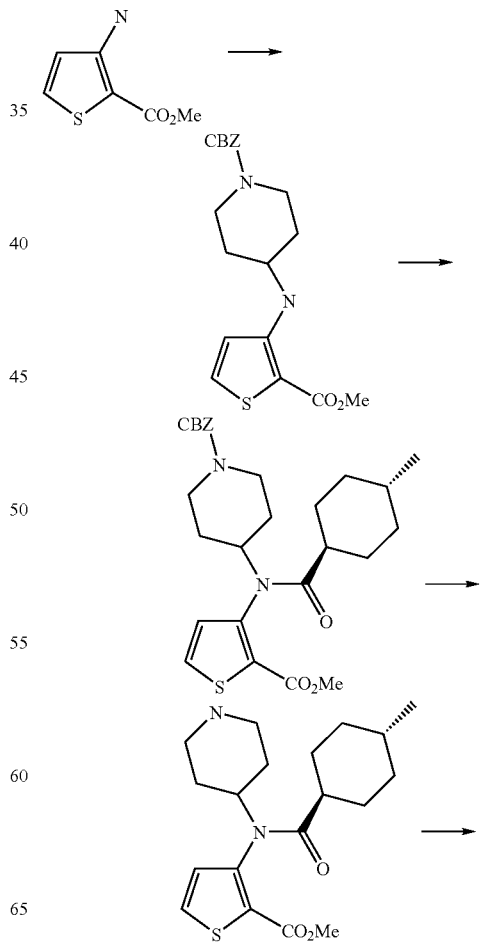

75

-continued

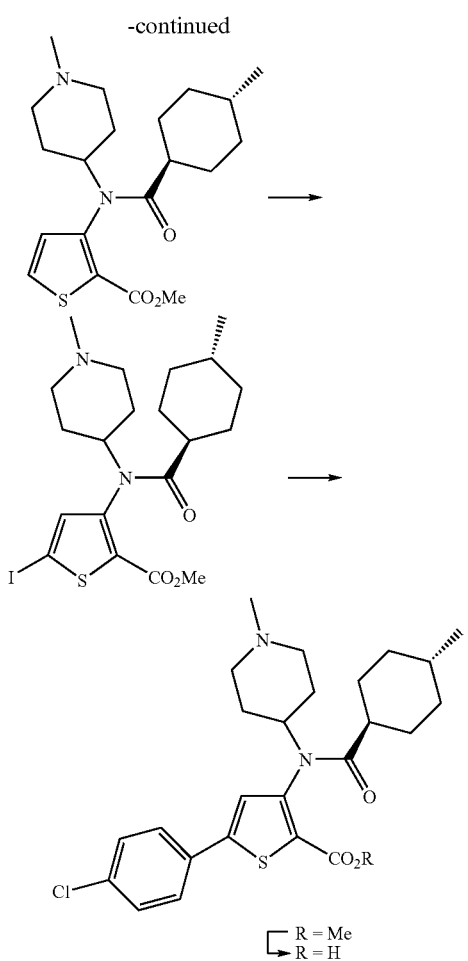

☐ R = Me
☐ R = H

Step I

Reductive amination of 3-amino-thiophene-2-carboxylic acid methyl ester (3.0 g, 19.1 mmol) and 4-oxo-piperidine-1-carboxylic acid benzyl ester (4.46 g, 19.1 mmol)in THF (4.6 mL) employing $Bu_2SnCl_2$ (0.598 g, 1.92 mmol) and $PhSiH_3$ (2.58 mL, 21.6 mmol) was carried out as described for example 19, step I gave 4-(2-methoxycarbonyl-thiophen-3-ylamino)-piperidine-1-carboxylic acid benzyl ester (7.25 g, quantitative). NMR $^1$H ($CDCl_3$, 400 MHz): 7.4-7.3 (m, 6H), 6.9-6.78 (m, 1H), 6.7-6.6 (m, 1H), 5.14 (s, 2H), 4.15-4.0 (m, 2H), 3.81 (s, 3H), 3.6-3.45 (m), 3.1 (brt, 2H), 2.1-1.9 (m, 2H), 1.6-1.45 (m, 2H).

Step II

Amidation of 4-(2-methoxycarbonyl-thiophen-3-ylamino)-piperidine-1-carboxylic acid benzyl ester (3.7 g, 10 mmol) and cyclochexyl chloride was carried out as described for example 19, step II gave 4-[(2-methoxycarbonyl-thiophen-3-yl)-(trans-4-methyl-cyclohexanecarbonyl)-amino]-piperidine-1-carboxylic acid benzyl ester (3.0 g, 60%). NMR $^1$H ($CDCl_3$, 400 MHz): 7.55 (d, 1H), 7.36-7.26 (m, 5H), 6.82 (d, 1H), 5.05 (brs, 2H), 4.82-4.7 (m, 1H), 4.31-4.1 (m, 2H), 3.82 (s, 3H), 2.8-2.75 (m, 2H), 1.9-0.9 (m, 11H), 0.78 (d, 3H), 0.74-0.5 (m, 2H).

Step III

Hydrogenation of 4-[(2-methoxycarbonyl-thiophen-3-yl)-(trans-4-methyl-cyclohexanecarbonyl)-amino]-piperidine-1-carboxylic acid benzyl ester (3.0 g, 6.02 mmol)with Pd/black in EtOAc was carried out for 36 h at 40 psi was carried out as described for example 19, step III gave

76

3-[(trans-4-methyl-cyclohexanecarbonyl)-piperidin-4-yl-amino]-thiophene-2-carboxylic acid methyl ester (1.0 g, 45.6%). NMR $^1$H ($CDCl_3$, 400 MHz): 7.525 (d, J=5.3, 1H), 6.84 (d, J=5.3, 1H), 4.674 (tt, 1H), 3.81 (s, 3H), 3.1-2.94 (m, 2H), 2.74-2.6 (m, 2H), 2.26-2.2 (m, 1H), 1.9-1.0 (m, 11H), 0.75 (d, J=6.6, 3H), 0.7-0.5 (m, 2H).

Step IV

To a stirred solution of 3-[(trans-4-methyl-cyclohexanecarbonyl)-piperidin-4-yl-amino]-thiophene-2-carboxylic acid methyl ester (1.0 g, 2.7 mmol), from step 3, in 1,2-dichloroethane (10 mL) was sequentially added aq. 37% HCHO solution (0.45 mL, 5.4 mmol) and $NaBH(OAc)_3$ (2.86 g, 13.5 mmol) in one portion, stirred for over night, reaction was then quenched with aq. 10% NaOH solution, extracted with DCM. The combined organic extract was washed with brine, dried, and concentrated to obtain 3-[(trans-4-methyl-cyclohexanecarbonyl)-(1-methyl-piperidin-4-yl)-amino]-thiophene-2-carboxylic acid ethyl ester (0.876 g, 85.5%) as a white solid. NMR $^1$H ($CDCl_3$, 400 MHz): 7.54 (d, 1H), 6.86 (d, 1H), 4.7-4.6 (m, 1H), 3.85 (s, 3H), 2.9-2.7 (m, 2H), 2.22 (s, 3H), 2.15-1.1 (m, 14 H), 0.8 (d, 3H), 0.75-0.5 (m, 2H).

Step V

To a stirred solution of diisopropyl amine (0.3 mL, 2.14 mmol) in THF (10 mL) was added n-BuMgCl (2.0 M in ether, 1.0 mL, 2.0 mol), stirred for 24 h. To the resultant solution was added drop wise a solution of 3-[(trans-4-methyl-cyclohexanecarbonyl)-(1-methyl-piperidin-4-yl)-amino]-thiophene-2-carboxylic acid methyl ester (0.189 g, 0.5 mmol) in THF (2.0 mL), stirred for 1 h at room temperature. It was then added a solution of Iodine (1.28 g, 5.0 mmol) in THF (2.0 mL), stirred for 1 h. Reaction mixture was then quenched with 10% aq $Na_2S_2O_3$ solution, extracted with EtOAc, washed with brine, dried, and concentrated. Purification of the residue on small plug of silica gel bond elute using DCM/$CHCl_3$/MeOH/$Et_3N$ (200:90:16:1) as eluent gave 5-iodo-3-[(trans-4-methyl-cyclohexanecarbonyl)-(1-methyl-piperidin-4-yl)-amino]-thiophene-2-carboxylic acid methyl ester (0.250 g, quantitative). NMR $^1$H ($CDCl_3$, 400 MHz): 7.05 (s, 1H), 4.68-4.55 (m, 1H), 3.83 (s, 3H), 2.95-2.8 (m, 2H), 2.26 (s, 3H), 2.2-1.1 (m, 14 H), 0.819 (d, J=6.3, 3H), 0.75-0.6 (m, 2H).

Step VI

To the mixture of 4-chlorophenylboronic acid (46.9 mg, 0.3 mmol) and 5-iodo-3-[(trans-4-methyl-cyclohexanecarbonyl)-(1-methyl-piperidin-4-yl)-amino]-thiophene-2-carboxylic acid methyl ester (50 mg, 0.099 mmol), from step 5, in 5:1 mixture of toluene/MeOH (2.0 mL) was added a solution of $Pd(PPh_3)_4$ (12.0 mg, 0.01 mmol, 10 mol %) in toluene (1.0 mL) followed by aqueous 2M $Na_2CO_3$ solution (0.1 mL, 0.2 mmol). The resultant reaction mixture was heated at 70° C. for 16 h, cooled to room temperature, filtered off through $MgSO_4$ and washed with EtOAc. Evaporation of the solvent and purification of the residue over preparative TLC (1 mm, 60A°) using DCM/$CHCl_3$/MeOH/$Et_3N$ (100:90:16:1) as an eluent furnished 5-(4-chloro-phenyl)-3-[(trans-4-methyl-cyclohexanecarbonyl)-(1-methyl-piperidin-4-yl)-amino-]-thiopene-2-carboxylic acid methyl ester (35.0 mg, 71.5% yield). NMR $^1$H ($CDCl_3$, 400 MHz): 7.53 (d, J=8.3, 2H), 7.4 (d, J=8.5, 2H), 7.0 (s, 1H), 4.67-4.58 (m, 1H), 3.84 (s, 3H), 2.82-2.64 (m, 1H), 2.2 (s, 3H), 2.14-1.35 (m), 0.763 (d, J=6.6, 3H), 0.76-0.56 (m, 2H).

Step VII

Hydrolysis of 5-(4-chloro-phenyl)-3-[(trans-4-methyl-cyclohexanecarbonyl)-(1-methyl-piperidin-4-yl)-amino]-thiophene-2-carboxylic acid methyl ester (19 mg, 0.039 mmol) with LiOH was carried out as described at example 25, step VII gave 5-(4-chloro-phenyl)-3-[(4-methyl-cyclohexanecarbonyl)-(1-methyl-piperidin-4-yl)-amino]-thiophene-2- carboxylic acid (Compound 57) (9.0 mg, 48.6%). NMR ¹H (CD₃OD 400 MHz): 7.761 (d, J=8.8, 2H), 7.487 (d, J=8.5, 2H), 7.476 (s, 1H), 4.7 (t, 1H), 3.59-3.49 (m, 2H), 3.2-3.11 (m, 2H), 2.81 (s, 3H), 2.3-1.2 (m, 12H), 0.791 (d, J=6.59, 3H), 0.88-0.5 (m, 2H). Using similar sequence, Compound 45, Compound 54, Compound 55, Compound 56 and Compound 58 have been prepared.

EXAMPLE 30

3-[[1-(4-Methoxy-benzyl)-2-oxo-piperidin-4-yl]-(4-methyl-cyclohexanecarbonyl)-amino]-5-phenyl-thiophene-2-carboxylic acid Compound 42

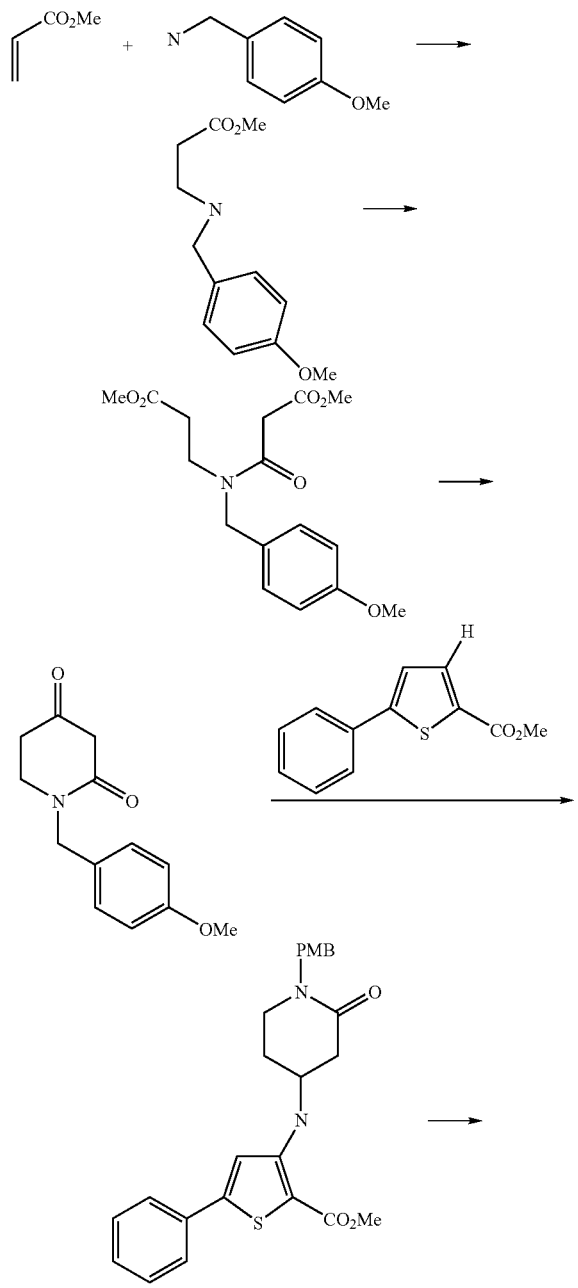

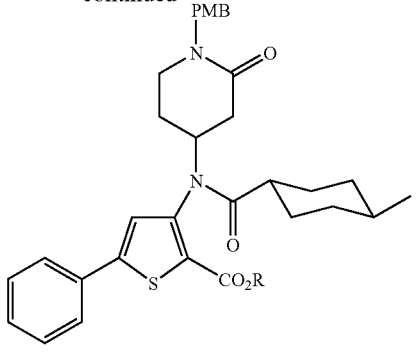

PMB = p-methoxybenzyl

Step I

A solution of p-methoxybenzyl amine (690 mg, 722 μL, 8.01 mmol) in dry methanol (5 ml), under nitrogen was cooled to 0° and treated drpwise with a solution of metacrylate (951 μL, 1.0 g, 7.28 mmol) in MeOH (1.0 ml) added over 2 min. After 15.5 h the clear solution was distilled at atmospheric pressure to remove MeOH. The high boiling residue (>170) formed 3-(4-Methoxy-benzylamino)-propionic acid methyl ester (1.88 g, Quantitative) ¹H (300 MHz, CDCl₃) 1.78 (bs, 1H), 2.45 and 2.53 (t, J=3.0 Hz, 2H), 2.77 and 2.87 (t, J=3.0 Hz, 2H), 3.46 and 3.67 (s, 3H), 3.64 and 3.73 (s, 3H), 3.88 (m, 2H), 6.78 and 6.85 (m, 2H), 7.17 and 7.23 (m, 2H).

Step II

A solution of neat dimethylmalonate (7.4 ml, 8.5 g, 64 mmol,8 eq) was heated in a flask to 170°, under and then treated dropwise, over 40 min, with a solution of 3-(4-Methoxy-benzylamino)-propionic acid methyl ester in dimethylmalonate (0.92 ml). The reaction was heated at 169-170 for 1.5 h when tlc showed complete loss of starting amine to a less polar compound. On cooling the crude material was applied to a column of silica and eluted first with CH₂Cl₂ to remove excess dimethylmalonate and then with (Hexane:CH₂Cl₂:EtOAc=1:1:1). N-(4-methoxy-benzyl)-N-(2-methoxycarbonyl-ethyl)-malonamic acid methyl ester was collected as a colourless oil (1.502 g, 58%); (300 MHz, CDCl₃) 2.52 and 2.61 (t, J=6.0 Hz, 2H), 3.62 and 3.70 (s, 3H), 3.65 and 3.74 (s, 3H), 3.77 and 3.78 (s, 3H), 4.50 and 4.54 (s, 2H), 6.82-6.88 (m, 2H), 7.68 and 7.18 (m, 2H).

Step III

A mixture of anhydrous K₂CO₃ (3.2 g, 23.2 mmol, 5 eq) and 18-crown-6 (azetroped several times with toluene) (122 mg, 0.464 mmol, 10 mol %) in dry toluene (4 ml), under nitrogen, was heated to reflux and then treated, dropwise, over 40 min, with a solution of N-(4-Methoxy-benzyl)-N-(2-methoxycarbonyl-ethyl)-malonamic acid methyl ester. After 7 h at reflux the reaction was diluted with water (4 ml) and toluene (4 ml), then cooled to 0° and carefully acudified to pH 1.7 with 0.1N HCl. The mixture was then extracted several times with CH₂Cl₂ (3×80 ml) and the combined organics dried and evaporated to a brown oil (1.33 g). The brown oil was treated with 10% aqueous oxalic acid and heated to reflux for 6.5 h. The mixture was then extracted reprated ly with CH$_2$Cl$_2$ and the combined organics dried and evaporated to a dirty yellow oil (1.03 g). The crude material was purified on silica gel using (CH$_2$Cl$_2$:MeOH=30:1) as eluent to give 1-(4-Methoxy-benzyl)-piperidine-2,4-dione as a pale brown solid (750 mg, 69%); (300 MHz, CDCl$_3$) 2.52 (t, J=5.7 HZ, 2H), 3.41 (s, 2H), 3.47 (t, J=5.7 Hz, 2H), 3.80 (s,3H), 4.62 (s, 2H), 6.16-6.88 (m, 2H), 7.20 (m, 2H).

Step IV

A suspension of methyl 3-amino,5-phenylthiophene 2-carboxylate (459 mg, 1.96 mmol) and 1-(4-Methoxy-benzyl)-piperidine-2,4-dione (457 mg, 1.96 mmol) at 21°, under N$_2$, was treated with dibutyltin dichloride (29 mg, 0.098 mmol, 5 mol %) followed after 5 min with phenylsilane (266□L, 233 mg, 2.15 mmol, 1.1 eq). The heterogenous mixture was stirred for 18 h at 21° when a clear solution resulted. The reaction was left a further 5 h, then evaporated to a thick oil (1.27 g). The crude material was purified over silica using (Hexanes:CH$_2$Cl$_2$:EtOAc=1:1:1) as eluent to deliver 3-[1-(4-Methoxy-benzyl)-2-oxo-piperidin-4-ylamino]-5-(1-methyl-hexa-1,3,5-trienyl)-thiophene-2-carboxylic acid methyl ester as a yellow foam (432 mg, 49%) (300 MHz, CDCl$_3$) 1.8-1.9 (m, 1H), 2.25-2.44 (m, 1H), 2.95 (dd, J=1.5 Hz, J=3.90 Hz, 1H), 3.98 (dd, J=1.5 Hz, J=3.90 Hz, 1H), 3.22-3.40 (m, 4H), 3.80 (s,3H), 3.33 (s,3H), 3.85-3.93 (m, 1H), 4.08 (m, 2H), 6.81 (s, 1H), 6.85-6.9 (m, 2H), 7.20-7.24 (m, 2H), 7.36-7.42 (m, 3H), 7.59-7.61 (m, 2H).

Step V

A solution of trans 4-methylcyclohexane carboxylic acid (56 mg, 0.399 mmol, 1.2 eq)in 1,2-dichloroethane (1 ml) at 0°, under N2, was treated with oxalyl chloride (2.0M solution in CH$_2$C$_{12}$)(231 μl, 0.46 mmol, 1.4 eq), followed by dimethylformamide (8 μl, 7 mg, 0.1 mmol, 30 mol %). After 1 h the reaction was treated with a solution of 3-[1-(4-Methoxy-benzyl)-2-oxo-piperidin-4-ylamino]-5-(1-methyl-hexa-1,3,5-trienyl)-thiophene-2-carboxylic acid methyl ester (150 mg, 0.33 mmol) in DCE (2 ml). The reaction was then placed in abth at 90° and left at reflux overnight for 21 h. The reaction was stripped-off solvent and the residue (212 mg) was purified by bond elute chromatography using (Hexane:CH$_2$Cl$_2$:EtOAc=1:1:1) as eluent to give 3-[[1-(4-Methoxy-benzyl)-2-oxo-piperidin-4-yl]-(4-methyl-cyclohexanecarbonyl)-amino]-5-(1-methyl-hexa-1,3,5-trienyl)-thiophene-2-carboxylic acid methyl ester (21 mg, 11%) as a yellow foam; (300 MHz, CDCl$_3$)0.55-0.73 (m, 1H), 0.77 (d, J=5.4 Hz, 3H), 1.26-1.30 (m, 12H), 1.94-2.12 (m, 1H), 2.14-2.19 (m, 1H), 2.40 (dd, J=9.0 Hz, J=12.0 Hz, 1H), 2.64-2.70 and 2.80 and 2.84 (m, 1H), 3.10-3.15 (m, 3H), 3.79-3.82 (m, 1H), 3.78 (s, 3H), 3.83 and 3.87 (s, 3H), 4.32 (t, J=12.0 Hz, 1H), 4.62 (dd, J=5.7 Hz, J=10.8 Hz, 1H), 4.50-5.0 (m, 1H), 6.79-6.83 (m, 2H), 6.99-7.14 (m, 2H), 7.26-7.48 (m, 3H), 7.61-7.65 (m, 2H).

Step VI

3-[[1-(4-Methoxy-benzyl)-2-oxo-piperidin-4-yl]-(4-methyl-cyclohexanecarbonyl)-amino]-5-phenyl-thiophene-2-carboxylic acid methyl ester (40 mg,0.069 mmol)was hydrolysed with LiOH as described previously at example 25, step VII to deliver 3-[[1-(4-Methoxy-benzyl)-2-oxo-piperidin-4-yl]-(4-methyl-cyclohexanecarbonyl)-amino]-5-phenyl-thiophene-2-carboxylic acid (Compound 42) as a white solid (8.4 mg, 21%); (300 MHz, Acetone-d$_6$) 0.42-0.62 (m, 1H), 0.64 (d, J=4.18 Hz, 3H), 1.16-1.34 (m, 7H), 1.40-1.54 (m, 4H), 1.58-1.66 (m, 2H), 1.76-1.78 (m, 1H), 1.87-1.90 (m, 1H), 1.98-1.99 (m, 1H), 2.08-2.09 (m, 1H), 3.63 (s, 3H), 4.23 (dd, J=5.7 Hz, J=12.0 Hz, 1H), 4.44(dd, J=1.5 Hz, J=11.7 Hz, 1H), 4.66-4.80 (m, 1H), 6.20-6.23 (m, 2H), 7.04-7.07 (m, 2H), 7.31-7.40 (m, 3H), 7.44 and 7.53 (s, 1H), 7.69-7.75(m, 2H).

EXAMPLE 31

3-[(1-Methanesulfonyl-piperidin-4-yl)-(4methylcyclohexanecarbonyl)-amino]-5-phenyl-thiophene-2-carboxylic acid Compound 70

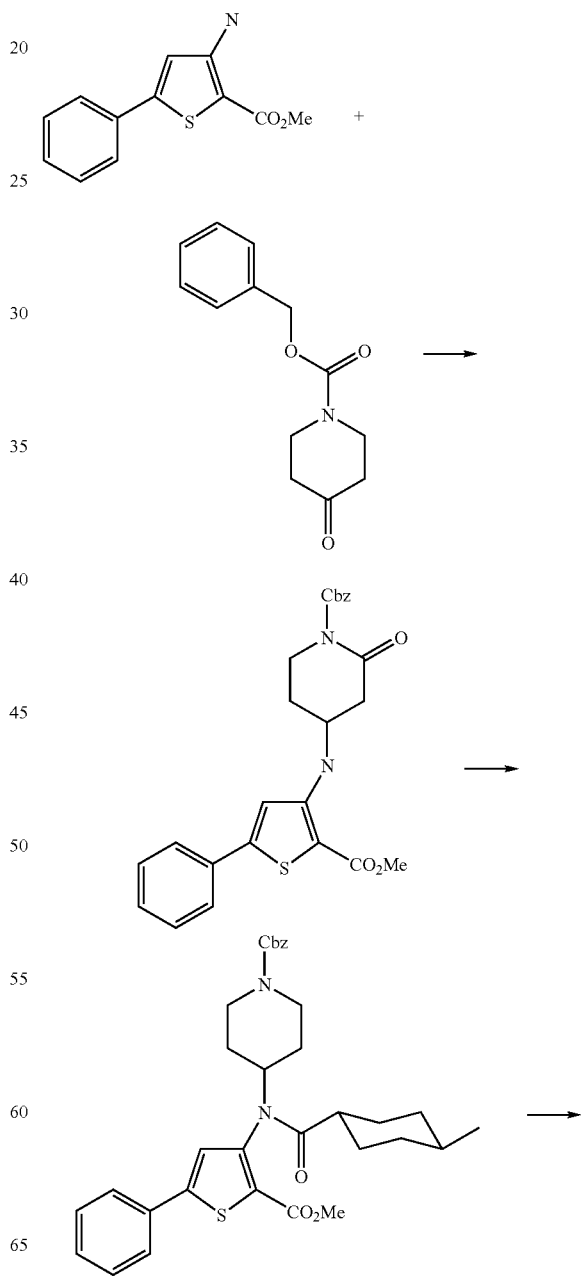

81

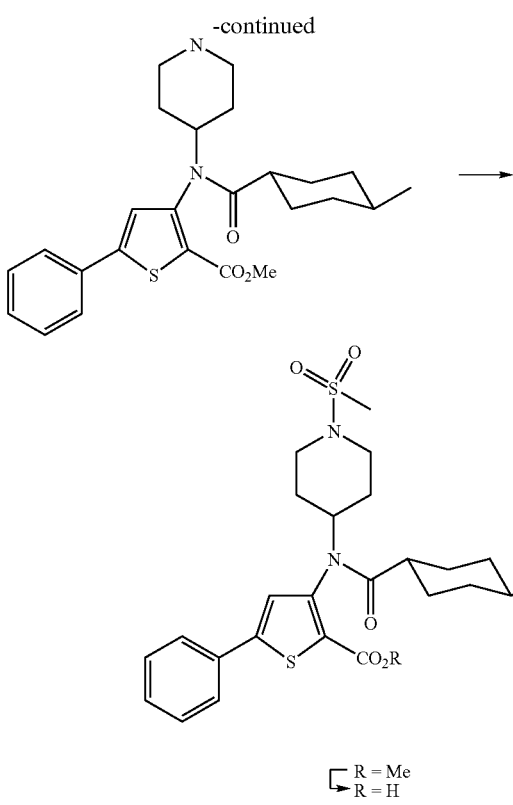

CBZ = benzyloxycarbonyl

Steps I to III were conducted in a similar manner as described in example 30.

Step IV

A solution of 3-[(1-piperidin-4-yl)-(4-methylcyclohexanecarbonyl)-amino]-5-phenyl-thiophene-2-carboxylic acid methyl ester (44 mg, 0.1 mmol) in DCM (1.0 ml, ca 0.1M) at 21° under $N_2$, was treated with triethylamine (29 □L, 21 mg, 0.21 mmol, 2.1 eq) followed by methanesufonyl chloride (15.5 □L, 23 mg, 0.2 mmol, 1.2 eq). A slight precipitate was evident. After 1.5 h the reaction was complete. The mixture was diluted with DCM and washed sequentially with N HCl, water, brine and dried. Evaporation of the organic extract yielded a gum (56 mg) which was purified on bond-elute silica using (Hexane:$CH_2C_{12}$:EtOAc=1:1:1) as eluent to afford 3-[(1-Methanesulfonyl-piperidin-4-yl)-(4-methylcyclohexanecarbonyl)-amino]-5-phenyl-thiophene-2-carboxylic acid methyl ester (40 mg, 78%); $^1$H (300 MHz, $CDCl_3$) 0.50-0.67 (m, 1H), 0.70 (d, J=4.8 Hz, 3H), 1.16-1.43 (m, 6H), 1.48-1.64 (m, 10H), 1.80-1.86 (m, 1H), 1.90-2.0 (m, 1H), 2.62-2.759 (m, 2H), 2.68 (s, 3H), 3.68-3.75 (m, 1H), 3.76-3.82 (m, 1H), 3.85 (s, 3H), 4.61-4.71 (m, 1H), 6.94 (s, 1H), 7.35-7.43 (m, 3H), 7.55-7.59 (m, 2H).

Step V

A solution of 3-[(1-Methanesulfonyl-piperidin-4-yl)-(4-methylcyclohexanecarbonyl)-amino]-5-phenyl-thiophene-2-carboxylic acid methyl ester (40 mg, 0.077 mmol) was hydrolysed as described before with lithium hydroxide (2M, 114 µL, 5.5 mg, 0.23 mmol) to give after acidic work-up 3-[(1-Methanesulfonyl-piperidin-4-yl)-(4-methylcyclohex-

82 ane-carbonyl)-amino]-5-phenyl-thiophene-2-carboxylic acid (29 mg, 74%) as a colourless powder; $^1$H (300 MHz, MeOD) 0.56-0.72 (m,$_1$H), 0.79 (d, J=4.8 Hz, 3H), 1.23-1.44 (m, 5H), 1.51-1.79 (m, 6H), 1.92-1.98 (m, 1H), 2.04-2.14 (m, 2H), 2.78-2.90 (m, 2H), 2.80 (s, 3H), 3.66-3.74 (m, 1H), 3.75-3.81 (m, 1H), 4.52-4.62 (m, 1H), 7.39 (s, 1H), 7.40-7.90 (m, 3H), 7.73-7.77 (m, 2H).

EXAMPLE 32

3-[(2-Amino-1-methyl-ethyl)-(4-methyl-cyclohexanecarbonyl)-amino]-5-(1-methyl-hexa-1,3,5-trienyl)-thiophene-2-carboxylic acid Compound 36.; 3-[(2-Azido-1-methyl-ethyl)-(4-methyl-cyclohexanecarbonyl)-amino]-5-(1-methyl-hexa-1,3,5-trienyl)-thiophene-2-carboxylic acid Compound 32.

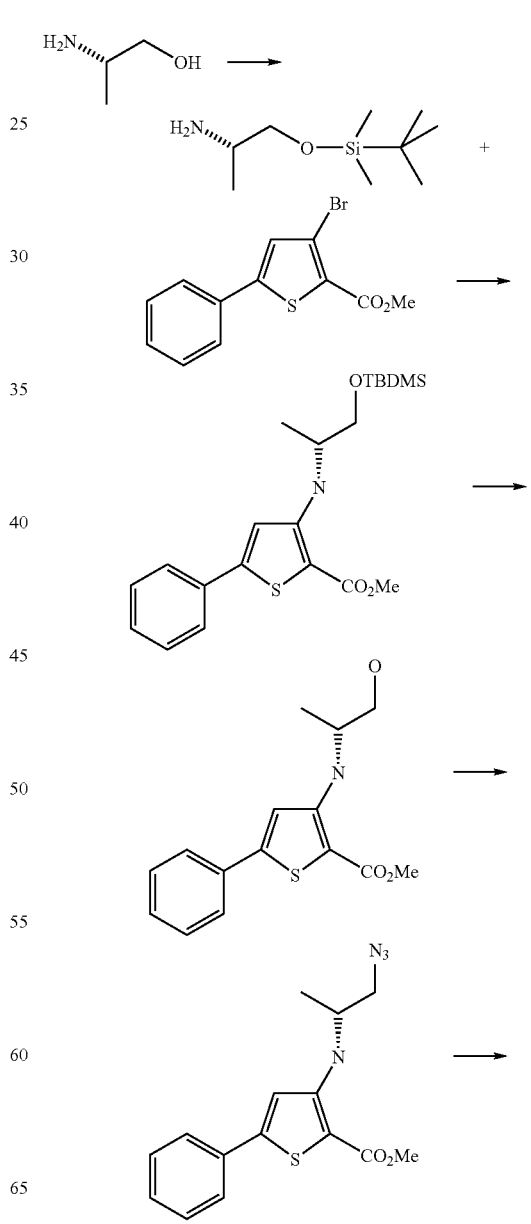

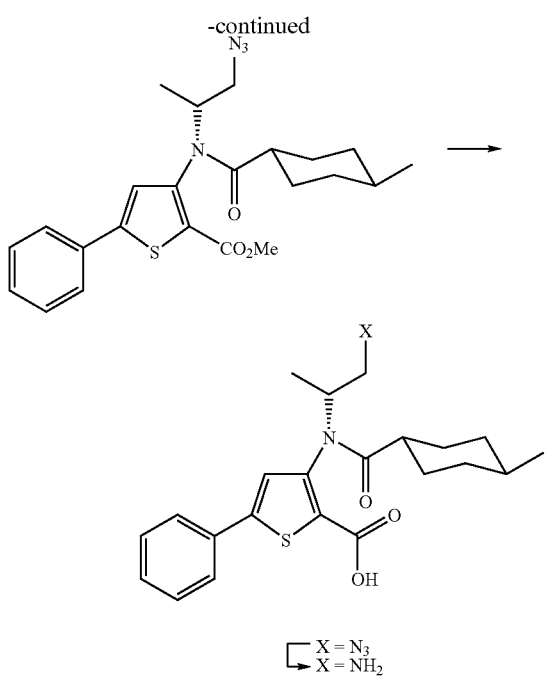

X = N₃
X = NH₂

Step I

A mixture of (S)-(+) 2-amino-1-propoanol (1.04 g, 13.85 mmol), tert butyldimethylsilyl chloride (2.09 g, 13.85 mmol) and triethylamine (2 ml, 1.05 eq) was stirred in DCM overnight ca 16 h. The reaction was diluted with DCM, washed with water, satd. NH₄Cl, brine, dried and evaporated to an oil. Silica gel purification of the crude using 3% MeOH/CH₂Cl₂ as eluent provided 2-(tert-Butyl-dimethyl-silanyloxy)-1-methyl-ethylamine (1.76 g, 80%); ¹H NMR (300 MHz, CDCl₃) 0.0 (s, 6H), 0.82 (s,9H), 0.99 (d, J=6.5 Hz, 3H), 2.22 (bs, 2H), 2.98 (bs, 1H), 3.30 (dd, J=10 Hz, J=17.0 Hz, 1H), 3.48 (dd, J=10.0 Hz, J=4.3 Hz, 1H).

Step II

A solution of methyl 3-bromo 5-phenylthiophene 2-carboxylate (0.5 g, 1.6 mmol) in toluene(10 ml) was treated at 21°, under N₂, with 2-(tert-Butyl-dimethyl-silanyloxy)-1-methyl-ethylamine (301 mg, 2.01 mmol, 1.2 eq) followed by palladium acetate (38 mg, 0.1 eq), BINAP (105 mg, 0.1 eq) and CsCO₃ (766 mg, 1.4 eq). The mixture was heated to reflux for 18 h then filtered through a pad of celite. The pad was washed with EtOAc and the combined washings dried and evaporated to a gum which was purified by silica chromatography using 3% EtOAc/Hexane as eluent to provide the desired compound 3-[2-(tert-Butyl-dimethyl-silanyloxy)-1-methyl-ethylamino]-5-phenyl-thiophene-2-carboxylic acid methyl ester (645 mg,95%); ¹H NMR (300 MHz, CDCl₃) 0.0 (s,6H), 0.82 (s,9H), 1.24 (d, J=6.0 Hz, 3H), 3.56-3.57 (m, 3H), 3.90 (s, 3H), 6.88 (bs, 1H), 6.84 (s, 1H), 7.30-7.40 (m, 3H), 7.56 (d, J=6.0 Hz, 2H).

Step III

To a solution of 3-[2-(tert-Butyl-dimethyl-silanyloxy)-1-methyl-ethylamino]-5-phenyl-thiophene-2-carboxylic acid methyl ester (1.08 g, 2.69 mmol) in MeOH (10 ml) at 21°, under N₂ was added a solution of acetylchloride premixed in MeOH (100 µL/1 mL, 210 µL 2.96 mmol, 1.1 eq). The reaction was followed by tlc. On completion the reaction was stripped-off solvent and the residue purified over silica using progressively 5%, 20%, and then 30% EtOAc/Hexane as eluent to give 3-(2-Hydroxy-1-methyl-ethylamino)-5-(1-methyl-hexa-1,3,5-trienyl)-thiophene-2-carboxylic acid methyl ester as a yellow solid (518 mg, 79%); ¹H NMR (300 MHz, CDCl₃) 1.25 (d, 6.6 Hz, 3H), 3.52-3.62 (m,1H), 3.73-3.77 (m, 2H), 3.84 (s, 3H), 6.92 (s, 1H), 7.36-7.42 (m, 3H), 3.62 (d, J=8.3 Hz, 2H).

Step IV

A mixture of 3-(2-Hydroxy-1-methyl-ethylamino)-5-phenyl-thiophene-2-carboxylic acid methyl ester (213 mg, 0.257 mmol), diethyldiazodicarboxylate (250 µL, 1.59 mmol, 2 eq), diphenylphosphoryl azide (343 µL, 1.59 mmol, 2 eq) and trphenyl phosphine (417 mg, 1.59 mmol, 2 eq) was stirred at 21° until all starting alcohol was consumed. The reaction was evaporated to dryness and the crude residue purified on biotage with 5% EtOAc/hexane followed by 100% toluene as eluent. 3-(2-Azido-1-methyl-ethylamino)-5-phenyl-thiophene-2-carboxylic acid methyl ester was isolated as a solid (181 mg, 78%); ¹H NMR (300 MHz, CDCl₃) 1.33 (d, J=6.6 Hz, 3H), 3.38-3.46 (m, 2H), 3.78-3.81 (m, 1H), 6.82 (s, 1H), 7.36-7.41 (m, 3H), 7.60-7.62 (m, 2H).

Step V

A solution of 3-(2-Azido-1-methyl-ethylamino)-5-phenyl-thiophene-2-carboxylic acid methyl ester (60 mg, 0.188 mmol) was treated as described in example 30, step V with freshly prepared trans 4-methylcyclohexane carboxylic acid chloride (25 mg, 0.176 mmol, 1.2 eq) to deliver 3-[(2-Azido-1-methyl-ethyl)-(4-methyl-cyclohexanecarbonyl)-amino]-5-phenyl-thiophene-2-carboxylic acid methyl ester (14.6 mg, 17%); ¹H NMR (300 MHz, CDCl₃) 0.5-0.7 (m, 4H), 0.71 (d, J=6.6 Hz, 3H), 1.23 (d, J=7.0 Hz, 3H), 1.2-1.42 (m, 4H), 2.12-2.25 (m, 1H), 3.24 (dd, , J=5.6 Hz, J=5.7 Hz, 1H), 3.52 (dd, J=5.6 Hz, J=5.7 Hz, 1H), 3.80 (s, 3H), 4.82-4.90 (m, 1H), 7.20 (s, 1H), 7.32-7.42 (m, 3H), 7.56-7.61 (m, 2H).

Step VI

A solution of 3-[(2-Azido-1-methyl-ethyl)-(4-methyl-cyclohexanecarbonyl)-amino]-5-phenyl-thiophene-2-carboxylic acid methyl ester (14 mg, 0.032 mmol) in dioxan:water=4:1, 0.5 ml) was treated as described in example 25, step 7 with LiOH (4 mg, 3 eq) to give after acidic work-up 3-[(2-Azido-1-methyl-ethyl)-(4-methyl-cyclohexanecarbonyl)-amino]-5-phenyl-thiophene-2-carboxylic acid (Compound 32) as a pale green foam (11.2 mg, 82%); ¹H NMR (300 MHz, Acetone-d₆) 0.43-0.62 and 0.77-0.86 (m, 1H), 0.63 and 0.75 (d, J=5.1 Hz, 3H), 0.93 and 1.20 (d, J=5.2 Hz, 3H), 1.78-1.85 and 1.97-2.10 (m, 2H), 3.20-3.68 (m, 1H), 3.32 and 3.50 (m, 1H), 4.40 and 4.50 (m, 1H), 7.3-7.4 (m, 3H), 7.44 (s, 1H), 7.67-7.69 (m, 2H).

Step VII

A solution of 3-[(2-Azido-1-methyl-ethyl)-(4-methyl-cyclohexanecarbonyl)-amino]-5-phenyl-thiophene-2-carboxylic acid (8 mg, 0.19 mmol) in EtOH (0.2 ml) at 21°, was treated with 10% Pd/C (4 mg, 50% w/w) and stirred under an atmosphere of H2 for 1.5 h. The reaction mixture was filtered through a pad of celite with hot EtOAc and the combined filtrate and washings dried and evaporated to a glass to provide 3-[(2-Amino-1-methyl-ethyl)-(4-methyl-cyclohexanecarbonyl)-amino]-5-phenyl-thiophene-2-carboxylic acid (Compound 36). (7 mg, %); ¹H NMR (300 MHz, Acetone-d₆) 0.43-0.65 and 0.75-0.90 (m, 4H), 1.17-1.64 (m, 6H), 1.81-1.90 and 2.01-2.40 (m, 3H), 2.54 (bs, 1H), 3.00 (bs, 1H), 3.50 and 3.70 (bs, 1H), 7.20 (s, 1H), 7.22-7.25 and 7.29-7.34 (m, 3H), 7.58-7.62 (m, 2H).

Similarly made were compound 43, compound 20, compound 19, compound 18, compound 7 and compound 8.

EXAMPLE 33

3-[(1-Cyano-piperidin-4-yl)-(4-methyl-cyclohexan-ecarbonyl)-amino]-5-phenyl-thiophene-2-carboxylic acid Compound 77.

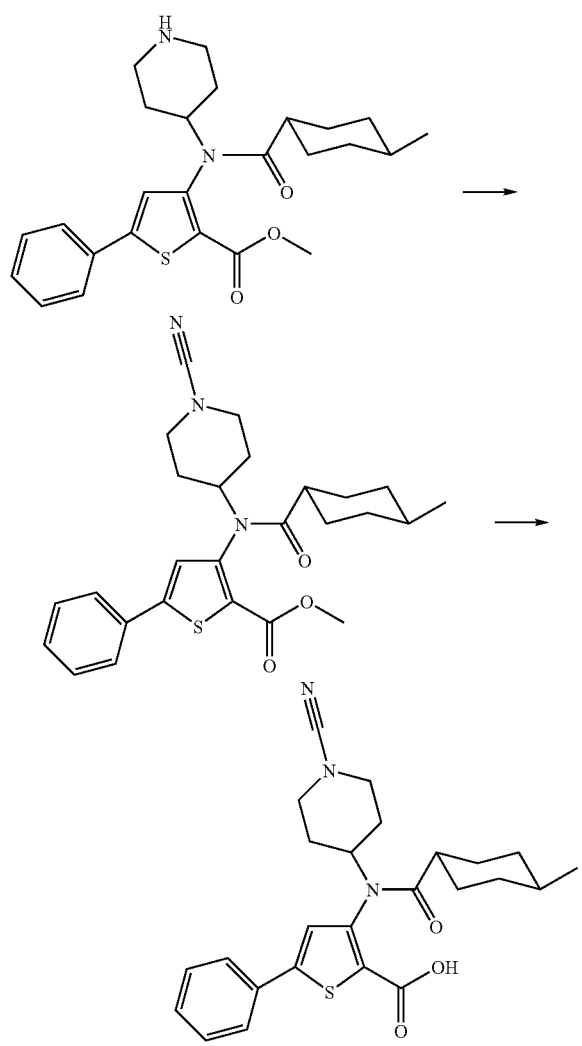

A solution of 3-[(4-methyl-cyclohexanecarbonyl)-piperidin-4-yl-amino]-5-phenyl-thiophene-2-carboxylic acid methyl ester (197 mg, 0.45 mmol) in $CH_2Cl_2$ (4.5 mL) was treated with $K_2CO_3$ (93 mg, 0.67 mmol) and cyanogen bromide (100 mg, 0.94 mmol). The reaction mixture was stirred at room temperature for 1 hour and heated at reflux for 18 h. The mixture was cooled at room temperature and filtered on celite. The filtrat was washed with AcOH (1N) and brine, dried ($Na_2SO_4$) and concentrated. The residue was purified by silica gel column chromatography using (2% MeOH/$CH_2Cl_2$) to provide 3-[(1-cyano-piperidin-4-yl)-(4-methyl cyclohexanecarbonyl)-amino]-5-phenyl-thiophene-2-carboxylic acid methyl ester (154 mg, 74% yield) as pale yellow foam.

Step II

3-[(1-cyano-piperidin-4-yl)-(4-methyl cyclohexanecarbonyl)-amino]-5-phenyl-thiophene-2-carboxylic acid methyl ester (150 mg, 0.32 mmol) was dissolved in a 4:1 mixture of dioxane:$H_2O$ (3.2 ml) and treated with LiOH.$H_2O$ (20 mg, 0.48 mmol). After 2 hours of stirring at 50° C., the solvents were removed and then partitioned between 5 ml of $H_2O$ acidified to pH 4 and 5 ml of EtOAc. The organic layer was separated and the aqueous phase as washed twice with ethyl acetate (2×5 mL). The combined ethyl acetate layer was dried ($Na_2SO_4$) and concentrated. The residue was purified by silica gel column chromatography using (5% MeOH/$CH_2Cl_2$) to provide 3-[(1-Cyano-piperidin-4-yl)-(4-methyl-cyclohexanecarbonyl)-amino]-5-phenyl-thiophene-2-carboxylic acid (114.3 mg, 78% yield) as pale green foam. $^1$H NMR (DMSO-$d_6$, 400 MHz): 7.80 (m, 2H), 7.45 (m, 4H), 4.44 (m, 1H), 3.35 (m, 2H), 3.13 (m, 2H), 1.96 (t, 1H), 1.88 (d, 1H), 1.75 (m, 1H), 1.70-1.40 (m, 6H), 1.20 (m, 3H), 0.70 (d, 3H), 0.60 (m, 2H).

EXAMPLE 34 cis-3-[(4-Hydroxy-4-methyl-cyclohexyl)-(4-methyl-cyclohexanecarbonyl)-amino]-5-phenyl-thiophene-2-carboxylic acid compound 86

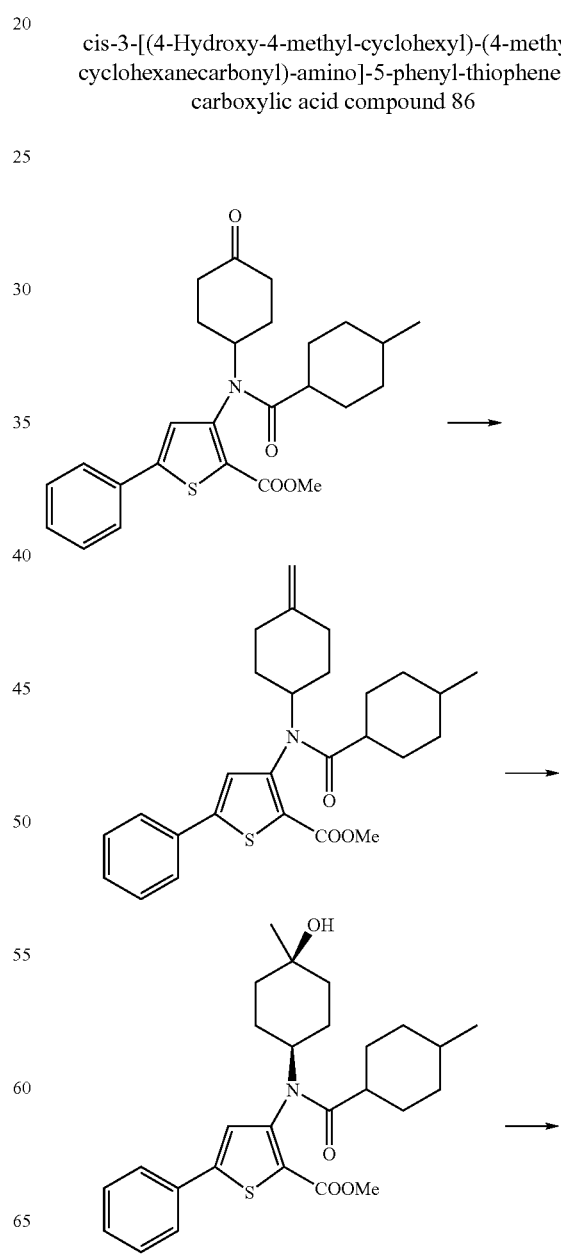

-continued

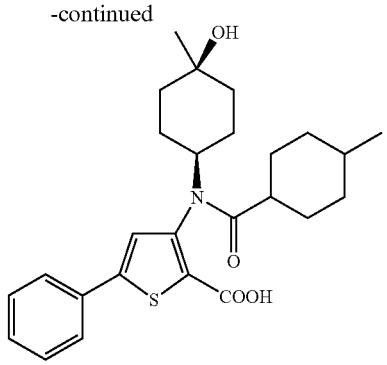

Step I

To a suspension of zinc dust (2.87 g, 44.0 mmol) and dibromoethane (1.00 mL, 14.4 mmol) in tetrahydrofuran (20 mL) stirred under a nitrogen atmosphere at −40° C. was added titane tetrachloride (10 mL of a solution 1M in dichloromethane, 10 mmol). The mixture was then allowed to warm to room temperature and was stirred for two days at this temperature. This methylation reagent (2.5 eq) was added to a solution of 3-[(4-Methyl-cyclohexanecarbonyl)-(4-oxo-cyclohexyl)-amino]-5-phenyl-thiophene-2-carboxylic acid methyl ester (0.200 g, 0.440 mmol, 1 eq) in dichloromethane (2 mL) and the resulting mixture was stirred 3 h at room temperature. A saturated solution of sodium bicarbonate was then added and reaction mixture was extracted with dichloromethane (3×30 mL). Organic phases were combined, dried over sodium sulfate and concentrated. The crude was purified by chromatography (30% ethyl acetate/hexanes) to give 160 mg (81%) of 3-[(4-Methyl-cyclohexanecarbonyl)-(4-methylene-cyclohexyl)-amino]-5-phenyl-thiophene-2-carboxylic acid methyl ester as a white solid. NMR $^1$H (CDCl$_3$, 400 MHz) 7.63 ppm (d, 2H); 7.40 ppm (m, 3H); 6.98 ppm (s, 1H); 4.82 ppm (tt, 1H); 4.78 ppm (d, 2H); 3.85 ppm (s, 3H); 2.20 ppm (m, 4H); 2.05 ppm (m, 2H); 1.90 ppm (d, 1H); 1.65 ppm (m, 4H); 1.42 ppm (m, 1H); 1.30 ppm (m, 2H); 1.00 ppm (m, 2H); 0.78 ppm (d, 3H); 0.64 ppm (m, 2H).

Step II

To a solution of water (1 mL) and tetrahydrofuran (1 mL) was added mercuric acetate (83.0 mg, 0.277 mmol, 1 eq) at room temperature. After stirring 10 min, the yellow solution was cooled to 0° C. and a solution of 3-[(4-Methyl-cyclohexanecarbonyl)-(4-methylene-cyclohexyl)-amino]-5-phenyl-thiophene-2-carboxylic acid methyl ester (125 mg, 0.277 mmol, 1 eq) was added dropwise. The resulting mixture was stirred 1 h at 0° C. NaOH 3M (1 mL) was then added, followed by sodium borohydride (10.0 mg, 0.277 mmol, 1 eq) and the reaction mixture was stirred 15 min at room temperature. The reaction mixture was extracted with dichloromethane (3×30 mL). Organic phases were combined, dried over sodium sulfate and concentrated. The crude was purified by chromatography (50% ethyl acetate/hexanes) and diastereoisomers were separated to give 90 mg of cis-3-[(4-Hydroxy-4-methyl-cyclohexyl)-(4-methyl-cyclohexanecarbonyl)-amino]-5-phenyl-thiophene-2-carboxylic acid methyl ester and 6.5 mg of trans-3-[(4-Hydroxy-4-methyl-cyclohexyl)-(4-methyl-cyclohexanecarbonyl)-amino]-5-phenyl-thiophene-2-carboxylic acid methyl ester (74%), both as a white solid. cis-3-[(4-Hydroxy-4-methyl-cyclohexyl)-(4-methyl-cyclohexanecarbonyl)-amino]-5-phenyl-thiophene-2-carboxylic acid methyl ester. NMR $^1$H (CDCl$_3$, 400 MHz): 7.63 ppm (d, 2H); 7.40 ppm (m, 3H); 6.98 ppm (s, 1H); 4.50 ppm (tt, 1H); 3.85 ppm (s, 3H); 2.00 ppm (m, 1H); 1.80-1.20 ppm (m, 15H); 1.18 ppm (s, H); 0.78 ppm (d, 3H); 0.64 ppm (m, 2H).

Step III

To a solution of cis-3-[(4-Hydroxy-4-methyl-cyclohexyl)-(4-methyl-cyclohexanecarbonyl)-amino]-5-phenyl-thiophene-2-carboxylic acid methyl ester (70.0 mg, 0.149 mmol, 1 eq) in tetrahydrofuran (1 mL), water (0.5 mL) and methanol (0.5 mL) was added lithium hydroxide (19.0 mg, 0.447 mmol, 3 eq). The resulting mixture was stirred 3 h at room temperature and was then extracted with ether (2×10 mL). Aqueous phase was separated and combined organic phases were discarded. Aqueous phase was acidified to pH 1 and extracted with dichloromethane (3×30 mL). Organic phases of dichloromethane were combined, dried over sodium sulfate and concentrated. The crude was purified by chromatography (10% methanol/dichloromethane) to give 50 mg (74%) of cis-3-[(4-Hydroxy-4-methyl-cyclohexyl)-(4-methyl-cyclohexanecarbonyl)-amino]-5-phenyl-thiophene-2-carboxylic acid. NMR $^1$H (CDCl$_3$, 400 MHz): 7.60 ppm (d, 2H); 7.39 ppm (m, 3H); 7.03 ppm (s, 1H); 4.51 ppm (bs, 2H); 2.00 ppm (m, 1H); 1.80-1.20 ppm (m, 15H); 1.12 ppm (s, 3H); 0.71 ppm (d, 3H); 0.60 ppm (m, 2H).

EXAMPLE 35

Preparation of Sodium Salt of the Compounds

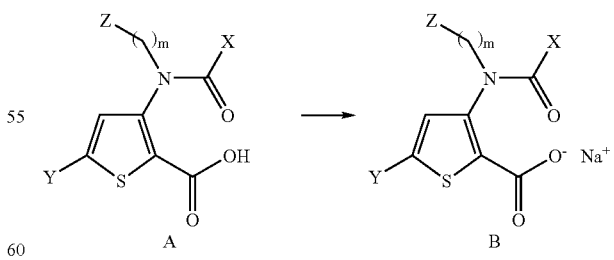

A solution of the carboxylic acid compound A (1 mmol) in 1:1 dioxane/water solution at 0° C. is treated with 0.1 N NaOH solution (1 mmol, 1 eq.). The reaction is stirred 15 min. The solution is then concentrated and lyophilized to obtain sodium; carboxylate compound B as a solid.

EXAMPLE 36

List of Compounds and Related Polymerase Activity

TABLE 1

| # | Structure | name | Activity |
|---|---|---|---|
| 1 | 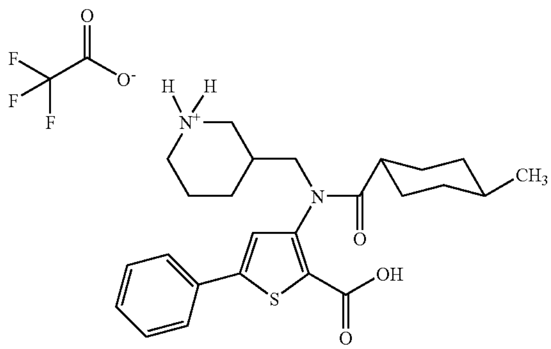 | 3-{[(2-CARBOXY--5-PHENYL-THIOPHEN-3-YL)-(4-METHYL-CYCLOHEXANECARBONYL)-AMINO]-METHYL}-PIPERIDINIUM; TRIFLUORO-ACETATE | +++ |
| 2 | 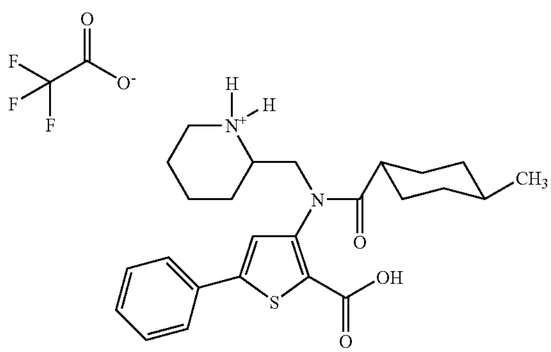 | 2-{[(2-CARBOXY-5-PHENYL-THIOPHEN-3-YL)-(4-METHYL-CYCLOHEXANECARBONYL)-AMINO]-METHYL}-PIPERIDINIUM; TRIFLUORO-ACETATE | +++ |
| 3 | 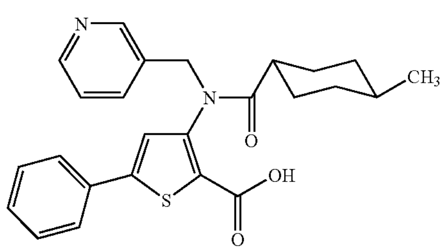 | 3-[(4-METHYL-CYCLOHEXANECARBONYL)-PYRIDIN-3-YLMETHYL-AMINO]-5-PHENYL-THIOPHENE-2-CARBOXYLIC ACID | +++ |
| 4 | 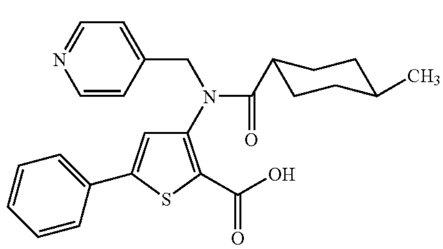 | 3-[(4-METHYL-CYCLOHEXANECARBONYL)-PYRIDIN-4-YLMETHYL-AMINO]-5-PHENYL-CARBOXYLIC ACID | +++ |

TABLE 1-continued

| # | Structure | Name | Activity |
|---|---|---|---|
| 5 | 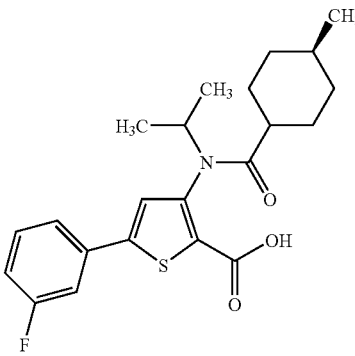 | 5-(3-FLUORO-PHENYL)-3-[ISOPROPYL-(4-METHYL-CYCLOHEXANECARBONYL)-AMINO]-THIOPHENE-2-CARBOXYLIC ACID | +++ |
| 6 | 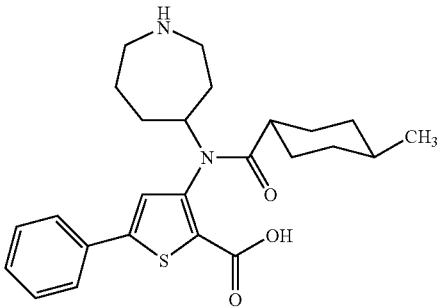 | 3-[AZEPAN-4-YL-(4-METHYL-CYCLOHEXANECARBONYL)-AMINO]-5-PHENYL-THIOPHENE-2-CARBOXYLIC ACID | +++ |
| 7 | 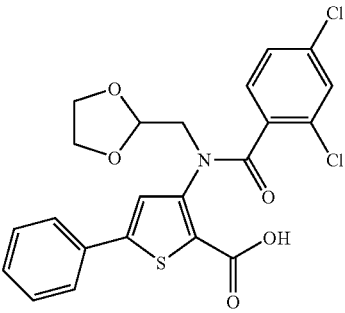 | 3-[(2,4-DICHLORO-BENZOYL)-[1,3]DIOXOLAN-2-YLMETHYL-AMINO]-5-PHENYL-THIOPHENE-2-CARBOXYLIC ACID | +++ |
| 8 | 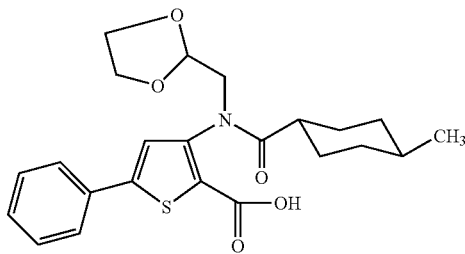 | 3-[[1,3]DIOXOLAN-2-YLMETHYL-(4-METHYL-CYCLOHEXANECARBONYL)-AMINO]-5-PHENYL-THIOPHENE-2-CARBOXYLIC ACID | +++ |
| 9 | 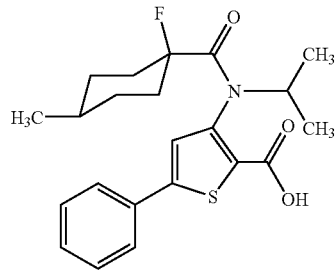 | 3-[(1-FLUORO-4-METHYL-CYCLOHEXANECARBONYL)-ISOPROPYL-AMINO]-5-PHENYL-THIOPHENE-2-CARBOXYLIC ACID | +++ |

TABLE 1-continued

| | | | |
|---|---|---|---|
| 10 | 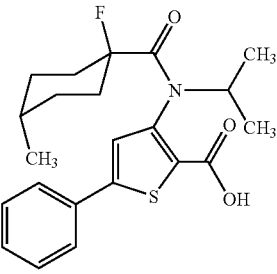 | 3-[(1-FLUORO-4-METHYL-CYCLOHEXANECARBONYL)-ISOPROPYL-AMINO]-5-PHENYL-THIOPHENE-2-CARBOXYLIC ACID | + |
| 11 | 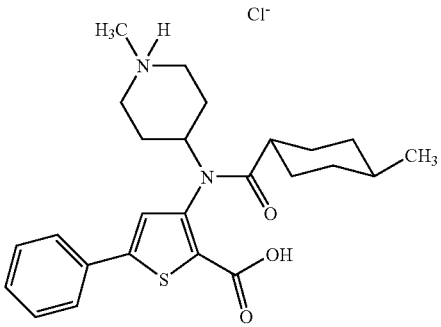 | 4-[(2-CARBOXY-5-PHENYL-THIOPHEN-3-YL)-(4-METHYL-CYCLOHEXANECARBONYL)-AMINO]-1-METHYL-PIPERIDINIUM; CHLORIDE | +++ |
| 12 | 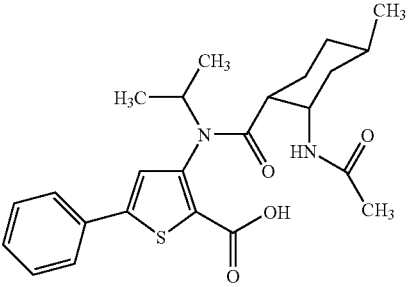 | 3-[(2-ACETYLAMINO-4-METHYL-CYCLOHEXANECARBONYL)-PHENYL-THIOPHENE-2-CARBOXYLIC ACID | ++ |
| 13 | 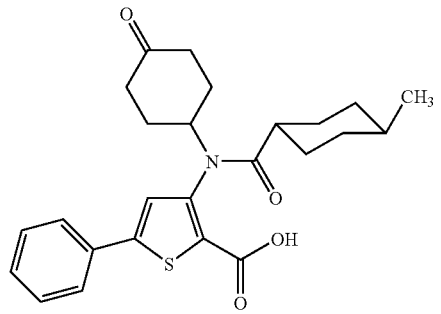 | 3-[(4-METHYL-CYCLOHEXANECARBONYL)-(4-OXO-CYCLOHEXYL)-AMINO]-5-PHENYL-THIOPHENE-2-CARBOXYLIC ACID | +++ |
| 14 | 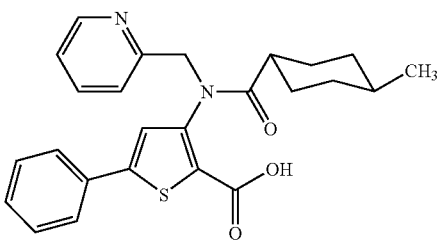 | 3-[(4-METHYL-CYCLOHEXANECARBONYL)-PYRIDIN-2-YLMETHYL-AMINO]-5-PHENYL-THIOPHENE-2-CARBOXYLIC ACID | +++ |

TABLE 1-continued

| | Structure | Name | Activity |
|---|---|---|---|
| 15 | 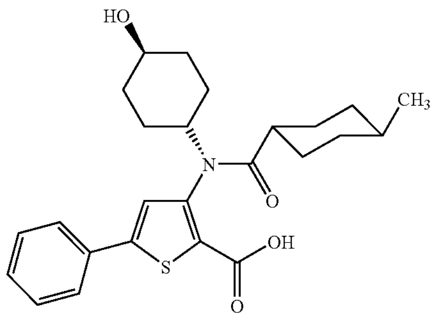 | 3-[(4-HYDROXY-CYCLOHEXYL)-(4-METHYL-CYCLOHEXANECARBONYL)-AMINO]-5-PHENYL-THIOPHENE-2-CARBOXYLIC ACID | +++ |
| 16 | 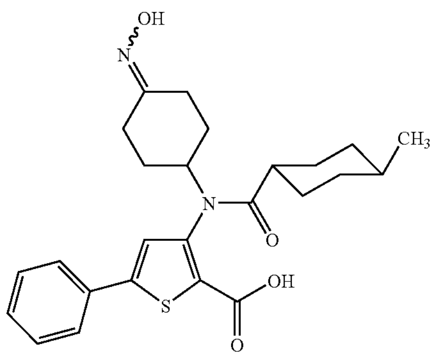 | 3-[(4-HYDROXYIMINO-CYCLOHEXYL)-(4-METHYL-CYCLOHEXANECARBONYL)-AMINO]-5-PHENYL-THIOPHENE-2-CARBOXYLIC ACID | +++ |
| 17 | 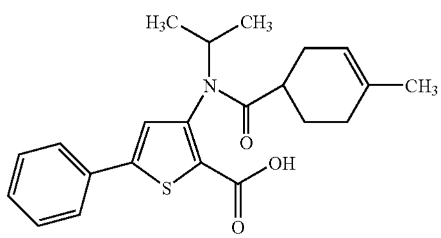 | 3-[ISOPROPYL-(4-METHYL-CYCLOHEX-3-ENECARBONYL)-AMINO]-5-PHENYL-THIOPHENE-2-CARBOXYLIC ACID | +++ |
| 18 | 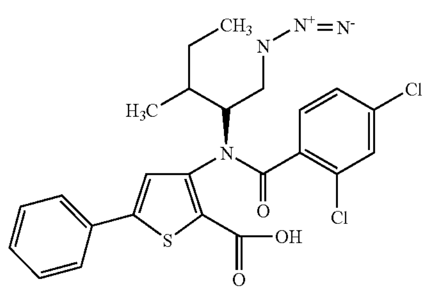 | 3-[(1-AZIDOMETHYL-2-METHYL-BUTYL)-(2,4-DICHLORO-BENZOYL)-AMINO]-5-PHENYL-THIOPHENE-2-CARBOXYLIC ACID | +++ |
| 19 | 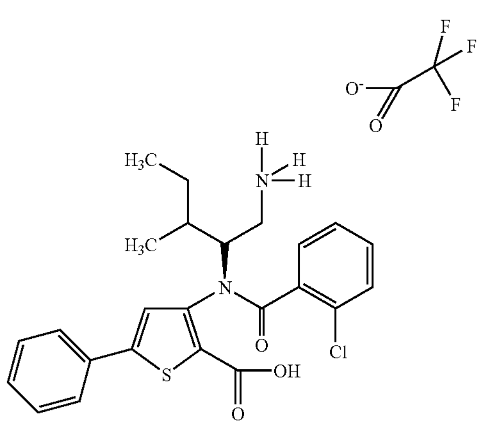 | 2-[(2-Carboxy-5-phenyl-thiophen-3-yl)-(2-chloro-benzoyl)-amino]-3-methyl-pentyl-ammonium | + |

TABLE 1-continued

| 20 | 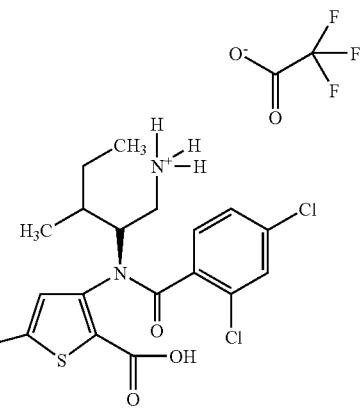 | 3-[(1-AMINOMETHYL-2-METHYL-BUTYL)-(2,4-DICHLORO-BENZOYL)-AMINO]-5-PHENYL-THIOPHENE-2-CARBOXYLIC ACID | ++ |
| 21 | 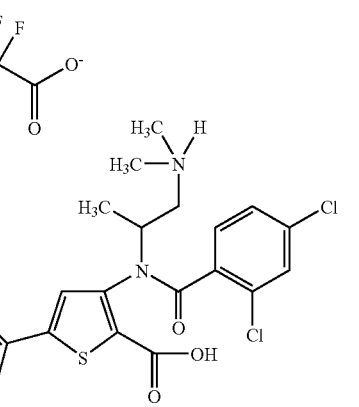 | {2-[(2-CARBOXY-5-PHENYL-THIOPHEN-3-YL)-(2,4-DICHLORO-BENZOYL)-AMINO]-PROPYL}-TRIMETHYL-AMMONIUM; TRIFLUORO-ACETATE | +++ |
| 22 | 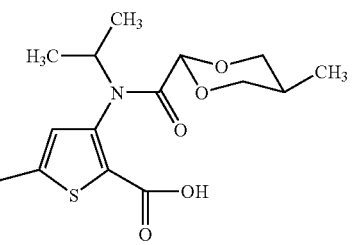 | 3-[ISOPROPYL-(5-METHYL-[1,3]DIOXANE-2-CARBONYL)-AMINO]-5-PHENYL-THIOPHENE-2-CARBOXYLIC ACID | ++ |
| 23 | 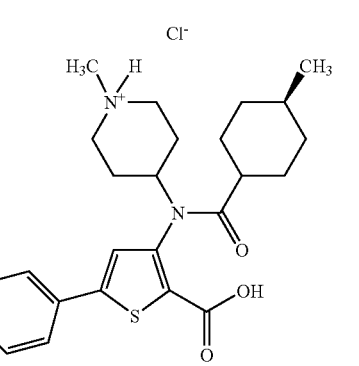 | 4-[(2-CARBOXY-5-(4-FLUORO-PHENYL)-THIOPHEN-3-YL]-(4-METHYL-CYCLOHEXANECARBONYL)-AMINO]-1-METHYL-PIPERIDINIUM; CHLORIDE | +++ |

TABLE 1-continued

| | | | |
|---|---|---|---|
| 24 | 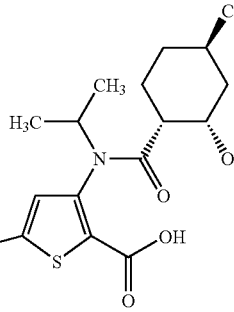 | 5-(4-FLUORO-PHENYL)-3-[(2-HYDROXY-4-METHYL-CYCLOHEXANECARBONYL)-ISOPROPYL-AMINO]-THIOPHENE-2-CARBOXYLIC ACID | +++ |
| 25 | 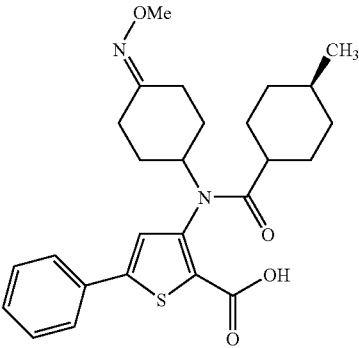 | 3-[(4-METHOXYIMINO-CYCLOHEXYL)-(4-METHYL-CYCLOHEXANECARBONYL)-AMINO]-5-PHENYL-THIOPHENE-2-CARBOXYLIC ACID | +++ |
| 26 | 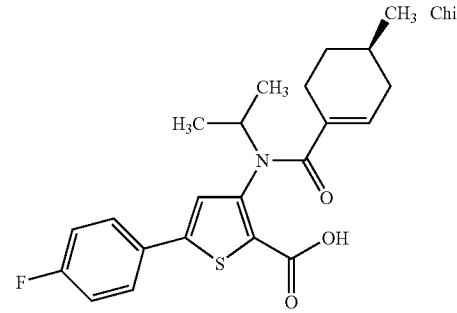 | 5-(4-FLUORO-PHENYL)-3-[ISOPROPYL-(4-METHYL-CYCLOHEX-1-ENECARBONYL)-AMINO]-THIOPHENE-2-CARBOXYLIC ACID | +++ |
| 27 | 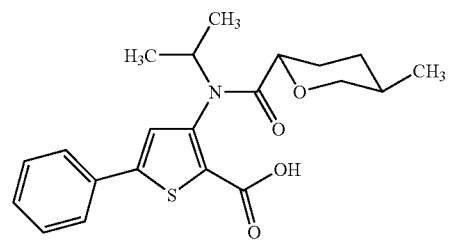 | 3-[ISOPROPYL-(5-METHYL-TETRAHYDRO-PYRAN-2-CARBONYL)-AMINO]-5-PHENYL-THIOPHENE-2-CARBOXYLIC ACID | +++ |
| 28 | 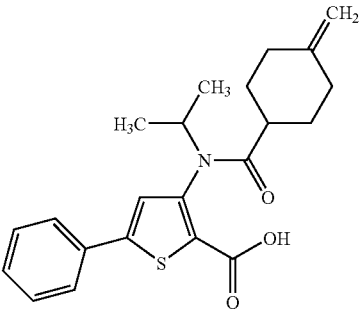 | 3-[ISOPROPYL-(4-METHYLENE-CYCLOHEXANECARBONYL)-AMINO]-5-PHENYL-THIOPHENE-2-CARBOXYLIC ACID | +++ |

TABLE 1-continued

| | | | |
|---|---|---|---|
| 29 | 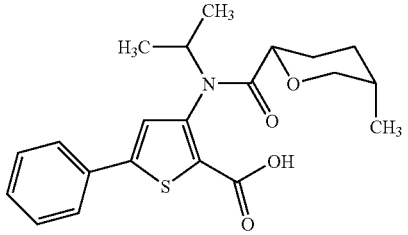 | 3-[ISOPROPYL-(5-METHYL-TETRAHYDRO-PYRAN-2-CARBONYL)-AMINO]-5-PHENYL-THIOPHENE-2-CARBOXYLIC ACID | ++ |
| 30 | 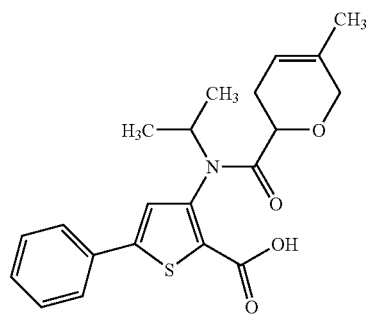 | 3-[ISOPROPYL-(5-METHYL-3,6-DIHYDRO-2H-PYRAN-2-CARBONYL)-AMINO]-5-PHENYL-THIOPHENE-2-CARBOXYLIC ACID | +++ |
| 31 | 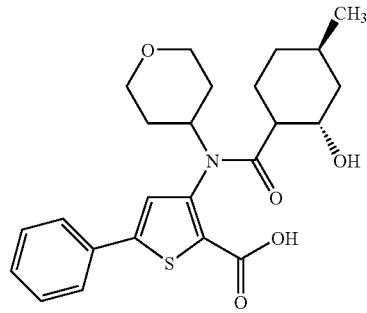 | 3-[(2-HYDROXY-4-METHYL-CYCLOHEXANECARBONYL)-(TETRAHYDRO-PYRAN-4-YL)-AMINO]-5-PHENYL-THIOPHENE-2-CARBOXYLIC ACID | +++ |
| 32 | 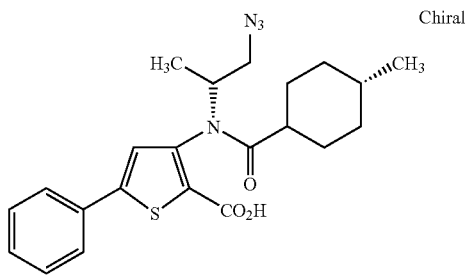 Chiral | 3-[(2-AZIDO-1-METHYL-ETHYL)-(4-METHYL-CYCLOHEXANECARBONYL)-AMINO]-5-PHENYL-THIOPHENE-2-CARBOXYLIC ACID | +++ |
| 33 | 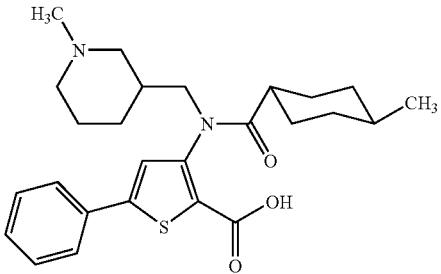 | 3-[(4-METHYL-CYCLOHEXANECARBONYL)-(1-METHYL-PIPERIDIN-4-YLMETHYL)-ANINO]-5-PHENYL-THIOPHENE-2-CARBOXYLIC ACID | +++ |

TABLE 1-continued

| | | | |
|---|---|---|---|
| 34 | 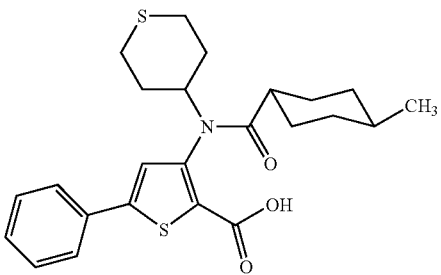 | 3-[(4-METHYL-CYCLOHEXANECARBONYL)-(TETRAHYDRO-THIOPYRAN-4-YL)-AMINO]-5-PHENYL-THIOPHENE-2-CARBOXYLIC ACID | +++ |
| 35 | 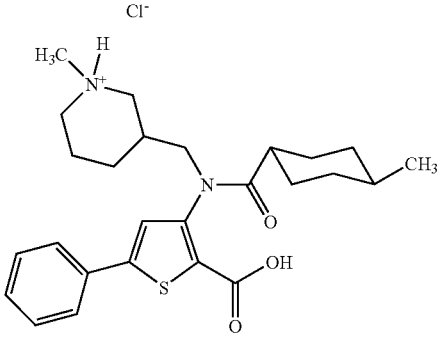 | 3-{[(2-CARBOXY-5-PHENYL-THIOPHEN-3-YL)-(4-METHYL-CYCLOHEXANECARBONYL)-AMINO]-METHYL}-1-METHYL-PIPERIDINIUM; CHLORIDE | +++ |
| 36 | 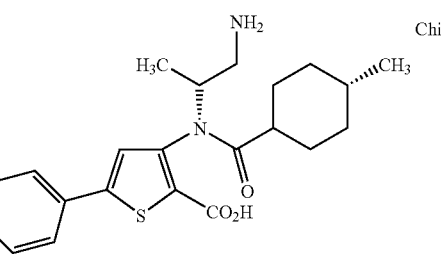 | 3-[(2-AMINO-1-METHYL-ETHYL)-(4-METHYL-CYCLOHEXANECARBONYL)-AMINO]-5-PHENYL-THIOPHENE-2-CARBOXYLIC ACID | +++ |
| 37 | 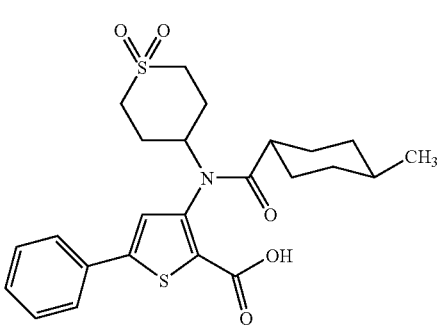 | 3-[(4-METHYL-CYCLOHEXANECARBONYL)-(1,1-DIOXO-TETRAHYDRO-THIOPYRAN-4-YL)-AMINO]-5-PHENYL-THIOPHENE-2-CARBOXYLIC ACID | +++ |
| 38 | 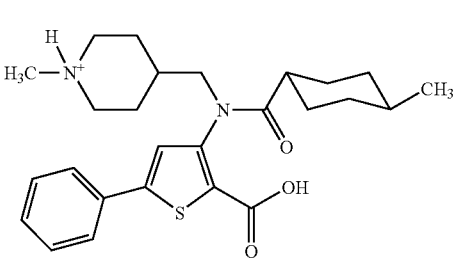 | 4-{[(2-CARBOXY-5-PHENYL-THIOPHEN-3-YL)-(4-METHYL-CYCLOHEXANECARBONYL)-AMINO]-METHYL}-1-METHYL-PIPERIDINIUM; CHLORIDE | +++ |

TABLE 1-continued

| | | | |
|---|---|---|---|
| 39 | 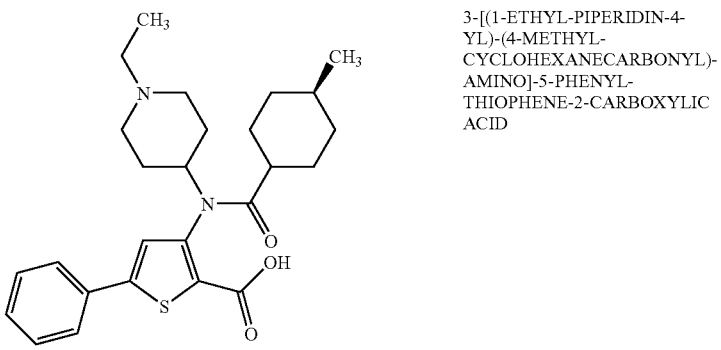 | 3-[(1-ETHYL-PIPERIDIN-4-YL)-(4-METHYL-CYCLOHEXANECARBONYL)-AMINO]-5-PHENYL-THIOPHENE-2-CARBOXYLIC ACID | +++ |
| 40 | 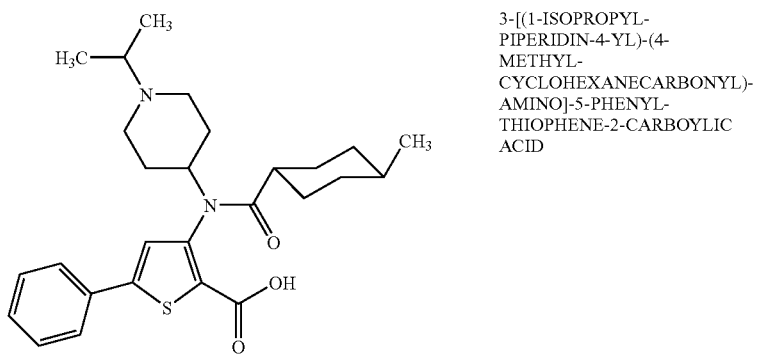 | 3-[(1-ISOPROPYL-PIPERIDIN-4-YL)-(4-METHYL-CYCLOHEXANECARBONYL)-AMINO]-5-PHENYL-THIOPHENE-2-CARBOYLIC ACID | +++ |
| 41 | 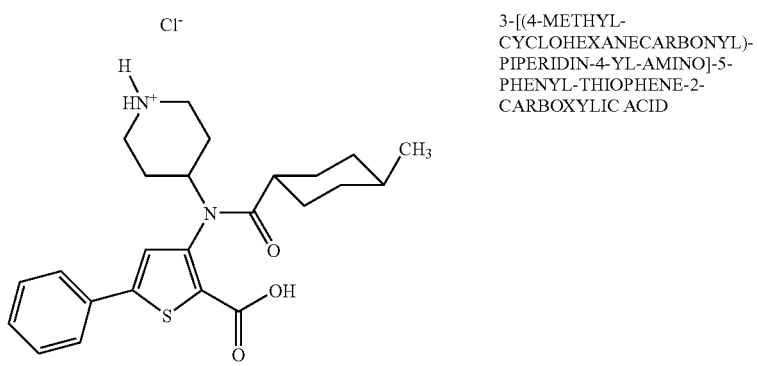 | 3-[(4-METHYL-CYCLOHEXANECARBONYL)-PIPERIDIN-4-YL-AMINO]-5-PHENYL-THIOPHENE-2-CARBOXYLIC ACID | +++ |
| 42 | 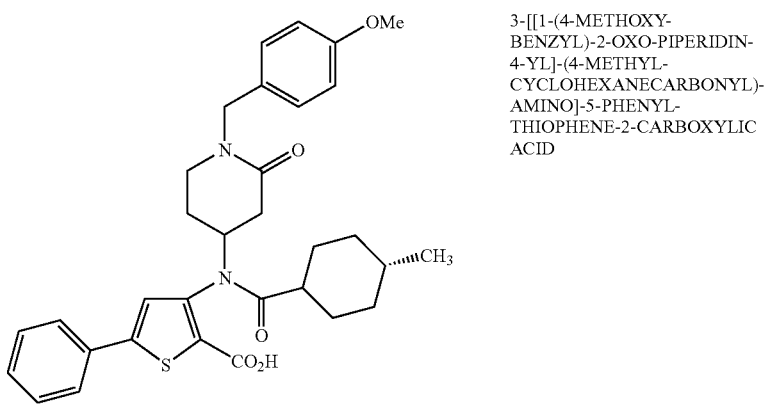 | 3-[[1-(4-METHOXY-BENZYL)-2-OXO-PIPERIDIN-4-YL]-(4-METHYL-CYCLOHEXANECARBONYL)-AMINO]-5-PHENYL-THIOPHENE-2-CARBOXYLIC ACID | +++ |

TABLE 1-continued

| 43 | 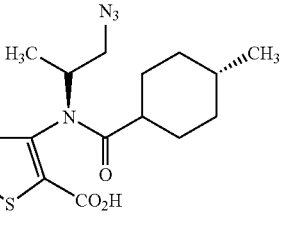 Chiral | 3-[(2-AZIDO-1-METHYL-ETHYL)-(4-METHYL-CYCLOHEXANECARBONYL)-AMINO]-5-PHENYL-THIOPHENE-2-CARBOXYLIC ACID | +++ |
| --- | --- | --- | --- |
| 44 | 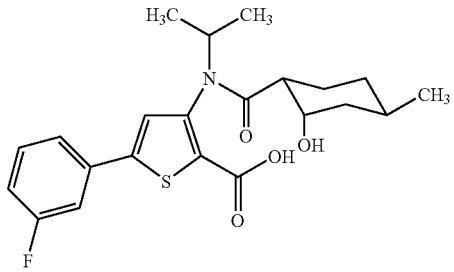 | 5-(3-FLUORO-PHENYL)-3-[(2-HYDROXY-4-METHYL-CYCLOHEXANECARBONYL)-ISOPROPYL-AMINO]-THIOPHENE-2-CARBOXYLIC ACID | +++ |
| 45 | 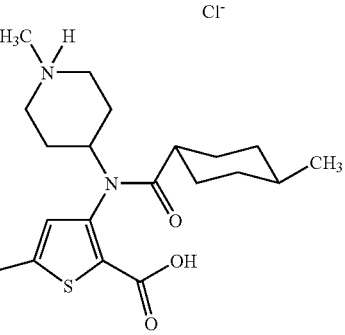 Cl⁻ | 4-[(2-CARBOXY-5-p-TOLYL-THIOPHEN-3-YL)-(4-METHYL-CYCLOHEXANECARBONYL)-AMINO]-1-METHYL-PIPERIDINIUM; CHLORIDE | +++ |
| 46 | 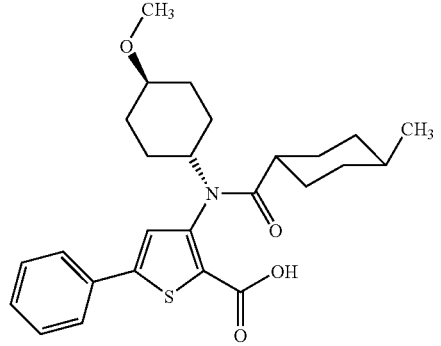 | 3-[(4-METHOXY-CYCLOHEXYL)-(4-METHYL-CYCLOHEXANECARBONYL)-AMINO]-5-PHENYL-THIOPHENE-2-CARBOXYLIC ACID | +++ |
| 47 | 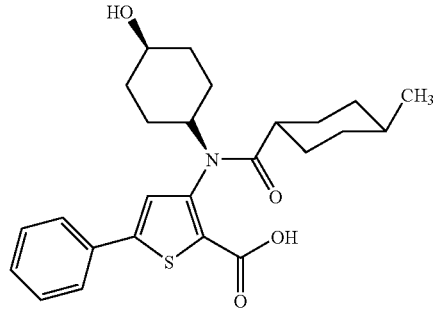 | 3-[(4-METHYL-CYCLOHEXANECARBONYL)-(4-HYDROXY-CYCLOHEXYL)-AMINO]-5-PHENYL-THIOPHENE-2-CARBOXYLIC ACID | +++ |

TABLE 1-continued

| | | | |
|---|---|---|---|
| 48 | 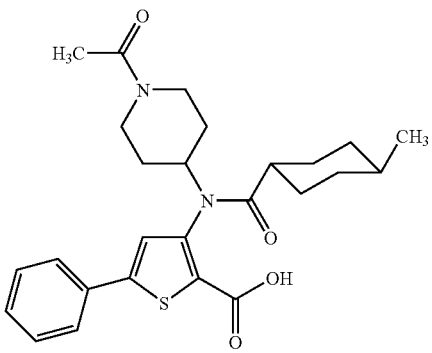 | 3-[(1-ACETYL-PIPERIDIN-4-YL)-(4-METHYL-CYCLOHEXANECARBONYL)-AMINO]-5-PHENYL-THIOPHENE-2-CARBOXYLIC ACID | +++ |
| 49 | 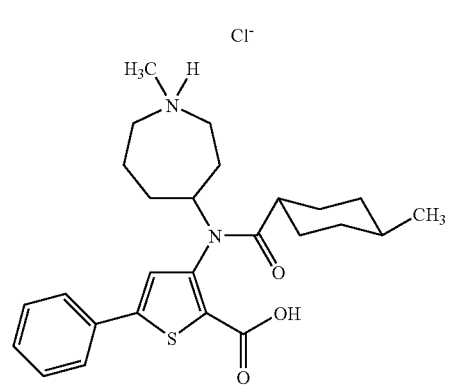 | 4-[(2-CARBOXY-5-PHENYL-THIOPHEN-3-YL)-(4-METHYL-CYCLOHEXANECARBONYL)-AMINO]-1-METHYL-AZEPANIUM; CHLORIDE | +++ |
| 50 | 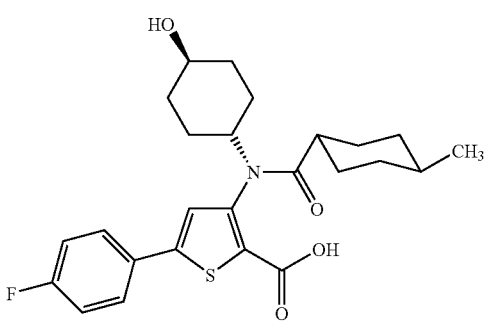 | 5-(4-FLUORO-PHENYL)-3-[(4-HYDROXY-CYCLOHEXYL)-(4-METHYL-CYCLOHEXANECARBONYL)-AMINO]-THIOPHENE-2-CARBOXYLIC ACID | +++ |
| 51 | 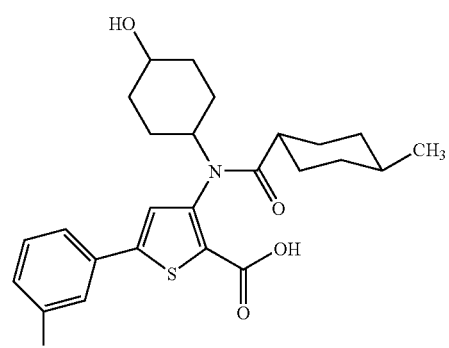 | 5-(3-FLUORO-PHENYL)-3-[(4-HYDROXY-CYCLOHEXYL)-(4-METHYL-CYCLOHEXANECARBONYL)-AMINO]-THIOPHENE-2-CARBOXYLIC ACID | +++ |

TABLE 1-continued

| | | | |
|---|---|---|---|
| 52 | 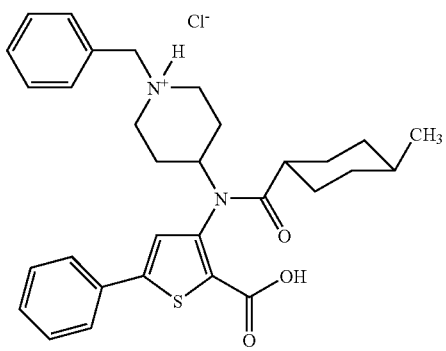 | 3-[(1-BENZYL-PIPERIDIN-4-YL)-(4-METHYL-CYCLOHEXANECARBONYL)-AMINO]-5-PHENYL-THIOPHENE-2-CARBOXYLIC ACID | +++ |
| 53 | 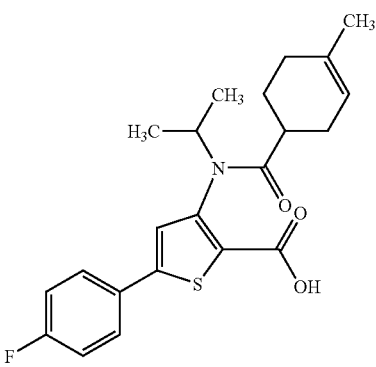 | 5-(4-FLUORO-PHENYL)-3-[ISOPROPYL-(4-METHYL-CYCLOHEX-3-ENECARBONYL)-AMINO]-THIOPHENE-2-CARBOXYLIC ACID | +++ |
| 54 | 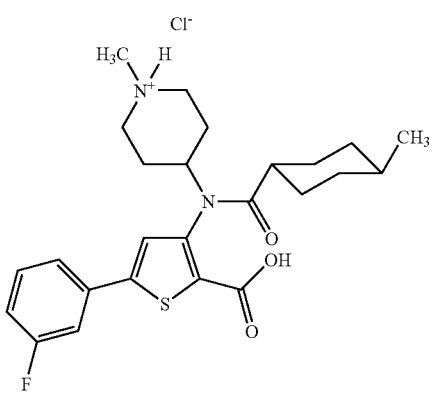 | 4-[[2-CARBOXY-5-(3-FLUORO-PHENYL)-THIOPHEN-3-YL]-(4-METHYL-CYCLOHEXANECARBONYL)-AMINO]-1-METHYL-PIPERIDINIUM; CHLORIDE | +++ |
| 55 | 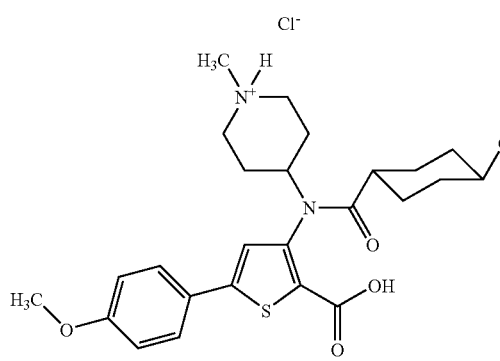 | 4-[[2-CARBOXY-5-(4-METHOXY-PHENYL)-THIOPHEN-3-YL]-(4-METHYL-CYCLOHEXANECARBONYL)-AMINO]-1-METHYL-PIPERIDINIUM; CHLORIDE | +++ |

TABLE 1-continued

| 56 | 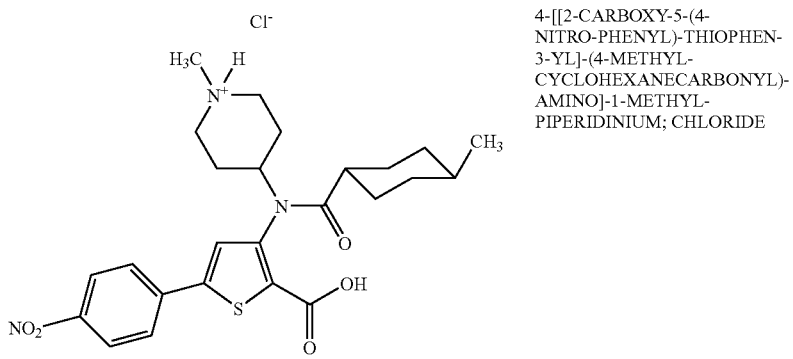 | 4-[[2-CARBOXY-5-(4-NITRO-PHENYL)-THIOPHEN-3-YL]-(4-METHYL-CYCLOHEXANECARBONYL)-AMINO]-1-METHYL-PIPERIDINIUM; CHLORIDE | +++ |
| --- | --- | --- | --- |
| 57 | 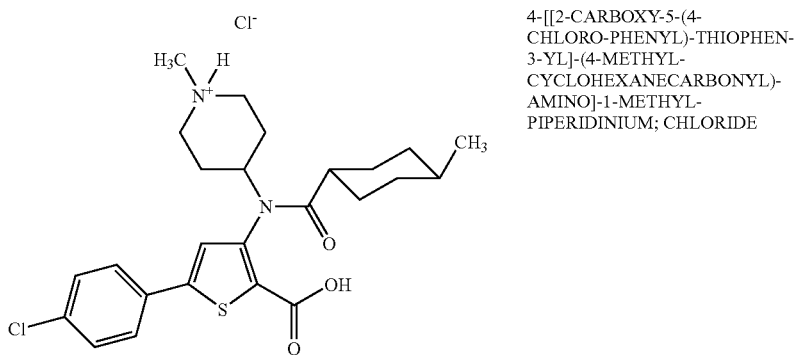 | 4-[[2-CARBOXY-5-(4-CHLORO-PHENYL)-THIOPHEN-3-YL]-(4-METHYL-CYCLOHEXANECARBONYL)-AMINO]-1-METHYL-PIPERIDINIUM; CHLORIDE | +++ |
| 58 | 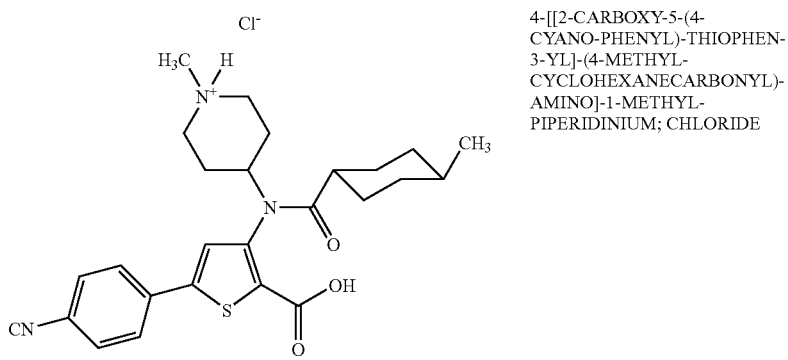 | 4-[[2-CARBOXY-5-(4-CYANO-PHENYL)-THIOPHEN-3-YL]-(4-METHYL-CYCLOHEXANECARBONYL)-AMINO]-1-METHYL-PIPERIDINIUM; CHLORIDE | +++ |
| 59 | 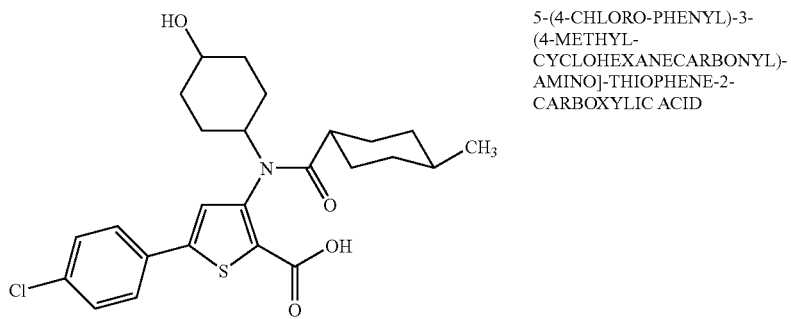 | 5-(4-CHLORO-PHENYL)-3-(4-METHYL-CYCLOHEXANECARBONYL)-AMINO]-THIOPHENE-2-CARBOXYLIC ACID | +++ |

TABLE 1-continued

| | | | |
|---|---|---|---|
| 60 | 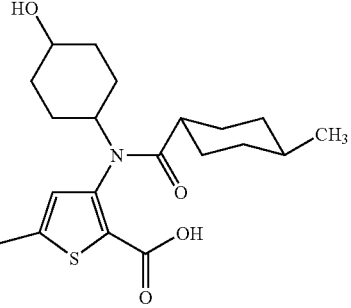 | 3-[(4-HYDROXY-CYCLOHEXYL)-(4-METHYL-CYCLOHEXANECARBONYL)-AMINO]-5-(4-METHOXY-PHENYL)-THIOPHENE-2-CARBOXYLIC ACID | +++ |
| 61 | 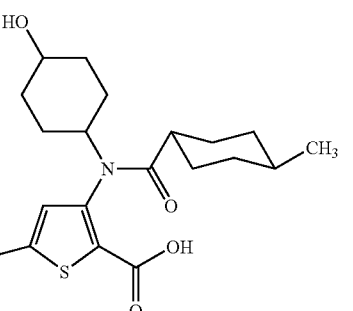 | 5-(4-CYANO-PHENYL)-3-[(4-HYDROXY-CYCLOHEXYL)-(4-METHYL-CYCLOHEXANECARBONYL)-AMINO]-THIOPHENE-2-CARBOXYLIC ACID | +++ |
| 62 | 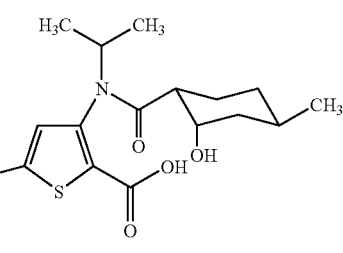 | 3-[(2-HYDROXY-4-METHYL-CYCLOHEXANECARBONYL)-ISOPROPYL-ANINO]-5-(4-METHOXY-PHENYL)-THIOPHENE-2-CARBOXYLIC ACID | +++ |
| 63 | 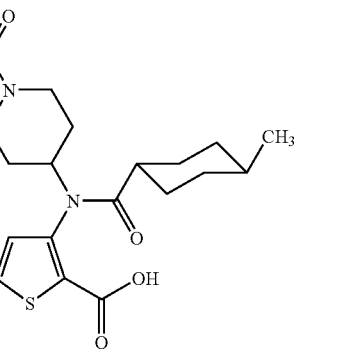 | 3-[(1-FORMYL-PIPERIDIN-4-YL)-(4-METHYL-CYCLOHEXANECARBONYL)-AMINO]-5-PHENYL-THIOPHENE-2-CARBOXYLIC ACID | +++ |
| 64 | 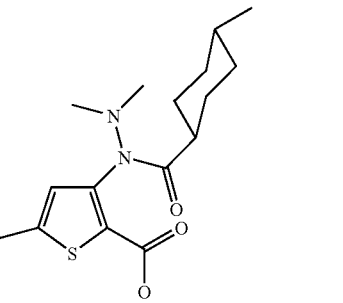 | 3-[N',N'-Dimethyl-N-(4-methyl-cyclohexanecarbonyl)-hydrazino]-5-phenyl-thiophene-2-carboxylic acid | +++ |

TABLE 1-continued

| | | | |
|---|---|---|---|
| 65 | 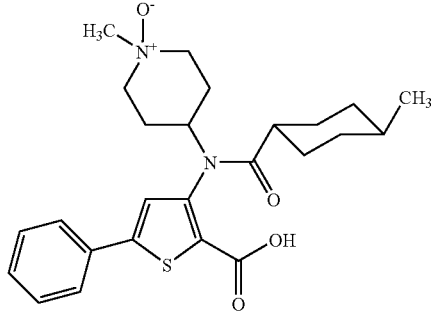 | 3-[(4-METHYL-CYCLOHEXANECARBONYL)-(1-METHYL-1-OXY-PIPERIDIN-4-YL)-AMINO]-5-PHENYL-THIOPHENE-2-CARBOXYLIC ACID | +++ |
| 66 | 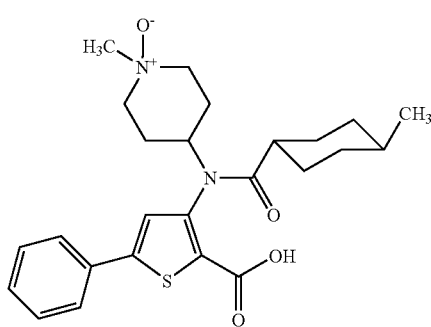 | 3-[(4-METHYL-CYCLOHEXANECARBONYL)-(1-METHYL-1-OXY-PIPERIDIN-4-YL)-AMINO]-5-PHENYL-THIOPHENE-2-CARBOXYLIC ACID | +++ |
| 67 | 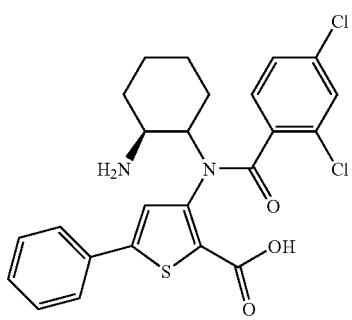 | 3-[(2-AMINO-CYCLOHEXYL)-(2,4-DICHLORO-BENZOYL)-AMINO]-5-PHENYL-THIOPHENE-2-CARBOXYLIC ACID | — |
| 68 | 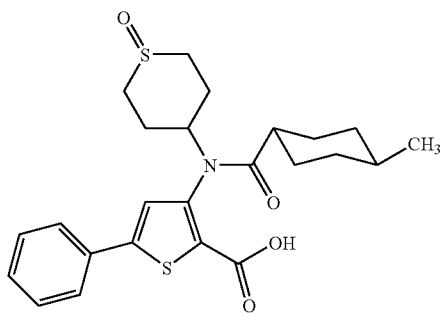 | 3-[(4-METHYL-CYCLOHEXANECARBONYL)-(1-OXO-TETRAHYDRO-THIOPYRAN-4-YL)-AMINO]-5-PHENYL-THIOPHENE-2-CARBOXYLIC ACID | +++ |

TABLE 1-continued

| | | | |
|---|---|---|---|
| 69 | 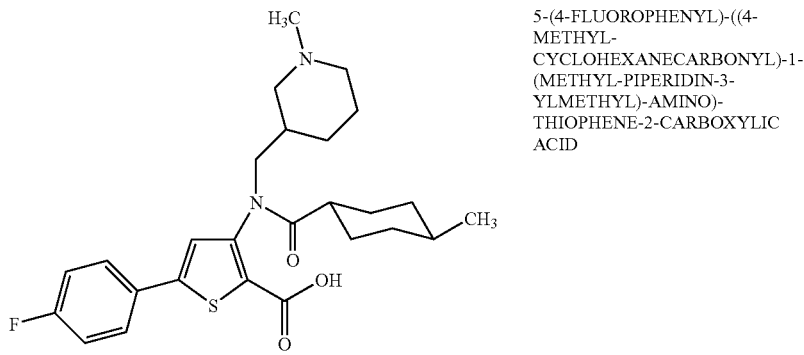 | 5-(4-FLUOROPHENYL)-((4-METHYL-CYCLOHEXANECARBONYL)-1-(METHYL-PIPERIDIN-3-YLMETHYL)-AMINO)-THIOPHENE-2-CARBOXYLIC ACID | +++ |
| 70 | 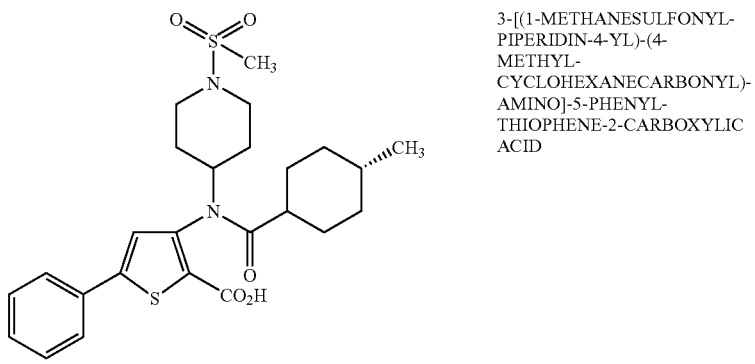 | 3-[(1-METHANESULFONYL-PIPERIDIN-4-YL)-(4-METHYL-CYCLOHEXANECARBONYL)-AMINO]-5-PHENYL-THIOPHENE-2-CARBOXYLIC ACID | +++ |
| 71 | 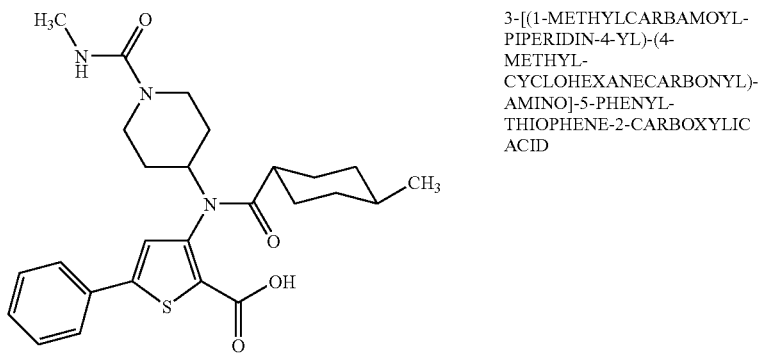 | 3-[(1-METHYLCARBAMOYL-PIPERIDIN-4-YL)-(4-METHYL-CYCLOHEXANECARBONYL)-AMINO]-5-PHENYL-THIOPHENE-2-CARBOXYLIC ACID | +++ |
| 72 | 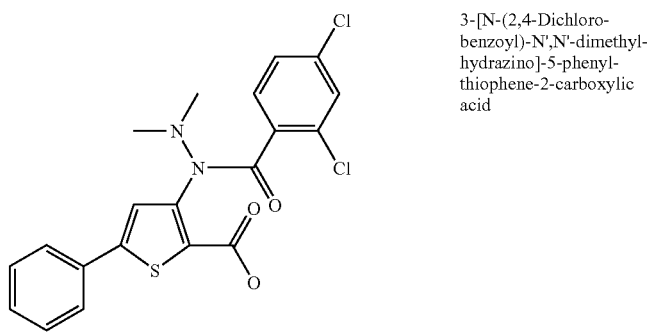 | 3-[N-(2,4-Dichloro-benzoyl)-N',N'-dimethyl-hydrazino]-5-phenyl-thiophene-2-carboxylic acid | +++ |

TABLE 1-continued

| | | | |
|---|---|---|---|
| 73 | 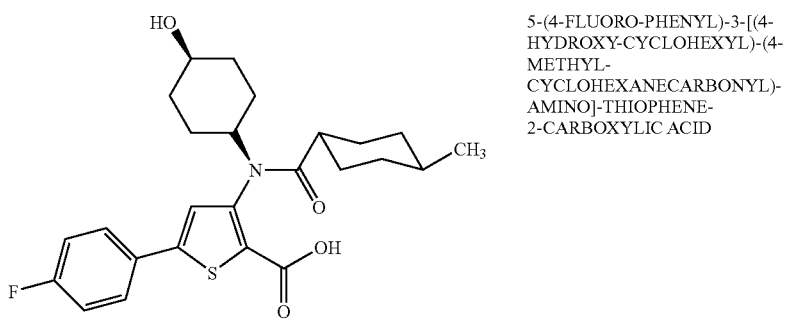 | 5-(4-FLUORO-PHENYL)-3-[(4-HYDROXY-CYCLOHEXYL)-(4-METHYL-CYCLOHEXANECARBONYL)-AMINO]-THIOPHENE-2-CARBOXYLIC ACID | +++ |
| 74 | 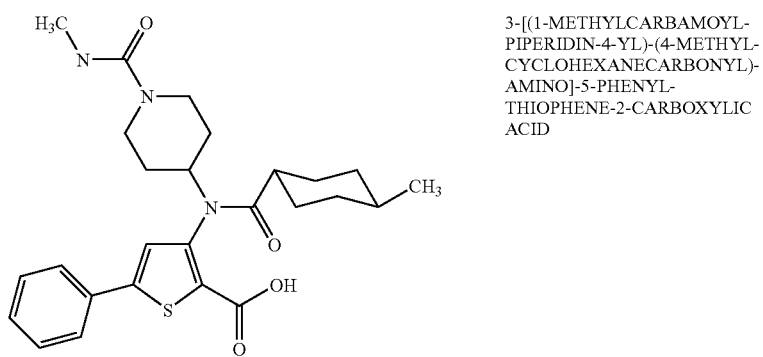 | 3-[(1-METHYLCARBAMOYL-PIPERIDIN-4-YL)-(4-METHYL-CYCLOHEXANECARBONYL)-AMINO]-5-PHENYL-THIOPHENE-2-CARBOXYLIC ACID | +++ |
| 75 | 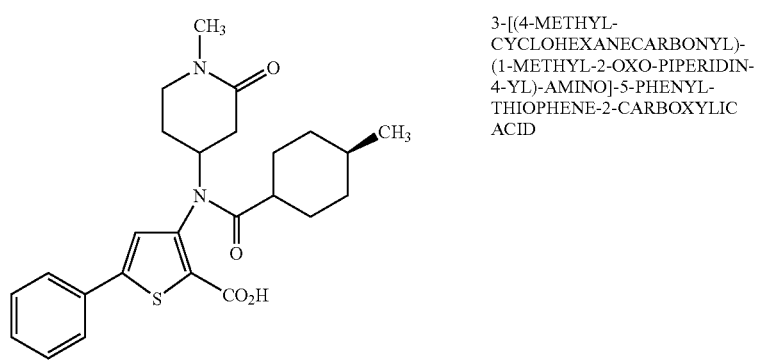 | 3-[(4-METHYL-CYCLOHEXANECARBONYL)-(1-METHYL-2-OXO-PIPERIDIN-4-YL)-AMINO]-5-PHENYL-THIOPHENE-2-CARBOXYLIC ACID | +++ |
| 76 | 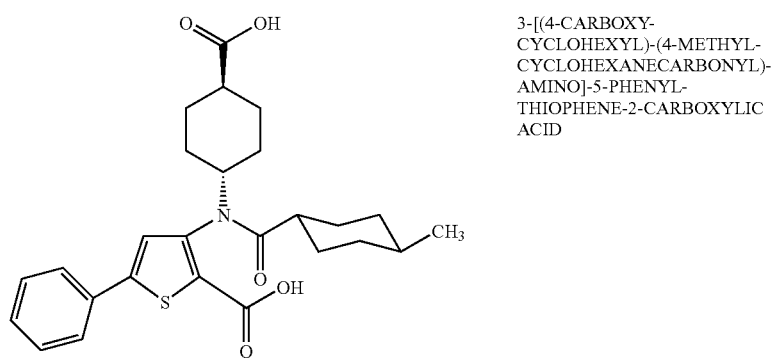 | 3-[(4-CARBOXY-CYCLOHEXYL)-(4-METHYL-CYCLOHEXANECARBONYL)-AMINO]-5-PHENYL-THIOPHENE-2-CARBOXYLIC ACID | +++ |

TABLE 1-continued

| 77 | 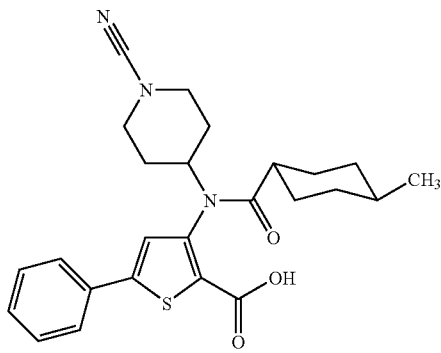 | 3-[(1-CYANO-PIPERIDIN-4-YL)-(4-METHYL-CYCLOHEXANECARBONYL)-AMINO]-5-PHENYL-THIOPHENE-2-CARBOXYLIC ACID | +++ |
| 78 | 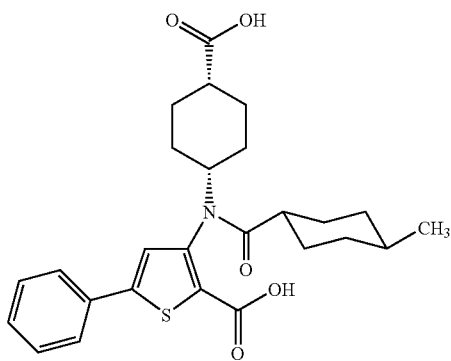 | 3-[(4-CARBOXY-CYCLOHEXYL)-(4-METHYL-CYCLOHEXANECARBONYL)-AMINO]-5-PHENYL-THIOPHENE-2-CARBOXYLIC ACID | +++ |
| 79 | 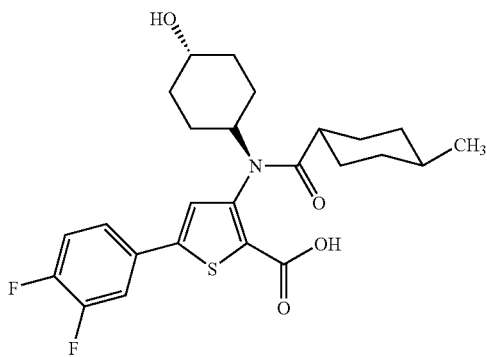 | 5-(3,4-DIFLUORO-PHENYL)-3-[(4-HYDROXY-CYCLOHEXYL)-(4-METHYL-CYCLOHEXANE-CARBONYL)-AMINO]-THIOPHENE-2-CARBOXYLIC ACID | +++ |
| 80 | 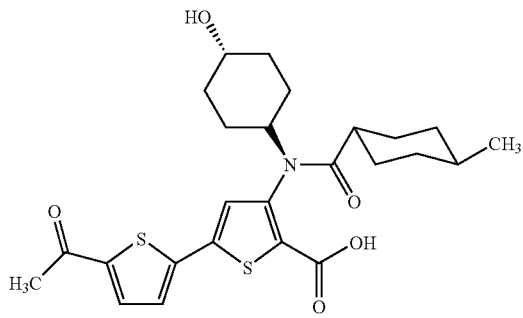 | 5'-ACETYL-4-[(4-HYDROXY-CYCLOHEXYL)-(4-METHYL-CYCLOHEXANECARBONYL)-AMINO]-[2,2']BITHIOPHENYL-5-CARBOXYLIC ACID | +++ |

TABLE 1-continued

| 81 | 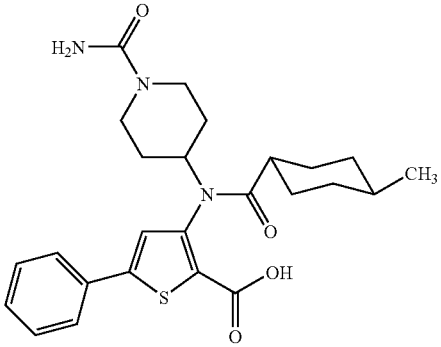 | 3-[(1-CARBAMOYL-PIPERIDIN-4-YL)-(4-METHYL-CYCLOHEXANECARBONYL)-AMINO]-5-PHENYL-THIOPHENE-2-CARBOXYLIC ACID | +++ |
| 82 | 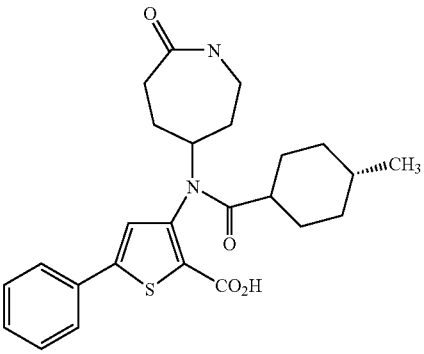 | 3-[(4-METHYL-CYCLOHEXANECARBONYL)-(7-OXO-AZEPAN-A-YL)-AMINO]-5-PHENYL-THIOPHENE-2-CARBOXYLIC ACID | +++ |
| 83 | 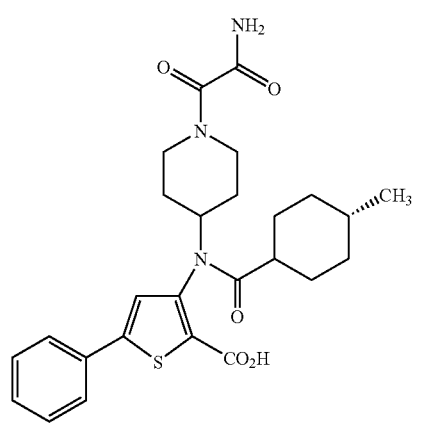 | 3-[(1-AMINOOXALYL-PIPERIDIN-4-YL)-(4-METHYL-CYCLOHEXANECARBONYL)-AMINO]-5-PHENYL-THIOPHENE-2-CARBOXYLIC ACID | +++ |
| 84 | 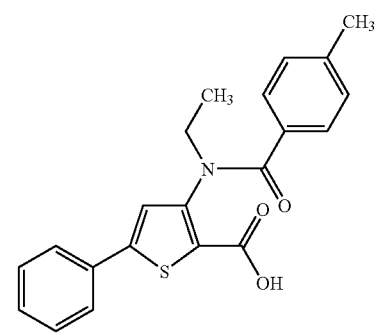 | 3-[ETHYL-(4-METHYL-BENZOYL)-AMINO]-5-PHENYL-THIOPHENE-2-CARBOXYLIC ACID | +++ |

TABLE 1-continued

| | | | |
|---|---|---|---|
| 85 | (structure) | 5-(4-ACETYL-PHENYL)-3-[(4-HYDROXY-CYCLOHEXYL)-(4-METHYL-CYCLOHEXANECARBONYL)-AMINO]-THIOPHENE-2-CARBOXYLIC ACID | +++ |
| 86 | (structure) | 3-[(4-HYDROXY-4-METHYL-CYCLOHEXYL)-(4-METHYL-CYCLOHEXANECARBONYL)-AMINO]-5-PHENYL-THIOPHENE-2-CARBOXYLIC ACID | +++ |
| 87 | (structure) | 3-[(3-HYDROXY-CYCLOHEXYL)-(4-METHYL-CYCLOHEXANECARBONYL)-AMINO]-5-PHENYL-THIOPHENE-2-CARBOXYLIC ACID | +++ |
| 88 | (structure) | 3-[(4-HYDROXY-4-METHYL-CYCLOHEXYL)-(4-METHYL-CYCLOHEXANECARBONYL)-AMINO]-5-PHENYL-THIOPHENE-2-CARBOXYLIC ACID | +++ |
| 89 | (structure) | 3-[(3-HYDROXY-CYCLOHEXYL)-(4-METHYL-CYCLOHEXANECARBONYL)-AMINO]-5-PHENYL-THIOPHENE-2-CARBOXYLIC ACID | +++ |

TABLE 1-continued

| | | |
|---|---|---|
| 90 | 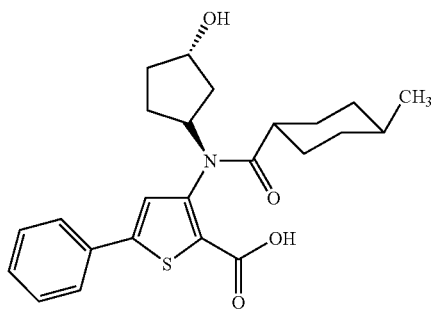 | 3-[(3-HYDROXY-CYCLOPENTYL)-(4-METHYL-CYCLOHEXANECARBONYL)-AMINO]-5-PHENYL-THIOPHE-2-CARBOXYLIC ACID +++ |

+++ $IC_{50} < 5\ \mu M$
++ $IC_{50}\ 5\ \mu M\text{-}20\ \mu M$
+ $IC_{50} > 20\ \mu M$

EXAMPLE 37

Evaluation of Compounds in the HCV RNA-Dependent RNA Polymerase Assay

The following references are all incorporated by reference:
1. Behrens, S., Tomei, L., De Francesco, R. (1996) *EMBO* 15, 12-22
2. Harlow, E, and Lane, D. (1988) *Antibodies: A Laboratory Manual*. Cold Spring Harbord Laboratory. Cold Spring Harbord. N.Y.
3. Lohmann, V., Körner, F., Herian, U., and Bartenschlager, R. (1997) *J. Virol.* 71, 8416-8428
4. Tomei, L., Failla, C., Santolini, E., De Francesco, R., and La Monica, N. (1993) *J Virol* 67, 4017-4026

Compounds were evaluated using an in vitro polymerase assay containing purified recombinant HCV RNA-dependent RNA polymerase (NS5B protein). HCV NS5B was expressed in insect cells using a recombinant baculovirus as vector. The experimental procedures used for the cloning, expression and purification of the HCV NS5B protein are described below. Follows, are details of the RNA-dependent RNA polymerase assays used to test the compounds.

Expression of the HCV NS5B Protein in Insect Cells:

The cDNA encoding the entire NS5B protein of HCV-Bk strain, genotype 1b, was amplified by PCR using the primers NS5Nhe5' (5'-GCTAGCGCTAGCTCAATGTCCTACA-CATGG-3') (SEQ ID NO: 1) and XhoNS53' (5'-CTC-GAGCTCGAGCGTCCATCGQTTGGGGAG-3') (SEQ ID NO: 2) and the plasmid pCD 3.8-9.4 as template (Tomei et al, 1993). NS5Nhe5' and XhoNS53' contain two NheI and XhoI sites (underlined sequences), respectively, at their 5' end. The amplified DNA fragment was cloned in the bacterial expression plasmid pET-21b (Novagen) between the restriction sites NheI and XhoI, to generate the plasmid pET/NS5B. This plasmid was later used as template to PCR-amplify the NS5B coding region, using the primers NS5B-H9 (5'-ATA-CATATGGCTAGCATGTCAATGTCCTACACATGG-3') (SEQ ID NO: 3) and NS5B-R4 (5'-GGATCCGGATCGCGT-TCATCGGTTGGGGAG-3') (SEQ ID NO: 4). NS5B-H9 spans a region of 15 nucleotides in the plasmid pET-21b followed by the translation initiation codon (ATG) and 8 nucleotides corresponding to the 5' end of the NS5B coding region (nt. 7590-7607 in the HCV sequence with the accession number M58335). NS5B-R4 contains two BamHI sites (underlined) followed by 18 nucleotides corresponding to the region around the stop codon in the HCV genome (nt. 9365-9347). The amplified sequence, of 1.8 kb, was digested with NheI and BamHI and ligated to a predigested pBlueBacII plasmid (Invitrogen). The resulting recombinant plasmid was designated pBac/NS5B. Sf9 cells were co-transfected with 3 μg of pBac/NS5B, together with 1 μg of linearized baculovirus DNA (Invitrogen), as described in the manufacturer's protocol. Following two rounds of plaque purification, an NS5B-recombinant baculovirus, BacNS5B, was isolated. The presence of the recombinant NS5B protein was determined by western blot analysis (Harlow and Lane, 1988) of BacNS5B-infected Sf9 cells, using a rabbit polyclonal antiserum (anti-NS5B) raised against a His-tagged version of the NS5B protein expressed in *E. coli*. Infections of Sf9 cells with this plaque purified virus were performed in one-liter spinner flasks at a cell density of $1.2 \times 10^6$ cells/ml and a multiplicity of infection of 5.

Preparation of a Soluble Recombinant NS5B Protein

Sf9 cells were infected as described above. Sixty hours post-infection, cells were harvested then washed twice with phosphate buffer saline (PBS). Total proteins were solubilized as described in Lohmann et al. (1997) with some modifications. In brief, proteins were extracted in three steps, S1, S2, S3, sing lysis buffers (LB) I, LB II and LB III (Lohmann et al, 1997). The composition of LBII was modified to contain 0.1% triton X-100 and 150 mM NaCl to reduce the amount of solubilized NS5B protein at this step. In addition, sonication of cell extracts was avoided throughout the protocol to reserve the integrity of the protein structure.

Purification of Recombinant NS5B Using Fast Protein Liquid Chromatography (FPLC):

Soluble NS5B protein in the S3 fraction was diluted to lower the NaCl concentration to 300 mM, then it incubated batchwise with DEAE sepharose beads (Amersham-Pharmacia) for 2 hrs at 4° C., as described by Behrens et al. (1996). Unbound material was cleared by centrifugation for 15 min at 4° C., at 25 000 rpm using a SW41 rotor (Beckman). The supernatant was further diluted to lower the NaCl concentration to 200 mM and subsequently loaded, with a flow rate of 1 ml/min, on a 5 ml HiTrap® heparin column (Amersham- Pharmacia) connected to an FPLC® system (Amersham-Pharmacia). Bound proteins were eluted in 1 ml fractions, using a continuous NaCl gradient of 0.2 to 1 M, over a 25 ml volume. NS5B-containing fractions were identified by sodium dodecyl sulfate polyacrylamide gel electrophoresis (SDS-PAGE), followed by western blotting using the anti-NS5B antiserum at a dilution of 1:2000. Positive fractions were pooled and the elution buffer was exchanged against a 50 mM $NaPO_4$ pH 7.0, 20% glycerol, 0.5% triton X-100 and 10 mM DTT, using a PD-10 column (Amersham-Pharmacia). The sample was then loaded onto a 1 ml HiTrap® SP column (Amersham-Pharmacia), with a flow rate of 0.1 ml/min. Bound proteins were eluted using a continuous 0 to 1 M NaCl gradient over a 15 ml volume. Eluted fractions were analyzed by SDS-PAGE and western blotting. Alternatively, proteins were visualized, following SDS-PAGE, by silver staining using the Silver Stain Plus kit (BioRad) as described by the manufacturer. Positive fractions were tested for RdRp activity (see below) and the most active ones were pooled, and stored as a 40% glycerol solution at −70° C.

In vitro HCV RdRp Flashplate Scintillation Proximity Assay (STREP-FLASH ASSAY) Used to Evaluate Analogues:

This assay consists on measuring the incorporation of [$^3$H] radiolabelled UTP in a polyrA/biotinylated-oligo dT template-primer, captured on the surface of streptavidin-coated scintillant-embedded microtiter Flashplates™ (NEN Life Science Products inc, MA, USA, SMP 103A). In brief, a 400 ng/µl polyrA solution (Amersham Pharmacia Biotech) was mixed volume-to-volume with 5' biotin-oligo $dT_{15}$ at 20 pmol/µl. The template and primers were denatured at 95 C for 5 minutes then incubated at 37 C for 10 minutes. Annealed template-primers were subsequently diluted in a Tris-HCl containing buffer and allowed to bind to streptavidin-coated flashplates overnight. Unbound material was discarded, compounds were added in a 10 µl solution followed by a 10 µl of a solution containing 50 mM $MgCl_2$, 100 mM Tris-HCl pH 7.5, 250 mM NaCl and 5 mM DTT. The enzymatic reaction was initiated upon addition of a 30 µl solution containing the enzyme and substrate to obtain the following concentrations: 25 µM UTP, 1 µCi [$^3$H] UTP and 100 nM recombinant HCV NS5B. RdRp reactions were allowed to proceed for 2 hrs at room temperature after which wells were washed three times with a 250 µL of 0.15 M NaCl solution, air dried at 37 C, and counted using a liquid scintillation counter (Wallac Microbeta Trilex, Perkin-Elmer, MA, USA). Results are shown in Table 1.

The preceeding examples can be repeated with similar success by substituting the generically or specifically described reactants and/or operating conditions of this invention for those used in the preceeding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A compound selected from:
3-[(4-METHYL-CYCLOHEXANECARBONYL)-(4-OXO-CYCLOHEXYL)-AMINO]-5-PHENYL-THIOPHENE-2-CARBOXYLIC ACID;
3-[(4-HYDROXY-CYCLOHEXYL)-(4-METHYL-CYCLOHEXANECARBONYL)-AMINO]-5-PHENYL-THIOPHENE-2-CARBOXYLIC ACID;
3-[(4-HYDROXYIMINO-CYCLOHEXYL)-(4-METHYL-CYCLOHEXANECARBONYL)-AMINO]-5-PHENYL-THIOPHENE-2-CARBOXYLIC ACID;
3-[(4-METHOXYIMINO-CYCLOHEXYL)-(4-METHYL-CYCLOHEXANECARBONYL)-AMINO]-5-PHENYL-THIOPHENE-2-CARBOXYLIC ACID;
3-[(4-METHOXY-CYCLOHEXYL)-(4-METHYL-CYCLOHEXANECARBONYL)-AMINO]-5-PHENYL-THIOPHENE-2-CARBOXYLIC ACID;
5-(4-FLUORO-PHENYL)-3-[(4-HYDROXY-CYCLOHEXYL)-(4-METHYL-CYCLOHEXANECARBONYL)-AMINO]-THIOPHENE-2-CARBOXYLIC ACID;
5-(3-FLUORO-PHENYL)-3-[(4-HYDROXY-CYCLOHEXYL)-(4-METHYL-CYCLOHEXANECARBONYL)-AMINO]-THIOPHENE-2-CARBOXYLIC ACID;
5-(4-CHLORO-PHENYL)-3-[(4-HYDROXY-CYCLOHEXYL)-(4-METHYL-CYCLOHEXANECARBONYL)-AMINO]-THIOPHENE-2-CARBOXYLIC ACID;
3-[(4-HYDROXY-CYCLOHEXYL)-(4-METHYL-CYCLOHEXANECARBONYL)-AMINO]-5-(4-METHOXY-PHENYL)-THIOPHENE-2-CARBOXYLIC ACID;
5-(4-CYANO-PHENYL)-3-[(4-HYDROXY-CYCLOHEXYL)-(4-METHYL-CYCLOHEXANECARBONYL)-AMINO]-THIOPHENE-2-CARBOXYLIC ACID;
3-[(4-CARBOXY-CYCLOHEXYL)-(4-METHYL-CYCLOHEXANECARBONYL)-AMINO]-5-PHENYL-THIOPHENE-2-CARBOXYLIC ACID;
5-(3,4-DIFLUORO-PHENYL)-3-[(4-HYDROXY-CYCLOHEXYL)-(4-METHYL-CYCLOHEXANECARBONYL)-AMINO]-THIOPHENE-2-CARBOXYLIC ACID;
5-(4-ACETYL-PHENYL)-3-[(4-HYDROXY-CYCLOHEXYL)-(4METHYL-CYCLOHEXANECARBONYL)-AMINO]-THIOPHENE-2-CARBOXYLIC ACID;
3-[(4-HYDROXY-4-METHYL-CYCLOHEXYL)-(4-METHYL-CYCLOHEXANECARBONYL)-AMINO]-5-PHENYL-THIOPHENE-2-CARBOXYLIC ACID;
3-[(3-HYDROXY-CYCLOHEXYL)-(4-METHYL-CYCLOHEXANECARBONYL)-AMINO]-5-PHENYL-THIOPHENE-2-CARBOXYLIC ACID;
and
pharmaceutically acceptable salts thereof.

2. A compound according to claim 1, wherein said compound is 3-[(4-METHYL-CYCLOHEXANECARBONYL)-(4-OXO-CYCLOHEXYL)-AMINO]-5-PHENYL-THIOPHENE-2-CARBOXYLIC ACID, or a pharmaceutically acceptable salt thereof.

3. A compound according to claim 1, wherein said compound is 3-[(4-HYDROXY-CYCLOHEXYL)-(4-METHYL-CYCLOHEXANECARBONYL)-AMINO]-5-PHENYL-THIOPHENE-2-CARBOXYLIC ACID, or a pharmaceutically acceptable salt thereof.

4. A compound according to claim 1, wherein said compound is 3-[(4-HYDROXYIMINO-CYCLOHEXYL)-(4-METHYL-CYCLOHXANECARBONYL)-AMINO]-5-PHENYL-THIOPHENE-2-CARBOXYLIC ACID, or a pharmaceutically acceptable salt thereof.

5. A compound according to claim 1, wherein said compound is 3-[(4-METHOXYIMINO-CYCLOHEXYL)-(4-METHYL-CYCLOHEXANECARBONYL)-AMINO]-5-PHENYL-THIOPHENE-2-CARBOXYLIC ACID, or a pharmaceutically acceptable salt thereof.

6. A compound according to claim 1, wherein said compound is 3-[(4-METHOXY-CYCLOHEXYL)-(4-METHYL-CYCLOHEXANECARBONYL)-AMINO]-5-PHENYL-THIOPHENE-2-CARBOXYLIC ACID, or a pharmaceutically acceptable salt thereof.

7. A compound according to claim 1, wherein said compound is 5-(4-FLUORO-PHENYL)-3-[(4-HYDROXY-CYCLOHEXYL)-(4-METHYL-CYCLOHEXANECARBONYL)-AMINO]-THIOPHENE-2-CARBOXYLIC ACID, or a pharmaceutically acceptable salt thereof.

8. A compound according to claim 1, wherein said compound is 5-(3-FLUORO-PHENYL)-3-[(4-HYDROXY-CYCLOHEXYL)-(4-METHYL-CYCLOHEXANECARBONYL)-AMINO]-THIOPHENE-2-CARBOXYLIC ACID, or a pharmaceutically acceptable salt thereof.

9. A compound according to claim 1, wherein said compound is 5-(4-CHLORO-PHENYL)-3-[(4-HYDROXY-CYCLOHEXYL)-(4-METHYL-CYCLOHEXANECARBONYL)-AMINO]-THIOPENE-2-CARBOXYLIC ACID, or a pharmaceutically acceptable salt thereof.

10. A compound according to claim 1, wherein said compound is 3-[(4-HYDROXY-CYCLOHEXYL)-(4-METHYL-CYCLOHEXANECARBONYL)-AMINO]-5-(4-METHOXY-PHENYL)-THIOPHENE-2-CARBOXYLIC ACID, or a pharmaceutically acceptable salt thereof.

11. A compound according to claim 1, wherein said compound is 5-(4-CYANO-PHENYL)-3-[(4-HYDROXY-CYCLOHEXYL)-(4-METHYL-CYCLOHEXANECARBONYL)-AMINO]-THIOPHENE-2-CARBOXYLIC ACID, or a pharmaceutically acceptable salt thereof.

12. A compound according to claim 1, wherein said compound is 3-[(4-CARBOXY-CYCLOHEXYL)-(4-METHYL-CYCLOHEXANECARBONYL)-AMINO]-5-PHENYL-THIOPHENE-2-CARBOXYLIC ACID, or a pharmaceutically acceptable salt thereof.

13. A compound according to claim 1, wherein said compound is 5-(3,4-DIFLUORO-PHENYL)-3-[(4-HYDROXY- CYCLOHEXYL)-(4-METHYL-CYCLOHEXANECARBONYL)-AMINO]-THIOPHENE-2-CARBOXYLIC ACID, or a pharmaceutically acceptable salt thereof.

14. A compound according to claim 1, wherein said compound is 5-(4-ACETYL-PHENYL)-3-[(4-HYDROXY-CYCLOHEXYL)-(4-METHYL-CYCLOHEXANECARBONYL)-AMINO]-THIOPHENE-2-CARBOXYLIC ACID, or a pharmaceutically acceptable salt thereof.

15. A compound according to claim 1, wherein said compound is 3-[(4-HYDROXY-4-METHYL-CYCLOHEXYL)-(4-METHYL-CYCLOHEXANECARBONYL)-AMINO]-5-PHENYL-THIOPHENE-2-CARBOXYLIC ACID, or a pharmaceutically acceptable salt thereof.

16. A compound according to claim 1, wherein said compound is 3-[(3-HYDROXY-CYCLOHEXYL)-(4-METHYL-CYCLOHEXANECARBONYL)-AMINO]-5-PHENYL-THIOPHENE-2-CARBOXYLIC ACID, or a pharmaceutically acceptable salt thereof.

17. A compound according to claim 1, wherein said compound has a monosubstituted-cyclohexyl group attached to the amino and the mono-substituent group of the cyclohexyl group attached to the amino is in the trans position relative to the amino.

18. A compound according to claim 17, wherein said compound has a 3-substituted-cyclohexyl group or 4-substituted-cyclohexyl group attached to the amino.

19. A compound according to claim 18, wherein said compound has a 4-hydroxy-cyclohexyl group attached to the amino.

20. A compound according to claim 1, wherein said compound has a monosubstituted-cyclohexyl group attached to the amino and the mono-substituent group of the cyclohexyl group attached to the amino is in the cis position relative to the amino.

21. A compound according to claim 20, wherein said compound has a 3-substituted-cyclohexyl group or 4-substituted-cyclohexyl group attached to the amino.

22. A compound according to claim 21, wherein said compound has a 4-hydroxy-cyclohexyl group attached to the amino.

23. A compound according to claim 17, wherein said compound has a monosubstituted-cyclohexyl group attached to the carbonyl and the mono-substituent of the cyclohexyl group attached to the carbonyl is in the trans position relative to the carbonyl.

24. A compound according to claim 18, wherein said compound has a monosubstituted-cyclohexyl group attached to the carbonyl and the mono-substituent of the cyclohexyl group attached to the carbonyl is in the trans position relative to the carbonyl.

25. A compound according to claim 19, wherein said compound has a monosubstituted-cyclohexyl group attached to the carbonyl and the mono-substituent of the cyclohexyl group attached to the carbonyl is in the trans position relative to the carbonyl.

26. A compound according to claim 23, wherein said compound has a 4-hydroxy-cyclohexyl group attached to the carbonyl.

27. A compound according to claim 24, wherein said compound has a 4-hydroxy-cyclohexyl group attached to the carbonyl.

28. A compound according to claim 25, wherein said compound has a 4-hydroxy-cyclohexyl group attached to the carbonyl.

29. A compound according to claim 18, wherein said compound is selected from compounds of the following formulas and pharmaceutically acceptable salts thereof:

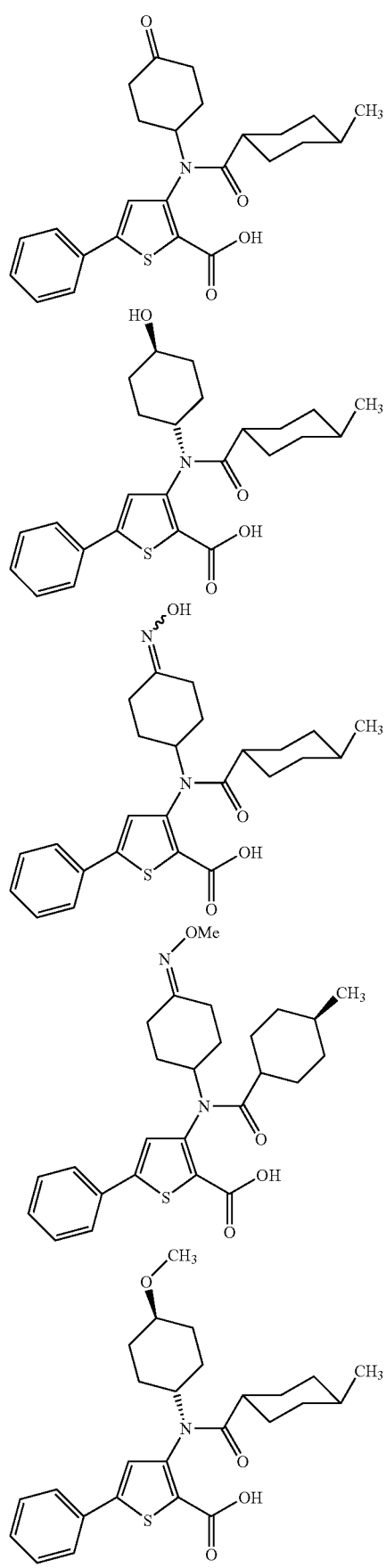

137
-continued
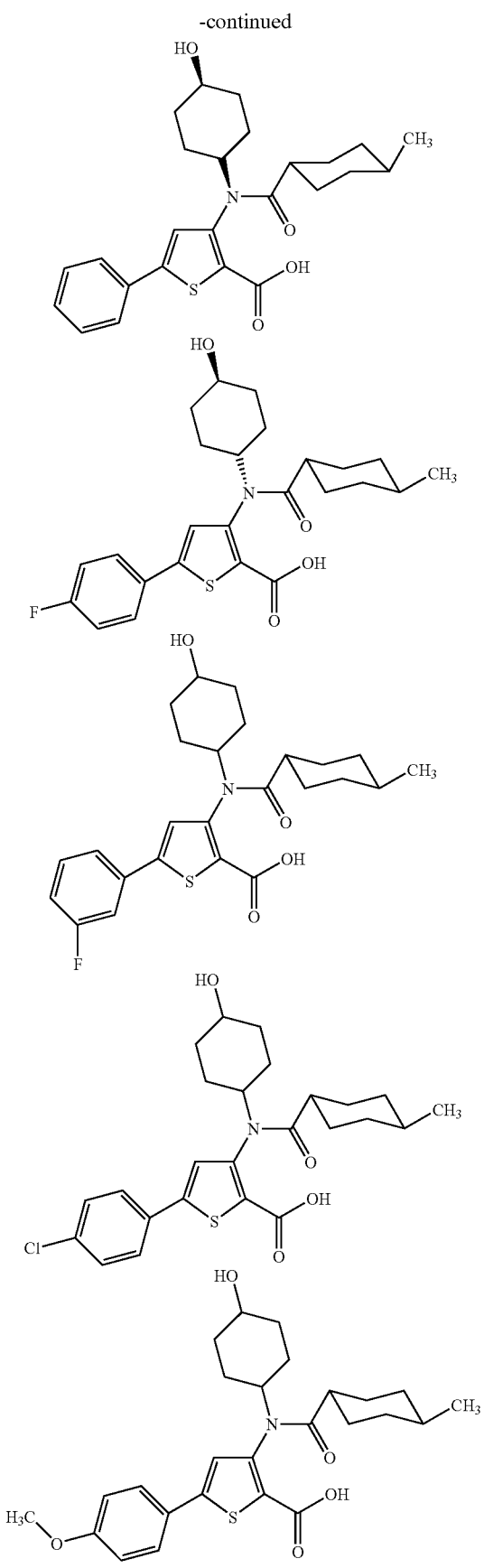
138
-continued
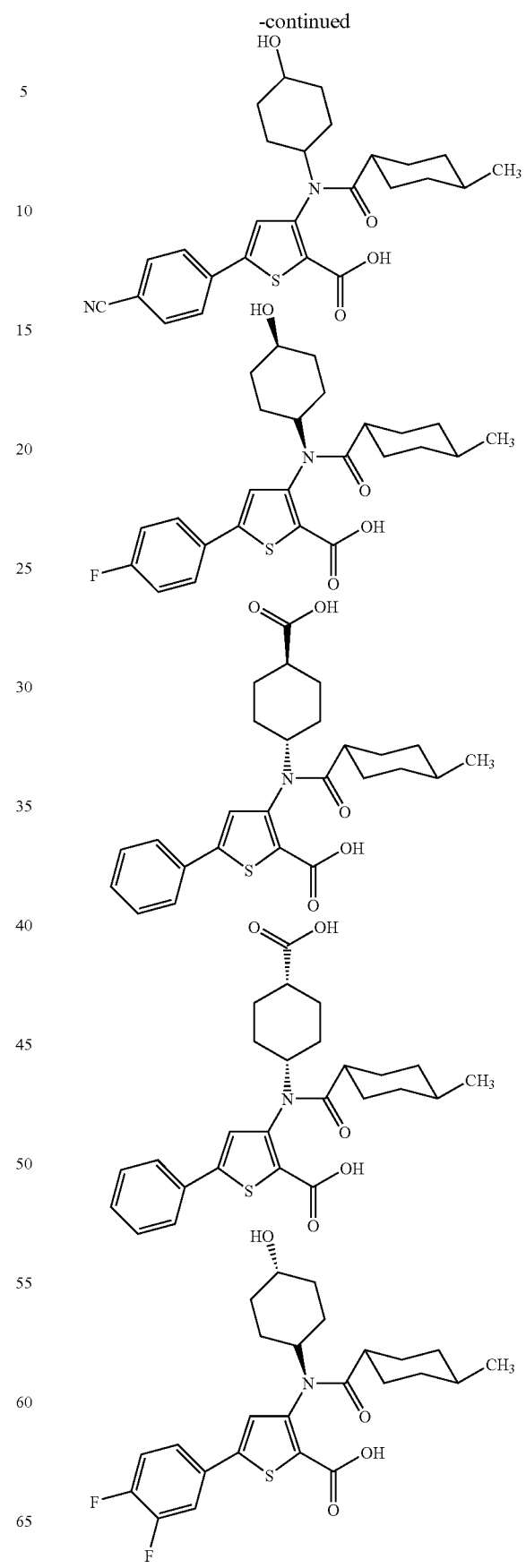

-continued
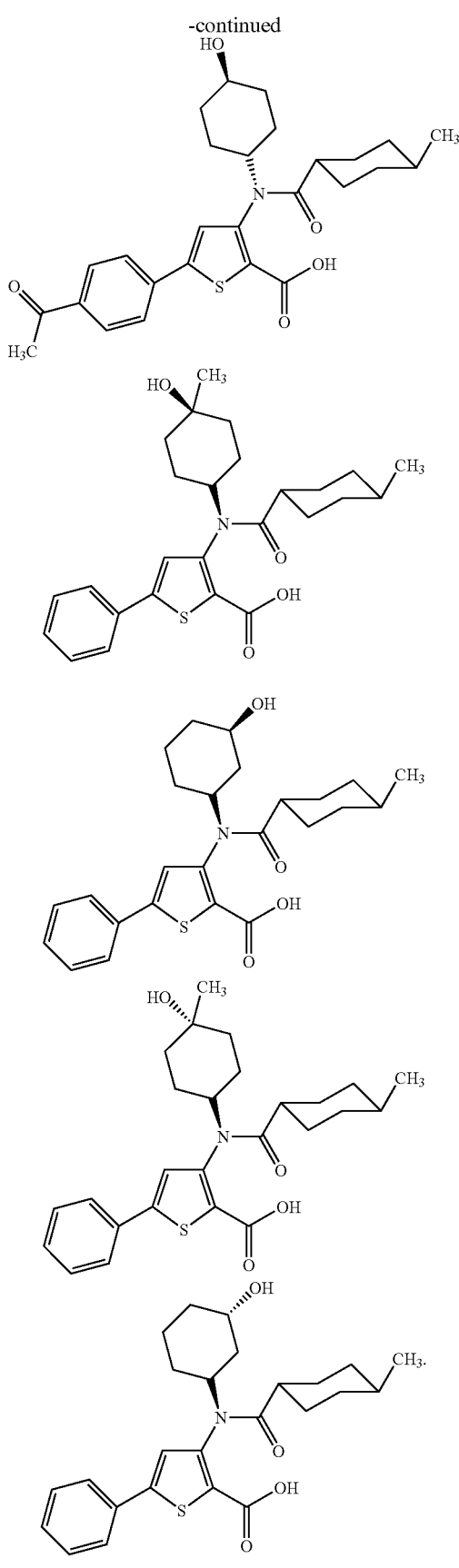
30. A compound according to claim 29, wherein said compound is selected from compounds of the following formulas and pharmaceutically acceptable salts thereof:
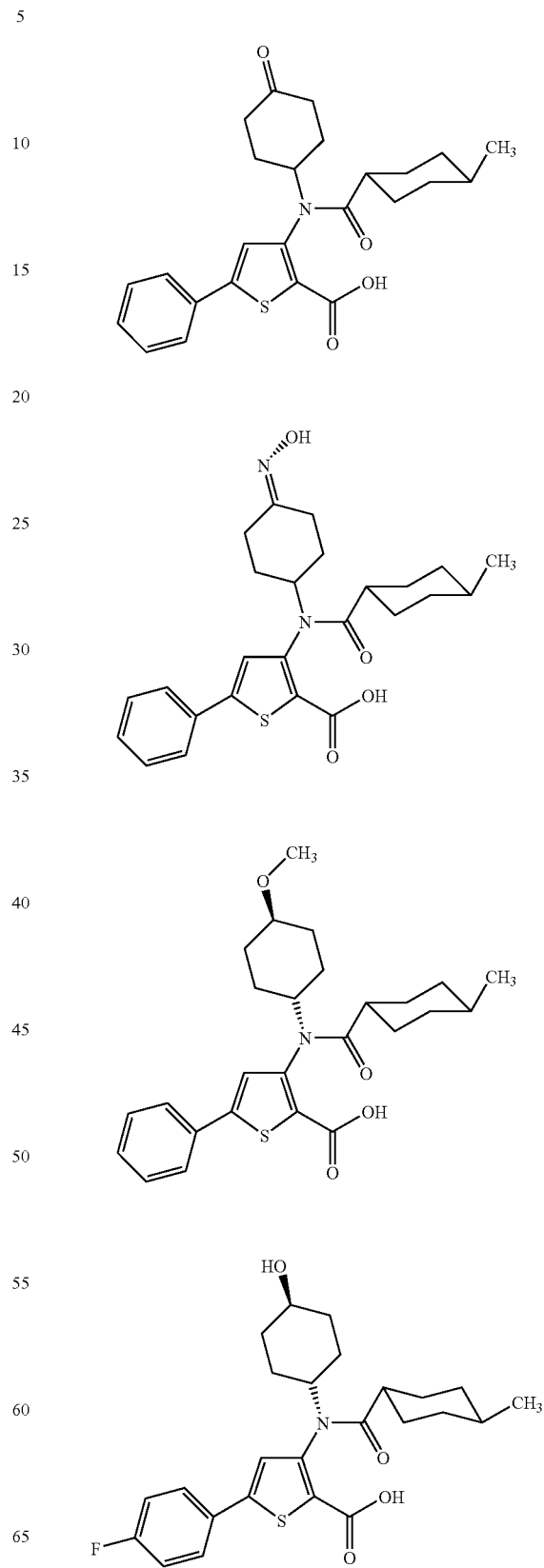

-continued

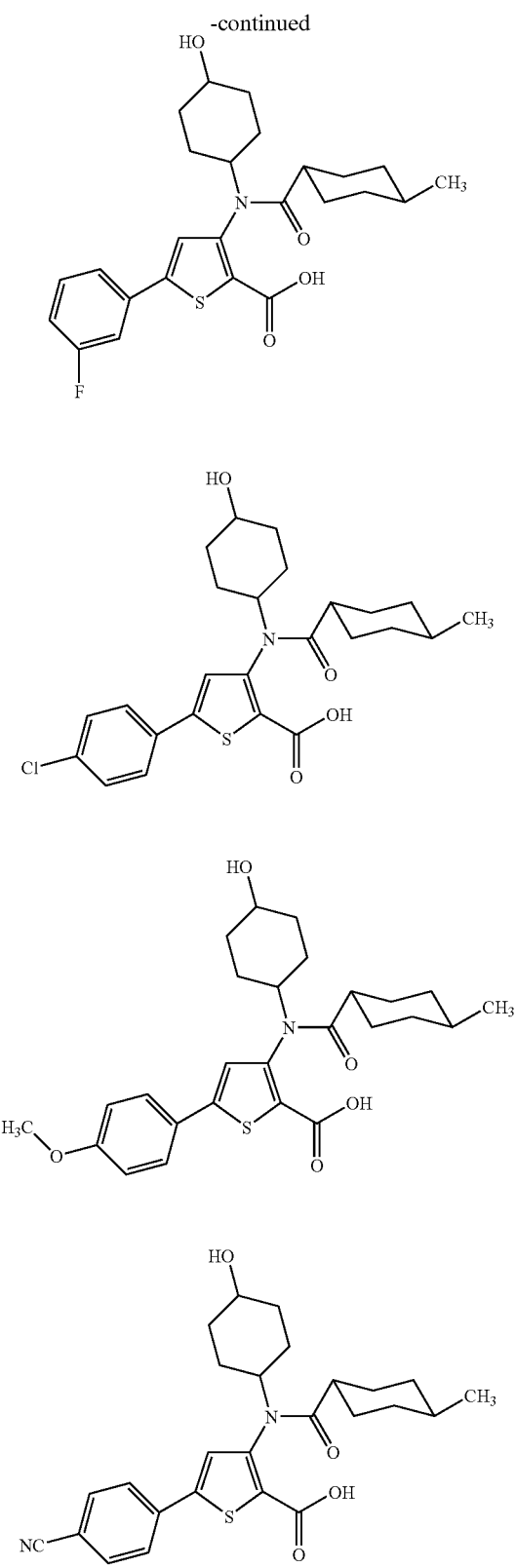

-continued

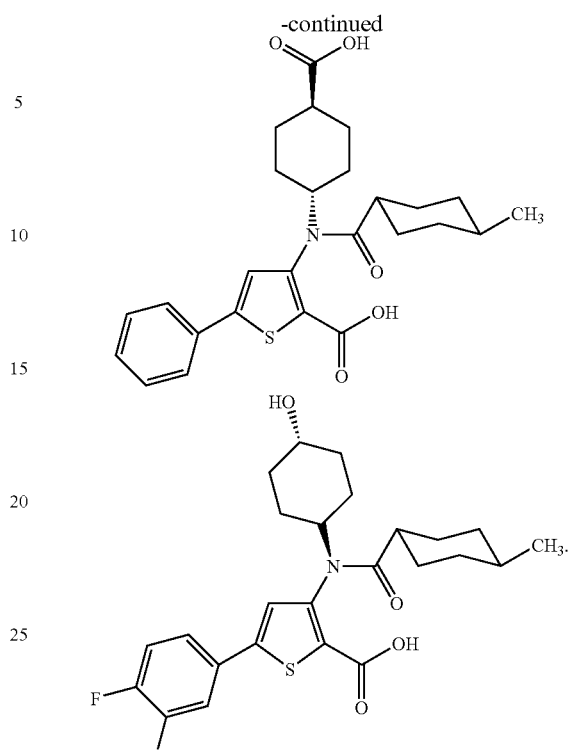

31. A compound according to claim 3, wherein said compound is 3-[trans-4-HYDROXY-CYCLOHEXYL)-(trans-4-METHYL-CYCLOHEXANECARBONYL)-AMINO]-5-PHENYL-THIOPHENE-2-CARBOXYLIC ACID, or a pharmaceutically acceptable salt thereof.

32. A compound according to claim 3, wherein said compound is 3-[(cis-4-HYDROXY-CYCLOHEXYL)-(trans-4-METHYL-CYCLOHEXANECARBONYL)-AMINO]-5-PHENYL-THIOPHENE-2-CARBOXYLIC ACID, or a pharmaceutically acceptable salt thereof.

33. A compound according to any one of claims any one of claims 1, 29, 31 and 32, wherein said compound is a sodium salt.

34. A pharmaceutical composition comprising at least one compound according to any one of claims 1, 29, 31 and 32 and at least one pharmaceutically acceptable carrier or excipient.

35. A composition according to claim 34, wherein said compound is a sodium salt.

36. A method for treating a HCV infection in a host comprising administering to the host a therapeutically effective amount of at least one compound according to any one of claims 1, 29, 31 and 32.

37. A method according to claim 36, wherein said pharmaceutically acceptable salt is a sodium salt.

38. A method according to claim 36, wherein said HCV of genotype 1b.

39. A method for inhibiting or reducing the activity of HCV polymerase in a host comprising administering to said host a therapeutically effective amount of at least one compound according to any one of claims 1, 29, 31 and 32.

40. A method according to claim 39, wherein said compound is a sodium salt.

* * * * *